United States Patent
Cheng et al.

(10) Patent No.: US 9,238,646 B2
(45) Date of Patent: *Jan. 19, 2016

(54) N-(HETERO)ARYL, 2-(HETERO)ARYL-SUBSTITUTED ACETAMIDES FOR USE AS WNT SIGNALING MODULATORS

(71) Applicants: Dai Cheng, San Diego, CA (US); Guobao Zhang, San Diego, CA (US); Dong Han, San Diego, CA (US); Wenqi Gao, San Diego, CA (US); Shifeng Pan, San Diego, CA (US)

(72) Inventors: Dai Cheng, San Diego, CA (US); Guobao Zhang, San Diego, CA (US); Dong Han, San Diego, CA (US); Wenqi Gao, San Diego, CA (US); Shifeng Pan, San Diego, CA (US)

(73) Assignee: NOVARTIS AG, Basel (CH)

(*) Notice: Subject to any disclaimer, the term of this patent is extended or adjusted under 35 U.S.C. 154(b) by 15 days.

This patent is subject to a terminal disclaimer.

(21) Appl. No.: 13/948,038

(22) Filed: Jul. 22, 2013

(65) Prior Publication Data

US 2013/0310375 A1  Nov. 21, 2013

Related U.S. Application Data

(62) Division of application No. 13/132,294, filed as application No. PCT/US2010/025813 on Mar. 1, 2010, now Pat. No. 8,546,396.

(60) Provisional application No. 61/156,599, filed on Mar. 2, 2009, provisional application No. 61/245,187, filed on Sep. 23, 2009.

(51) Int. Cl.
| | |
|---|---|
| A61K 31/496 | (2006.01) |
| A61K 31/497 | (2006.01) |
| A61K 31/501 | (2006.01) |
| A61K 31/5377 | (2006.01) |
| A61K 31/444 | (2006.01) |
| C07D 401/12 | (2006.01) |
| C07D 401/14 | (2006.01) |
| C07D 403/14 | (2006.01) |
| C07D 413/14 | (2006.01) |
| C07D 417/12 | (2006.01) |
| C07D 213/75 | (2006.01) |
| C07D 403/12 | (2006.01) |
| C07D 417/14 | (2006.01) |

(52) U.S. Cl.
CPC ............ *C07D 417/12* (2013.01); *C07D 213/75* (2013.01); *C07D 401/12* (2013.01); *C07D 401/14* (2013.01); *C07D 403/12* (2013.01); *C07D 403/14* (2013.01); *C07D 413/14* (2013.01); *C07D 417/14* (2013.01)

(58) Field of Classification Search
None
See application file for complete search history.

(56) References Cited

FOREIGN PATENT DOCUMENTS

| AU | 1993035694 | 10/1993 |
|---|---|---|
| WO | WO9903854 | 1/1999 |
| WO | WO2004046117 | 6/2004 |
| WO | WO2004046130 | 6/2004 |
| WO | WO2004058758 | 7/2004 |
| WO | WO2004072025 | 8/2004 |
| WO | WO2006116503 | 11/2006 |
| WO | WO2008058037 | 5/2008 |
| WO | WO2008152094 | 12/2008 |
| WO | WO2009075874 | 6/2009 |
| WO | WO2012003189 | 1/2012 |

OTHER PUBLICATIONS

Logan, et al., "The WNT Signaling Pathway in Development and Disease", Annual Review of Cell and Developmental Biology, 2004, pp. 781-810, vol. 20.

Kypta, et al., "GSK-3 inhibitors and their potential in the treatment of Alzheimer's disease", Expert Opinion on Therapeutic Patents, Jan. 1, 2005, pp. 1315-1331, vol. 15, No. 10, Ashley Publications Ltd.

Chen, et al., "Small molecule-mediated disruption of Wnt-dependent signaling in tissue regeneration and cancer", Nature Chemical Biology, Feb. 2009, pp. 100-107, vol. 5, No. 2, Nature America, Inc.

Russell, et al., "Epigenetically Altered Wound Healing in Keloid Fibroblasts", Journal of Investigative Dermatology, 2010, pp. 2489-2496, vol. 130, The Society for Investigative Dermatology.

Velasco, et al., "Wnt pathway genes in osteoporosis and osteoarthritis: differential expression and genetic associaton study", Osteoporosis Int., 2010, pp. 109-118, vol. 21, International Osteoporosis Foundation and National Osteoporosis Foundation.

Mazieres, et al., "Wnt Inhibitory Factor-1 is Silenced by Promoter Hypermethylation in Human Lung Cancer", Cancer Research, Jul. 15, 2004, pp. 4717-4720, vol. 64.

Nager, et al., "B-Catenin Signalling in Glioblastoma Multiforme and Glioma-Initiating Cells", Chemotherapy Research and Practice, 2011, pp. 1-7, vol. 2012, Article ID 192362.

*Primary Examiner* — Emily Bernhardt
(74) *Attorney, Agent, or Firm* — Emily T. Wu; Genomics Insititute of the Novartis Research Foundation

(57) ABSTRACT

The present invention relates to compositions and methods for modulating the Wnt signaling pathway.

7 Claims, No Drawings

N-(HETERO)ARYL, 2-(HETERO)ARYL-SUBSTITUTED ACETAMIDES FOR USE AS WNT SIGNALING MODULATORS

CROSS-REFERENCE TO RELATED APPLICATIONS

This application is a divisional of U.S. patent application Ser. No. 13/132,294, a 371 U.S. national phase application of international application number PCT/US2010/025813 filed Mar. 1, 2010, which claims the benefit of U.S. provisional application Ser. No. 61/156,599, filed Mar. 2, 2009; and of U.S. provisional application Ser. No. 61/245,187, filed Sep. 23, 2009. Each of these applications is incorporated herein by reference in their entirety.

TECHNICAL FIELD

The present invention relates to compositions and methods for modulating the Wnt signaling pathway.

BACKGROUND

The Wnt gene family encodes a large class of secreted proteins related to the Int1/Wnt1 proto-oncogene and *Drosophila* wingless ("Wg"), a *Drosophila* Wnt1 homologue (Cadigan et al. (1997) Genes & Development 11:3286-3305). Wnts are expressed in a variety of tissues and organs and play a major role in many developmental processes, including segmentation in *Drosophila*; endoderm development in *C. elegans*; and establishment of limb polarity, neural crest differentiation, kidney morphogenesis, sex determination, and brain development in mammals (Parr, et al. (1994) Curr. Opinion Genetics & Devel. 4:523-528). The Wnt pathway is a master regulator in animal development, both during embryogenesis and in the mature organism (Eastman, et al. (1999) Curr Opin Cell Biol 11: 233-240; Peifer, et al. (2000) Science 287: 1606-1609).

Wnt signals are transduced by the Frizzled ("Fz") family of seven transmembrane domain receptors (Bhanot et al. (1996) Nature 382:225-230). Wnt ligands bind to Fzd, and in so doing, activate the cytoplasmic protein Dishevelled (Dvl-1, 2 and 3 in humans and mice)(Boutros, et al. (1999) Mech Dev 83: 27-37) and phosphorylate LRP5/6. A signal is thereby generated which prevents the phosphorylation and degradation of Armadillo/β(beta)-catenin, in turn leading to the stabilization of β-catenin (Perrimon (1994) Cell 76:781-784). This stabilization is occasioned by Dvl's association with axin (Zeng et al. (1997) Cell 90:181-192), a scaffolding protein that brings various proteins together, including GSK3, APC, CK1, and β-catenin, to form the β-catenin destruction complex.

The Wingless-type (Wnt) Frizzled protein receptor pathway involves important regulatory genes that carry polymorphisms associated with primary carcinomas. In the course of downstream signaling, cytosolic β-catenin accumulates, translocates into the nucleus, and then enhances gene expression by complexing with other transcription factors Uthoff et al., *Mol Carcinog*, 31:56-62 (2001). In the absence of Wnt signals, free cytosolic β-catenin is incorporated into a complex consisting of Axin, the adenomatous polyposis coli (APC) gene product, and glycogen synthase kinase (GSK)-3β. Conjunctional phosphorylation of Axin, APC, and β-catenin by GSK-3β designates β-catenin for the ubiquitin pathway and degradation by proteasomes Uthoff et al., *Mol Carcinog*, 31:56-62 (2001); Matsuzawa et al., *Mol Cell*, 7:915-926 (2001).

Disheveled (Dvl) is a positive mediator of Wnt signalling positioned downstream of the frizzled receptors and upstream of βcatenin. GSK-3 phosphorylates several proteins in the Wnt pathway and is instrumental in the downstream regulation of βcatenin. Mutations in the gene APC are an initiating event for both sporadic and hereditary colorectal tumorigenesis. APC mutants are relevant in tumorigenesis, since the aberrant protein is an integral part of the Wnt-signaling cascade. The protein product contains several functional domains acting as binding and degradation sites for βcatenin Mutations that occur in the amino-terminal segment of βcatenin are usually involved in phosphorylation-dependent, ubiquitin-mediated degradation and, thus, stabilize βcatenin. When stabilized cytoplasmic-catenin accumulates, it translocates to the nucleus interacting with the Tcf/Lef high-mobility group of transcription factors that modulate expression of oncogenes such as c-myc.

It is known that Wnt/β-catenin signaling promotes cell survival in various cell types Orford et al., *J Cell Biol*, 146: 855-868 (1999); Cox et al., *Genetics*, 155:1725-1740 (2000); Reya et al., *Immunity*, 13:15-24 (2000); Satoh et al., *Nat Genet*, 24:245-250 (2000); Shin et al., *Journal of Biological Chemistry*, 274:2780-2785 (1999); Chen et al., *J Cell Biol*, 152:87-96 (2001); Ioannidis et al., *Nat Immunol*, 2:691-697 (2001). Wnt signaling pathway is also thought to be associated with tumor development and/or progression (Polakis et al., *Genes Dev*, 14:1837-1851 (2000); Cox et al., *Genetics*, 155:1725-1740 (2000); Bienz et al., *Cell*, 103:311-320 (2000); You et al., *J Cell Biol*, 157:429-440 (2002)). Aberrant activation of the Wnt signaling pathway is associated with a variety of human cancers, correlating with the over-expression or amplification of c-Myc (Polakis et al., *Genes Dev*, 14:1837-1851 (2000); Bienz et al., *Cell*, 103:311-320 (2000); Brown et al., *Breast Cancer Res*, 3:351-355 (2001); He et al., *Science*, 281:1509-1512 (1998); Miller et al., *Oncogene*, 18:7860-7872 (1999). In addition, c-Myc was identified as one of the transcriptional targets of the β-catenin/Tcf in colorectal cancer cells (He et al., *Science*, 281:1509-1512 (1998); de La Coste et al., *Proc Natl Acad Sci USA*, 95:8847-8851 (1998); Miller et al., *Oncogene*, 18:7860-7872 (1999); You et al., *J Cell Biol*, 157:429-440 (2002)).

Thus, a need exists for agents and methods that modulate the Wnt signaling pathway, thereby treating, diagnosing, preventing, and/or ameliorating Wnt signaling-related disorders.

DISCLOSURE OF THE INVENTION

The present invention relates to compositions and methods for modulating the Wnt signaling pathway.

In one aspect, the present invention provides a compound having Formula (1) or (2):

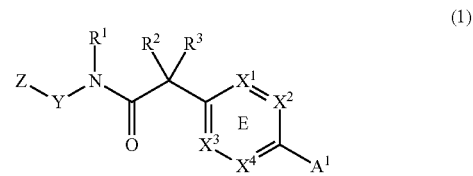

-continued

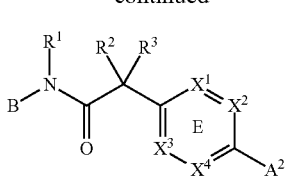

(2)

or a physiologically acceptable salt thereof, wherein:
ring E is an optionally substituted aryl or heteroaryl;
$A^1$ and $A^2$ are independently a $C_{1-5}$ heterocycle, quinolinyl, or a heteroaryl selected from:

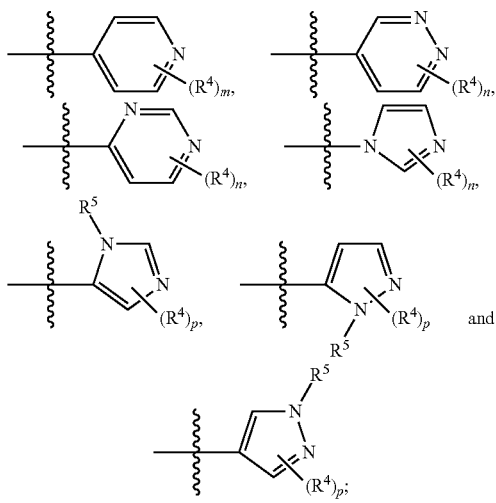

wherein any heterocycle of $A^1$ and $A^2$ can be optionally substituted with $-LC(O)R^{10}$;

wherein the nitrogen can be optionally oxidized (see, for example, compound 156 of table 1).

B is benzothiazolyl, quinolinyl or isoquinolinyl, each of which is optionally substituted with 1-3 $R^6$ groups;

$X^1$, $X^2$, $X^3$ and $X^4$ are independently $CR^7$ or N;

Y is phenyl or a 5-6 member heteroaryl containing 1-2 heteroatoms selected from N, O and S;

Z is aryl, $C_{1-5}$ heterocycle, or a 5-6 member heteroaryl containing 1-2 heteroatoms selected from N, O and S;

each Y and Z are optionally substituted with 1-3 $R^6$ groups;

$R^1$ and $R^5$ are independently H or $C_{1-6}$ alkyl;

$R^2$ and $R^3$ are independently H, $C_{1-6}$ alkyl or halo;

$R^4$ is halo, cyano, $C_{1-6}$alkoxy, or a $C_{1-6}$ alkyl optionally substituted with halo, alkoxy or amino;

$R^6$ is hydrogen, halo, $C_{1-6}$alkoxy, $-S(O)_2R^{10}$, $-C(O)OR^{10}$, $-C(O)R^{10}$, $-C(O)NR^8R^9$, $C_{1-6}$ alkyl, $C_{2-6}$ alkenyl or $C_{2-6}$ alkynyl, each of which may be optionally substituted with halo, amino, hydroxyl, alkoxy or cyano; halo, CN, -L-W, $NR^8R^9$, $-L-C(O)R^{10}$, $-L-C(O)OR^{10}$, $-L-C(O)NR^8R^9$, $OR^{10}$; $-L-S(O)_2R^{10}$ or $-L-S(O)_2NR^8R^9$;

$R^7$ is H, halo, $C_{1-6}$ alkoxy, $-L-S(O)_2R^{10}$, cyano, $C_{1-6}$ alkoxy, $C_{1-6}$ alkyl, optionally substituted with halo, amino, hydroxyl, alkoxy or cyano; $NR^8R^9$, $-L-C(O)R^{10}$, $-L-C(O)NR^8R^9$, $OR^{10}$; $-L-S(O)_2R^{10}$ or $-L-S(O)_2NR^8R^9$;

$R^8$ and $R^9$ are independently H, -L-W, or $C_{1-6}$ alkyl, $C_{2-6}$ alkenyl or $C_{2-6}$ alkynyl, each of which may be optionally substituted with halo, amino, hydroxyl, alkoxy or cyano; or $R^8$ and $R^9$ together with the atoms to which they are attached may form a ring;

$R^{10}$ is H, -L-W, or $C_{1-6}$ alkyl, $C_{2-6}$ alkenyl or $C_{2-6}$ alkynyl, each of which may be optionally substituted with halo, amino, hydroxyl, alkoxy or cyano;

L is a bond or $(CR_2)_{1-4}$ wherein R is H or $C_{1-6}$ alkyl;

W is $C_{3-7}$cycloalkyl, $C_{1-5}$heterocycle, aryl or heteroaryl;

m is 0-4; n is 0-3; and p is 0-2; and the solvates, hydrates, n-oxide derivative or prodrugs thereof.

In the above Formula (1), Y is phenyl, thiazolyl, pyridinyl, pyridazinyl, pyrimidinyl or pyrazinyl, each of which is optionally substituted with 1-2 $R^6$ groups. In other examples, Z is phenyl, pyridyl, pyridazine, pyrimidine, pyrazine, piperazinyl, piperidinyl, morpholinyl, pyrazole or 1,2,3,6-tetrahydropyridine, each of which is optionally substituted with 1-2 $R^6$ groups.

In one embodiment, the invention provides a compound of Formula (3):

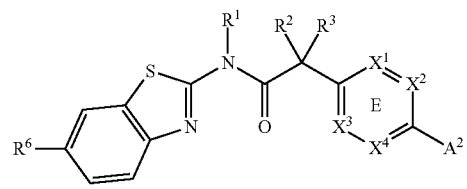

(3)

wherein $R^1$, $R^2$, $R^3$, $X^1$, $X^2$, $X^3$, $X^4$, $A^2$ and $R^6$ are as defined above.

In another embodiment, the invention provides a compound of Formula (4):

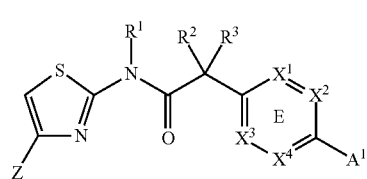

(4)

wherein $R^1$, $R^2$, $R^3$, $X^1$, $X^2$, $X^3$, $X^4$, $A^1$ and Z are as defined above.

In any of the above Formula (1), (2), (3) or (4), $A^1$ and $A^2$ are independently morpholinyl, piperazinyl, quinolinyl,

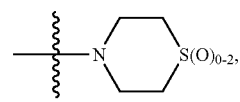

or a heteroaryl selected from the group:

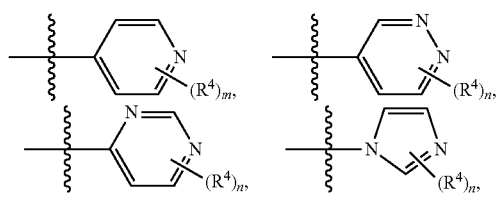

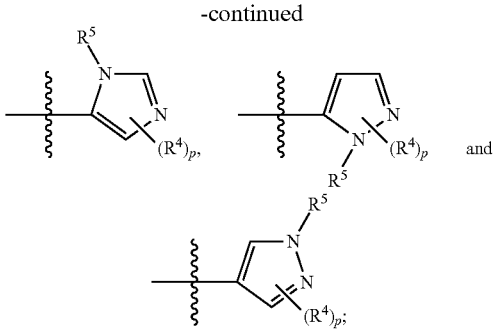

wherein any heterocycle of $A^1$ and $A^2$ can be optionally substituted with —C(O)CH$_3$; wherein $R^4$ and n are as defined above.

In some examples, ring E in any of the above Formula (1), (2), (3) or (4) is phenyl, pyridyl or pyrimidinyl, each of which optionally substituted with $R^7$, wherein $R^7$ is as defined above. In particular examples, $R^7$ may be H, halo, cyano or an optionally halogenated C$_{1-6}$ alkyl.

In yet another embodiment, the invention provides a compound of Formula (5):

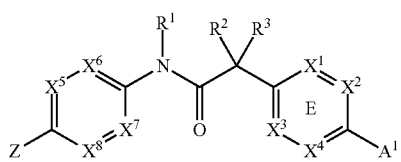

(5)

wherein $A^1$ is piperazinyl substituted with —C(O)CH$_3$

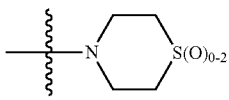

or selected from:

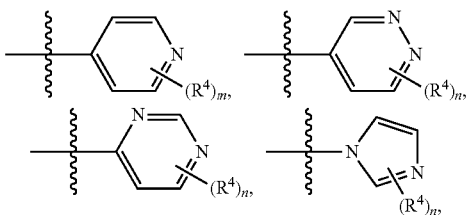

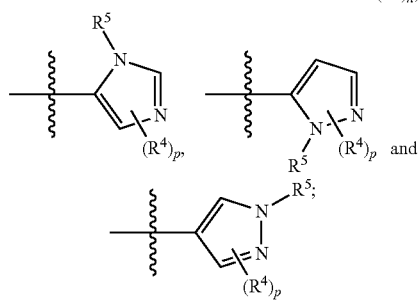

ring E is phenyl or one of $X^1$, $X^2$, $X^3$ and $X^4$ is N and the others are CR$^7$;

one of $X^5$, $X^6$, $X^7$ and $X^8$ is N and the others are CR$^{11}$;

Z is a 6-membered heterocycle or a 6-membered heteroaryl, each containing 1-2 nitrogen heteroatoms and each of which is optionally substituted with 1-2 R$^6$ groups;

$R^1$, $R^2$ and $R^3$ are H or C$_{1-6}$ alkyl;

$R^4$ and $R^6$ are independently hydrogen, cyano, C$_{1-6}$alkoxy, —S(O)$_2$R$^{10}$, —C(O)NR$^8$R$^9$, -L-C(O)R$^{10}$, -L-C(O)OR$^{10}$, C$_{1-6}$ alkyl, C$_{2-6}$ alkenyl or C$_{2-6}$ alkynyl;

$R^{10}$ is C$_{1-6}$ alkyl or -L-W;

L is a bond or (CR$_2$)$_{1-4}$ wherein R is H or C$_{1-6}$ alkyl;

W is C$_{3-7}$cycloalkyl;

$R^7$ and $R^{11}$ are independently H, halo, cyano, C$_{1-6}$alkoxy, —S(O)$_2$R$^{10}$, or an optionally halogenated C$_{1-6}$ alkyl; and m and n are independently 0-1.

In another embodiment, with reference to Formula (5), $A^1$ is piperazinyl substituted with —C(O)CH$_3$,

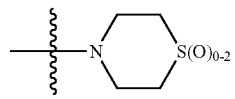

or selected from:

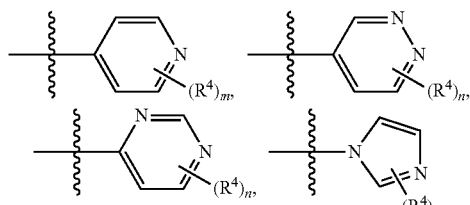

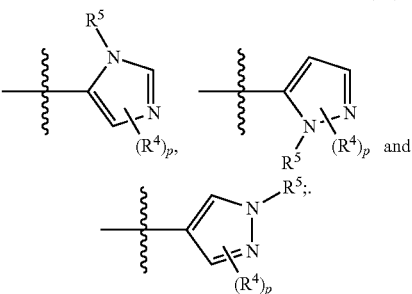

ring E is phenyl or one of $X^1$, $X^2$, $X^3$ and $X^4$ is N and the others are CR$^7$;

one of $X^5$, $X^6$, $X^7$ and $X^8$ is N and the others are CR$^{11}$; Z is a 6-membered heterocycle or a 6-membered heteroaryl, each containing 1-2 nitrogen heteroatoms and each of which is optionally substituted with 1-2 R$^6$ groups; $R^1$, $R^2$ and $R^3$ are H or C$_{1-6}$ alkyl; $R^4$ and $R^6$ are independently hydrogen, cyano, C$_{1-6}$alkoxy, —S(O)$_2$R$^{10}$, —C(O)NR$^8$R$^9$, -L-C(O)R$^{10}$, -L-C(O)OR$^{10}$, C$_{1-6}$ alkyl optionally substituted with halo, C$_{2-6}$ alkenyl or C$_{2-6}$ alkynyl; R$^{10}$ is C$_{1-6}$ alkyl or -L-W; L is a bond or (CR$_2$)$_{1-4}$ wherein R is H or C$_{1-6}$ alkyl; W is C$_{3-7}$cycloalkyl; $R^7$ and $R^{11}$ are independently H, halo, cyano, C$_{1-6}$alkoxy, —S(O)$_2$R$^{10}$, or an optionally halogenated C$_{1-6}$ alkyl; and m and n are independently 0-2.

In some examples, $R^{10}$ in Formula (5) is C$_{1-6}$ alkyl. In other examples, Z in Formula (5) is a 6-membered heteroaryl containing 2 nitrogen heteroatoms, or a 6-membered C$_4$ heterocycle containing 2 nitrogen heteroatoms. In yet other examples, one of $X^1$, $X^2$, $X^3$ and $X^4$ is N and the others are CR$^7$.

In yet another embodiment, the invention provides a compound of Formula (6):

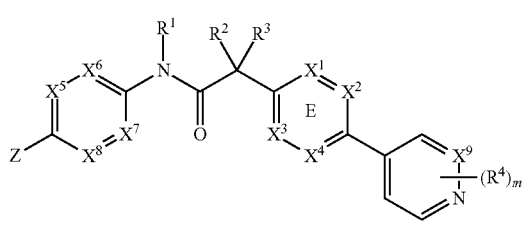

(6)

wherein $X^1$, $X^2$, $X^3$ and $X^4$ is selected from N and $CR_7$; one of $X^5$, $X^6$, $X^7$ and $X^8$ is N and the others are CH; $X^9$ is selected from N and CH; Z is selected from phenyl, pyrazinyl, pyridinyl and piperazinyl; wherein each phenyl, pyrazinyl, pyridinyl or piperazinyl of Z is optionally substituted with an $R^6$ group; $R^1$, $R^2$ and $R^3$ are hydrogen; m is 1; $R^4$ is selected from hydrogen, halo, difluoromethyl, trifluoromethyl and methyl; $R^6$ is selected from hydrogen, halo and —C(O)$R^{10}$; wherein $R^{10}$ is methyl; and $R^7$ is selected from hydrogen, halo, cyano, methyl and trifluoromethyl.

In any of the above Formula (1), (2), (3), (4), (5) or (6), $R^1$, $R^2$ and $R^3$ may be H. In other examples, $R^4$ and $R^6$ are independently selected from hydrogen, halo, trifluoromethyl, methyl and —C(O)CH$_3$.

Examples of the compounds of the invention include but are not limited to: tert-butyl 4-(5-{2-[4-(2-methylpyridin-4-yl)phenyl]acetamido}pyridin-2-yl)-1,2,3,6-tetrahydropyridine-1-carboxylate; N-[6-(3-fluorophenyl)pyridin-3-yl]-2-[4-(2-methylpyridin-4-yl)phenyl]acetamide; N-(6-methoxy-1,3-benzothiazol-2-yl)-2-[4-(pyridin-4-yl)phenyl]acetamide; N-(6-methoxy-1,3-benzothiazol-2-yl)-2-[6-(morpholin-4-yl)pyridin-3-yl]acetamide; N-(6-methoxy-1,3-benzothiazol-2-yl)-2-[4-(quinolin-4-yl)phenyl]acetamide; N-(6-methoxy-1,3-benzothiazol-2-yl)-2-[4-(2-methylpyridin-4-yl)phenyl]acetamide; N-(6-methoxy-1,3-benzothiazol-2-yl)-2-[6-(quinolin-4-yl)pyridin-3-yl]acetamide; N-(6-methanesulfonyl-1,3-benzothiazol-2-yl)-2-[4-(pyridin-4-yl)phenyl]acetamide; N-(6-fluoro-1,3-benzothiazol-2-yl)-2-[4-(pyridin-4-yl)phenyl]acetamide; N-(1,3-benzothiazol-2-yl)-2-[4-(pyridin-4-yl)phenyl]acetamide; N-(6-methoxy-1,3-benzothiazol-2-yl)-2-[6-(pyridin-4-yl)pyridin-3-yl]acetamide; N-(6-methoxy-1,3-benzothiazol-2-yl)-2-[4-methyl-4-(2-methylpyridin-4-yl)phenyl]acetamide; N-(6-methoxy-1,3-benzothiazol-2-yl)-2-[6-(2-methylpyridin-4-yl)pyridin-3-yl]acetamide; N-(6-methoxy-1,3-benzothiazol-2-yl)-2-[4-(2-methylpyrimidin-4-yl)phenyl]acetamide; N-[4-(pyridin-2-yl)-1,3-thiazol-2-yl]-2-[4-(pyridin-4-yl)phenyl]acetamide; N-[4-(pyridin-4-yl)-1,3-thiazol-2-yl]-2-[4-(pyridin-4-yl)phenyl]acetamide; N-(6-methoxy-1,3-benzothiazol-2-yl)-2-[2-methyl-4-(2-methylpyridin-4-yl)phenyl]acetamide; 2-[6-(2-methylpyridin-4-yl)pyridin-3-yl]-N-(4-phenyl-1,3-thiazol-2-yl)acetamide; N-(isoquinolin-3-yl)-2-[4-(pyridin-4-yl)phenyl]acetamide; N-(6-fluoro-1,3-benzothiazol-2-yl)-2-[6-(2-methylpyridin-4-yl)pyridin-3-yl]acetamide; 2-[4-(pyridin-4-yl)phenyl]-N-(quinolin-2-yl)acetamide; N-(6-methoxy-1,3-benzothiazol-2-yl)-2-[5-(2-methylpyridin-4-yl)pyrimidin-2-yl]acetamide; N-(6-methoxy-1,3-benzothiazol-2-yl)-2-[5-(2-methylpyridin-4-yl)pyridin-2-yl]acetamide; 2-[3-methyl-4-(2-methylpyridin-4-yl)phenyl]-N-(4-phenyl-1,3-thiazol-2-yl)acetamide; 2-[4-(2-methylpyridin-4-yl)phenyl]-N-(4-phenyl-1,3-thiazol-2-yl)acetamide; 2-[4-(2-methylpyridin-4-yl)phenyl]-N-(5-phenylpyridin-2-yl)acetamide; 2-[4-(2-methylpyridin-4-yl)phenyl]-N-(4-phenylpyridin-2-yl)acetamide; 2-[4-(2-methylpyridin-4-yl)phenyl]-N-[6-(trifluoromethoxy)-1,3-benzothiazol-2-yl]acetamide; 2-[4-(2-methylpyridin-4-yl)phenyl]-N-(5-phenyl-1,3-thiazol-2-yl)acetamide; N-(6-methoxy-1,3-benzothiazol-2-yl)-2-[4-(2-methoxypyridin-4-yl)phenyl]acetamide; 2-[4-(2-ethylpyridin-4-yl)phenyl]-N-(6-methoxy-1,3-benzothiazol-2-yl)acetamide; 2-[2-methyl-4-(2-methylpyridin-4-yl)phenyl]-N-(4-phenyl-1,3-thiazol-2-yl)acetamide; N-[4-(4-methoxyphenyl)-1,3-thiazol-2-yl]-2-[4-(2-methylpyridin-4-yl)phenyl]acetamide; N-[4-(4-fluorophenyl)-1,3-thiazol-2-yl]-2-[4-(2-methylpyridin-4-yl)phenyl]acetamide; N-[4-(3,4-difluorophenyl)-1,3-thiazol-2-yl]-2-[4-(2-methylpyridin-4-yl)phenyl]acetamide; 2-[4-(2-methylpyridin-4-yl)phenyl]-N-(6-phenylpyridin-3-yl)acetamide; N-(5-phenylpyridin-2-yl)-2-[4-(pyridazin-4-yl)phenyl]acetamide; N-[5-(4-methylphenyl)pyridin-2-yl]-2-[4-(2-methylpyridin-4-yl)phenyl]acetamide; N-[5-(3-methoxyphenyl)pyridin-2-yl]-2-[4-(2-methylpyridin-4-yl)phenyl]acetamide; N-[5-(2-methoxyphenyl)pyridin-2-yl]-2-[4-(2-methylpyridin-4-yl)phenyl]acetamide; N-[5-(4-methoxyphenyl)pyridin-2-yl]-2-[4-(2-methylpyridin-4-yl)phenyl]acetamide; 2-[4-(2-methylpyridin-4-yl)phenyl]-N-(5-phenylpyrazin-2-yl)acetamide; 2-[4-(2-methylpyridin-4-yl)phenyl]-N-[5-(pyridin-2-yl)pyridin-2-yl]acetamide; 2-[4-(2-methylpyridin-4-yl)-3-(trifluoromethyl)phenyl]-N-(4-phenyl-1,3-thiazol-2-yl)acetamide; N-[5-(3-methylphenyl)pyridin-2-yl]-2-[4-(2-methylpyridin-4-yl)phenyl]acetamide; 2-[4-(2-methylpyridin-4-yl)-3-(trifluoromethyl)phenyl]-N-(5-phenylpyridin-2-yl)acetamide; 2-[4-(2-methylpyridin-4-yl)phenyl]-N-[5-(pyridin-3-yl)pyridin-2-yl]acetamide; 2-[4-(2-methylpyridin-4-yl)phenyl]-N-[5-(pyridin-4-yl)pyridin-2-yl]acetamide; 2-[4-(2-methylpyridin-4-yl)phenyl]-N-(6-phenylpyridazin-3-yl)acetamide; 2-[4-(2-methylpyridin-4-yl)phenyl]-N-(4-phenylphenyl)acetamide; 2-[6-(2-methylpyridin-4-yl)pyridin-3-yl]-N-(5-phenylpyridin-2-yl)acetamide; 2-[4-(2-methylpyridin-4-yl)phenyl]-N-(2-phenylpyrimidin-5-yl)acetamide; 2-[4-(1H-imidazol-1-yl)phenyl]-N-(5-phenylpyridin-2-yl)acetamide; N-(6-phenylpyridin-3-yl)-2-[4-(pyridazin-4-yl)phenyl]acetamide; N-[5-(4-fluorophenyl)pyridin-2-yl]-2-[4-(2-methylpyridin-4-yl)phenyl]acetamide; N-[5-(3-fluorophenyl)pyridin-2-yl]-2-[4-(2-methylpyridin-4-yl)phenyl]acetamide; N-[5-(4-ethylpiperazin-1-yl)pyridin-2-yl]-2-[4-(2-methylpyridin-4-yl)phenyl]acetamide; N-{5-[(2R,6S)-2,6-dimethylmorpholin-4-yl]pyridin-2-yl}-2-[4-(2-methylpyridin-4-yl)phenyl]acetamide; 2-[4-(2-methylpyridin-4-yl)phenyl]-N-[4-(pyridin-3-yl)phenyl]acetamide; N-(6-fluoro-1,3-benzothiazol-2-yl)-2-[4-(pyridazin-4-yl)phenyl]acetamide; 2-[4-(2-methylpyridin-4-yl)phenyl]-N-(5-phenylpyrimidin-2-yl)acetamide; N-(6-methoxy-1,3-benzothiazol-2-yl)-N-methyl-2-[4-(pyridin-4-yl)phenyl]acetamide; 2-[4-(pyridazin-4-yl)phenyl]-N-[4-(pyridin-3-yl)phenyl]acetamide; N-(6-phenylpyridazin-3-yl)-2-[4-(pyridazin-4-yl)phenyl]acetamide; 2-[4-(2-methylpyridin-4-yl)phenyl]-N-[5-(1H-pyrazol-4-yl)pyridin-2-yl]acetamide; 2-[4-(2-methylpyridin-4-yl)phenyl]-N-[5-(pyrazin-2-yl)pyridin-2-yl]acetamide; 2-[4-(2-methylpyridin-4-yl)phenyl]-N-[5-(pyrimidin-5-yl)pyridin-2-yl]acetamide; 2-[4-(2-methylpyridin-4-yl)phenyl]-N-[4-(pyridazin-4-yl)phenyl]acetamide; 2-[4-(2-methylpyridin-4-yl)phenyl]-N-[5-(1,2,3,6-tetrahydropyridin-4-yl)pyridin-2-yl]acetamide; 2-[4-(2-methylpyridin-4-yl)phenyl]-N-[5-(pyridazin-3-yl)pyridin-2-yl]acetamide; 2-[5-methyl-6-(2-methylpyridin-4-yl)pyridin-3-yl]-N-(6-phenylpyridin-3-yl)acetamide; 2-[4-(2-methylpyridin-4-yl)phenyl]-N-[5-(pyridazin-2-yl)pyridin-2-yl]acetamide; 2-[4-(2-methylpyridin-4-yl)phenyl]-N-[6-

(morpholin-4-yl)pyridin-3-yl]acetamide; N-[5-(3-fluorophenyl)pyridin-2-yl]-2-[5-methyl-6-(pyridazin-4-yl)pyridin-3-yl]acetamide; 2-[3-methyl-4-(2-methylpyridin-4-yl)phenyl]-N-[5-(pyridin-2-yl)pyridin-2-yl]acetamide; 2-[3-methyl-4-(pyridazin-4-yl)phenyl]-N-[5-(pyridin-2-yl)pyridin-2-yl]acetamide; 2-[6-(2-methylpyridin-4-yl)pyridin-3-yl]-N-[5-(pyridazin-3-yl)pyridin-2-yl]acetamide; N-[5-(pyridazin-3-yl)pyridin-2-yl]-2-[6-(pyridazin-4-yl)pyridin-3-yl]acetamide; 2-[4-(2-methylpyridin-4-yl)-3-(trifluoromethyl)phenyl]-N-[5-(pyrazin-2-yl)pyridin-2-yl]acetamide; N-[5-(3-fluorophenyl)pyridin-2-yl]-2-[5-methyl-6-(2-methylpyridin-4-yl)pyridin-3-yl]acetamide; N-[5-(3-fluorophenyl)pyridin-2-yl]-2-[4-(2-methylpyridin-4-yl)-3-(trifluoromethyl)phenyl]acetamide; 2-[4-(2-methylpyridin-4-yl)phenyl]-N-[5-(pyridazin-4-yl)pyridin-2-yl]acetamide; N-[5-(3-fluorophenyl)pyridin-2-yl]-2-[6-(2-methylpyridin-4-yl)pyridin-3-yl]acetamide; N-[6-(3-fluorophenyl)pyridin-3-yl]-2-[6-(2-methylpyridin-4-yl)pyridin-3-yl]acetamide; 2-[4-(2-methylpyridin-4-yl)phenyl]-N-[6-(pyridazin-4-yl)pyridin-3-yl]acetamide; 2-[5-methyl-6-(2-methylpyridin-4-yl)pyridin-3-yl]-N-[5-(pyrazin-2-yl)pyridin-2-yl]acetamide; 2-[5-methyl-6-(pyridazin-4-yl)pyridin-3-yl]-N-(6-phenylpyridin-3-yl)acetamide; 2-[6-(2-methylpyridin-4-yl)pyridin-3-yl]-N-(6-phenylpyridin-3-yl)acetamide; N-(6-phenylpyridin-3-yl)-2-[6-(pyridazin-4-yl)pyridin-3-yl]acetamide; N-[6-(1-acetyl-1,2,3,6-tetrahydropyridin-4-yl)pyridin-3-yl]-2-[4-(2-methylpyridin-4-yl)phenyl]acetamide; methyl 4-(5-{2-[4-(2-methylpyridin-4-yl)phenyl]acetamido}pyridin-2-yl)-1,2,3,6-tetrahydropyridine-1-carboxylate; N-[6-(1-methanesulfonyl-1,2,3,6-tetrahydropyridin-4-yl)pyridin-3-yl]-2-[4-(2-methylpyridin-4-yl)phenyl]acetamide; N—[6-(1-methylpiperidin-4-yl)pyridin-3-yl]-2-[4-(2-methylpyridin-4-yl)phenyl]acetamide; 2-[5-methyl-6-(pyridazin-4-yl)pyridin-3-yl]-N-[5-(pyridin-2-yl)pyridin-2-yl]acetamide; 2-[6-(pyridazin-4-yl)pyridin-3-yl]-N-[5-(pyridin-2-yl)pyridin-2-yl]acetamide; 2-[6-(2-methylpyridin-4-yl)pyridin-3-yl]-N-(5-phenylpyrimidin-2-yl)acetamide; N-[5-(3-fluorophenyl)pyrimidin-2-yl]-2-[6-(pyridazin-4-yl)pyridin-3-yl]acetamide; ethyl 4-(5-{2-[4-(2-methylpyridin-4-yl)phenyl]acetamido}pyridin-2-yl)-1,2,3,6-tetrahydropyridine-1-carboxylate; propan-2-yl 4-(5-{2-[4-(2-methylpyridin-4-yl)phenyl]acetamido}pyridin-2-yl)-1,2,3,6-tetrahydropyridine-1-carboxylate; 1-methylcyclopropyl 4-(5-{2-[4-(2-methylpyridin-4-yl)phenyl]acetamido}pyridin-2-yl)-1,2,3,6-tetrahydropyridine-1-carboxylate; 2-[4-(2-methylpyridin-4-yl)phenyl]-N-[6-(1,2,3,6-tetrahydropyridin-4-yl)pyridin-3-yl]acetamide; N-[6-(3-fluorophenyl)pyridin-3-yl]-2-[5-methyl-6-(2-methylpyridin-4-yl)pyridin-3-yl]acetamide; N-[6-(3-fluorophenyl)pyridin-3-yl]-2-[5-methyl-6-(pyridazin-4-yl)pyridin-3-yl]acetamide; N-[6-(3-fluorophenyl)pyridin-3-yl]-2-[4-(2-methylpyridin-4-yl)-3-(trifluoromethyl)phenyl]acetamide; N-[6-(3-fluorophenyl)pyridin-3-yl]-2-[4-(pyridazin-4-yl)-3-(trifluoromethyl)phenyl]acetamide; N-[6-(1-methyl-1,2,3,6-tetrahydropyridin-4-yl)pyridin-3-yl]-2-[4-(2-methylpyridin-4-yl)phenyl]acetamide; N-[6-(1-ethyl-1,2,3,6-tetrahydropyridin-4-yl)pyridin-3-yl]-2-[4-(2-methylpyridin-4-yl)phenyl]acetamide; N-[6-(3-fluorophenyl)pyridin-3-yl]-2-[6-(2-methylpyridin-4-yl)pyridin-3-yl]acetamide; N-(6-phenylpyridazin-3-yl)-2-[6-(pyridazin-4-yl)pyridin-3-yl]acetamide; 2-[6-(2-methylpyridin-4-yl)pyridin-3-yl]-N-(6-phenylpyridazin-3-yl)acetamide; and N-(5-(4-acetylpiperazin-1-yl)pyridin-2-yl)-2-(3-cyano-4-(2-methylpyridin-4-yl)phenyl)acetamide; N-(2,3'-bipyridin-6'-yl)-2-(4-(pyridazin-4-yl)-3-(trifluoromethyl)phenyl)acetamide; N-(5-(pyridazin-3-yl)pyridin-2-yl)-2-(4-(pyridazin-4-yl)phenyl)acetamide; N-(5-(3-fluorophenyl)pyridin-2-yl)-2-(6-(pyridazin-4-yl)pyridin-3-yl)acetamide; N-(6-(3-fluorophenyl)pyridin-3-yl)-2-(6-(pyridazin-4-yl)pyridin-3-yl)acetamide; N-(6-(1-(2-amino-2-oxoethyl)-1,2,3,6-tetrahydropyridin-4-yl)pyridin-3-yl)-2-(4-(2-methylpyridin-4-yl)phenyl)acetamide; N-(6-(3-fluorophenyl)pyridin-3-yl)-2-(4-(pyridazin-4-yl)phenyl)acetamide; N-(5-(pyrazin-2-yl)pyridin-2-yl)-2-(4-(pyridazin-4-yl)-3-(trifluoromethyl)phenyl)acetamide; tert-butyl 4-(5-(2-(4-(2-methylpyridin-4-yl)phenyl)acetamido)pyridin-2-yl)piperazine-1-carboxylate; N-(5-(3-fluorophenyl)pyridin-2-yl)-2-(4-(pyridazin-4-yl)phenyl)acetamide; N-(2,3'-bipyridin-6'-yl)-2-(4-(2-methylpyridin-4-yl)-3-(trifluoromethyl)phenyl)acetamide; N-(5-(pyridazin-3-yl)pyridin-2-yl)-2-(4-(pyridazin-4-yl)-3-(trifluoromethyl)phenyl)acetamide; N-(2-(3-fluorophenyl)pyrimidin-5-yl)-2-(4-(2-methylpyridin-4-yl)phenyl)acetamide; N-(2,3'-bipyridin-6'-yl)-2-(2',3-dimethyl-2,4'-bipyridin-5-yl)acetamide; tert-butyl 4-(6-(2-(4-(2-methylpyridin-4-yl)phenyl)acetamido)pyridin-3-yl)piperazine-1-carboxylate; N-(2,3'-bipyridin-6'-yl)-2-(2'-methyl-2,4'-bipyridin-5-yl)acetamide; N-(6-(1-acetylpiperidin-4-yl)pyridin-3-yl)-2-(4-(2-methylpyridin-4-yl)phenyl)acetamide; 2-(2'-methyl-2,4'-bipyridin-5-yl)-N-(5-(pyrazin-2-yl)pyridin-2-yl)acetamide; N-(5-(pyrazin-2-yl)pyridin-2-yl)-2-(6-(pyridazin-4-yl)pyridin-3-yl)acetamide; 2-(5-methyl-6-(pyridazin-4-yl)pyridin-3-yl)-N-(5-(pyrazin-2-yl)pyridin-2-yl)acetamide; N-(5-(4-acetylpiperazin-1-yl)pyridin-2-yl)-2-(4-(2-methylpyridin-4-yl)phenyl)acetamide; methyl 4-(6-(2-(4-(2-methylpyridin-4-yl)phenyl)acetamido)pyridin-3-yl)piperazine-1-carboxylate; 2-(3-methyl-4-(pyridazin-4-yl)phenyl)-N-(5-(pyrazin-2-yl)pyridin-2-yl)acetamide; 2-(3-methyl-4-(pyridazin-4-yl)phenyl)-N-(5-(pyridazin-4-yl)pyridin-2-yl)acetamide; 2-(2',3-dimethyl-2,4'-bipyridin-5-yl)-N-(5-(pyridazin-4-yl)pyridin-2-yl)acetamide; 2-(2',3-dimethyl-2,4'-bipyridin-5-yl)-N-(6-(pyridazin-4-yl)pyridin-3-yl)acetamide; 2-(3-methyl-4-(pyridazin-4-yl)phenyl)-N-(5-(pyridazin-3-yl)pyridin-2-yl)acetamide; tert-butyl 4-(6-(2-(4-(2-methylpyridin-4-yl)phenyl)acetamido)pyridin-3-yl)piperidine-1-carboxylate; 2-(3-methyl-4-(pyridazin-4-yl)phenyl)-N-(6-(pyridazin-4-yl)pyridin-3-yl)acetamide; 2-(6-(4-acetylpiperazin-1-yl)pyridin-3-yl)-N-(5-(3-fluorophenyl)pyridin-2-yl)acetamide; 2-(4-(2-methylpyridin-4-yl)phenyl)-N-(5-(3-oxopiperazin-1-yl)pyridin-2-yl)acetamide; 4-(6-(2-(4-(2-methylpyridin-4-yl)phenyl)acetamido)pyridin-3-yl)piperazine-1-carboxamide; N-(5-(4-methyl-1H-imidazol-1-yl)pyridin-2-yl)-2-(4-(2-methylpyridin-4-yl)phenyl)acetamide; 2-(4-(4-methyl-1H-imidazol-1-yl)phenyl)-N-(5-(pyrazin-2-yl)pyridin-2-yl)acetamide; 2-(2',3-dimethyl-2,4'-bipyridin-5-yl)-N-(5-(pyridazin-3-yl)pyridin-2-yl)acetamide; 2-(5-methyl-6-(pyridazin-4-yl)pyridin-3-yl)-N-(5-(pyridazin-3-yl)pyridin-2-yl)acetamide; 2-(5-methyl-6-(pyridazin-4-yl)pyridin-3-yl)-N-(5-(pyridazin-4-yl)pyridin-2-yl)acetamide; N-(5-(4-acetylpiperazin-1-yl)pyridin-2-yl)-2-(2',3-dimethyl-2,4'-bipyridin-5-yl)acetamide; N-(5-((3S,5R)-4-acetyl-3,5-dimethylpiperazin-1-yl)pyridin-2-yl)-2-(4-(2-methylpyridin-4-yl)phenyl)acetamide; N-(4-(1-acetylpiperidin-4-yl)phenyl)-2-(4-(2-methylpyridin-4-yl)phenyl)acetamide; N-(6-(4-(2-hydroxyethyl)piperazin-1-yl)pyridin-3-yl)-2-(4-(2-methylpyridin-4-yl)phenyl)acetamide; N-(6-(3-fluorophenyl)pyridin-3-yl)-2-(5-methyl-6-(pyridazin-4-yl)pyridin-3-yl)acetamide; 2-(2',3-dimethyl-2,4'-bipyridin-5-yl)-N-(4-(pyrazin-2-yl)phenyl)acetamide; 2-(2',3-dimethyl-2,4'-bipyridin-5-yl)-N-(4-(pyridazin-3-yl)phenyl)acetamide; 2-(2-(2',3-dimethyl-2,4'-bipyridin-5-yl)acetamido)-5-(pyrazin-2-yl)pyridine 1-oxide; 2',3-dimethyl-5-(2-oxo-2-(5-(pyrazin-2-yl)pyridin-2-ylamino)ethyl)-2,4'-bipyridine 1'-oxide; 2-(2',3-dimethyl-2,4'-bipyridin-5-yl)-N-(6-(pyrazin-2-yl)pyridin-3-yl)acetamide; N-(5-(4-isobutyrylpiperazin-1-yl)pyridin-2-yl)-2-(4-(2-methylpyridin-4-yl)phenyl)acetamide; N-(5-(4-acetylpiperazin-1-yl)pyridin-2-yl)-2-(3-methyl-4-(2-methylpyridin-4-yl)phenyl)acetamide; N-(6-(4-acetylpiperazin-1-yl)pyridin-3-yl)-2-(2',3-dimethyl-2,4'-bipyridin-5-yl)acetamide; (R)—N-(6-(4-acetyl-3-methylpiperazin-1-yl)pyridin-3-yl)-2-(4-(2-methylpyridin-4-yl)phenyl)acetamide; (S)—N-(6-(4-acetyl-3-methylpiperazin-1-yl)pyridin-3-yl)-2-(4-(2-methylpyridin-4-yl)phenyl)acetamide; (S)—N-(6-(4-acetyl-3-methylpiperazin-1-yl)pyridin-3-yl)-2-(2',3-dimethyl-2,4'-bipyridin-5-yl)acetamide; (R)—N-(6-(4-acetyl-3-methylpiperazin-1-yl)pyridin-3-yl)-2-(2',3-dimethyl-2,4'-bipyridin-5-yl)acetamide; N-(5-((3S,5R)-4-acetyl-3,5-dimethylpiperazin-1-yl)pyridin-2-yl)-2-(2',3-dimethyl-2,4'-bipyridin-5-yl)acetamide; methyl 4-(6-(2-(2',3-dimethyl-2,4'-bipyridin-5-yl)acetamido)pyridin-3-yl)piperazine-1-carboxylate; methyl 4-(6-(2-(3-methyl-4-(2-methylpyridin-4-yl)phenyl)acetamido)pyridin-3-yl)piperazine-1-carboxylate; N-(5-(4-acetylpiperazin-1-yl)pyridin-2-yl)-2-(3-fluoro-4-(2-methylpyridin-4-yl)phenyl)acetamide; N-(5-(4-acetylpiperazin-1-yl)pyridin-2-yl)-2-(2'-methyl-2,4'-bipyridin-5-yl)acetamide; N-(5-(4-acetylpiperazin-1-yl)pyridin-2-yl)-2-(3-chloro-4-(2-methylpyridin-4-yl)phenyl)acetamide; ethyl 4-(6-(2-(2',3-dimethyl-2,4'-bipyridin-5-yl)acetamido)pyridin-3-yl)piperazine-1-carboxylate; N-(5-(4-acetylpiperazin-1-yl)pyridin-2-yl)-2-(4-(2-methylpyridin-4-yl)-3-(trifluoromethyl)phenyl)acetamide; 2-(3-cyano-4-(2-methylpyridin-4-yl)phenyl)-N-(6-phenylpyridin-3-yl)acetamide; 2-(2',3-dimethyl-2,4'-bipyridin-5-yl)-N-(5-(4-propionylpiperazin-1-yl)pyridin-2-yl)acetamide; N-(5-(4-(cyanomethyl)piperazin-1-yl)pyridin-2-yl)-2-(4-(2-methylpyridin-4-yl)phenyl)acetamide; N-(5-(4-cyanopiperazin-1-yl)pyridin-2-yl)-2-(4-(2-methylpyridin-4-yl)phenyl)acetamide; N-(5-(4-acetylpiperazin-1-yl)pyridin-2-yl)-2-(4-(2-chloropyridin-4-yl)phenyl)acetamide; N-(5-(4-acetylpiperazin-1-yl)pyridin-2-yl)-2-(4-(2-fluoropyridin-4-yl)phenyl)acetamide; 2-(3-cyano-4-(2-methylpyridin-4-yl)phenyl)-N-(5-(pyrazin-2-yl)pyridin-2-yl)acetamide; 2-(3-cyano-4-(2-methylpyridin-4-yl)phenyl)-N-(6-(pyrazin-2-yl)pyridin-3-yl)acetamide; 2-(3-cyano-4-(2-methylpyridin-4-yl)phenyl)-N-(5-(pyridazin-3-yl)pyridin-2-yl)acetamide; N-(5-(4-acetylpiperazin-1-yl)pyridin-2-yl)-2-(3-methoxy-4-(2-methylpyridin-4-yl)phenyl)acetamide; N-(5-(4-acetylpiperazin-1-yl)pyridin-2-yl)-2-(3-chloro-2'-methyl-2,4'-bipyridin-5-yl)acetamide; (S)—N-(5-(4-acetyl-3-methylpiperazin-1-yl)pyridin-2-yl)-2-(3-cyano-4-(2-methylpyridin-4-yl)phenyl)acetamide; (R)—N-(5-(4-acetyl-3-methylpiperazin-1-yl)pyridin-2-yl)-2-(2',3-dimethyl-2,4'-bipyridin-5-yl)acetamide; isopropyl 4-(6-(2-(2',3-dimethyl-2,4'-bipyridin-5-yl)acetamido)pyridin-3-yl)piperazine-1-carboxylate; N-(5-(4-acetylpiperazin-1-yl)pyridin-2-yl)-2-(3-cyano-2'-methyl-2,4'-bipyridin-5-yl)acetamide; N-(5-(4-acetylpiperazin-1-yl)pyridin-2-yl)-2-(2'-methyl-3-(trifluoromethyl)-2,4'-bipyridin-5-yl)acetamide; N-(5-(4-acetylpiperazin-1-yl)pyridin-2-yl)-2-(3-fluoro-2'-methyl-2,4'-bipyridin-5-yl)acetamide; N-(5-(4-acetylpiperazin-1-yl)pyridin-2-yl)-2-(2-fluoro-5-methyl-4-(2-methylpyridin-4-yl)phenyl)acetamide; N-(5-(4-acetylpiperazin-1-yl)pyridin-2-yl)-2-(4-(2-methylpyrimidin-4-yl)-3-(trifluoromethyl)phenyl)acetamide; N-(5-(4-acetylpiperazin-1-yl)pyridin-2-yl)-2-(2'-fluoro-3-methyl-2,4'-bipyridin-5-yl)acetamide; N-(5-(4-acetylpiperazin-1-yl)pyridin-2-yl)-2-(2',3-difluoro-2,4'-bipyridin-5-yl)acetamide; N-(5-(4-acetylpiperazin-1-yl)pyridin-2-yl)-2-(4-(2-methylpyrimidin-4-yl)phenyl)acetamide; N-(5-(4-acetylpiperazin-1-yl)pyridin-2-yl)-2-(4-(5-fluoropyrimidin-4-yl)phenyl)acetamide; N-(5-(4-acetylpiperazin-1-yl)pyridin-2-yl)-2-(2'-methyl-3-(methylsulfonyl)-2,4'-bipyridin-5-yl)acetamide; N-(5-(4-acetylpiperazin-1-yl)pyridin-2-yl)-2-(4-(6-methylpyrimidin-4-yl)phenyl)acetamide; 2-(2'-fluoro-3-methyl-2,4'-bipyridin-5-yl)-N-(5-(pyrazin-2-yl)pyridin-2-yl)acetamide; 2-(4-(2-fluoropyridin-4-yl)phenyl)-N-(5-(pyrazin-2-yl)pyridin-2-yl)acetamide; N-(5-(4-acetylpiperazin-1-yl)pyridin-2-yl)-2-(4-(2-(difluoromethyl)pyridin-4-yl)phenyl)acetamide; N-(6-(4-acetylpiperazin-1-yl)pyridin-3-yl)-2-(4-(2-(difluoromethyl)pyridin-4-yl)phenyl)acetamide; 2-(4-(2-(difluoromethyl)pyridin-4-yl)phenyl)-N-(5-(pyrazin-2-yl)pyridin-2-yl)acetamide; N-(5-(4-acetylpiperazin-1-yl)pyridin-2-yl)-2-(4-(5-fluoropyrimidin-4-yl)-3-methylphenyl)acetamide; 2-(2',3-difluoro-2,4'-bipyridin-5-yl)-N-(5-(pyrazin-2-yl)pyridin-2-yl)acetamide; 2-(3-cyano-4-(2-fluoropyridin-4-yl)phenyl)-N-(5-(pyrazin-2-yl)pyridin-2-yl)acetamide; N-(5-(4-acetylpiperazin-1-yl)pyridin-2-yl)-2-(3-fluoro-4-(2-fluoropyridin-4-yl)phenyl)acetamide; 2-(2'-fluoro-2,4'-bipyridin-5-yl)-N-(5-(pyrazin-2-yl)pyridin-2-yl)acetamide; N-(5-(4-acetylpiperazin-1-yl)pyridin-2-yl)-2-(2'-fluoro-2,4'-bipyridin-5-yl)acetamide; 2-(2',3-difluoro-2,4'-bipyridin-5-yl)-N-(5-(pyridazin-3-yl)pyridin-2-yl)acetamide; N-(5-(4-acetylpiperazin-1-yl)pyridin-2-yl)-2-(3-cyano-4-(2-fluoropyridin-4-yl)phenyl)acetamide; 2-(3-fluoro-4-(2-fluoropyridin-4-yl)phenyl)-N-(5-(pyrazin-2-yl)pyridin-2-yl)acetamide; 2-(3-fluoro-4-(2-fluoropyridin-4-yl)phenyl)-N-(5-(pyridazin-3-yl)pyridin-2-yl)acetamide; 2-(3-cyano-4-(2-fluoropyridin-4-yl)phenyl)-N-(5-(pyridazin-3-yl)pyridin-2-yl)acetamide; 2-(4-(2-fluoropyridin-4-yl)phenyl)-N-(5-(pyridazin-3-yl)pyridin-2-yl)acetamide; and 2-(2'-fluoro-3-methyl-2,4'-bipyridin-5-yl)-N-(5-(pyridazin-3-yl)pyridin-2-yl)acetamide; or physiologically acceptable salts thereof.

In another embodiment are compounds selected from the group consisting of:

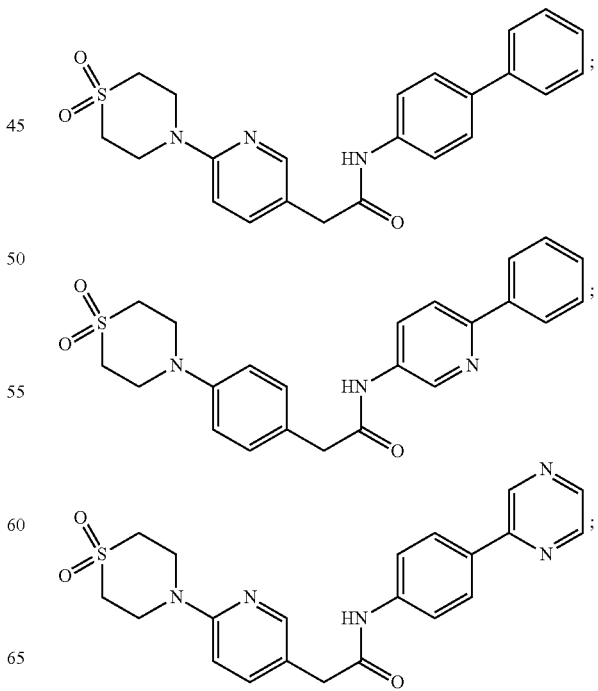

-continued

In another embodiment are compounds having Formula (10) or (11):

(10)

(11)

or a physiologically acceptable salt thereof, wherein:

ring E is an optionally substituted aryl or heteroaryl;

$A^1$ and $A^2$ are independently a $C_{1-5}$ heterocycle, quinolinyl, or a heteroaryl selected from the group:

wherein any heterocycle of $A^1$ and $A^2$ can be optionally substituted with -LC(O)$R^{10}$;

wherein the nitrogen can be optionally oxidized (see, for example, compound 156 of table 1).

B is benzothiazolyl, quinolinyl or isoquinolinyl, each of which is optionally substituted with 1-3 $R^6$ groups;

$X^1$, $X^2$, $X^3$ and $X^4$ are independently $CR^7$ or N;

Y is phenyl or a 5-6 member heteroaryl containing 1-2 heteroatoms selected from N, O and S;

Z is aryl, $C_{1-5}$ heterocycle, or a 5-6 member heteroaryl containing 1-2 heteroatoms selected from N, O and S;

each Y and Z are optionally substituted with 1-3 $R^6$ groups;

$R^1$ and $R^5$ are independently H or $C_{1-6}$ alkyl;

$R^2$ and $R^3$ are independently H, $C_{1-6}$ alkyl or halo;

$R^4$ is halo, cyano, $C_{1-6}$alkoxy, or a $C_{1-6}$ alkyl optionally substituted with halo, alkoxy or amino;

$R^6$ is hydrogen, halo, $C_{1-6}$alkoxy, —S(O)$_2R^{10}$, —C(O)O$R^{10}$, —C(O)$R^{10}$, —C(O)N$R^8R^9$, $C_{1-6}$ alkyl, $C_{2-6}$ alkenyl or $C_{2-6}$ alkynyl, each of which may be optionally substituted with halo, amino, hydroxyl, alkoxy or cyano; halo, CN, -L-W, N$R^8R^9$, -L-C(O)$R^{10}$, -L-C(O)O$R^{10}$, -L-C(O)N$R^8R^9$, O$R^{10}$; -L-S(O)$_2R^{10}$ or -L-S(O)$_2$N$R^8R^9$;

$R^7$ is H, halo, $C_{1-6}$ alkoxy, -L-S(O)$_2R^{10}$, cyano, $C_{1-6}$ alkoxy, $C_{1-6}$ alkyl, optionally substituted with halo, amino, hydroxyl, alkoxy or cyano; N$R^8R^9$, -L-C(O)$R^{10}$, -L-C(O)N$R^8R^9$, O$R^{10}$; -L-S(O)$_2R^{10}$ or -L-S(O)$_2$N$R^8R^9$;

$R^8$ and $R^9$ are independently H, -L-W, or $C_{1-6}$ alkyl, $C_{2-6}$ alkenyl or $C_{2-6}$ alkynyl, each of which may be optionally substituted with halo, amino, hydroxyl, alkoxy or cyano; or $R^8$ and $R^9$ together with the atoms to which they are attached may form a ring;

$R^{10}$ is H, -L-W, or $C_{1-6}$ alkyl, $C_{2-6}$ alkenyl or $C_{2-6}$ alkynyl, each of which may be optionally substituted with halo, amino, hydroxyl, alkoxy or cyano;

L is a bond or $(CR_2)_{1-4}$ wherein R is H or $C_{1-6}$ alkyl;

W is $C_{3-7}$cycloalkyl, $C_{1-5}$heterocycle, aryl or heteroaryl;

m is 0-4; n is 0-3; and p is 0-2; and the solvates, hydrates, n-oxide derivative or prodrugs thereof.

In another embodiment are compounds of Formulae 10 and 11 selected from the group consisting of: N-(6-methoxybenzo[d]thiazol-2-yl)-2-(3-(pyridin-4-yl)phenyl)acetamide; N-(6-phenylpyridin-3-yl)-2-(3-(pyridin-4-yl)phenyl)acetamide; 2-(3-(2-methylpyridin-4-yl)phenyl)-N-(6-phenylpyridin-3-yl)acetamide; N-(6-phenylpyridin-3-yl)-2-(3-(pyridazin-4-yl)phenyl)acetamide; 2-(3-(2-methoxypyridin-4-yl)phenyl)-N-(6-phenylpyridin-3-yl)acetamide; N-(5-(4-acetylpiperazin-1-yl)pyridin-2-yl)-2-(3-(2-methylpyridin-4-yl)phenyl)acetamide; 2-(3-(2-methylpyridin-4-yl)phenyl)-N-(4-(pyridazin-3-yl)phenyl)acetamide; 2-(3-(2-methylpyridin-4-yl)phenyl)-N-(4-(pyrazin-2-yl)phenyl)acetamide; 2-(3-(2-methylpyridin-4-yl)phenyl)-N-(6-(pyrazin-2-yl)pyridin-3-yl)acetamide; 2-(2'-methyl-2,4'-bipyridin-6-yl)-N-(6-phenylpyridin-3-yl)acetamide; 2-(2'-methyl-2,4'-bipyridin-4-yl)-N-(6-phenylpyridin-3-yl)acetamide; 2-(4-cyano-3-(2-methylpyridin-4-yl)phenyl)-N-(6-phenylpyridin-3-yl)acetamide; N-(5-(4-acetylpiperazin-1-yl)pyridin-2-yl)-2-(4-cyano-3-(2-methylpyridin-4-yl)phenyl)acetamide; 2-(2'-methyl-2,4'-bipyridin-4-yl)-N-(5-(pyrazin-2-yl)pyridin-2-yl)acetamide; N-(5-(4- acetylpiperazin-1-yl)pyridin-2-yl)-2-(2'-methyl-2,4'-bipyridin-4-yl)acetamide; and N-(5-(4-acetylpiperazin-1-yl)pyridin-2-yl)-2-(2-cyano-2'-methyl-3,4'-bipyridin-5-yl)acetamide, or a pharmaceutically acceptable salt thereof.

In another aspect, the present invention provides pharmaceutical compositions comprising a compound having Formula (1), (2), (3), (4), (5) or (6), and a physiologically acceptable carrier.

In yet another aspect, the invention provides methods for inhibiting Wnt signaling in a cell, comprising contacting the cell with an effective amount of a compound having Formula (1), (2), (3), (4), (5) or (6), or a pharmaceutical composition thereof.

In yet another aspect, the invention provides methods for inhibiting a Porcupine gene in a cell, comprising contacting the cell with an effective amount of a compound having Formula (1), (2), (3), (4), (5) or (6), or a pharmaceutical composition thereof.

The invention also provides methods to treat, ameliorate or prevent a Wnt-mediated disorder in a mammal suffering there from, comprising administering to the mammal a therapeutically effective amount of a compound having Formula (1), (2), (3), (4), (5) or (6), or a pharmaceutical composition thereof, and optionally in combination with a second therapeutic agent. Alternatively, the present invention provides for the use of a compound having Formula (1), (2), (3), (4), (5) or (6), and optionally in combination with a second therapeutic agent, in the manufacture of a medicament for treating a Wnt-mediated disorder.

The compounds of the invention may be administered, for example, to a mammal suffering from a Wnt-mediated disorder selected from keloids, fibrosis such as skin fibrosis, idiopathic pulmonary fibrosis, renal interstitial fibrosis and liver fibrosis; proteinuria, kidney graft rejection, osteoarthritis, Parkinson's disease, cystoid macular edema (CME) such as uveitis-associated CME; retinopathy such as diabetic retinopathy or retinopathy of prematurity; macular degeneration and a cell proliferative disorder associated with aberrant Wnt signaling activity.

In particular examples, the compounds of the invention may be used alone or in combination with a chemotherapeutic agent to treat a cell proliferative disorder, including but not limited to, colorectal cancer, breast cancer, head and neck squamous cell carcinoma, esophageal squamous cell carcinoma, non-small cell lung cancer, gastric cancer, pancreatic cancer, leukemia, lymphoma, neuroblastoma, retinoblastoma, sarcoma, osteosarcoma, chondosarcoma, Ewing's sarcoma, rhabdomysarcoma, brain tumor, Wilm's tumor, basal cell carcinoma, melanoma, head and neck cancer, cervical cancer and prostate cancer.

Definitions

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., $CF_3$), or may have one or more carbons that is substituted or replaced with a heteroatom, such as NR, O or S (e.g., $-OCH_2CH_2O-$, alkylthiols, thioalkoxy, alkylamines, etc).

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring may contain N, O, S, $-N=$, $C(O)$ (see for example, compound 141, table 1), $-S-$, $-S(O)-$, $-S(O)_2-$, or $-NR-$ wherein R may be hydrogen, $C_{1-4}$alkyl or a protecting group. Examples of heterocyclic rings include but are not limited to morpholino, pyrrolidinyl, pyrrolidinyl-2-one, piperazinyl, piperidinyl, piperidinylone, 1,4-dioxa-8-aza-spiro[4.5]dec-8-yl, etc.

As used herein, an H atom in any substituent groups (e.g., $CH_2$) encompasses all suitable isotopic variations, e.g., H, $^2H$ and $^3H$.

A "Wnt protein" is a ligand of the Wnt signaling pathway component which binds to a Frizzled receptor so as to activate Wnt signaling. Specific examples of Wnt proteins include at least 19 members, including: Wnt-1 (RefSeq.: NM_005430), Wnt-2 (RefSeq.: NM_003391), Wnt-2B (Wnt-13) (RefSeq.: NM_004185), Wnt-3 (ReSeq.: NM_030753), Wnt3a (RefSeq.: NM_033131), Wnt-4 (RefSeq.: NM_030761), Wnt-5A (RefSeq.: NM_003392), Wnt-5B (RefSeq.: NM_032642), Wnt-6 (RefSeq.: NM_006522), Wnt-7A (RefSeq.: NM_004625), Wnt-7B (RefSeq.: NM_058238), Wnt-8A (RefSeq.: NM_058244), Wnt-8B (RefSeq.: NM 003393), Wnt-9A (Wnt-14) (RefSeq.: NM_003395), Wnt-9B (Wnt-15) (RefSeq.: NM_003396), Wnt-10A (RefSeq.: NM_025216), Wnt-10B (RefSeq.: NM_003394), Wnt-11 (RefSeq.: NM_004626), Wnt-16 (RefSeq.: NM_016087)). While each member has varying degrees of sequence identity, each contain 23-24 conserved cysteine residues which show highly conserved spacing. McMahon, A P et al, Trends Genet. 8: 236-242 (1992); Miller J R., *Genome Biol.* 3(1): 3001.1-3001.15 (2002). For purposes of this invention, a Wnt protein and active variants thereof is a protein that binds to a Frizzled ECD or the CRD component of such an Frz ECD.

A "Wnt-mediated disorder" is a disorder, condition, or disease state characterized by aberrant Wnt signaling. In a specific aspect, the aberrant Wnt signaling is a level of Wnt signaling in a cell or tissue suspected of being diseased that exceeds the level of Wnt signaling in a similar non-diseased cell or tissue. In a specific aspect, a Wnt-mediated disorder includes cancer.

The term "cancer" refers to the physiological condition in mammals that is typically characterized by unregulated cell growth/proliferation. Examples of cancer include, but are not limited to: carcinoma, lymphoma, blastoma, and leukemia. More particular examples of cancers include, but are not limited to: chronic lymphocytic leukemia (CLL), lung, including non small cell (NSCLC), breast, ovarian, cervical, endometrial, prostate, colorectal, intestinal carcinoid, bladder, gastric, pancreatic, hepatic (hepatocellular), hepatoblastoma, esophageal, pulmonary adenocarcinoma, mesothelioma, synovial sarcoma, osteosarcoma, head and neck squamous cell carcinoma, juvenile nasopharyngeal angiofibromas, liposarcoma, thyroid, melanoma, basal cell carcinoma (BCC), medulloblastoma and desmoid.

"Treating" or "treatment" or "alleviation" refers to both therapeutic treatment and prophylactic or preventative measures, wherein the object is to prevent or slow down (lessen) the targeted pathologic disease or condition or disorder. Those in need of treatment include those already with the disorder as well as those prone to having the disorder or those in whom the disorder is to be prevented (prophylaxis). When the Wnt-mediated disorder is cancer, a subject or mammal is successfully "treated" or shows a reduced tumor burden if, after receiving a therapeutic amount of a Wnt antagonist according to the methods of the present invention, the patient shows observable and/or measurable reduction in or absence of one or more of the following: reduction in the number of cancer cells or absence of the cancer cells; reduction in the tumor size; inhibition of cancer cell infiltration into peripheral organs including the spread of cancer into soft tissue and bone; inhibition of tumor metastasis; inhibition, to some extent, of tumor growth; and/or relief to some extent, one or more of the symptoms associated with the specific cancer; reduced morbidity and mortality, and improvement in quality of life issues. To the extent the Wnt antagonist may prevent growth and/or kill existing cancer cells, it may be cytostatic and/or cytotoxic. Reduction of these signs or symptoms may also be felt by the patient.

"Mammal" refers to any animal classified as a mammal, including humans, domestic and farm animals, and zoo, sports, or pet animals, such as dogs, cats, cattle, horses, sheep, pigs, goats, rabbits, etc. In certain embodiments, the mammal is human.

Administration "in combination with" one or more further therapeutic agents includes simultaneous (concurrent) and consecutive administration in any order.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

An "effective amount" of a compound (e.g., a Wnt antagonist) is an amount sufficient to carry out a specifically stated purpose. An "effective amount" may be determined empirically and in a routine manner, in relation to the stated purpose.

The term "therapeutically effective amount" refers to an amount of a Wnt antagonist effective to "treat" a Wnt-mediated disorder in a subject or mammal In the case of cancer, the therapeutically effective amount of the drug may reduce the number of cancer cells; reduce the tumor size; inhibit (i.e., slow to some extent or stop) cancer cell infiltration into peripheral organs; inhibit tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Furthermore, a "chemotherapeutic agent" may include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; antiprogesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Modes of Carrying Out the Invention

The present invention relates to compositions and methods for modulating the Wnt signaling pathway.

In one aspect, the present invention provides A compound having Formula (1) or (2):

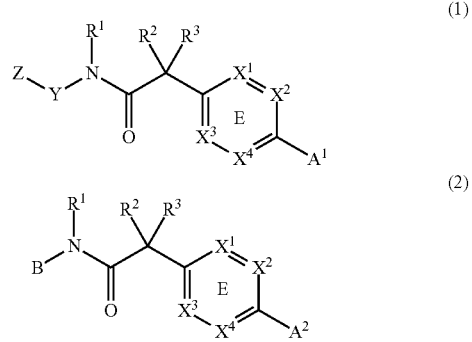

or a physiologically acceptable salt thereof, wherein: ring E is an optionally substituted aryl or heteroaryl; $A^1$ and $A^2$ are independently a $C_{1-5}$ heterocycle, quinolinyl, or a heteroaryl selected from the group:

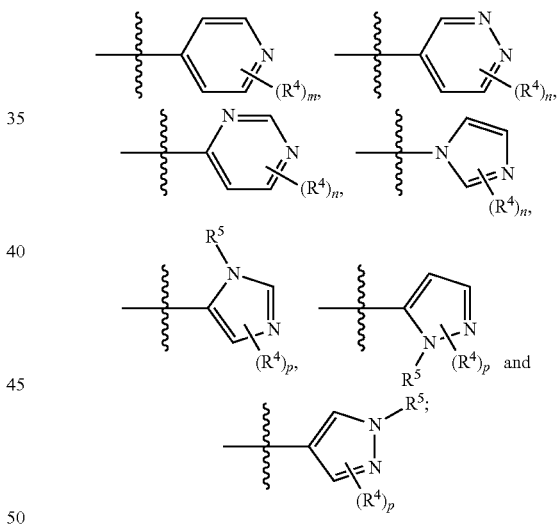

wherein any heterocycle of $A^1$ and $A^2$ can be optionally substituted with -LC(O)$R^{10}$; B is benzothiazolyl, quinolinyl or isoquinolinyl, each of which is optionally substituted with 1-3 $R^6$ groups; $X^1$, $X^2$, $X^3$ and $X^4$ are independently $CR^7$ or N; Y is phenyl or a 5-6 membered heteroaryl containing 1-2 heteroatoms selected from N, O and S; Z is aryl, $C_{1-5}$ heterocycle, or a 5-6 membered heteroaryl containing 1-2 heteroatoms selected from N, O and S; each Y and Z are optionally substituted with 1-3 $R^6$ groups; $R^1$ and $R^5$ are independently H or $C_{1-6}$ alkyl; $R^2$ and $R^3$ are independently H, $C_{1-6}$ alkyl or halo; $R^4$ is halo, cyano, $C_{1-6}$alkoxy, or a $C_{1-6}$ alkyl optionally substituted with halo, alkoxy or amino; $R^6$ is hydrogen, halo, $C_{1-6}$alkoxy, —S(O)$_2R^{10}$, —C(O)O$R^{10}$, —C(O)$R^{10}$, —C(O)N$R^8R^9$, $C_{1-6}$ alkyl, $C_{2-6}$ alkenyl or $C_{2-6}$ alkynyl, each of which can be optionally substituted with halo, amino, hydroxyl, alkoxy or cyano; halo, CN, -L-W, N$R^8R^9$, -L-C(O)$R^{10}$, -L-C (O)OR$^{10}$, -L-C(O)NR$^8$R$^9$, OR$^{10}$; -L-S(O)$_2$R$^{10}$ or -L-S(O)$_2$NR$^8$R$^9$; R$^7$ is H, halo, C$_{1-6}$ alkoxy, -L-S(O)$_2$R$^{10}$, C$_{1-6}$ alkyl optionally substituted with halo, amino, hydroxyl, alkoxy or cyano; NR$^8$R$^9$, -L-C(O)R$^{10}$, -L-C(O)NR$^8$R$^9$, OR$^{10}$; -L-S(O)$_2$R$^{10}$ or -L-S(O)$_2$NR$^8$R$^9$; R$^8$ and R$^9$ are independently H, -L-W, or C$_{1-6}$ alkyl, C$_{2-6}$ alkenyl or C$_{2-6}$ alkynyl, each of which may be optionally substituted with halo, amino, hydroxyl, alkoxy or cyano; or R$^8$ and R$^9$ together with the atoms to which they are attached may form a ring; R$^{10}$ is H, -L-W, or C$_{1-6}$ alkyl, C$_{2-6}$ alkenyl or C$_{2-6}$ alkynyl, each of which may be optionally substituted with halo, amino, hydroxyl, alkoxy or cyano; L is a bond or (CR$_2$)$_{1-4}$ wherein R is H or C$_{1-6}$ alkyl; W is C$_{3-7}$cycloalkyl, C$_{1-5}$heterocycle, aryl or heteroaryl; m is 0-4; n is 0-3; and p is 0-2.

In another aspect, Y is phenyl, thiazolyl, pyridinyl, pyridazinyl, pyrimidinyl or pyrazinyl, each of which is optionally substituted with 1-2 R$^6$ groups and R$^6$ is as defined in the disclosure of the invention.

In another aspect, Z is phenyl, pyridinyl, pyridazine, pyrimidine, pyrazine, piperazinyl, piperidinyl, morpholinyl, pyrazole or 1,2,3,6-tetrahydropyridine, each of which is optionally substituted with 1-2 R$^6$ groups and R$^6$ is as defined in the disclosure of the invention.

In another aspect, A$^1$ and A$^2$ are independently morpholinyl, piperazinyl, quinolinyl,

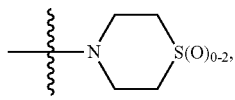

or a heteroaryl selected from the group:

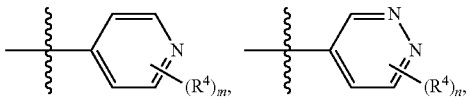

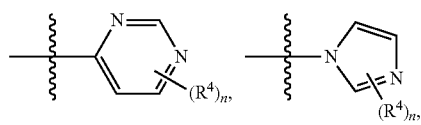

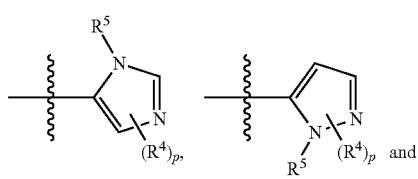

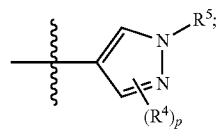

wherein any heterocycle of A$^1$ and A$^2$ can be optionally substituted with —C(O)CH$_3$; R$^4$, m, n and p are as defined in the disclosure of the invention.

Another aspect is a compound of Formula (3):

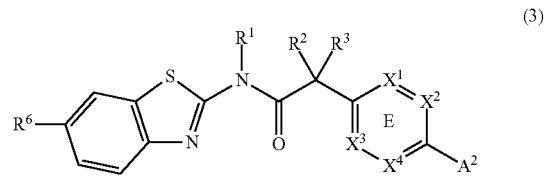

wherein R$^1$, R$^2$, R$^3$, X$^1$, X$^2$, X$^3$, X$^4$, A$^2$ and R$^6$ are as defined in the disclosure of the invention.

Another aspect is a compound of Formula (4):

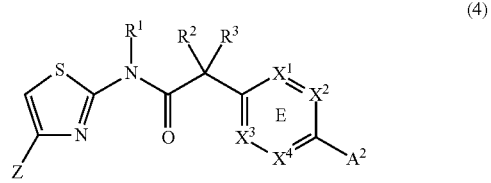

wherein R$^1$, R$^2$, R$^3$, X$^1$, X$^2$, X$^3$, X$^4$, A$^1$ and Z are as defined in the disclosure of the invention.

In another aspect, ring E is phenyl, pyridyl or pyrimidinyl, each of which optionally substituted with R$^7$.

In another aspect, R$^7$ is H, halo, cyano, C$_{1-6}$alkoxy, —S(O)$_2$R$^{10}$, or an optionally halogenated C$_{1-6}$ alkyl.

Another aspect is a compound is of Formula (5):

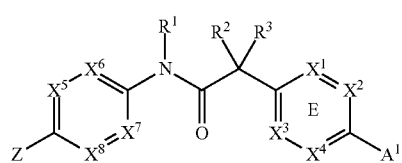

wherein A$^1$ is piperazinyl substituted with —C(O)CH$_3$,

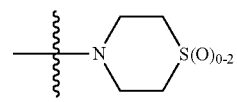

or selected from:

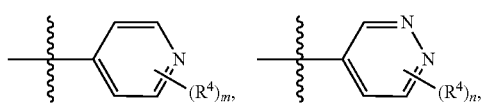

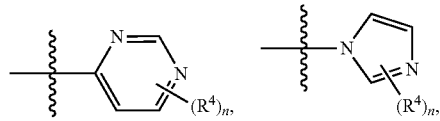

-continued

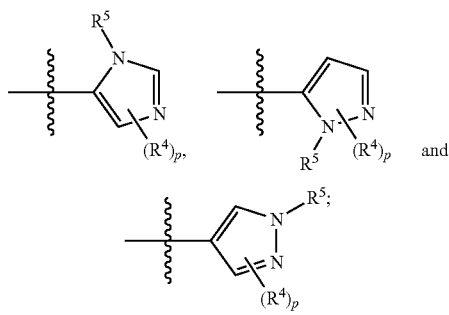

ring E is phenyl or one of $X^1$, $X^2$, $X^3$ and $X^4$ is N and the others are $CR^7$; one of $X^5$, $X^6$, $X^7$ and $X^8$ is N and the others are $CR^{11}$; Z is a 6-membered heterocycle or a 6-membered heteroaryl, each containing 1-2 nitrogen heteroatoms and each of which is optionally substituted with 1-2 $R^6$ groups; $R^1$, $R^2$ and $R^3$ are H or $C_{1-6}$ alkyl; $R^4$ and $R^6$ are independently hydrogen, cyano, $C_{1-6}$alkoxy, —$S(O)_2R^{10}$, —$C(O)NR^8R^9$, -L-C(O)$R^{10}$, -L-C(O)O$R^{10}$, $C_{1-6}$ alkyl optionally substituted with halo, $C_{2-6}$ alkenyl or $C_{2-6}$ alkynyl; $R^{10}$ is $C_{1-6}$ alkyl or -L-W; L is a bond or $(CR_2)_{1-4}$ wherein R is H or $C_{1-6}$ alkyl; W is $C_{3-7}$cycloalkyl; $R^7$ and $R^{11}$ are independently H, halo, cyano, $C_{1-6}$alkoxy, —$S(O)_2R^{10}$, or an optionally halogenated $C_{1-6}$ alkyl; and m, n and p are independently 0-2.

In another aspect, $A^1$ is piperazinyl substituted with —C(O)CH$_3$,

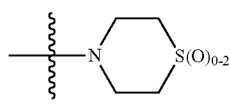

or selected from:

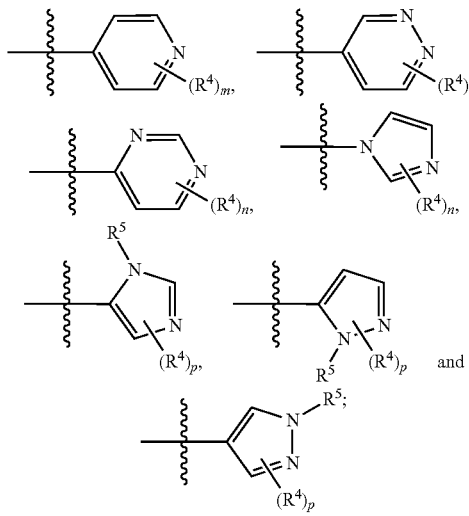

and m is 0-2; n is 0-2; and p is 0-1.

In a further aspect, one of $X^1$, $X^2$, $X^3$ and $X^4$ is N and the others are $CR^7$.

Another aspect is a compound of Formula (6):

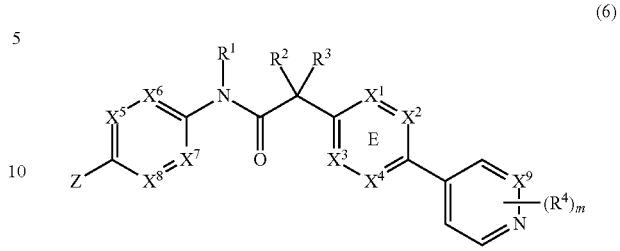

(6)

wherein $X^1$, $X^2$, $X^3$ and $X^4$ is selected from N and $CR_7$; one of $X^5$, $X^6$, $X^7$ and $X^8$ is N and the others are CH; $X^9$ is selected from N and CH; Z is selected from phenyl, pyrazinyl, pyridinyl and piperazinyl; wherein each phenyl, pyrazinyl, pyridinyl or piperazinyl of Z is optionally substituted with an $R^6$ group; $R^1$, $R^2$ and $R^3$ are hydrogen; m is 1; $R^4$ is selected from hydrogen, halo and methyl; $R^6$ is selected from hydrogen, halo and —C(O)$R^{10}$; wherein $R^{10}$ is methyl; and $R^7$ is selected from hydrogen, methyl and trifluoromethyl.

In another aspect, $R^1$, $R^2$ and $R^3$ are H; and $R^4$ and $R^6$ are independently selected from hydrogen, halo, methyl and —C(O)CH$_3$.

In each of the above formula, any asymmetric carbon atoms may be present in the (R)-, (S)- or (R,S)-configuration. The compounds may thus be present as mixtures of isomers or as pure isomers, for example, as pure enantiomers or diastereomers. The invention further encompasses possible tautomers of the inventive compounds.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies.

In particular examples, $^2$H, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents. Isotopic variations of the compounds have the potential to change a compound's metabolic fate and/or create small changes in physical properties such as hydrophobicity, and the like. Isotopic variation have the potential to enhance efficacy and safety, enhance bioavailability and half-life, alter protein binding, change biodistribution, increase the proportion of active metabolites and/or decrease the formation of reactive or toxic metabolites.

The invention also provides for a method of inhibiting Wnt-signaling in a cell comprising contacting the cell with an effective amount of a Wnt antagonist. In one embodiment, the cell is contained within a mammal, and the administered amount is a therapeutically effective amount. In one embodiment, the inhibition of Wnt signaling further results in the inhibition of the growth of the cell. In a further embodiment, the cell is a cancer cell.

Inhibition of cell proliferation is measured using methods known to those skilled in the art. For example, a convenient assay for measuring cell proliferation is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) *J. Immunol. Meth.* 160: 81-88, U.S. Pat. No. 6,602,677. The assay may be conducted in 96- or 384-well format, making it amenable to automated high-throughput screening (HTS). See Cree et al (1995) *Anti-Cancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU) Inhibition of cell proliferation may also be measured using colony formation assays known in the art.

Furthermore, the invention provides for methods of treating a Wnt-mediated disorder in a mammal suffering therefrom, comprising administering to the mammal a therapeutically effective amount of a Wnt antagonist. In one embodiment, the disorder is a cell proliferative disorder associated with aberrant, e.g., increased, expression of activity of Wnt signaling. In another embodiment, the disorder results from increased expression of a Wnt protein. In yet another embodiment, the cell proliferative disorder is cancer, such as for example, colon cancer, colorectal cancer, breast cancer, cancer associated with various disorders relating to HSC's, such as leukemias and various other blood related cancers, and cancer related to neuronal proliferative disorders, including brain tumors, such as gliomas, astrocytomas, meningiomas, Schwannomas, pituitary tumors, primitive neuroectodermal tumors (PNET), medulloblastomas, craniopharyngioma, pineal region tumors, and skin cancers, including basal cell carcinoma and squamous cell carcinoma.

Treatment of the cell proliferative disorder by administration of a Wnt antagonist results in an observable and/or measurable reduction in or absence of one or more of the following: reduction in the number of cancer cells or absence of the cancer cells; reduction in the tumor size; inhibition of cancer cell infiltration into peripheral organs including the spread of cancer into soft tissue and bone; inhibition of tumor metastasis; inhibition, to some extent, of tumor growth; and/or relief to some extent, one or more of the symptoms associated with the specific cancer; reduced morbidity and mortality, and improvement in quality of life issues. To the extent the Wnt antagonist may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TDP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB). In a specific embodiment, the administration of Wnt antagonist decreases tumor burden (e.g., reduces size or severity of the cancer). In yet another specific embodiment, the administration of Wnt antagonist kills the cancer.

Pharmacology and Utility

The present invention relates to compositions and methods for modulating the Wnt signaling pathway. In particular embodiments, the present invention provides compositions and methods that inhibit Wnt signal transduction activity by modulating activation of the Wnt pathway, thereby treating, diagnosing, preventing, and/or ameliorating Wnt signaling-related disorders.

The current paradigm for developing therapies for Wnt signaling-related disorders relies on targeting β-cat or Wnt pathway components downstream of β-cat. Recent studies, however, suggest that inhibition of the extracellular ligand-receptor interaction component is effective in reducing the tumorigenicity, even though the event initiating the Wnt signaling may have occurred downstream. Moreover, the transfection of inoperative frizzled receptor (Frz7 ectodomain) into carcinoma cell line (SK-CO-1) restored a normal β-catenin phenotype. This cell line has active Wnt signaling due to a homozygous APC$^{-/-}$ mutation. Such cells also did not demonstrate tumor formation when transferred in vivo. Vincan et al., Differentiation 2005; 73: 142-153. This demonstrates that the inhibition of Wnt signaling at the extracellular level can downregulate Wnt signaling resulting from activation of a downstream intracellular Wnt signaling pathway component. This further suggests that inhibitors of the Wnt signaling pathway may be used in the treatment of any Wnt-mediated disorder, regardless of the particular manner in which Wnt signaling has been activated.

Disorders Associated with Wnt Signaling Activity

Deregulation of the Wnt signaling pathway may be caused by somatic mutations in genes encoding various Wnt signaling pathway components. For example, aberrant Wnt signaling activity has been associated with Wnt ligand overexpression in non small cell lung cancer (NSCLC) [You et al., *Oncogene* 2004; 23: 6170-6174], chronic lymphocytic leukemia (CLL) [Lu et al., *Proc. Natl. Acad. Sci. USA* 2004; 101: 3118-3123], gastric cancer [Kim et al., *Exp. Oncol.* 2003; 25: 211-215; Saitoh et al., *Int. J. Mol. Med.* 2002; 9: 515-519], head and neck squamous cell carcinoma (HNSCC) [Rhee et al., *Oncogene* 2002; 21: 6598-6605], colorectal cancer [Holcombe et al., *J. Clin. Pathol—Mol. Pathol.* 2002; 55: 220-226], ovarian cancer [Ricken et al., *Endocrinology* 2002; 143: 2741-2749], basal cell carcinoma (BCC) [Lo Muzio et al., *Anticancer Res.* 2002; 22: 565-576] and breast cancer. Moreover, the reduction of various Wnt ligand regulatory molecules such as sFRP and WIF-1 have been associated with breast cancer [Klopocki et al., *Int. J. Oncol.* 2004; 25: 641-649; Ugolini et al., *Oncogene* 2001; 20: 5810-5817; Wissmann et al., *J. Pathol* 2003; 201: 204-212], bladder cancer [Stoehr et al., *Lab Invest.* 2004; 84: 465-478; Wissmann et al., supra], mesothelioma [Lee et al., *Oncogene* 2004; 23: 6672-6676], colorectal cancer [Suzuki et al., *Nature Genet.* 2004; 36: 417-422; Kim et al., *Mol. Cancer. Ther.* 2002; 1: 1355-1359; Caldwell et al., *Cancer Res.* 2004; 64: 883-888], prostate cancer [Wissman et al., supra], NSCLC [Mazieres et al., *Cancer Res.* 2004; 64: 4717-4720], and lung cancer [Wissman et al., supra].

Aberrant Wnt signaling resulting from overexpression of various components of the Frz-LRP receptor complex have also been associated with certain cancers. For example, LRP5 overexpression has been associated with osteosarcoma [Hoang et al., *Int. J. Cancer* 2004; 109: 106-111], while Frz overexpression has been associated with cancers such as prostate [Wissmann et al., supra], HNSCC [Rhee et al., *Oncogene* 2002; 21: 6598-6605], colorectal [Holcombe et al., supra], ovarian cancer [Wissman et al., supra], esophageal [Tanaka et al., *Proc. Natl. Acad. Sci. USA* 1998; 95: 10164-10169] and gastric [Kirikoshi et al., *Int. J. Oncol.* 2001; 19: 111-115]. Additionally, overexpression of Wnt signaling pathway components such as Dishevelled have been associated with cancers such as prostate [Wissman et al, supra], breast [Nagahata et al., *Cancer Sci.* 2003; 94: 515-518], mesothelioma [Uematsu et al., *Cancer Res.* 2003; 63: 4547-4551] and cervical [Okino et al, *Oncol Rep.* 2003; 10: 1219-1223]. Frat-1 overexpression has been associated with cancers such as pancreatic, esophageal, cervical, breast and gastric. [Saitoh et al., *Int. J. Oncol.* 2002; 20: 785-789; Saitoh et al., *Int. J. Oncol* 2001; 19: 311-315]. Axin loss of function (LOF) mutations have been associated with hepatocellular cancer [Satoh et al., *Nature Genet.* 2000; 24: 245-250; Taniguchi et al., *Oncogene* 2002; 21: 4863-4871] and medulloblastoma [Dahmen et al., *Cancer Res.* 2001; 61: 7039-7043; Yokota et al., *Int. J. Cancer* 2002; 101: 198-201].

Furthermore, a multitude of cancers has been associated with activating β-catenin through disruption of the "degradation complex" such as gain-of-function mutations in β-catenin or loss-of-function mutations in APC. A reduction in the degradation of β-catenin results in greater amounts of functional β-catenin in the cell, which then causes increased transcription of the target genes, resulting in aberrant cell proliferation. For example, mutations in the gene encoding β-catenin (i.e., CTNNB1) have been associated with cancers such as gastric [Clements et al., *Cancer Res.* 2002; 62: 3503-3506; Park et al., *Cancer Res.* 1999; 59: 4257-4260], colorectal [Morin et al., *Science* 1997; 275: 1787-1790; Ilyas et al., *Proc. Natl. Acad. Sci. USA* 1997; 94: 10330-10334], intestinal carcinoid [Fujimori et al., *Cancer Res.* 2001; 61: 6656-6659], ovarian [Sunaga et al., *Genes Chrom. Cancer* 2001; 30: 316-321], pulmonary adenocarcinoma [Sunaga et al., supra], endometrial [Fukuchi et al., *Cancer Res.* 1998; 58: 3526-3528; Kobayashi et al., *Japan. J. Cancer Res.* 1999; 90: 55-59; Mirabelli-Primdahl et al., *Cancer Res.* 1999; 59: 3346-3351], hepatocellular [Satoh et al., supra.; Wong et al., *Cancer* 2001; 92: 136-145], hepatoblastoma [Koch et al., *Cancer Res.* 1999; 59: 269-273], medulloblastoma [Koch et al., *Int. J. Cancer* 2001; 93: 445-449], pancreatic [Abraham et al., *Am. J. Pathol* 2002; 160: 1361-1369], thyroid [Garcia-Rostan et al., *Cancer Res.* 1999; 59: 1811-1815; Garcia-Rostan et al., *Am. J. Pathol* 2001; 158: 987-996], prostate [Chesire et al., *Prostate* 2000; 45: 323-334; Voeller et al., *Cancer Res.* 1998; 58: 2520-2523], melanoma [Reifenberger et al., *Int. J. Cancer* 2002; 100: 549-556], pilomatricoma [Chan et al., *Nature Genet.* 1999; 21: 410-413], Wilms' tumor [Koesters et al., *J. Pathol* 2003; 199: 68-76], pancreatoblastomas [Abraham et al., *Am. J. Pathol.* 2001; 159: 1619-1627], liposarcomas [Sakamoto et al., *Arch. Pathol. Lab Med.* 2002; 126: 1071-1078], juvenile nasopharyngeal angiofibromas [Abraham et al., *Am. J. Pathol.* 2001; 158: 1073-1078], desmoid [Tejpar et al., *Oncogene* 1999; 18: 6615-6620; Miyoshi et al., *Oncol. Res.* 1998; 10: 591-594], synovial sarcoma [Saito et al., *J. Pathol* 2000; 192: 342-350]. While loss-of-function mutations have been associated with cancers such as colorectal [Fearon et al., *Cell* 1990; 61: 759-767; Rowan et al., *Proc. Natl. Acad. Sci. USA* 2000; 97: 3352-3357], melanoma [Reifenberger et al., *Int. J. Cancer* 2002; 100: 549-556; Rubinfeld et al., *Science* 1997; 275: 1790-1792], medulloblastoma [Koch et al., *Int. J. Cancer* 2001; 93: 445-449; Huang et al., *Am. J. Pathol* 2000; 156: 433-437] and desmoids [Tejpar et al., *Oncogene* 1999; 18: 6615-6620; Alman et al., *Am J. Pathol.* 1997; 151: 329-334].

Other disorders associated with aberrant Wnt signaling, include but are not limited to osteoporosis, osteoarthritis, polycystic kidney disease, diabetes, schizophrenia, vascular disease, cardiac disease, non-oncogenic proliferative diseases, and neurodegenerative diseases such as Alzheimer's disease.

Aberrant Wnt Signaling in Cancers and Leukemia

Aberrant Wnt pathway activation, through the stabilization of β-catenin, plays a central role in tumorigenesis for many colorectal carcinomas. It is estimated that 80% of colorectal carcinomas (CRCs) harbor inactivating mutations in the tumor repressor APC, which allows for uninterrupted Wnt signaling. Furthermore, there is a growing body of evidence that suggests that the Wnt-pathway activation may be involved in melanoma, breast, liver, lung, gastric cancer, and other cancers.

Unregulated activation of the Wnt signaling pathway is also a precursor to the development of leukemia. Experimental evidence exists supporting the oncogenic growth of both myeloid and lymphoid lineages as dependent on Wnt signaling. Wnt signaling has been implicated in regulating both the chronic and acute forms of myeloid leukemia. Granulocyte-macrophage progenitors (GMPs) from chronic myelogenous leukemia patients and blast crisis cells from patients resistant to therapy display activated Wnt signaling. Moreover, inhibition of β-catenin through ectopic expression of Axin decreases the replating capacity of leukemic cells in vitro, suggesting that chronic myelogenous leukemia precursors are dependent on Wnt signaling for growth and renewal. Wnt overexpression also caused GMPs to acquire stem-cell-like properties of long-term self renewal, supporting the hypothesis that Wnt signaling is important for the normal development of blood lineages, but that aberrant Wnt signaling results in the transformation of progenitor cells.

Recent studies also suggest that lymphoid neoplasias may also be influenced by Wnt signaling. Wnt-16 is overexpressed in pre-B-cell leukemia cell lines carrying the E2A-PbX translocation, suggesting that autocrine Wnt activity may contribute to oncogenesis. McWhirter, et al., *Proc. Natl. Acad. Sci. USA* 96: 11464-11469 (1999). The role of Wnt signaling in the growth and survival of normal B-cell progenitors further supports this notion. Reya et al., *Immunity* 13: 15-24 (2000); Ranheim et al., *Blood* 105: 2487-2494 (2005). Autocrine dependence on Wnt has also been proposed for regulating the growth of multiple myeloma, a cancer of terminally differentiated B-cells. Derksen et al., *Proc. Natl. Acad. Sci. USA* 101: 6122-6127 (2004). Primary myelomas and myeloma cell lines were also found to express stabilized (i.e., independent of degradation complex). Although no mutations in Wnt signaling components was present, the overexpression of several components, including Wnt-5A and Wnt-10B suggest that tumor dependency and cancer self-renewal is not necessarily dependent on mutations appearing in Wnt signaling pathway components, but rather only upon constitutive activation of the pathway itself.

The transition of self-renewing, pluripotent stem cells to myeloid progenitors is accompanied by the downregulation of Wnt signaling. Reya et al, *Nature* 423: 409-414 (2003). Similarly, the stable expression of β-catenin in lymphoid progenitors restored multiple differentiation options, albeit such cells lacked markers typically associated with either cell type. Baba et al, *Immunity* 23: 599-609 (2005).

Aberrant Wnt Signaling in Neural Disorders

It has also been observed that the activation of Wnt signaling through β-catenin can increase cycling and expansion of neural progenitors, and that loss of such signaling can result in a loss of progenitor compartment. Chenn et al., *Science* 297: 365-369 (2002); Zechner et al., *Dev. Biol.* 258: 406-418 (2003). Just as normal activation of Wnt signaling may promote self-renewal of neuronal stem cells, aberrant Wnt pathway activation may be tumorigenic in the nervous system. Experimental evidence supporting this conclusion is the discovery that medulloblastoma, a pediatric brain tumor of the cerebellum, contains mutations in both β-catenin and Axin—thereby suggesting that medulloblastomas arise from primitive progenitors that become transformed in response to uncontrolled Wnt signaling. Zurawel et al., *Cancer Res.* 58: 896-899 (1998); Dahmen et al., *Cancer Res.* 61: 7039-7043 (2001); Baeza et al., *Oncogene* 22: 632-636 (2003). Thus, it is strongly suggested that the inhibition of Wnt signaling by the Wnt antagonists of the invention may be an effective therapeutic in the treatment of various neuronal proliferative disorders, including brain tumors, such as gliomas, astrocytomas, meningiomas, Schwannomas, pituitary tumors, primitive neuroectodermal tumors (PNET), medulloblastomas, craniopharyngioma, pineal region tumors, and non cancerous neurofibromatoses.

Wnt Signaling in Hematopoietic Stem Cells

Hematopoietic stem cells give rise to the adult blood cells of the circulatory system in a process of lineage-committed progenitor cells from multipotential hematopoietic stem cells (HSC). It is also apparent that Wnt signaling contributes to the self-renewal and maintenance of HSC's, and that dysfunctional Wnt signaling is responsible for various disorders resulting from HSC's, such as leukemias and various other blood related cancers. Reya et al., *Nature* 434: 843-850 (2005); Baba et al., *Immunity* 23: 599-609 (2005); Jamieson et al., *N. Engl. J. Med.* 351(7): 657-667 (2004). Wnt signaling is normally reduced as stem cells convert to committed myeloid progenitor cells. Reya et al., *Nature* 423: 409-414 (2003).

Not only are Wnt ligands themselves produced by HSC's, but Wnt signaling is also active, thereby suggesting autocrine or paracrine regulation. Rattis et al., *Curr. Opin. Hematol.* 11: 88-94 (2004); Reya et al., *Nature* 423: 409-414 (2003). Additionally, both β-catenin and Wnt3a promote self renewal of murine HSCs and progenitor cells, while application of Wnt-5A to human hematopoietic progenitors promotes the expansion of undifferentiated progenitors in vitro. Reya et al., supra.; Willert et al., *Nature* 423: 448-452 (2003); Van Den Berg et al., *Blood* 92: 3189-3202 (1998).

In addition to HSC's, it is apparent that embryonic stem cells, epidermal stem cells and epithelial stem cells are responsive or dependent on Wnt signaling for maintenance in an undifferentiated, proliferating state. Willert et al., supra; Korinek et al., *Nat. Genet.* 19: 379-383 (1998); Sato et al., *Nat. Med.* 10: 55-63 (2004); Gat et al., *Cell* 95: 605-614 (1998); Zhu et al., *Development* 126: 2285-2298 (1999). Therefore the inhibition of Wnt signaling with the Wnt antagonists of the present invention may be a therapeutic in the treatment of disorders resulting from dysfunctional hematopoieses, such as leukemias and various blood related cancers, such as acute, chronic, lymphoid and myelogenous leukemias, myelodysplastic syndrome and myeloproliferative disorders. These include myeloma, lymphoma (e.g., Hodgkin's and non-Hodgkin's) chronic and nonprogressive anemia, progressive and symptomatic blood cell deficiencies, polycythemia vera, essential or primary thrombocythemia, idiopathic myelofibrosis, chronic myelomonocytic leukemia (CMML), mantle cell lymphoma, cutaneous T-cell lymphoma, Waldenstrom macroglobinemia, Wnt Signaling in Aging The Wnt signaling pathway may also play a critical role in aging and age-related disorders. As reported in Brack A S, et al., *Science*, 317(5839):807-10 (2007), muscle stem cells from aged mice were observed to convert from a myogenic to a fibrogenic lineage as they begin to proliferate. This conversion is associated with an increase in canonical Wnt signaling pathway activity in aged myogenic progenitors and can be suppressed by Wnt inhibitors. Additionally, components of serum from aged mice bind to the Frizzled proteins and may account for the elevated Wnt signaling in aged cells. Injection of Wnt3A into young regenerating muscle reduced proliferation and increased deposition of connective tissue.

The Wnt signaling pathway has been further implicated in aging process in studies using the Klotho mouse model of accelerated aging in which it was determined that the Klotho protein physically interacted with and inhibited Wnt proteins. Liu H, et al., Science, 317(5839):803-6 (2007). In a cell culture model, the Wnt-Klotho interaction resulted in the suppression of Wnt biological activity while tissues and organs from Klotho-deficient animals showed evidence of increased Wnt signaling.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention may be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form.

Pharmaceutical compositions comprising a compound of the present invention in free form or in a pharmaceutically acceptable salt form in association with at least one pharmaceutically acceptable carrier or diluent may be manufactured in a conventional manner by mixing, granulating or coating methods. For example, oral compositions may be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets, together with c) binders, e.g., magnesium aluminum silicate, starch paste, gelatin, tragamayth, methylcellulose, sodium carboxymethylcellulose and or polyvinylpyrrolidone; and if desired, d) disintegrants, e.g., starches, agar, alginic acid or its sodium salt, or effervescent mixtures; and/or e) absorbents, colorants, flavors and sweeteners. Injectable compositions may be aqueous isotonic solutions or suspensions, and suppositories may be prepared from fatty emulsions or suspensions.

The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier may include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, may be aqueous solutions, ointments, creams or gels well-known in the art. Such may contain solubilizers, stabilizers, tonicity enhancing agents, buffers and preservatives.

Compounds of the invention may be administered in therapeutically effective amounts in combination with one or more therapeutic agents (pharmaceutical combinations). For example, synergistic effects may occur when a compound of the invention is used in combination with a chemotherapeutic agent. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit may comprise instructions for its administration.

Processes for Making Compounds of the Invention

In general, compounds having Formula (1) may be prepared following any one of the synthetic methodologies described in Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry", John Wiley and Sons, 1991). Suitable leaving groups for use in the synthetic methodologies described include halogen leaving groups (e.g., chloro or bromo), and other conventional leaving groups within the knowledge of those skilled in the art.

The compounds of the invention, including their salts, are also obtainable in the form of hydrates, or their crystals may include for example the solvent used for crystallization (present as solvates). Salts can usually be converted to compounds in free form, e.g., by treating with suitable basic agents, for example with alkali metal carbonates, alkali metal hydrogen carbonates, or alkali metal hydroxides, such as potassium carbonate or sodium hydroxide. A compound of the invention in a base addition salt form may be converted to the corresponding free acid by treating with a suitable acid (e.g., hydrochloric acid, etc.). In view of the close relationship between the novel compounds in free form and those in the form of their salts, including those salts that may be used as intermediates, for example in the purification or identification of the novel compounds, any reference to the free compounds is to be understood as referring also to the corresponding salts, as appropriate.

Salts of the inventive compounds with a salt-forming group may be prepared in a manner known per se. Acid addition salts of compounds of Formula (1), (2), (3), (4) or (5) may thus be obtained by treatment with an acid or with a suitable anion exchange reagent. Pharmaceutically acceptable salts of the compounds of the invention may be formed, for example, as acid addition salts, with organic or inorganic acids, from compounds of Formula (1), (2), (3), (4) or (5) with a basic nitrogen atom.

Suitable inorganic acids include, but are not limited to, halogen acids, such as hydrochloric acid, sulfuric acid, or phosphoric acid. Suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid,-malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4 methylbenzenesulfonic acid, methylsulfuric acid, ethylsulfuric acid, dodecylsulfuric acid, N cyclohexylsulfamic acid, N-methyl-, N-ethyl- or N-propyl-sulfamic acid, or other organic protonic acids, such as ascorbic acid. For isolation or purification purposes, it is also possible to use pharmaceutically unacceptable salts, for example picrates or perchlorates. For therapeutic use, only pharmaceutically acceptable salts or free compounds are employed (where applicable in the form of pharmaceutical preparations).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal may be found in T. W. Greene, "Protecting Groups in Organic Chemistry", 3rd edition, John Wiley and Sons, Inc., 1999.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubilities, reactivity, etc.) and may be readily separated by taking advantage of these dissimilarities. The diastereomers may be separated by fractionated crystallization, chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In summary, the compounds of the invention may be made by a process as described in the Examples; and (a) optionally converting a compound of the invention into a pharmaceutically acceptable salt;

(b) optionally converting a salt form of a compound of the invention to a non-salt form;

(c) optionally converting an unoxidized form of a compound of the invention into a pharmaceutically acceptable N-oxide;

(d) optionally converting an N-oxide form of a compound of the invention to its unoxidized form;

(e) optionally resolving an individual isomer of a compound of the invention from a mixture of isomers;

(f) optionally converting a non-derivatized compound of the invention into a pharmaceutically acceptable prodrug derivative; and (g) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter. One of skill in the art will appreciate that the above transformations are only representative of methods for preparation of the compounds of the present invention, and that other well known methods can similarly be used. The present invention is further exemplified, but not limited, by the following and Examples that illustrate the preparation of the compounds of the invention.

EXAMPLE 1

N-(6-methoxybenzo[d]thiazol-2-yl)-2-(4-(pyridin-4-yl)phenyl)acetamide (3)

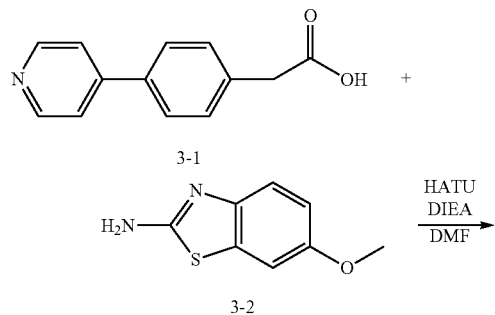

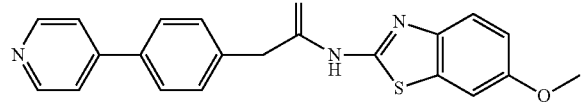

Compound 3

To a mixture of 2-(4-(pyridin-4-yl)phenyl)acetic acid 3-1 (45 mg, 0.21 mmol), 6-methoxybenzo[d]thiazol-2-amine 3-2 (36 mg, 0.20 mmol), and DIEA (32 mg, 0.25 mmol) in DMF (0.5 mL) under stiffing was added HATU (84 mg, 0.22 mmol). The solution was stirred for 2 hours before it was subject to reverse phase HPLC for purification to give compound 3 as white solid. MS m/z 376.1 (M+1); $^1$H NMR 400 MHz (DMSO-$d_6$) δ 12.60(s, 1H), 8.70(m, 2H), 7.87(m, 2H), 7.78(m, 2H), 7.72(d, 1H, J=8.8 Hz), 7.63(d, 1H, J=2.8 Hz), 7.58(m, 2H), 7.11(dd, 1H, J1=8.8 Hz, J2=2.4 Hz), 3.96(s, 2H), 3.86(s, 3H).

EXAMPLE 2

2-(3-methyl-4-(2-methylpyridin-4-yl)phenyl)-N-(4-phenylthiazol-2-yl)acetamide (24)

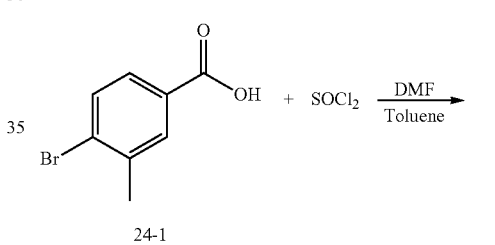

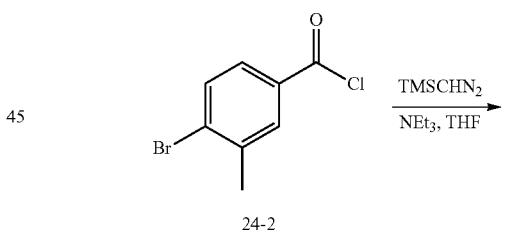

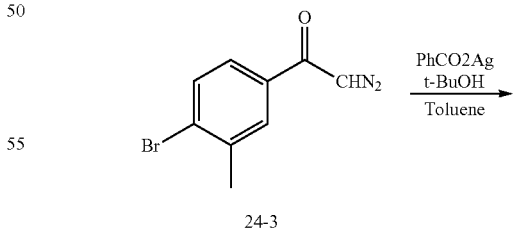

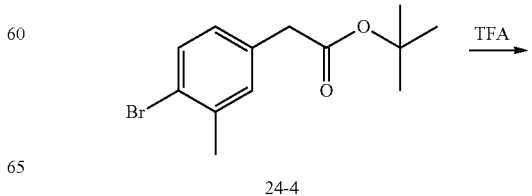

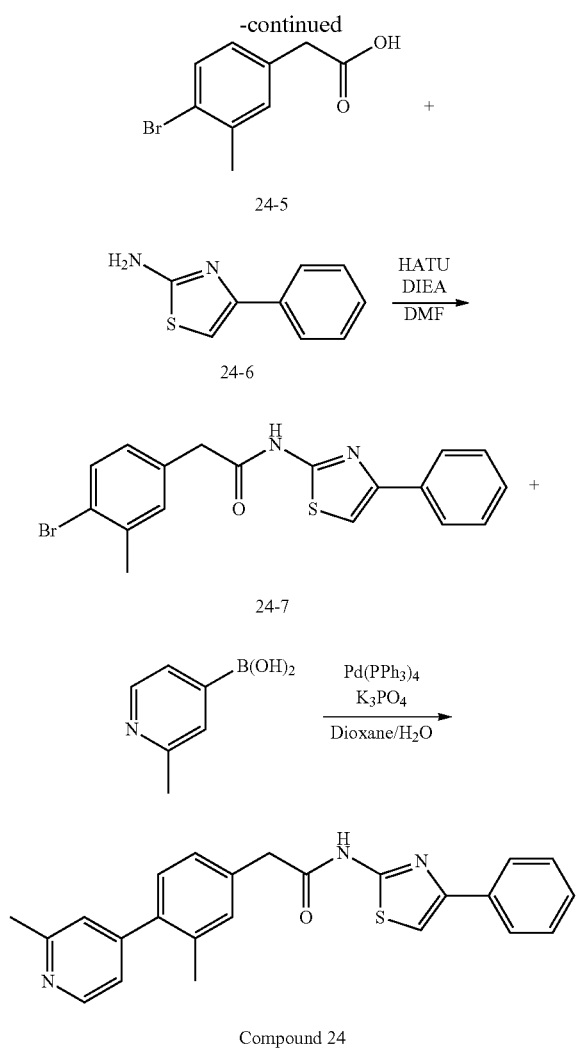

Compound 24

Step 1: To a suspension of 3-methyl-4-bromobenzoic acid 24-1 (2.15 g, 10 mmol) in toluene (15 mL, anhydrous) were added $SOCl_2$ (1.4 mL, ~1.9 eq) and 3 drops of DMF at room temperature. The mixture was refluxed 2 hours with stiffing. After cooling to room temperature, the reaction mixture was concentrated under reduced pressure. The resulting residue was dissolved in THF (25 mL, anhydrous) and then at 0° C. $NEt_3$ (2.2 mL) and $TMSCHN_2$ (8.2 mLx2.0 M in hexanes) were added. After 12 hours of stirring the mixture was poured into saturated $NaHCO_3$ solution (60 mL) and extracted with ethyl acetate (3×60 mL). The combined extracts were washed with brine, dried over $Na_2SO_4$ and evaporated to give the crude intermediate 24-3. This crude intermediate was added in small portions to a refluxed solution of $NEt_3$ (4.2 mL), $PhCO_2Ag$ (0.70 g) in t-butanol (50 mL) and toluene (20 mL) with stirring. After 1 hour of refluxing, the reaction mixture was cooled to room temperature. Activated carbon powder was added to the reaction mixture which was then filtered through Celite. The filtrate was diluted with ethyl acetate (100 mL) and washed with brine. After dried over $Na_2SO_4$, the resulting solution was concentrated under reduced pressure. The residue was purified by column chromatography on silica gel with DCM-EtOAc (30:1) as eluent to afford the t-butyl ester 24-4.

Step 2: Ester 24-4 (810 mg, 2.84 mmol) was dissolved in DCM (16 mL) and trifluoroacetic acid (2 mL) was added. The mixture was stiffed at room temperature overnight. Solvent DCM was evaporated and the residue was dissolved in ethyl acetate (50 mL) and this organic solution was extracted with $Na_2CO_3$ solution (10% aqueous, 50 mL). The aqueous phase was acidified with HCl solution to pH2 and the precipitate was extracted with ethyl acetate (50 mL). After it was dried over $Na_2SO_4$, the organic solvent was evaporated to give acid 24-5.

Step 3: To a mixture of compound 24-5 (92 mg, 0.4 mmole), 4-phenyl-2-aminothiazole 24-6 (76 mg, 0.44 mmole) and HATU (167 mg, 0.44 mmole) in DMF (1.6 mL) was added DIEA (100 uL, 0.58 mmole) and the mixture was stirred at room temperature over night. Then it was redistributed between ethyl acetate (50 mL) and water (40 mL). The organic phase was dried over $Na_2SO_4$ and the solvent was evaporated. The residue was subject to silica gel chromatography to give compound 24-7.

Step 4: A mixture of compound 24-7 (33 mg, 0.085 mmole), 2-methylpyridin-4-ylboronic acid (23 mg, 0.17 mmole), $Pd(PPh_3)_4$ (9.8 mg, 0.0085 mmole) and $K_3PO_4$ (36 mg, 0.17 mmole) in dioxane (0.6 mL) and water (0.06 mL) under argon was stirred at 96° C. overnight. After it was cooled down to room temperature, the reaction mixture was filtered through celite, diluted with ethyl acetate (50 mL) and the organic solution washed with water (50 mLx2) and dried over $Na_2SO_4$. After evaporation, the residue obtained was subjecte to reverse phase HPLC to give compound 24 as white solid. MS m/z 400.14 (M+1); $^1H$ NMR 400 MHz (DMSO-$d_6$) δ 12.58(s, 1H), 8.56(d, 1H, J=5.6 Hz), 7.92(m, 2H), 7.63(s, 1H), 7.46(m, 2H), 7.36(m, 1H), 7.33(m, 4H), 7.24(d, 1H, J=8.0 Hz), 3.83(s, 2H), 2.56(s, 3H), 2.27(s, 3H).

EXAMPLE 3

2-(4-(2-methylpyridin-4-yl)phenyl)-N-(5-phenylpyridin-2-yl)acetamide (26)

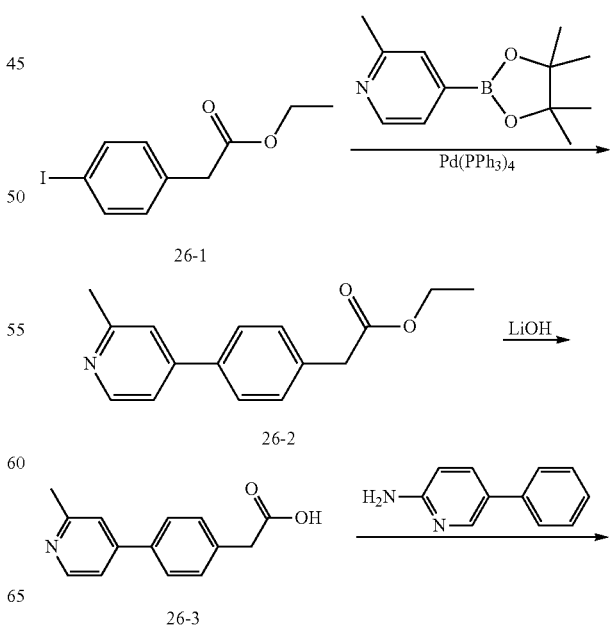

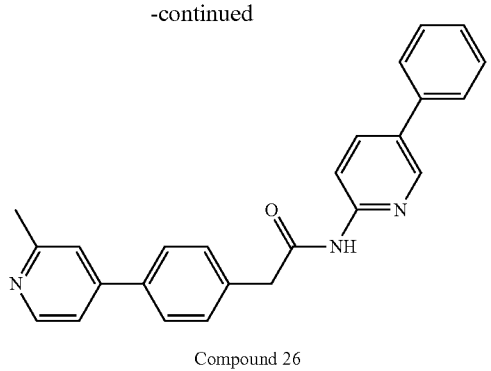

Compound 26

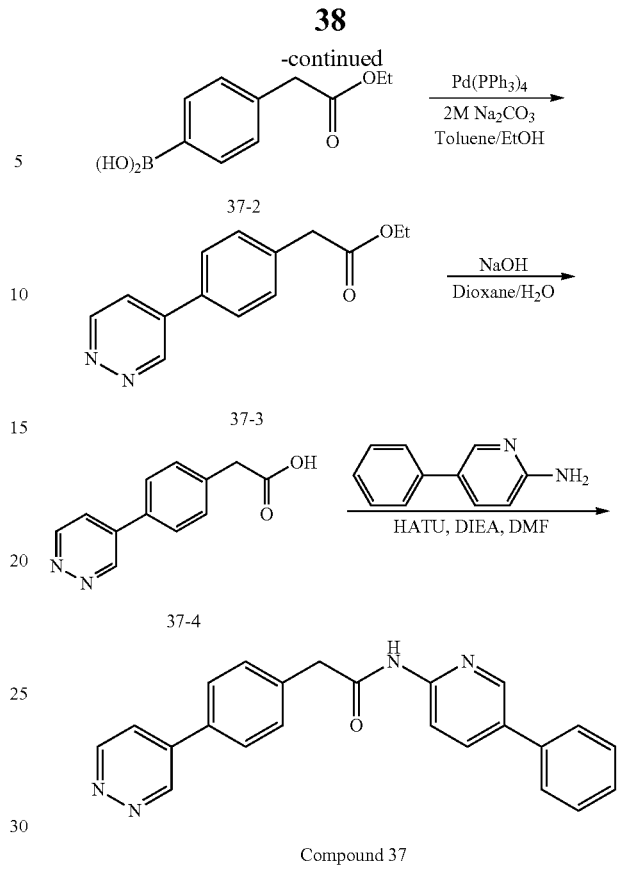

Compound 37

Step 1: To a sealed tube were added 2-methyl-4-(4,4,5,5-tetramethyl-1,3,2-dioxaborolan-2-yl)pyridine (2.2 g, 10 mmol), ethyl 2-(4-iodophenyl)acetate 26-1 (2.9 g, 10 mmol), Pd(PPh$_3$)$_4$ (0.231 g, 0.2 mmol), toluene (30 mL), ethanol (10 mL) and 2M Na$_2$CO$_3$ (10 mL). The reaction mixture was flushed with nitrogen and stirred at 90° C. for 10 hours. After cooled down to room temperature, the reaction mixture was diluted into 200 mL ethyl acetate and washed with saturated sodium bicarbonate solution and then brine. The organic phase was dried over Na$_2$SO$_4$ and then taken to dryness by rotary evaporation. The crude product was purified by silica gel flash chromatography, eluted with 50% ethyl acetate in hexane to give ethyl 2-(4-(2-methylpyridin-4-yl)phenyl)acetate 26-2 as an oil. MS m/z 256.1 (M+1).

Step 2: A mixture of ethyl 2-(4-(2-methylpyridin-4-yl)phenyl)acetate 26-2 (1.81 g, 7.1 mmol), LiOH (0.17 g, 7.1 mmol) in THF (30 mL), methanol (10 mL) and H$_2$O (10 mL) was stirred at 60° C. for 1 hour. After cooled down to 0° C., the mixture was neutralized with 1 N HCl at 0° C. and then taken to dryness by rotary evaporation to yield 2-(4-(2-methylpyridin-4-yl)phenyl)acetic acid 26-3. The product was used for next step without further purification. MS m/z 228.1 (M+1).

Step 3: A mixture of 2-(4-(2-methylpyridin-4-yl)phenyl) acetic acid 26-3 (50 mg, 0.2 mmol), 5-phenylpyridin-2-amine (41 mg, 0.24 mmol) and O-(7-azabenzotriazol-1-yl)-N,N,N',N'-tetramethyluroniumhexafluorophosphate (HATU) (114 mg, 0.3 mmol) in 1.5 mL DMF was added N,N-diisopropylethylamine (DIEA, 104 μL, 0.6 mmol) at room temperature. The mixture was stirred at room temperature for 2 hours. The solvent was removed by rotary evaporation. The crude product was purified by reverse phase HPLC to give 2-(4-(2-methylpyridin-4-yl)phenyl)-N-(5-phenylpyridin-2-yl)acetamide 26 as white solid. MS m/z 380.17 (M+1); $^1$H NMR 400 MHz (DMSO-d$_6$) δ 10.84(s, 1H), 8.60(d, 1H, J=2.4 Hz), 8.42(d, 1H, J=6.4 Hz), 8.10(d, 1H, J=8.8 Hz), 8.04(dd, 1H, J$_1$=8.8 Hz, J$_2$=2.4 Hz), 7.70(m, 2H), 7.65(m, 2H), 7.51(m, 1H), 7.44(m, 5H), 7.33(m, 1H), 3.76(s, 2H), 2.46(s, 3H).

EXAMPLE 4

N-(5-phenylpyridin-2-yl)-2-(4-(pyridazin-4-yl)phenyl)acetamide (37)

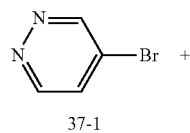

37-1

Step 1: To a sealed tube were added 4-(2-ethoxy-2-oxoethyl)phenylboronic acid 37-2 (310 mg, 1.5 mmol), 4-bromopyridazine 37-1 (158 mg, 1 mmol), Pd(PPh$_3$)$_4$ (70 mg, 0.1 mmol), toluene (4 mL), ethanol (1 mL) and 2M Na$_2$CO$_3$ (1.5 mL). The reaction mixture was bubbled with nitrogen for 2 minutes and stirred at 90° C. for 10 hours. After cooled down to room temperature, the reaction mixture was diluted with ethyl acetate (50 mL), washed with saturated sodium bicarbonate aqueous solution and brine. The organic phase was dried over Na$_2$SO$_4$ and then concentrated to dryness by rotary evaporation. The crude product was purified by silica gel flash chromatography, eluted with 50% ethyl acetate in hexane to give ethyl 2-(4-(pyridazin-4-yl)phenyl)acetate 37-3 as pale yellow solid. MS m/z 243.1 (M+1)

Step 2: Ethyl 2-(4-(pyridazin-4-yl)phenyl)acetate 37-3 (150 mg, 0.62 mmol) and NaOH (120 mg, 3 mmol) was mixed in dioxane (1.5 mL) and H$_2$O (1.5 mL) and stirred at 80° C. for 1 hour. After cooled down to 0° C., the mixture was treated with 1 N HCl aqueous solution to pH 1, and taken to dryness by rotary evaporation. The crude product was extracted with ethyl acetate (100 mL×3). The combined organic phases were concentrated to give 2-(4-(pyridazin-4-yl)phenyl)acetic acid 37-4 as pale yellow solid. MS m/z 215.1 (M+1)

Step 3: To a mixture of 2-(4-(pyridazin-4-yl)phenyl)acetic acid 37-4 (43 mg, 0.2 mmol), 5-phenylpyridin-2-amine (41 mg, 0.24 mmol) and O-(7-azabenzotriazol-1-yl)-N,N,N',N'-tetramethyluroniumhexafluorophosphate (HATU) (117 mg, 0.3 mmol) in DMF (1 mL) was added DIEA (104 μL, 0.6 mmol) at room temperature. The mixture was stirred at room temperature for 2 hours. The crude product was purified by reverse phase HPLC to give N-(5-phenylpyridin-2-yl)-2-2(4-pyridazin-4-yl)phenyl)acetamide 37 as white solid. MS m/z 367.1 (M+1); $^1$H NMR 400 MHz (CDCl$_3$) δ 9.45-9.44 (m, 1H), 9.22 (dd, 1H, J$_1$=1.2 Hz, J$_2$=11.2 Hz), 8.44 (d, 1H, J=2.4 Hz), 8.29 (d, 1H, J=8.8 Hz), 7.92 (dd, 1H, J$_1$=16.8 Hz, J$_2$=2.4 Hz), 7.70-7.66 (m, 3H), 7.56-7.51 (m, 4H), 7.46-7.43 (m, 2H), 7.39-7.35 (m, 1H), 3.85 (s, 2H).

EXAMPLE 5

2-(4-(2-methylpyridin-4-yl)-3-(trifluoromethyl)phenyl)-N-(5-phenylpyridin-2-yl)acetamide (46)

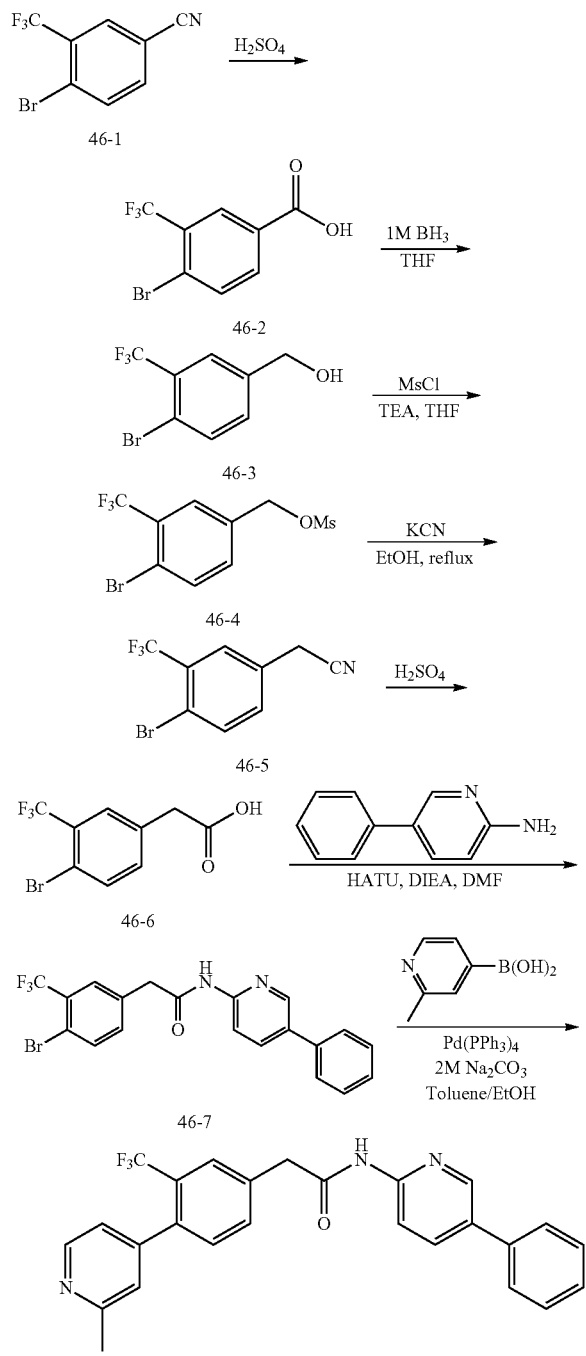

Step 1: To a flask containing 3-trifluoromethyl-4-bromobenzonitrile 46-1 (5.0 g, 20 mmol) were added water (20 mL) and dropwise concentrated sulfuric acid (20 mL). The reaction mixture was stirred at 100° C. for 10 hours. After cooled down to room temperature, the reaction mixture was poured into dichloromethane (150 mL) and water (100 mL). The mixture was neutralized with powder sodium carbonate to pH 9. The aqueous layer was acidified with 1N hydrochloric acid aqueous solution to pH 1, and extracted with ethyl acetate (50 mL×3). The combined organic layers were washed with brine, dried over Na$_2$SO$_4$ and then taken to dryness by rotary evaporation to 4-bromo-3-(trifluoromethyl)benzoic acid 46-2 as white solid. MS m/z 269.1 (M+1)

Step 2: To a solution of 4-bromo-3-(trifluoromethyl)benzoic acid 46-2 (1.35 g, 5 mmol) in THF (10 mL) was added 1M BH$_3$.THF in THF (20 mL) slowly at 0° C. The mixture was warmed up to room temperature and stirred for 4 hours. The reaction was quenched with water at 0° C. All the solvents were evaporated and the residue was redissolved in ethyl acetate (100 mL), washed with saturated NaHCO$_3$ aqueous solution, water and brine, dried over Na$_2$SO$_4$, and then concentrated. The crude product was purified by silica gel flash chromatography, eluted with 40% ethyl acetate in hexane to give (4-bromo-3-(trifluoromethyl)phenyl)methanol 46-3 as white solid. MS m/z 237.1 (M+1)

Step 3: To a solution of (4-bromo-3-(trifluoromethyl)phenyl)methanol 46-3 (956 mg, 3.75 mmol) and triethylamine (455 mg, 4.5 mmol) in THF (9 mL) was added a solution of methanesulfonyl chloride (430 mg, 3.75 mmol) in THF (1 mL) at 10° C. slowly. The mixture was stirred for 1 hour. The solid was filtered and washed with ethyl ether. The filtrate was evaporated to 4-bromo-3-(trifluoromethyl)benzyl methanesulfonate 46-4 as pale yellow solid. MS m/z 233.1 (M+1)

Step 4: To a solution of 4-bromo-3-(trifluoromethyl)benzyl methanesulfonate 46-4 (1.295 g, 3.75 mmol) in ethanol (10 mL) was added a solution of potassium cyanide (364 mg, 5.6 mmol) in water (2 mL). The mixture was refluxed for 2 hours. After the mixture was cooled down to the room temperature, all the solvents were evaporated and the residue was redissolved in dichloromethane (50 mL), washed with water and brine, dried over Na$_2$SO$_4$, and concentrated to dryness to give 2-(4-bromo-3-(trifluoromethyl)phenyl)acetonitrile 46-5 as dark brown oil, which was used for next step directly. MS m/z 264.1 (M+1)

Step 5: To a flask containing 2-(4-bromo-3-(trifluoromethyl)phenyl)acetonitrile 46-5 (880 mg, 3.3 mmol) were added water (4.5 mL) and dropwise concentrated sulfuric acid (4.5 mL). The reaction mixture was stirred at 115° C. for 4 hours. After cooled down to room temperature, the reaction mixture was poured into water (100 mL). The resulting solution was neutralized with powder sodium carbonate to pH 12, treated with 1N HCl aqueous solution to pH around 2, and extracted with dichloromethane (50 mL×3). The combined organic layers were washed with brine, dried over Na$_2$SO$_4$ and then taken to dryness by rotary evaporation give 2-(4-bromo-3-(trifluoromethyl)phenyl)acetic acid 46-6 as pale yellow solid. MS m/z 283.1 (M+1)

Step 6: To a mixture of 2-(4-bromo-3-(trifluoromethyl)phenyl)acetic acid 46-6 (71 mg, 0.25 mmol), 5-phenylpyridin-2-amine (64 mg, 0.38 mmol) and HATU (148 mg, 0.38 mmol) in DMF (1 mL) was added DIEA (125 μL, 0.75 mmol) at room temperature. The mixture was stirred at room temperature for 2 hours. The mixture was diluted with ethyl acetate (50 mL), washed with saturated NaHCO$_3$ aqueous solution, water and brine, dried over Na$_2$SO$_4$, and concentrated by rotary evaporation. The crude product was purified by silica gel flash chromatography, eluted with 40% ethyl acetate in hexane to give 2-(4-bromo-3-(trifluoromethyl)phenyl)-N-(5-phenylpyridin-2-yl)acetamide 46-7 as pale yellow solid. MS m/z 435.2 (M+1)

Step 7: To a sealed tube were added 2-(4-bromo-3-(trifluoromethyl)phenyl)-N-(5-phenylpyridin-2-yl)acetamide 46-7 (73 mg, 0.17 mmol), 2-methylpyridin-4-ylboronic acid (35 mg, 0.255 mmol), Pd(PPh$_3$)$_4$ (12 mg, 0.017 mmol), toluene (0.8 mL), ethanol (0.2 mL) and 2M Na$_2$CO$_3$ (0.5 mL). The reaction mixture was bubbled with nitrogen for 2 minutes and stirred at 90° C. for 10 hours. After cooled down to room temperature, the reaction mixture was diluted with ethyl acetate (50 mL) and washed with saturated NaHCO$_3$ aqueous solution and brine. The organic phase was dried over Na$_2$SO$_4$ and concentrated to dryness by rotary evaporation. The crude product was purified by reverse phase HPLC to give 2-(4-(2-methylpyridin-4-yl)-3-(trifluoromethyl)phenyl)-N-(5-phenylpyridin-2-yl)acetamide 46 as white solid. MS m/z 448.1 (M+1); $^1$H NMR 400 MHz (CDCl$_3$) δ 8.48-8.45 (m, 2H), 8.28 (d, 1H, J=8.4 Hz), 7.92 (dd, 1H, J$_1$=8.4 Hz, J$_2$=2.4 Hz), 7.75 (s, 1H), 7.61 (dd, 1H, J$_1$=8.0 Hz, J$_2$=1.2 Hz), 7.54-7.52 (m, 2H), 7.47-7.43 (m, 2H), 7.39-7.37 (m, 1H), 7.28 (d, 1H, J=7.6 Hz), 7.14 (s, 1H), 7.10 (d, 1H, J=5.2 Hz), 3.86 (s, 2H), 2.59 (s, 3H).

EXAMPLE 6

2-(4-(1H-imidazol-1-yl)phenyl)-N-(5-phenylpyridin-2-yl)acetamide (53)

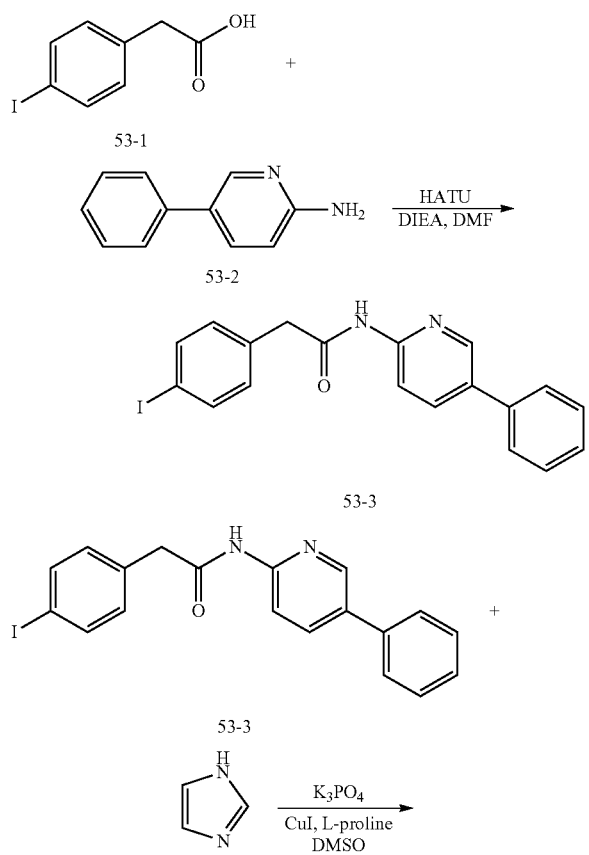

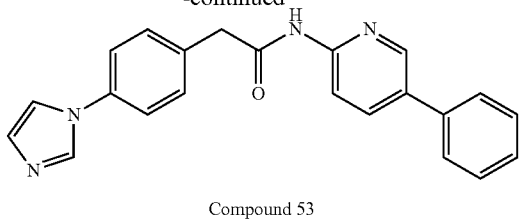

Compound 53

Step 1: To a solution of 2-(4-iodophenyl)acetic acid 53-1 (816 mg, 3.14 mmol), 5-phenylpyridin-2-amine 53-2 (534 mg, 3.14 mmol) and HATU (1.19 g, 3.14 mmol) in DMF (1 mL) was added DIEA (1.57 mL, 9.42 mmol) at room temperature. The mixture was stirred at room temperature for 2 hours. The mixture was diluted with ethyl acetate (50 mL), washed with saturated NaHCO$_3$ aqueous solution, water and brine, dried over Na$_2$SO$_4$, and concentrated by rotary evaporation. The crude product was purified by silica gel flash chromatography, eluted with 40% ethyl acetate in hexane to give 2-(4-Iodophenyl)-N-(5-phenylpyridin-2-yl)acetamide 53-3 as pale yellow solid. MS m/z 415.2 (M+1)

Step 2: A mixture of 2-(4-iodophenyl)-N-(5-phenylpyridin-2-yl)acetamide 53-3 (41 mg, 0.1 mmol), imidazole (10 mg, 0.15 mmol), potassium phosphate (41 mg, 0.3 mmol), CuI (2 mg, 0.01 mmol) and L-proline (2.3 mg, 0.02 mmol) in DMSO (0.5 mL) was stirred under an atmosphere of dry Argon at 100° C. for 10 hours. The crude product was purified by reverse phase HPLC to give 2-(4-(1H-imidazol-1-yl)phenyl)-N-(5-phenylpyridin-2-yl)acetamide 53 as white solid. MS m/z 355.1 (M+1); $^1$H NMR 400 MHz (CDCl$_3$) δ 8.47-8.46 (m, 1H), 8.29 (d, 1H, J=8.8 Hz), 7.99 (s, 1H), 7.92 (dd, 1H, J$_1$=16.8 Hz, J$_2$=2.4 Hz), 7.88 (s, 1H), 7.55-7.53 (m, 2H), 7.49-7.38 (m, 6H), 7.29 (s, 1H), 7.23 (s, 1H), 3.83 (s, 2H).

EXAMPLE 7

N-(5-(1H-pyrazol-4-yl)pyridin-2-yl)-2-(4-(2-methylpyridin-4-yl)phenyl)acetamide (65)

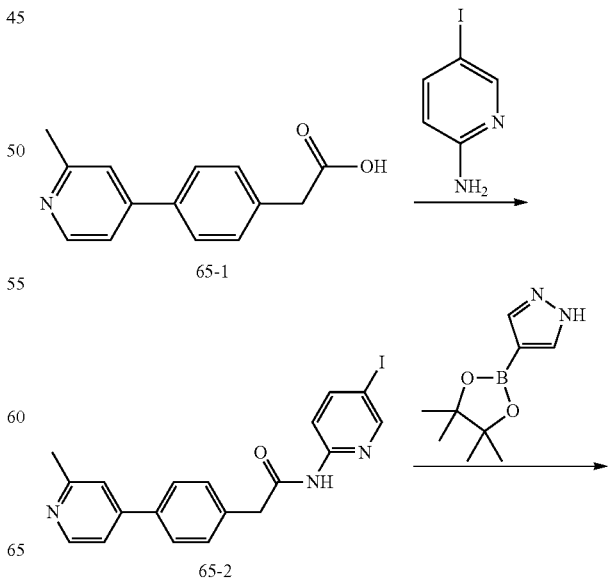

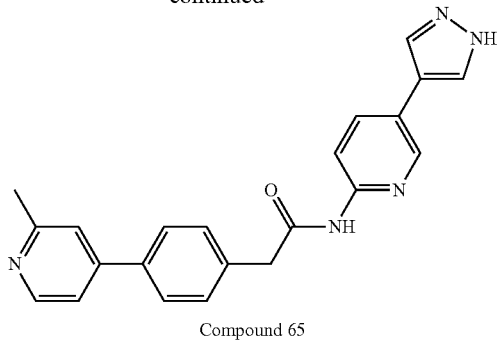

Compound 65

Step 1: To a solution of 2-(4-(2-methylpyridin-4-yl)phenyl)acetic acid 65-1 (300 mg, 1.3 mmol), 5-iodopyridin-2-amine (344 mg, 1.6 mmol) and HATU (590 mg, 1.6 mmol) in DMF (8 mL) was added DIEA (503 mg, 3.9 mmol) at room temperature. After stirred at room temperature for 2 hours, the reaction mixture was diluted into ethyl acetate and washed with saturated NaHCO$_3$ solution and then brine. The organic phase was dried over MgSO$_4$. The solvent was removed and the crude product was purified by silica gel flash chromatography to afford N-(5-iodopyridin-2-yl)-2-(4-(2-methylpyridin-4-yl)phenyl)acetamide 65-2 as off-white solid. MS m/z 430.1 (M+1).

Step 2: N-(5-Iodopyridin-2-yl)-2-(4-(2-methylpyridin-4-yl)phenyl)acetamide 65-2 (20 mg, 0.046 mmol), 4-(4,4,5,5-tetramethyl-1,3,2-dioxaborolan-2-yl)-1H-pyrazole (13.5 mg, 0.07 mmol) and Pd(PPh$_3$)$_4$ (5 mg, 0.004 mmol) was mixed in toluene (3 mL)/ethanol (1 mL)/Na$_2$CO$_3$(2M, 1 mL). The reaction mixture was stirred at 90° C. for 10 hours. The solvent was removed by rotary evaporation and the residue was dissolved in DMSO. The inorganic salt was removed by filtration. The crude product in DMSO was purified by reverse phase HPLC to give N-(5-(1H-pyrazol-4-yl)pyridin-2-yl)-2-(4-(2-methylpyridin-4-yl)phenyl)acetamide 65 as off-white solid. MS m/z 370.2 (M+1).

EXAMPLE 8

2-(4-(2-methylpyridin-4-yl)phenyl)-N-(6-morpholinopyridin-3-yl)acetamide (73)

A mixture of 2-(4-(2-methylpyridin-4-yl)phenyl)acetic acid 73-1 (40 mg, 0.18 mmol), 6-morpholinopyridin-3-amine (40 mg, 0.22 mmol) and HATU (80 mg, 0.21 mmol) in 2 mL DMF was added DIEA (104 μL, 0.6 mmol) at room temperature. The mixture was stirred at room temperature for 2 hours. The solvent was removed by rotary evaporation. The crude product was purified by reverse phase HPLC to give the title compound 73 as white solid. MS m/z 389.19 (M+1); $^1$H NMR 400 MHz (DMSO-d$_6$) δ11.30(s, 1H), 8.82(d, 1H, J=6.4 Hz), 8.57(d, 1H, J=2.4 Hz), 8.35(m, 1H), 8.24(dd, 1H, J$_1$=6.4 Hz, J$_2$=1.6 Hz), 8.19(dd, 1H, J$_1$=10.0 Hz, J$_2$=2.8 Hz), 8.02(m, 2H), 7.63(m, 2H), 7.42(d, 2H, J=9.6 Hz), 3.87(s, 2H), 3.75(m, 4H), 3.66(m, 4H), 2.80(s, 3H).

EXAMPLE 9

N-(5-(3-fluorophenyl)pyridin-2-yl)-2-(5-methyl-6-(pyridazin-4-yl)pyridin-3-yl)acetamide (74)

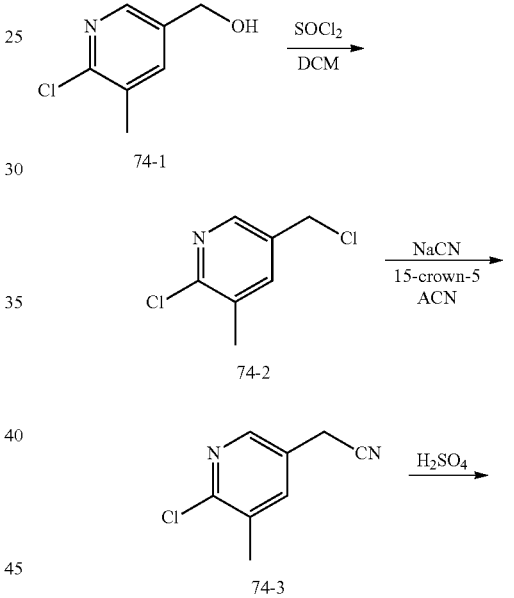

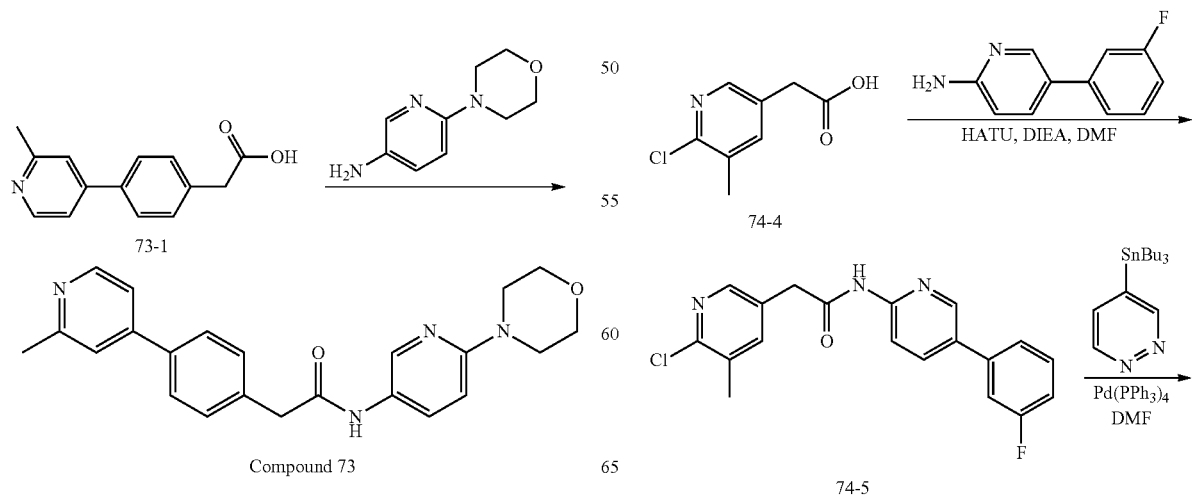

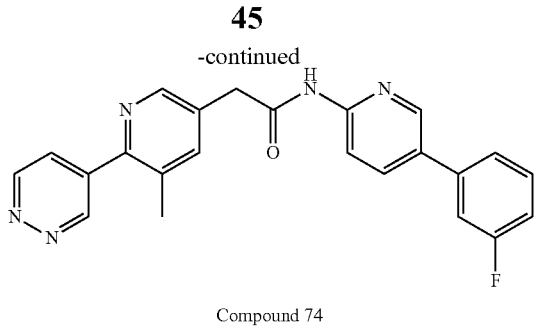

Compound 74

Step 1: To a solution of (6-chloro-5-methylpyridin-3-yl)methanol 74-1 (1.57 g, 10 mmol) in dichloromethane (15 mL) was added dropwise thionyl chloride (3.6 mL, 50 mmol) at 0° C. slowly. The mixture was stirred for 2 hours at room temperature, diluted with dichloromethane (100 mL) and water (100 mL), neutralized with powder sodium carbonate to pH 8. The aqueous layer was further extracted with dichloromethane (50 mL). The combined organic layers were washed with brine, dried over $Na_2SO_4$, and concentrated to dryness by rotary evaporation to afford 2-chloro-5-(chloromethyl)-3-methylpyridine 74-2 as pale yellow solid, which was used for next step directly. MS m/z 176.1 (M+1)

Step 2: A mixture of 2-chloro-5-(chloromethyl)-3-methylpyridine 74-2 (1.64 g, 9.4 mmol), sodium cyanide (1.85 g, 37 mmol) and 15-crown-5 (0.1 mL, 0.47 mmol) in acetonitrile (30 mL) was stirred at 40° C. for 4 hours. After the mixture was cooled down to room temperature, the solvent was evaporated and the residue was redissolved in ethyl acetate (100 mL), washed with water and brine, dried over $Na_2SO_4$, and concentrated to dryness to 2-(6-chloro-5-methylpyridin-3-yl)acetonitrile 74-3 as pale red solid, which was used for next step without further purification. MS m/z 167.1 (M+1)

Step 3: To a flask containing 2-(6-chloro-5-methylpyridin-3-yl)acetonitrile 74-3 (1.12 g, 6.75 mmol) were added water (9.0 mL) and dropwise concentrated sulfuric acid (9.0 mL). The reaction mixture was stirred at 100° C. for 4 hours. After cooled down to room temperature, the reaction mixture was poured into water (100 mL). The resulting solution was neutralized with powder sodium carbonate to pH around 3, and extracted with ethyl acetate (50 mL×3). The combined organic layers were washed with brine, dried over $Na_2SO_4$ and then taken to dryness by rotary evaporation give 2-(6-Chloro-5-methylpyridin-3-yl)acetic acid 74-4 as pale yellow solid, which was used directly for next step. MS m/z 186.1 (M+1)

Step 4: To a mixture of 2-(6-chloro-5-methylpyridin-3-yl)acetic acid 74-4 (222 mg, 1.2 mmol), 5-phenylpyridin-2-amine (336 mg, 1.8 mmol) and HATU (684 mg, 1.8 mmol) in DMF (5 mL) was added DIEA (600 μL, 3.6 mmol) at room temperature. The mixture was stirred at room temperature for 2 hours. The mixture was diluted with ethyl acetate (100 mL), washed with saturated $NaHCO_3$ aqueous solution, water and brine, dried over $Na_2SO_4$, and concentrated by rotary evaporation. The crude product was purified by silica gel flash chromatography, eluted with 40% ethyl acetate in dichloromethane to give 2-(6-chloro-5-methylpyridin-3-yl)-N-(5-(3-fluorophenyl)pyridin-2-yl)acetamide 74-5 as dark yellow solid. MS m/z 356.1 (M+1).

Step 5: To a reaction tube containing 2-(6-chloro-5-methylpyridin-3-yl)-N-(5-(3-fluorophenyl)pyridin-2-yl)acetamide 74-5 (54 mg, 0.15 mmol), 4-(tributylstannyl)pyridazine (55 mg, 0.15 mmol) and $Pd(PPh_3)_4$ (16 mg, 0.015 mmol) under Argon was added DMF (0.8 mL). The mixture was stirred at 120° C. for 10 hours. The crude product was purified by reverse phase HPLC to give N-(5-(3-fluorophenyl)pyridin-2-yl)-2-(5-methyl-6-(pyridazin-4-yl)pyridin-3-yl)acetamide 74 as white solid. MS m/z 400.1 (M+1); $^1$H NMR 400 MHz (CDCl$_3$) δ 9.42 (dd, 1H, J$_1$=4.8 Hz, J$_2$=1.2 Hz), 9.29 (dd, 1H, J$_1$=10.4 Hz, J$_2$=1.2 Hz), 8.56 (d, 1H, J=1.6 Hz), 8.46 (d, 1H, J=1.6 Hz), 8.28 (d, 1H, J=8.8 Hz), 7.90 (dd, 1H, J$_1$=17.6 Hz, J$_2$=2.4 Hz), 7.72 (d, 1H, J=1.6 Hz), 7.70 (dd, 1H, J$_1$=10.8 Hz, J$_2$=2.0 Hz), 7.44-7.39 (m, 1H), 7.32-7.30 (m, 1H), 7.25-7.21 (m, 1H), 7.09-7.04 (m, 1H), 3.82 (s, 2H), 2.44 (s, 3H).

EXAMPLE 10

2-(2',3-dimethyl-2,4'-bipyridin-5-yl)-N-(5-(pyrazin-2-yl)pyridin-2-yl)acetamide (86)

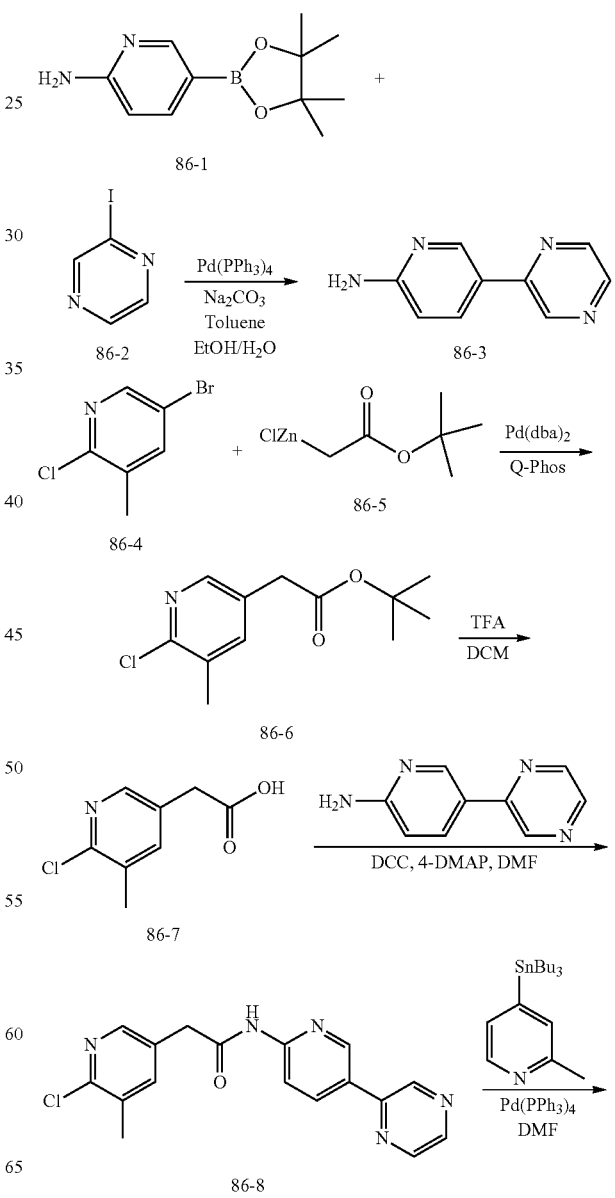

-continued

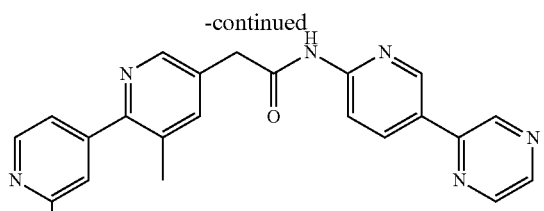

Compound 86

Step 1: To a sealed tube was added 5-(4,4,5,5-tetramethyl-1,3,2-dioxaborolan-2-yl)pyridin-2-amine 86-1 (2.2 g, 10 mmol), 2-iodopyrazine 86-2 (2.06 g, 10 mmol), Pd(PPh$_3$)$_4$ (577 mg, 0.5 mmol), toluene (70 mL), ethanol (15 mL) and 2M Na$_2$CO$_3$ (15 mL). The reaction mixture was bubbled with nitrogen for 2 minutes and stirred at 90° C. for 10 hours. After cooling to room temperature, the solvents were evaporated and the residue was redissolved in dichloromethane (200 ml) and treated with 1M HCl aqueous solution (50 mL). The two layers were separated and the aqueous layer was treated with 10% NaOH aqueous solution to adjust the pH to around 13. The resulting suspension was extracted with ethyl acetate (100 mL×3). The combined organic phases were washed with H$_2$O (50 mL) and brine (50 mL), dried over Na$_2$SO$_4$, and concentrated to give 5-(pyrazin-2-yl)pyridin-2-amine 86-3 as white solid. MS m/z 173.1 (M+1); $^1$H NMR 400 MHz (DMSO-d$_6$) δ 9.12(d, 1H, J=1.6 Hz), 8.73(m, 1H), 8.60(m, 1H), 8.46(d, 1H, J=2.8 Hz), 8.12(dd, 1H, J$_1$=8.8 Hz, J$_2$=2.4 Hz), 6.55(d, 1H, J=8.8 Hz), 6.46(s, 2H).

Step 2: To a sealed tube was added 5-bromo-2-chloro-3-methylpyridine 86-4 (4.69 g, 22.72 mmol), 0.5 M (2-tert-butoxy-2-oxoethyl) zinc(II) chloride in ether 86-5 (50 mL, 25 mmol), Pd(dba)$_2$ (262 mg, 0.45 mmol), Q-phos (320 mg, 0.45 mmol), and THF (75 mL). The reaction mixture was bubbled with nitrogen for 1 minute and stirred at 70° C. for 4 hours. After cooling to room temperature, all the solvents were evaporated and the residue was redissolved in ethyl acetate, washed with water and brine, dried over Na$_2$SO$_4$ and concentrated to dryness by rotary evaporation. The crude product was purified by silica gel flash chromatography and eluted with 20% ethyl acetate in hexane to give tert-butyl 2-(6-chloro-5-methylpyridin-3-yl)acetate 86-6 as red oil. MS m/z 242.1 (M+1)

Step 3: A mixture of tert-butyl 2-(6-chloro-5-methylpyridin-3-yl) acetate 86-6 (7.8 g, 32 mmol) and TFA (32 mL) in DCM (32 mL) was stirred at room temperature for 3 hours. The solution was adjusted to pH around 12 by sodium carbonate and extracted with dichloromethane. The aqueous phase was acidified to pH 3 by 1N HCl aqueous solution and stirred for 15 minutes. The suspension was extracted with dichloromethane (100 mL X3). The combined organic phases were washed with water and brine, dried over Na$_2$SO$_4$ and then dried to give 2-(6-chloro-5-methylpyridin-3-yl)acetic acid 86-7 as pale yellow solid. MS m/z 186.1 (M+1); $^1$H NMR 400 MHz (CD$_3$Cl) δ 8.17(d, 1H, J=2.0 Hz), 7.55(d, 1H, J=2.0 Hz), 3.63(s, 2H), 2.38(s, 3H).

Step 4: A mixture of 2-(6-chloro-5-methylpyridin-3-yl) acetic acid 86-7 (3.0 g, 16.2 mmol), 5-(pyrazin-2-yl)pyridin-2-amine 86-3 (2.80 g, 16.2 mmol), 1,3-dicyclohexylcarbodiimide (4 g, 19.44 mmol) and 4-(dimethylamino)pyridine (324 mg, 3.24 mmol) in DMF (45 mL) was stirred at room temperature for 10 hours. The reaction mixture was filtered to remove the solid and the filtrate was diluted with ethyl acetate, washed with water and brine, dried over Na$_2$SO$_4$ and concentrated to dryness by rotary evaporation. The crude product was purified by silica gel flash chromatography, eluted with 5% methanol in dichloromethane to give 2-(6-chloro-5-methylpyridin-3-yl)-N-(5-(pyrazin-2-yl)pyridin-2-yl)acetamide 86-8 as pale yellow solid. MS m/z 340.2 (M+1); $^1$H NMR 400 MHz (DMSO-d$_6$) δ 11.09(s 1H), 9.31(d, 1H, J=1.6 Hz), 9.11(d, 1H, J=1.6 Hz), 8.72(m, 1H), 8.63(m, 1H), 8.51(dd, 1H, J$_1$=8.6 Hz, J$_2$=2.4 Hz), 8.21(m, 2H), 7.76(d, 1H, J=1.6 Hz), 3.82(s, 2H), 2.33(s, 3H).

Step 5: To a reaction flask containing 2-(6-chloro-5-methylpyridin-3-yl)-N-(5-(3-fluorophenyl)pyridin-2-yl)acetamide 86-8 (3.34 g, 9.4 mmol), 2-methyl-4-(tributylstannyl)pyridine (3.47 g, 9.4 mmol) and Pd(PPh$_3$)$_4$ (1 g, 0.94 mmol) under argon was added DMF (45 mL). The mixture was stirred at 120° C. for 10 hours. 1N KF aqueous solution was added to the mixture and stirred for 15 minutes after it was cooled down to room temperature. The formed solid was collected by filtration and further purified by silica gel flash chromatography, eluted with 10% methanol in dichloromethane to give 2-(2',3-dimethyl-2,4'-bipyridin-5-yl)-N-(5-(pyrazin-2-yl)pyridin-2-yl)acetamide (Compound 86) as white solid. MS m/z 397.2 (M+1); $^1$H NMR 400 MHz (DMSO-d$_6$) δ 11.13(s 1H), 9.31(d, 1H, J=1.6 Hz), 9.11(d, 1H, J=1.6 Hz), 8.72(m, 1H), 8.62 (d, 1H, J=2.8 Hz), 8.53(m, 3H), 8.24(d, 1H, J=8.8 Hz), 7.73(d, 1H, J=1.6 Hz), 7.42(s, 1H), 7.35(dd, 1H, J$_1$=4.8 Hz, J$_2$=0.8 Hz), 3.87(s, 2H), 2.53(s, 3H), 2.34(s, 3H).

EXAMPLE 11

N-(5-(4-acetylpiperazin-1-yl)pyridin-2-yl)-2-(3-cyano-4-(2-methylpyridin-4-yl)-phenyl)acetamide (111)

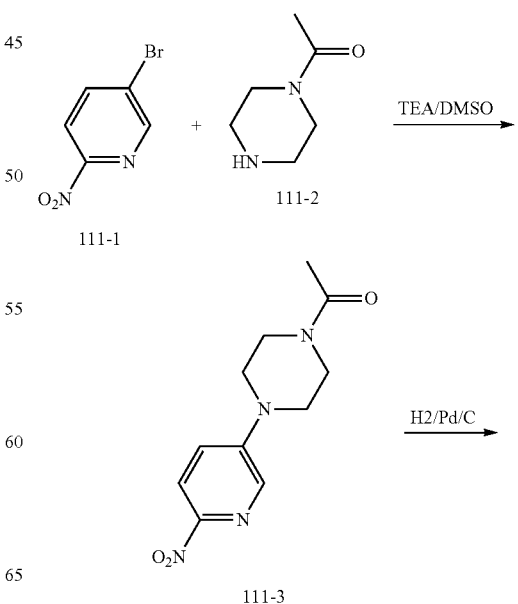

-continued

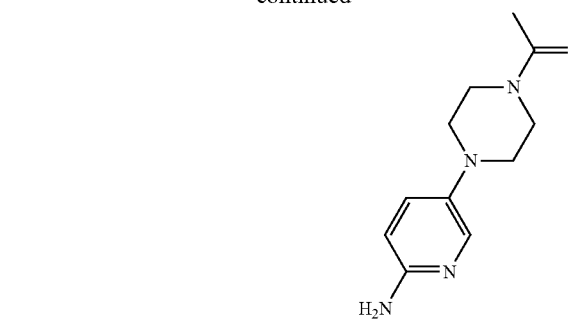

111-4

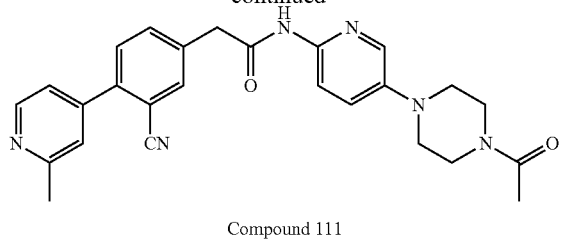

Compound 111

Step 1: To a sealed tube was added 5-bromo-2-nitropyridine 111-1 (2.3 g, 11.4 mmol), 1-(piperazin-1-yl)ethanone 111-2 (1.6 g, 12.8 mmol), triethylamine (4.8 mL, 34.2 mmol) and DMSO (5 mL). The reaction was heated to 120° C. and stirred for 16 hours. The reaction was cooled to room temperature. Triethylamine was removed by rotary evaporation. The residue was triturated in 15 mL ethyl acetate. The solid was collected by filtration and washed with small amount of ethyl acetate to give 1-(4-(6-nitropyridin-3-yl)piperazin-1-yl)ethanone 111-3 as a light yellow solid. MS m/z 251.1 (M+1).

Step 2: To a round-bottom flask was added 1-(4-(6-nitropyridin-3-yl)piperazin-1-yl)ethanone 111-3 (2.6 g, 10.4 mmol), Pd/C (0.5 g) and methanol (50 mL). The reaction was stirred for 4 hours under hydrogen atmosphere by attaching a hydrogen balloon. The reaction was flashed with nitrogen and the solid was removed by filtration. The solvent was removed by rotary evaporation. The crude product was purified by silica-gel flash chromatography to give 1-(4-(6-aminopyridin-3-yl)piperazin-1-yl)ethanone 111-4 as an off-white solid. MS m/z 221.1 (M+1). $^1$H NMR 400 MHz (DMSO-$d_6$) $\delta$7.62 (d, 1H, J=2.8 Hz), 7.20 (dd, 1H, J1=8.8 Hz, J2=2.8 Hz), 6.41 (d, 1H, J=8.8 Hz), 5.47 (s, 2H), 3.55 (m, 4H), 2.93 (t, 2H, J=5.2 Hz), 2.86 (t, 2H, J=5.2 Hz), 2.03 (s, 3H).

Step 3: In a sealed tube, a mixture of 2-chloro-5-iodobenonitrile 111-5 (1.30 g, 5 mmol), 0.5 M (2-tert-butoxy-2-oxoethyl) zinc(II) chloride 111-6 in ether (11 mL, 5.5 mmol), Pd(dba)$_2$ (144 mg, 0.25 mmol), Q-phos (178 mg, 0.25 mmol), and THF (20 mL) under argon was stirred at 70° C. for 18 hours. After cooling to room temperature, the solvents were evaporated and the residue was redissolved in ethyl acetate, washed with water and brine, dried over Na$_2$SO$_4$ and concentrated to dryness by rotary evaporation. The crude product was purified by silica gel flash chromatography, eluted with 30% ethyl acetate in hexane to give tert-butyl 2-(4-chloro-3-cyanophenyl)acetate 111-7 as a brown oil. MS m/z 252.1 (M+1).

Step 4: A mixture of tert-butyl 2-(4-chloro-3-cyanophenyl) acetate 111-7 (572 mg, 2.28 mmol), 2-methyl-4-(tributylstannyl)pyridine 111-8 (870 mg, 2.28 mmol) and Pd(PPh$_3$)$_4$ (220 mg, 0.2 mmol) and DMF (9 mL) was stirred at 120° C. for 10 hours under argon. After cooling to room temperature, the mixture was diluted with ethyl acetate, washed with saturated aqueous Na$_2$S$_2$O$_3$ solution, water and brine, dried over Na$_2$SO$_4$, and concentrated to dryness by rotary evaporation. The crude was purified by silica gel flash chromatography, eluted with 5% methanol in dichloromethane to give tert-butyl 2-(3-cyano-4-(2-methylpyridin-4-yl)phenyl)acetate 111-9 as a yellow oil. MS m/z 309.2 (M+1).

Step 5: A mixture of tert-butyl 2-(3-cyano-4-(2-methylpyridin-4-yl)phenyl)acetate 111-9 (656 mg, 2.13 mmol) and TFA (2 mL) in DCM (2 mL) was stirred at room temperature for 3 hours. The solution was adjusted to pH around 12 by Na$_2$CO$_3$ and extracted with dichloromethane. The aqueous phase was acidified to pH 3 by 1N HCl aqueous solution and

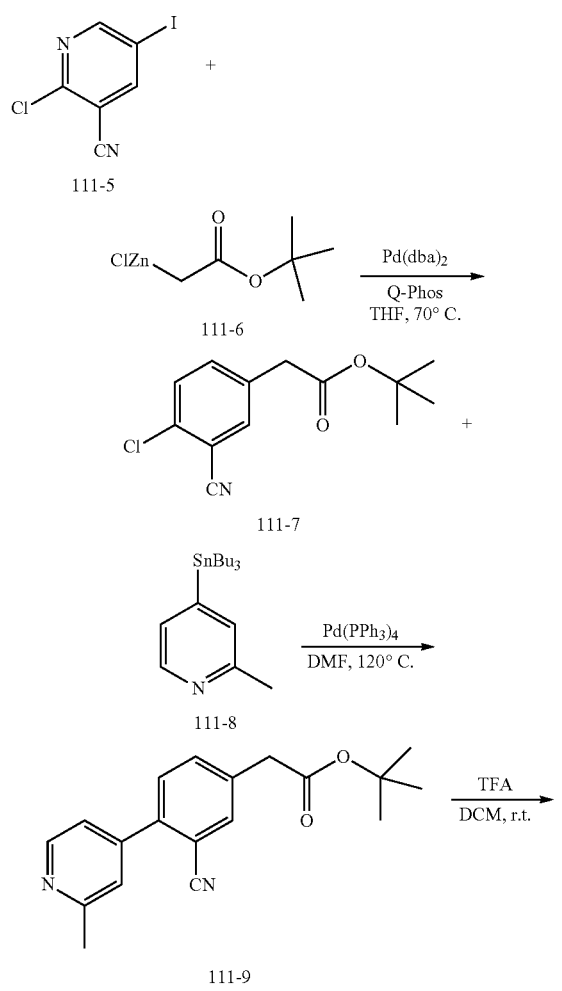

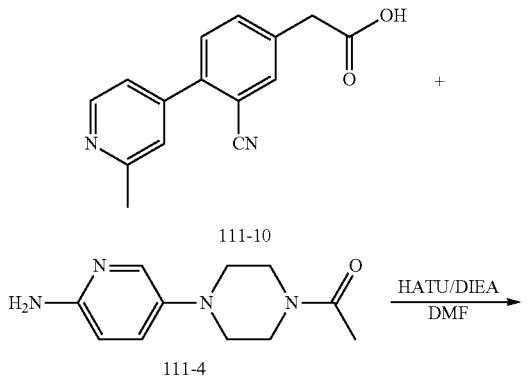

stirred for 15 minutes. The solvents were evaporated and the remaining solid was extracted with 20% methanol in ethyl acetate and filtered to remove the insoluble. The filtrate was concentrated to dryness by rotary evaporation to give a sticky solid containing 2-(3-cyano-4-(2-methylpyridin-4-yl)phenyl)acetic acid 111-10, which is used directly for next step. MS m/z 253.1 (M+1).

Step 6: To a mixture of acid 111-10 (150 mg crude from above containing about 25 mg, 0.1 mmol), 1-(4-(6-aminopyridin-3-yl)piperazin-1-yl)ethanone (22 mg, 0.1 mmol) 111-4, o-(7-azabenzotriazol-1-yl)-N,N,N',N'-tetramethyluronium hexafluorophosphate (HATU, 40 mg, 0.105 mmol) were added DMF (1 mL) and diispropylethyl amine (DIEA, 38.7 mg, 0.3 mmol) and the mixture was stirred at room temperature overnight. Then it was redistributed between water (30 mL) and ethyl acetate (30 mL). The organic phase was dried over $Na_2SO_4$ and concentrated to dryness by rotary evaporation. The oily reside was subjected to both reverse phase preparative HPLC and silica gel chromatography to give N-(5-(4-acetylpiperazin-1-yl)pyridin-2-yl)-2-(3-cyano-4-(2-methylpyridin-4-yl)phenyl)acetamide (Compound 111) as a white solid. MS m/z 455.3 (M+1).

EXAMPLE 12

N-(5-(pyrazin-2-yl)pyridin-2-yl)-2-(4-(pyridazin-4-yl)-3-(trifluoromethyl)phenyl)acetamide (118)

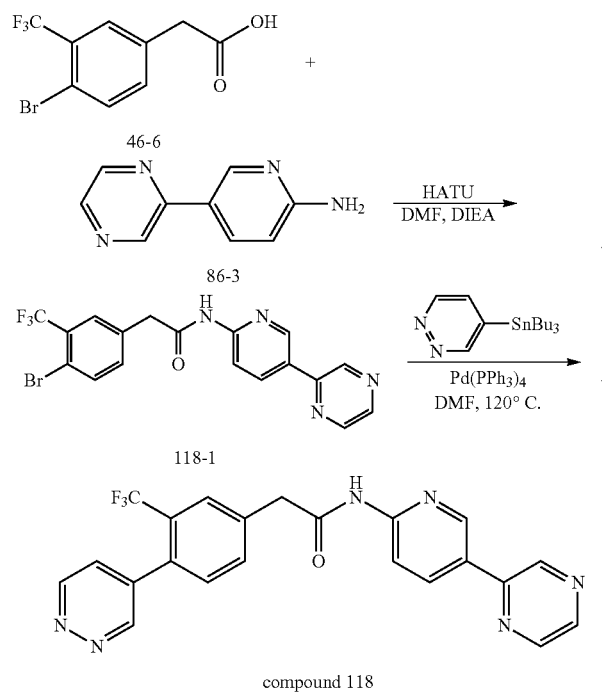

Step 1: To a mixture of 2-(4-bromo-3-(trifluoromethyl)phenyl)acetic acid 46-6 (128 mg, 0.5 mmol), 5-(pyrazin-2-yl)pyridin-2-amine 86-3 (95 mg, 0.55 mmol) and o-(7-azabenzotriazol-1-yl)-N,N,N',N'-tetramethyluronium hexafluorophosphate (HATU, 214 mg, 0.55 mmol) in DMF (2 mL) was added diispropylethyl amine (DIEA, 250 μL, 1.5 mmol). The mixture was stirred at room temperature for 2 hours. The mixture was diluted with ethyl acetate (50 mL), washed with saturated $NaHCO_3$ aqueous solution, water and brine, dried over $Na_2SO_4$, and concentrated by rotary evaporation. The crude product was purified by silica gel flash chromatography, eluted with 5% methanol in dichloromethane to give 2-(4-bromo-3-(trifluoromethyl)phenyl)-N-(5-(pyrazin-2-yl)pyridin-2-yl)acetamide 118-1 as pale orange solid. MS m/z 438.2 (M+1)

Step 2: To a reaction tube containing 2-(4-bromo-3-(trifluoromethyl)phenyl)-N-(5-(pyrazin-2-yl)pyridin-2-yl)acetamide 118-1 (53 mg, 0.12 mmol), 4-(tributylstannyl)pyridazine (54 mg, 0.14 mmol) and $Pd(PPh_3)_4$ (14 mg, 0.012 mmol) under argon was added DMF (0.6 mL). The mixture was stirred at 120° C. for 10 hours. The crude product, which was a solution, was subjected directly for reverse phase HPLC to give N-(5-(pyrazin-2-yl)pyridin-2-yl)-2-(4-(pyridazin-4-yl)-3-(trifluoromethyl)phenyl)acetamide 118 as white solid. MS m/z 437.1 (M+1); $^1$H NMR 400 MHz (DMSO-$d_6$) δ 11.14 (s, 1H), 9.35 (dd, 2H), 9.31 (d, 1H), 9.27 (s, 1H), 9.12 (d, 1H), 8.72 (dd, 1H), 8.62 (d, 1H), 8.52 (dd, 1H), 8.23 (d, 1H), 7.95 (s, 1H), 7.82-7.75 (m, 2H), 7.52 (d, 1H), 4.00 (s, 2H).

EXAMPLE 13

N-(2,3'-bipyridin-6'-yl)-2-(2',3-dimethyl-2,4'-bipyridin-5-yl)acetamide (124)

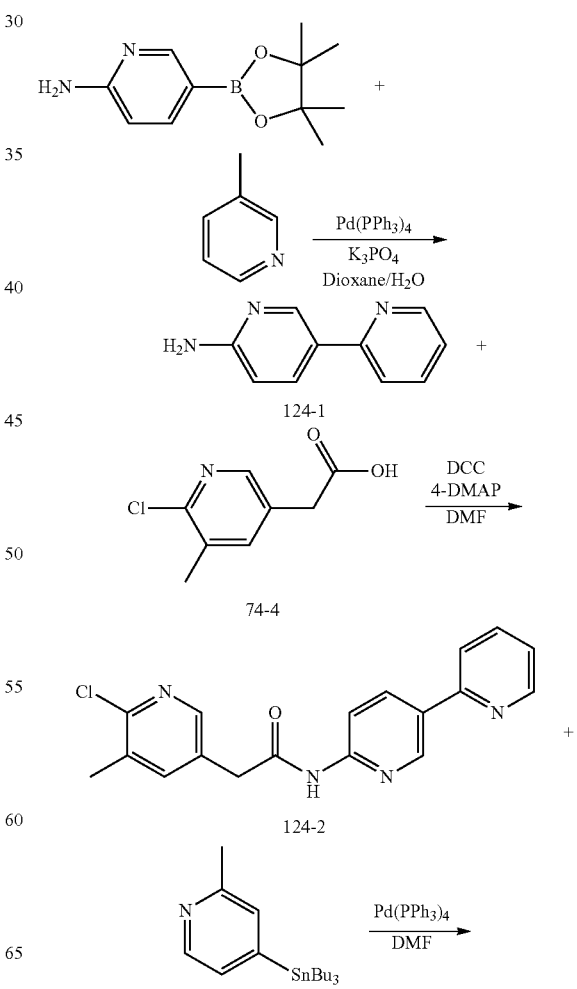

53

-continued

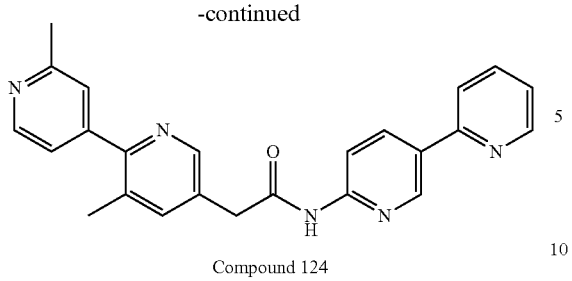

Compound 124

Step 1. To a reaction tube were added 5-(4,4,5,5-tetramethyl-1,3,2-dioxaborolan-2-yl)pyridin-2-amine (220 mg, 1.00 mmol), 2-iodopyridine (205 mg, 1.00 mmol), Pd(PPh$_3$)$_4$ (57.7 mg, 0.05 mmol) and K$_3$PO$_4$ (424 mg, 2.00 mmol). The tube was subjected to vacuum and back filled with argon. Dioxane (3.0 ml) and water (0.3 ml) were added and the mixture was heated at 96° C. overnight. After cooled to room temperature, the reaction mixture was filtered through celite (washed with ethyl acetate) and concentrated by evaporation. The residue was redistributed between ethyl acetate (40 ml) and 0.1 N HCl solution (40 mL). The acidic aqueous phase was further extracted with ethyl acetate (40 ml×2) and treated with Na$_2$CO$_3$ to have pH around 9 and concentrated by evaporation of water. The solid residue was extracted with refluxing ethyl acetate (40 ml) to give 2,3'-bipyridin-6'-amine (124-1) which is used for reaction without further purification.

Step 2. A mixture of 2-(6-chloro-5-methylpyridin-3-yl)acetic acid 74-4 (57 mg, 0.31 mmol), 2,3'-bipyridin-6'-amine 124-1 (51 mg, 0.30 mmol), 1,3-dicyclohexylcarbodiimide (75 mg, 0.36 mmol) and 4-(dimethylamino)pyridine (6 mg, 0.06 mmol) in DMF (1.2 mL) was stirred at room temperature for 10 hours. The reaction mixture was filtered through celite, washed and diluted with ethyl acetate (30 ml) and extracted with water 930 ml×2). The organic phase was dried over Na$_2$SO$_4$ and concentrated by evaporation. The residue was subjected to silica gel column chromatography with ethyl acetate as eluent to give N-(2,3'-bipyridin-6'-yl)-2-(6-chloro-5-methylpyridin-3-yl)acetamide 124-2 as white solid.

Step 3. To a reaction tube were added 5 N-(2,3'-bipyridin-6'-yl)-2-(6-chloro-5-methylpyridin-3-yl)acetamide 124-2 (52 mg, 0.15 mmol), 2-methyl-4-(tributylstannyl)pyridine (115 mg, 0.3 mmol), and Pd(PPh$_3$)$_4$ (35 mg, 0.03 mmol). The tube was subjected to vacuum and back filled with argon. DMF (1.0 ml) was added and the mixture was heated in 118° C. oil bath overnight. After cooled to room temperature, the mixture was filtered through celite, washed and diluted with ethyl acetate (30 ml) and extracted with 0.1 N HCl solution (30 ml). The acidic aqueous phase was treated with Na$_2$CO$_3$ to have pH around 9 and extracted with ethyl acetate (3×20 ml). The combined organic phase was dried over Na$_2$SO$_4$ and concentrated by evaporation. The residue was subjected to silica gel column chromatography with 5% MeOH in DCM as eluent to give N-(2,3'-bipyridin-6'-yl)-2-(2',3-dimethyl-2,4'-bipyridin-5-yl)acetamide 124 as white solid. MS m/z 396.3 (M+1); $^1$H NMR 400 MHz (CDCl$_3$) δ 8.93-8.89 (m, 1H), 8.72~8.67 (m, 1 H), 8.59 (d, 1 H), 8.51 (d, 1 H), 8.37~8.29 (m, 2 H), 8.23 (bs, 1 H), 7.76(m, 1H), 7.71 (m, 1 H), 7.65 (d, 1 H), 7.33 (bs, 1 H), 7.30~7.24 (m, 1 H), 3.81 (s, 2H), 2.63 (s, 3H), 2.38 (s, 3 H).

54

EXAMPLE 14 tert-butyl 4-(6-(2-(4-(2-methylpyridin-4-yl)phenyl)acetamido)pyridin-3-yl)piperazine-1-carboxylate (125)

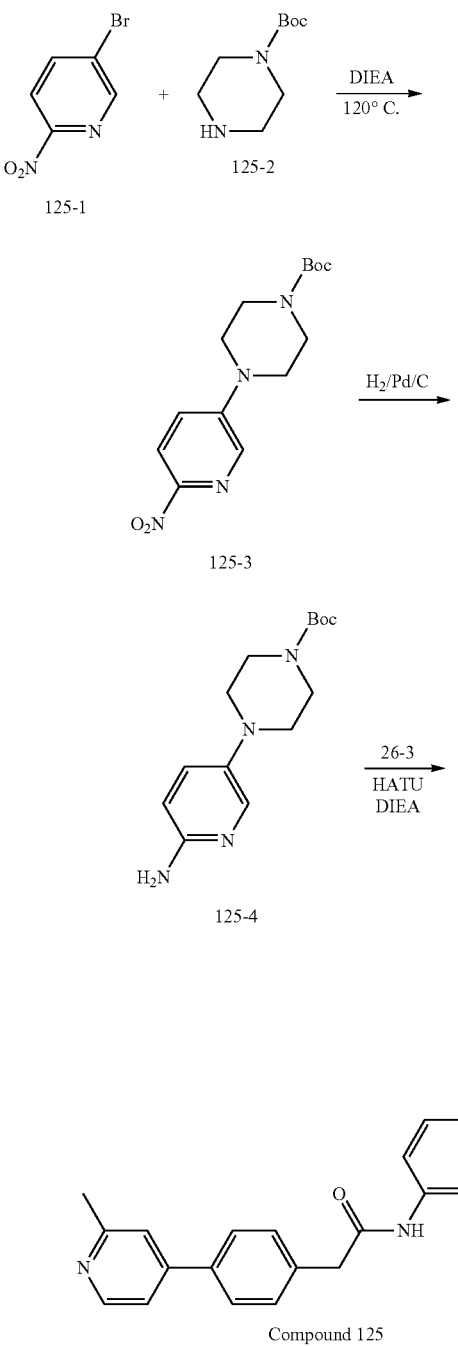

Compound 125

Step 1: To a sealed tube were added 5-bromo-2-nitropyridine 125-1 (5.1 g, 25.2 mmol), tert-butyl piperazine-1-carboxylate 125-2 (4.7 g, 25.2 mmol), DIEA (12 mL, 75 mmol) and DMSO (20 mL). The reaction was heated to 120° C. and stirred for 16 hours. The reaction was cooled down to room temperature. Triethylamine was removed by rotary evaporation. The residue was triturated in 15 mL ethyl acetate. The solid was collected by filtration and washed with small amount of ethyl acetate to give tert-butyl 4-(6-nitropyridin-3-yl)piperazine-1-carboxylate 125-3 as light yellow solid. MS m/z 309.2 (M+1).

Step 2: To a round-bottom flask was added tert-butyl 4-(6-nitropyridin-3-yl)piperazine-1-carboxylate 125-3 (3.4 g, 11 mmol), Pd/C (0.5 g) and methanol (100 mL). The reaction was stirred for 4 hours under hydrogen atmosphere by attaching a hydrogen balloon. The reaction was flushed with nitrogen and the solid was removed by filtration. The solvent was removed by rotary evaporation to give tert-butyl 4-(6-aminopyridin-3-yl)piperazine-1-carboxylate 125-4 as purple solid. MS m/z 279.2 (M+1).

Step 3: To a mixture of 2-(4-(2-methylpyridin-4-yl)phenyl) acetic acid 26-3 (1.1 g, 4.8 mmol), tert-butyl 4-(6-aminopyridin-3-yl)piperazine-1-carboxylate 125-4 (1.3 g, 4.6 mmol) and O-(7-azabenzotriazol-1-yl)-N,N,N',N'-tetramethyluroniumhexafluorophosphate (HATU) (2.0 g, 5.3 mmol) in DMF (15 mL) was added DIEA (2.4 mL, 13.8 mmol) at room temperature. The mixture was stirred at room temperature for 2 hours. The reaction mixture was diluted into ethyl acetate, washed with saturated NaHCO$_3$ then brine, dried over Na$_2$SO$_4$. The solvent was removed by rotary evaporation to give tert-butyl 4-(6-(2-(4-(2-methylpyridin-4-yl)phenyl)acetamido)pyridin-3-yl)piperazine-1-carboxylate 125. MS m/z 488.2 (M+1); $^1$H NMR 400 MHz (DMSO-d$_6$) δ 10.55 (s, 1H), 8.56 (d, 1H), 8.03 (s, 1H), 7.93 (d, 1H), 7.81 (d, 1H), 7.74 (s, 1H), 7.66 (d, 1H), 7.51 (d, 2H), 7.42 (m, 1H), 3.75 (s, 2H), 3.08 (b, 2H), 2.57 (s, 2H), 2.54 (s, 4H), 2.51 (s, 3H), 1.42 (s, 9H).

EXAMPLE 15

2-(5-methyl-6-(pyridazin-4-yl)pyridin-3-yl)-N-(5-(pyrazin-2-yl)pyridin-2-yl)acetamide (130)

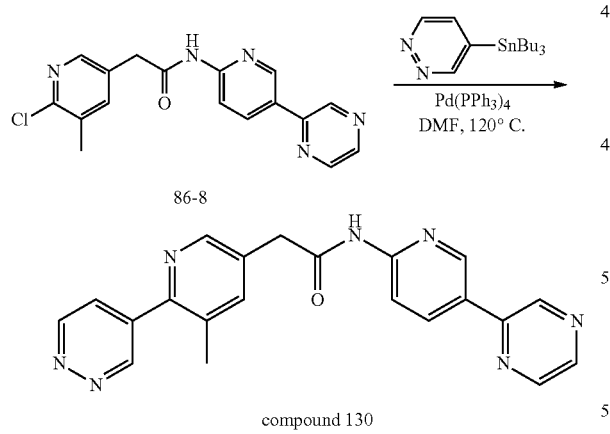

Step 1: To a reaction tube containing 2-(6-chloro-5-methylpyridin-3-yl)-N-(5-(pyrazin-2-yl)pyridin-2-yl)acetamide 86-8 (70 mg, 0.21 mmol), 4-(tributylstannyl) pyridazine (79 mg, 0.21 mmol) and Pd(PPh$_3$)$_4$ (22 mg, 0.021 mmol) under argon was added DMF (0.9 mL). The mixture was stirred at 120° C. for 10 hours. The crude DMF solution was purified by reverse phase HPLC to give 2-(5-methyl-6-(pyridazin-4-yl) pyridin-3-yl)-N-(5-(pyrazin-2-yl)pyridin-2-yl)acetamide 130 as white solid. MS m/z 384.2 (M+1); $^1$H NMR 400 MHz (DMSO-d$_6$) δ 11.15 (s, 1H), 9.47 (d, 1H), 9.34 (dd, 1H), 9.31 (d, 1H), 9.11 (dd, 1H), 8.72 (m, 1H), 8.62 (d, 1H), 8.56 (m, 1H), 8.52 (dd, 1H), 8.21 (d, 1H), 7.92 (dd, 1H), 7.79 (s, 1H), 3.90 (s, 2H), 2.42 (s, 3H).

EXAMPLE 16

N-(5-(4-acetylpiperazin-1-yl)pyridin-2-yl)-2-(4-(2-methylpyridin-4-yl)phenyl)acetamide (131)

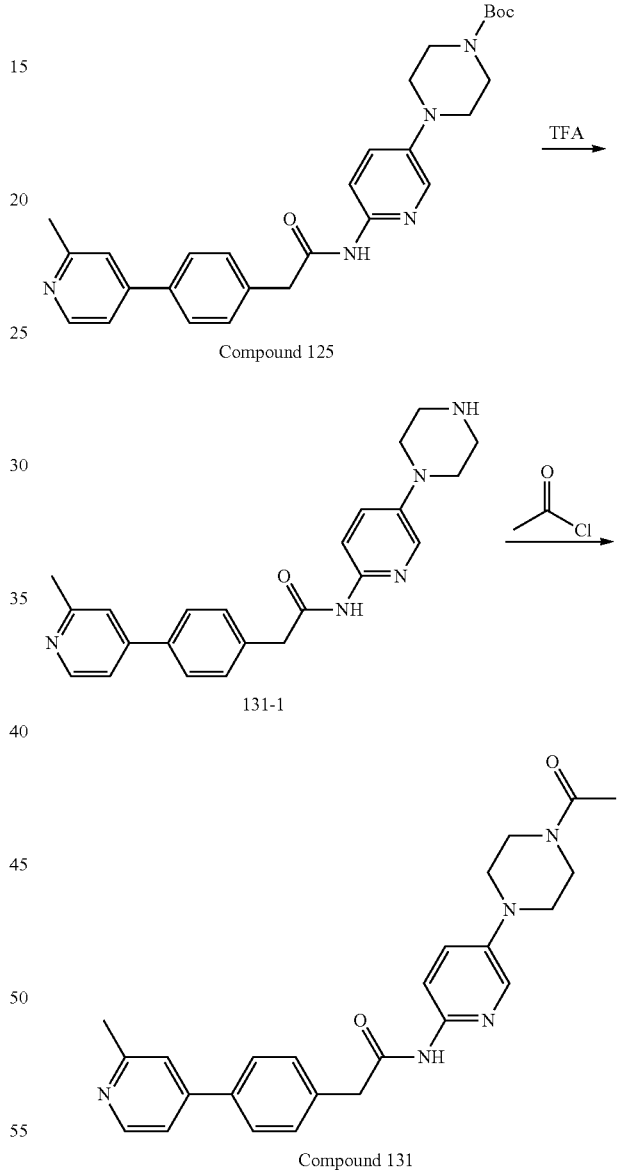

Step 1: To the solution of tert-butyl 4-(6-(2-(4-(2-methylpyridin-4-yl)phenyl)acetamido)pyridin-3-yl)piperazine-1-carboxylate (125) (1.5 g, 3 mmol) in DCM (10 mL) was added TFA (10 mL). The reaction was stirred for 2 hours. The excess TFA and solvent was removed by rotary evaporation to give 2-(4-(2-methylpyridin-4-yl)phenyl)-N-(5-(piperazin-1-yl)pyridin-2-yl)acetamide 131-1. The compound was used for next step without further purification. MS m/z 388.2 (M+1).

Step 2: To the solution of 2-(4-(2-methylpyridin-4-yl)phenyl)-N-(5-(piperazin-1-yl)pyridin-2-yl)acetamide 131-1 (20 mg, 0.05 mmol) in THF (1 mL) was added DIEA (19 mg, 0.15 mmol) and acetyl chloride (3.9 μL, 0.055 mmol). The reaction was stirred at room temperature for 40 min. The solvent was removed by rotary evaporation and the residue was purified by reverse phase HPLC to give N-(5-(4-acetylpiperazin-1-yl)pyridin-2-yl)-2-(4-(2-methylpyridin-4-yl)phenyl)acetamide 131 as off-white solid. MS m/z 430.2 (M+1); $^1$H NMR 400 MHz (DMSO-d$_6$) δ10.50 (s, 1H), 8.45 (d, 1H), 7.97 (d, 1H), 7.87 (d, 1H), 7.71 (d, 2H), 7.57 (s, 1H), 7.49 (d, 1H), 7.42 (d, 2H), 7.37 (dd, 1H), 3.68 (s, 2H), 3.52 (m, 4H), 3.09 (t, 2H), 3.02 (t, 2H), 2.48 (s, 3H), 1.97 (s, 3H).

EXAMPLE 17

Methyl 4-(6-(2-(4-(2-methylpyridin-4-yl)phenyl)acetamido)pyridin-3-yl)piperazine-1-carboxylate (132)

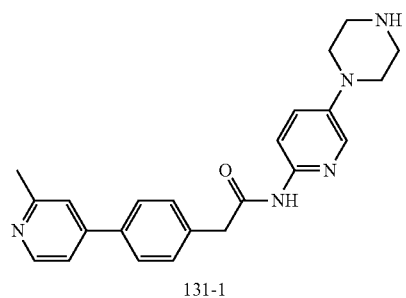
131-1

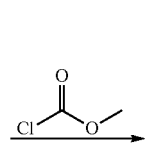

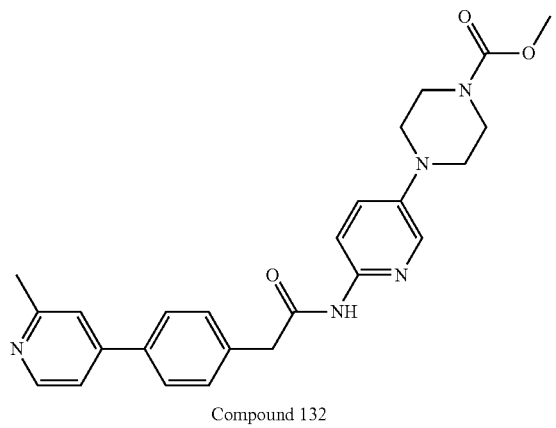
Compound 132

To the solution of 2-(4-(2-methylpyridin-4-yl)phenyl)-N-(5-(piperazin-1-yl)pyridin-2-yl)acetamide 131-1 (20 mg, 0.05 mmol) in THF (1 mL) was added DIEA (19 mg, 0.15 mmol) and methyl chloroformate (5.2 mg, 0.055 mmol). The reaction was stirred at room temperature for 40 min. The solvent was removed by rotary evaporation and the residue was purified by reverse phase HPLC to give N-(5-(4-acetylpiperazin-1-yl)pyridin-2-yl)-2-(4-(2-methylpyridin-4-yl)phenyl)acetamide 132 as off-white solid. MS m/z 446.2 (M+1); $^1$H NMR 400 MHz (DMSO-d$_6$) δ10.55 (s, 1H), 8.72 (d, 1H), 8.18 (s, 1H), 8.08 (m, 1H), 7.96 (d, 1H), 7.90 (d, 2H), 7.84 (d, 1H), 7.50 (d, 2H), 7.35 (dd, 1H), 3.72 (s, 2H), 3.54 (s, 3H), 3.43 (t, 4H), 3.03 (t, 3H), 2.65 (s, 3H).

EXAMPLE 18

2-(3-Methyl-4-(pyridazin-4-yl)phenyl)-N-(5-(pyridazin-4-yl)pyridin-2-yl)acetamide (134)

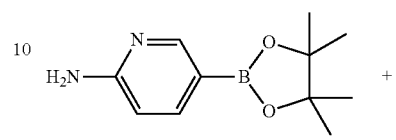

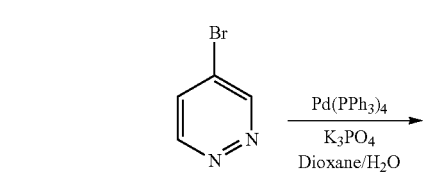

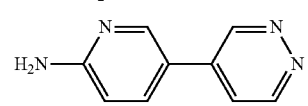
134-1

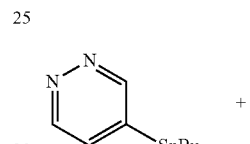

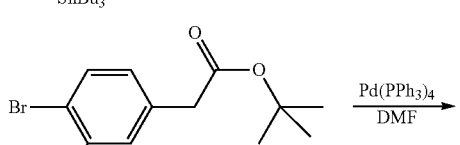

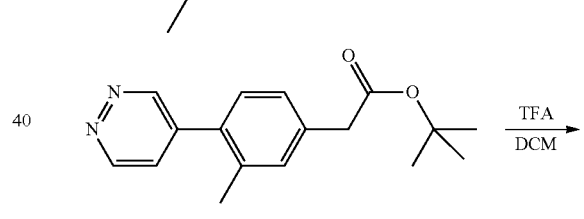
134-2

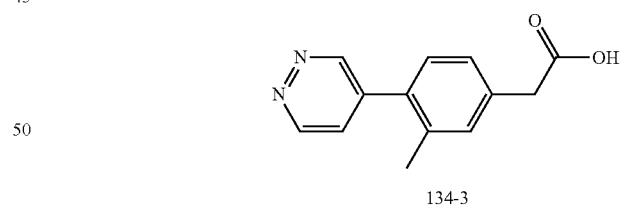
134-3

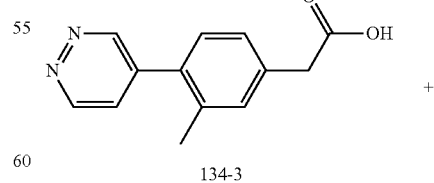
134-3

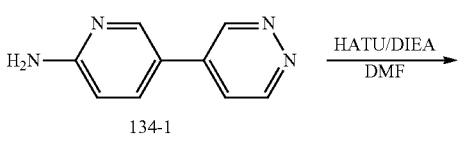
134-1

-continued

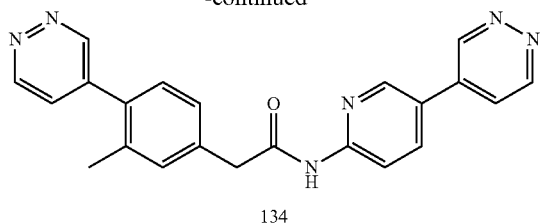

134

Step 1. To a reaction tube were added 5-(4,4,5,5-tetramethyl-1,3,2-dioxaborolan-2-yl)pyridin-2-amine (220 mg, 1.00 mmol), 4-bromopyridazine (159 mg, 1.00 mmol), Pd(PPh$_3$)$_4$ (57.7 mg, 0.05 mmol) and K$_3$PO$_4$ (424 mg, 2.00 mmol). The tube was subjected to vacuum and back filled with argon. Dioxane (3.0 ml) and water (0.3 ml) were added and the mixture was heated at 96° C. overnight. After cooled to room temperature, the reaction mixture was filtered through celite (washed with ethyl acetate) and concentrated by evaporation. Subsequent silica gel column chromatography with 5% methanol in DCM as eluent gave 5-(pyridazin-4-yl)pyridin-2-amine 134-1 as brown solid.

Step 2. A mixture of tert-butyl 2-(4-bromo-3-methylphenyl)acetate (855 mg, 3.00 mmol), 4-(tributylstannyl)pyridazine (1162 mg, 3.15 mmol), Pd(PPh$_3$)$_4$ (173 mg, 0.15 mmol) and DMF (10 ml) was stirred under argon atmosphere at 118° C. overnight. After cooled to room temperature, the mixture was concentrated by evaporation of DMF, redissolved in ethyl acetate (50 ml) and washed with water (50 ml×2). After dried over Na$_2$SO$_4$ and concentrated by evaporation, the mixture was subjected to silica gel column chromatography with ethyl acetate/hexanes (1:1) as eluent to give tert-butyl 2-(3-methyl-4-(pyridazin-4-yl)phenyl)acetate 134-2 as an oil.

Step 3. The ester 134-2 obtained in step 2 was stirred in DCM (15 ml) with trifluoroacetic acid (TFA, 3 ml) at room temperature overnight. After concentrated by evaporation, the residue was redistributed between ethyl acetate (30 ml) and 5% Na$_2$CO$_3$ aqueous solution (30 ml). The aqueous phase was acidified to pH around 2 with 6 N HCl solution and extracted with ethyl acetate (40 ml×2). The organic extraction was evaporated to give 2-(3-methyl-4-(pyridazin-4-yl)phenyl)acetic acid 134-3 as a solid which is used for reaction without further purification.

Step 4. A mixture of 5-(pyridazin-4-yl)pyridin-2-amine 134-1 (53 mg, 0.31 mmol), 2-(3-methyl-4-(pyridazin-4-yl)phenyl)acetic acid 134-3 (73 mg, 0.32 mmol), HATU (122 mg, 0.32 mmol) and DIEA (80 uL, 0.46 mmol) in DMF (1.0 ml) was stirred at room temperature overnight. Then it was distributed between ethyl acetate (40 ml) and 3% Na$_2$CO$_3$ aqueous solution (40 ml) and extracted with 0.5 N HCl solution (30 ml). The aqueous extraction was treated with Na$_2$CO$_3$ to adjust the pH to around 10 followed by extraction with ethyl acetate (30 ml×2). The combined organic extractions were dried over Na$_2$SO$_4$ and concentrated by evaporation. The residue was subjected to reverse phase HPLC to yield 2-(3-methyl-4-(pyridazin-4-yl)phenyl)-N-(5-(pyridazin-4-yl)pyridin-2-yl)acetamide 134 as off white solid. MS m/z 383.2 (M+1).

EXAMPLE 19

2-(6-(4-acetylpiperazin-1-yl)pyridin-3-yl)-N-(5-(3-fluorophenyl)pyridin-2-yl)acetamide (140)

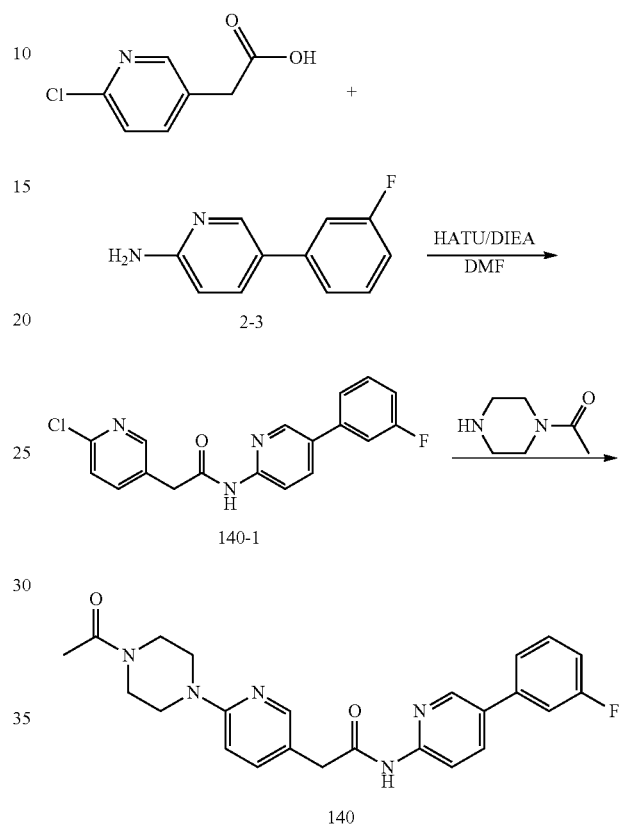

Step 1. A mixture of 2-(6-chloropyridin-3-yl)acetic acid (521 mg, 3.03 mmol), 5-(3-fluorophenyl)pyridin-2-amine (570 mg, 3.03 mmol), HATU (1250 mg, 3.29 mmol) and DIEA (784 µl, 4.50 mmol) in DMF (10 ml) was stirred at room temperature overnight. DMF was mostly removed by evaporation under reduced pressure. The residue was dissolved in EtOAc (50 ml), washed with 3% Na$_2$CO$_3$ solution (30 ml) and water (50 mL), and dried over Na$_2$SO$_4$. After concentration by evaporation, the residue was subjected to silica gel column chromatography to give 2-(6-chloropyridin-3-yl)-N-(5-(3-fluorophenyl)pyridin-2-yl)acetamide 140-1.

Step 2. 2-(6-Chloropyridin-3-yl)-N-(5-(3-fluorophenyl)pyridin-2-yl)acetamide 140-1 (100 mg, 0.29 mmol) was heated with 1-(piperazin-1-yl)ethanone (0.8 ml) at 108° C. for 4 hours. The mixture was dissolved in EtOAc (30 ml), washed with water (40 mL), and dried over Na$_2$SO$_4$. After concentration by evaporation, the residue was subjected to reverse phase HPLC to afford 2-(6-(4-acetylpiperazin-1-yl)pyridin-3-yl)-N-(5-(3-fluorophenyl)pyridin-2-yl)acetamide 140 as solid.

EXAMPLE 20

2-(4-(2-methylpyridin-4-yl)phenyl)-N-(5-(3-oxopiperazin-1-yl)pyridin-2-yl)acetamide (141)

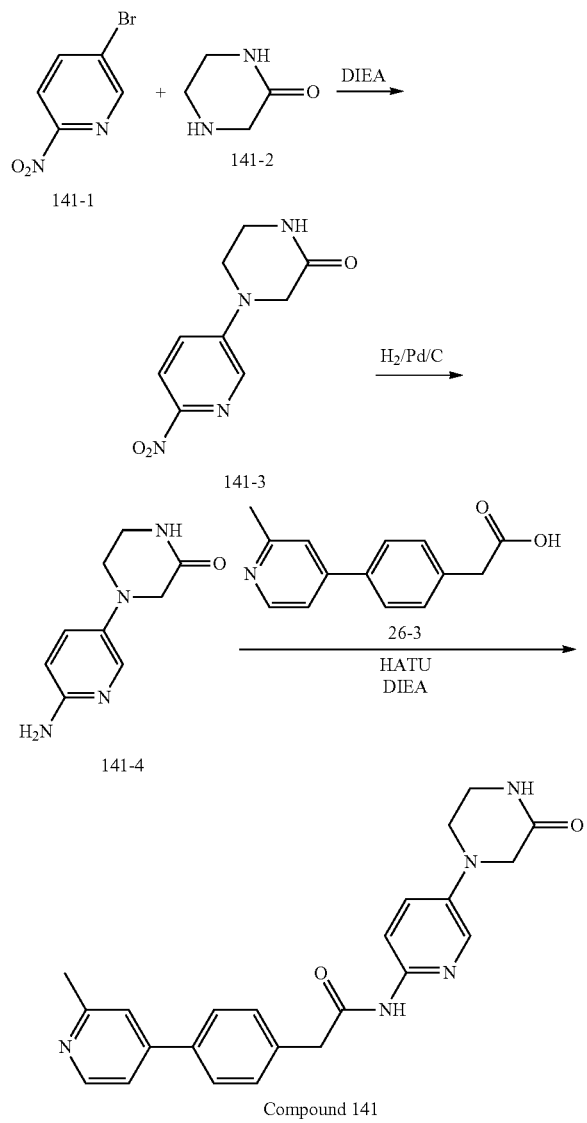

Compound 141

Step 1: To a sealed tube were added 5-bromo-2-nitropyridine 141-1 (1.01 g, 5 mmol), piperazin-2-one 141-2 (0.6 g, 6 mmol), DIEA (1.8 mL, 18 mmol) and DMSO (6 mL). The reaction was heated to 120° C. and stirred for 16 hours. The reaction was cooled down to room temperature. DIEA was removed by rotary evaporation. The residue was triturated in 15 mL ethyl acetate. The solid was collected by filtration and washed with small amount of ethyl acetate to give 4-(6-nitropyridin-3-yl)piperazin-2-one 141-3 as light yellow solid. MS m/z 223.2 (M+1).

Step 2: To a round-bottom flask was added 4-(6-nitropyridin-3-yl)piperazin-2-one 141-3 (0.7 g, 3.1 mmol), Pd/C (0.2 g) and methanol (20 mL). The reaction was stirred for 4 hours under hydrogen atmosphere by attaching a hydrogen balloon. The reaction was flashed with nitrogen and the solid was removed by filtration. The solvent was removed by rotary evaporation to give 4-(6-aminopyridin-3-yl)piperazin-2-one 141-4 as purple solid. MS m/z 193.2 (M+1).

Step 3: To a mixture of 2-(4-(2-methylpyridin-4-yl)phenyl)acetic acid 26-3 (22 mg, 0.1 mmol), 4-(6-aminopyridin-3-yl)piperazin-2-one 141-4 (19 mg, 0.1 mmol) and O-(7-azabenzotriazol-1-yl)-N,N,N',N'-tetramethyluroniumhexafluorophosphate (HATU) (40 mg, 0.1 mmol) in DMF (1 mL) was added DIEA (52 µL, 0.3 mmol) at room temperature. The mixture was stirred at room temperature for 2 hours. The reaction mixture was diluted into DMSO and purified by reverse phase HPLC to give 2-(4-(2-methylpyridin-4-yl)phenyl)-N-(5-(3-oxopiperazin-1-yl)pyridin-2-yl)acetamide 141. MS m/z 402.2 (M+1); $^1$H NMR 400 MHz (DMSO-$d_6$) δ10.53 (s, 1H), 8.49 (d, 1H), 8.05-8.01 (m, 2H), 7.94 (d, 1H), 7.75 (d, 2H), 7.57 (s, 1H), 7.48-7.48 (m, 3H), 7.41 (dd, 1H), 3.74 (s, 1H), 3.71 (s, 2H), 2.54-2.50 (m, 7H), 1.24 (s, 2H).

EXAMPLE 21

N-(5-(4-methyl-1H-imidazol-1-yl)pyridin-2-yl)-2-(4-(2-methylpyridin-4-yl)phenyl)acetamide (143)

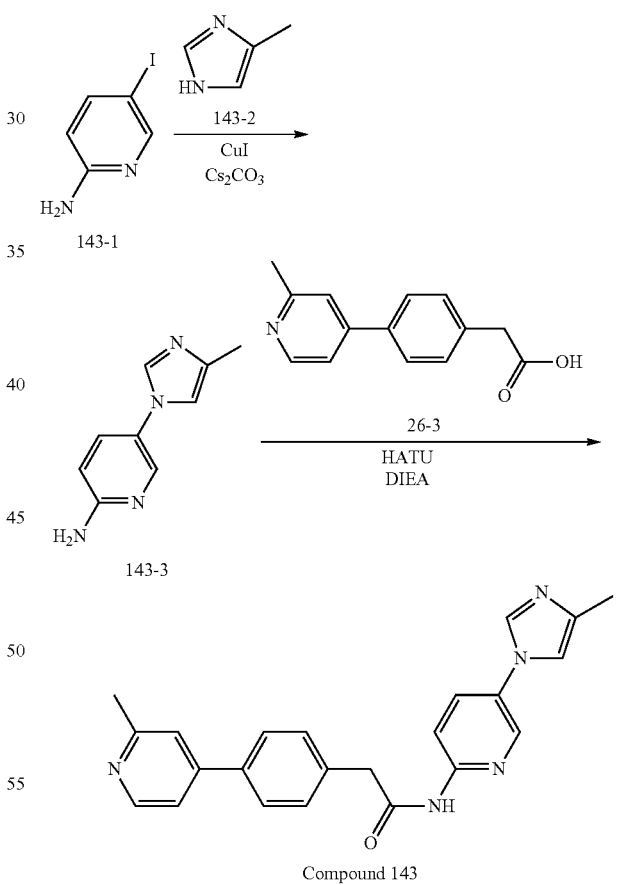

Compound 143

Step 1: To a seal tube charged with 5-iodopyridin-2-amine 143-1 (1.1 g, 5 mmol), 4-methyl-1H-imidazole 143-2 (0.61 g, 7.4 mmol), CuI (0.31 g, 1.63 mmol) and Cs$_2$CO$_3$ (3.25 g, 10 mmol) was added DMF (10 mL). The reaction vessel was flushed with nitrogen and sealed. The reaction was stirred at room temperature for 30 minutes before being heated up to 110° C. for 24 hours. The reaction was diluted into ethyl acetate and the salt was removed by filtration. The filtrate was dried and the residue was purified by silica gel flash chromatography, eluted with 10% methanol in ethyl acetate to give 5-(4-methyl-1H-imidazol-1-yl)pyridin-2-amine 143-3 as off-white solid. MS m/z 175.2 (M+1).

Step 2: To a mixture of 2-(4-(2-methylpyridin-4-yl)phenyl) acetic acid 26-3 (22 mg, 0.1 mmol), 5-(4-methyl-1H-imidazol-1-yl)pyridin-2-amine 143-3 (18 mg, 0.1 mmol) and O-(7-azabenzotriazol-1-yl)-N,N,N',N'-tetramethyluroniumhexafluorophosphate (HATU) (40 mg, 0.1 mmol) in DMF (1 mL) was added DIEA (52 μL, 0.3 mmol) at room temperature. The mixture was stirred at room temperature for 2 hours. The reaction mixture was diluted into DMSO and purified by reverse phase HPLC to give N-(5-(4-methyl-1H-imidazol-1-yl)pyridin-2-yl)-2-(4-(2-methylpyridin-4-yl)phenyl)acetamide 143. MS m/z 384.1 (M+1); $^1$H NMR 400 MHz (DMSO-$d_6$) δ10.91 (s, 1H), 8.58 (dd, 1H), 8.43 (d, 1H), 8.10 (m, 2H), 7.99 (m, 1H), 7.77 (d, 2H), 7.51 (s, 1H), 7.43-7.40 (m, 4H), 3.75 (s, 2H), 2.46 (s, 3H), 2.10 (s, 3H).

EXAMPLE 22

2-(2',3-dimethyl-2,4'-bipyridin-5-yl)-N-(5-(pyrazin-2-yl)pyridin-2-yl)acetamide (145)

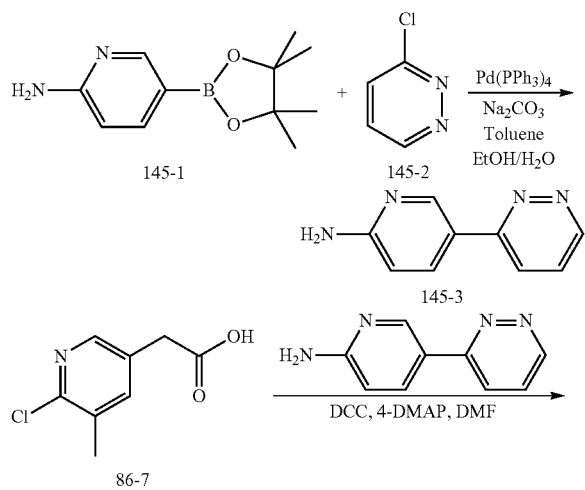

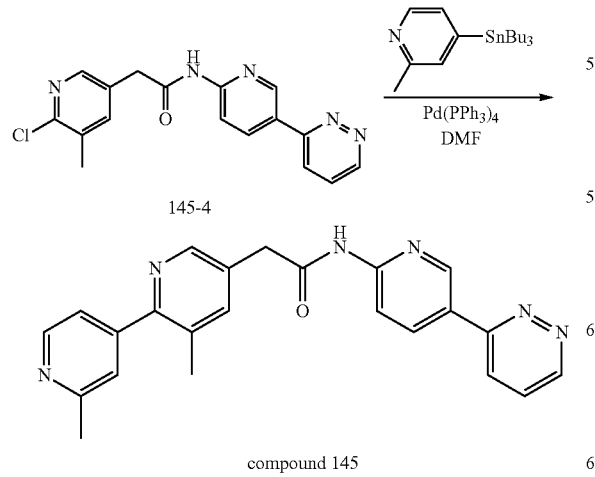

Step 1: To a sealed flask were added 5-(4,4,5,5-tetramethyl-1,3,2-dioxaborolan-2-yl)pyridin-2-amine 145-1 (1.54 g, 7 mmol), 3-chloropyridazine 145-2 (0.8 g, 7 mmol), Pd(PPh$_3$)$_4$ (500 mg, 0.7 mmol), toluene (50 mL), ethanol (12 mL) and 2M Na$_2$CO$_3$ (11 mL). The reaction mixture was bubbled with nitrogen for 2 minutes and stirred at 90° C. for 10 hours. After cooled to room temperature, the solvents were evaporated and the residue was redissolved in dichloromethane (200 ml) and treated with 1M HCl aqueous solution (50 mL). The two layers were separated and the aqueous layer was treated with 10% NaOH aqueous solution to adjust the pH to around 13. The resulting solution was evaporated and the remaining solid was exacted with ethyl acetate (100 mL×3). The combined organic phases were concentrated to give 5-(pyridazin-3-yl)pyridin-2-amine 145-3 as dark brown solid. MS m/z 173.1 (M+1).

Step 2: A mixture of 2-(6-chloro-5-methylpyridin-3-yl) acetic acid 86-7 (241 mg, 1.3 mmol), 5-(pyridazin-3-yl)pyridin-2-amine 145-3 (224 mg, 1.3 mmol), 1,3-dicyclohexylcarbodiimide (325 mg, 1.6 mmol) and 4-(dimethylamino) pyridine (26 mg, 0.26 mmol) in DMF (6 mL) was stirred at room temperature for 10 hours. The reaction mixture was filtered to remove the solid and the filtrate was diluted with ethyl acetate, washed with water and brine, dried over Na$_2$SO$_4$ and concentrated to dryness by rotary evaporation. The crude product was purified by silica gel flash chromatography, eluted with 5% methanol in dichloromethane to give 2-((6-chloro-5-methylpyridin-3-yl)-N-(5-(pyridazin-3-yl) pyridin-2-yl)acetamide 145-4 as pale yellow solid. MS m/z 340.2 (M+1)

Step 3: To a reaction tube containing 2-(6-chloro-5-methylpyridin-3-yl)-N-(5-(pyridazin-3-yl)pyridin-2-yl)acetamide 145-4 (68 mg, 0.2 mmol), 2-methyl-4-(tributylstannyl) pyridine (76 mg, 0.2 mmol) and Pd(PPh$_3$)$_4$ (22 mg, 0.02 mmol) under argon was added DMF (0.9 mL). The mixture was stirred at 120° C. for 10 hours. The crude product, a clear solution, was purified by reverse phase HPLC to give 2-(2', 3-dimethyl-2,4'-bipyridin-5-yl)-N-(5-(pyrazin-2-yl)pyridin-2-yl)acetamide 145 as white solid. MS m/z 397.2 (M+1); $^1$H NMR 400 MHz (DMSO-$d_6$) δ 11.14 (s, 1H), 9.22 (dd, 1H), 9.13 (d, 1H), 8.56 (dd, 1H), 8.52 (d, 1H), 8.49 (d, 1H), 8.29 (dd, 1H), 8.24 (d, 1H), 7.81 (dd, 1H), 7.73 (d, 1H), 7.42 (s, 1H), 7.35 (dd, 1H), 3.87 (s, 2H), 2.53 (s, 3H), 2.35 (s, 3H).

EXAMPLE 23

N-(5-(4-acetylpiperazin-1-yl)pyridin-2-yl)-2-(2',3-dimethyl-2,4'-bipyridin-5-yl)acetamide

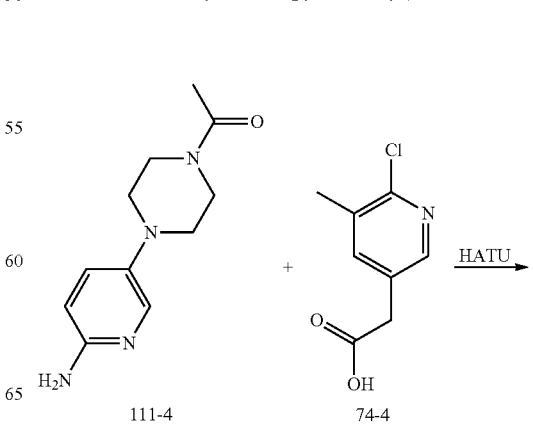

-continued

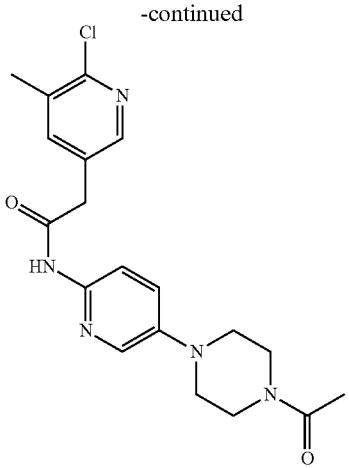

148-1

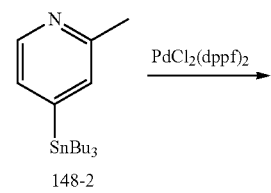

148-2

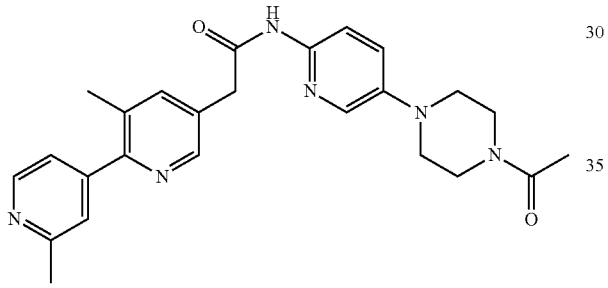

Compound 148

Step 1: To a mixture of 2-(6-chloro-5-methylpyridin-3-yl)acetic acid 74-4 (100 mg, 0.54 mmol), 1-(4-(6-aminopyridin-3-yl)piperazin-1-yl)ethanone 111-4 (140 mg, 0.64 mmol) and O-(7-azabenzotriazol-1-yl)-N,N,N',N'-tetramethyluroniumhexafluorophosphate (HATU) (220 mg, 0.58 mmol) in DMF (2 mL) was added DIEA (280 μL, 1.62 mmol) at room temperature. The mixture was stirred at room temperature for 2 hours. The reaction mixture was diluted into ethyl acetate, washed with saturated $NaHCO_3$ then brine, dried over $Na_2SO_4$. The solvent was removed by rotary evaporation to give N-(5-(4-acetylpiperazin-1-yl)pyridin-2-yl)-2-(6-chloro-5-methylpyridin-3-yl)acetamide 148-1 (210 mg, 100%). MS m/z 388.1 (M+1).

Step 2: To the mixture of N-(5-(4-acetylpiperazin-1-yl)pyridin-2-yl)-2-(6-chloro-5-methylpyridin-3-yl)acetamide 148-1 (80 mg, 0.21 mmol) and 2-methyl-4-(tributylstannyl)pyridine 148-2 (75 mg, 0.21 mmol) in DMF (1.5 mL) was added [1,1'-Bis(diphenylphosphino)ferrocene]dichloropalladium(II) (30 mg, 0.18 mmol). The reaction was stirred at 110° C. for 20 hours. After cooling down to room temperature, the reaction mixture was purified by reverse-phase HPLC to give N-(5-(4-acetylpiperazin-1-yl)pyridin-2-yl)-2-(2',3-dimethyl-2,4'-bipyridin-5-yl)acetamide 148 as off-white solid.

MS m/z 445.2 (M+1); $^1$H NMR 400 MHz (DMSO-$d_6$) δ10.57 (s, 1H), 8.49 (d, 1H), 8.40 (d, 1H), 7.98 (d, 1H), 7.87 (d, 1H), 7.64 (d, 1H), 7.42 (s, 1H), 7.36-7.34 (m, 2H), 3.70 (s, 2H), 3.50 (b, 4H), 3.09 (t, 2H), 3.02 (t, 2H), 2.49 (s, 3H), 2.28 (s, 3H), 1.97 (s, 3H).

EXAMPLE 24

2-methyl-4-(3-methyl-5-(2-oxo-2-(5-(pyrazin-2-yl)pyridin-2-ylamino)ethyl)pyridin-2-yl)pyridine 1-oxide (156)

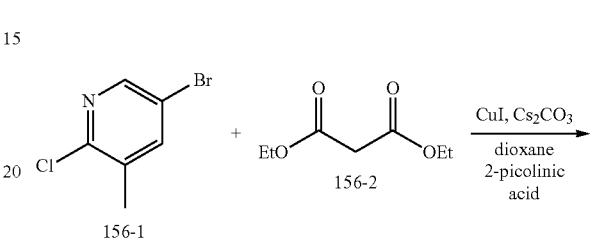

156-1 156-2

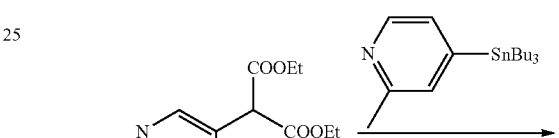

156-3

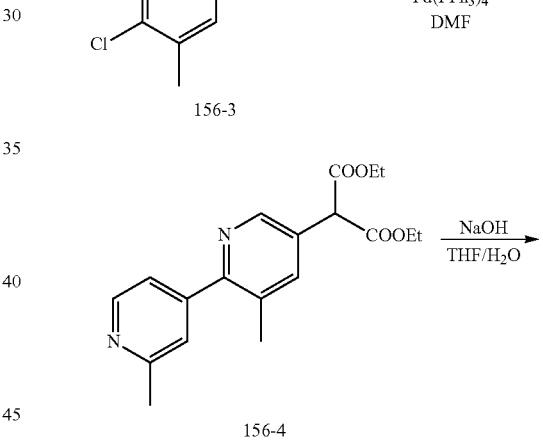

156-4

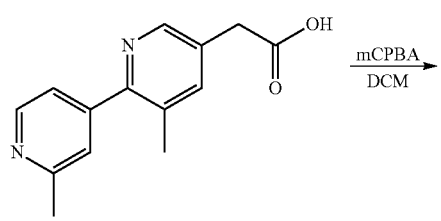

156-5

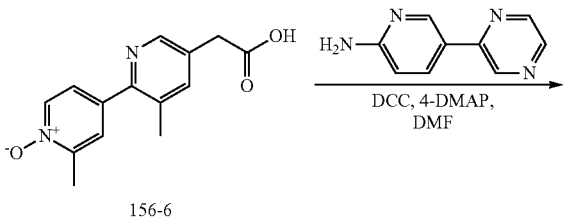

156-6

-continued

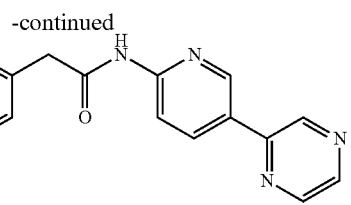

compound 156

Step 1: To a flask were added 5-bromo-2-chloro-3-methylpyridine 156-1 (4.13 g, 20 mmol), CuI (380 mg, 2.00 mmol), Cs$_2$CO$_3$ (18 g, 60 mmol), 2-picolinic acid (480 mg, 4.00 mmol). The flask was evacuated and backfilled with argon 3 times. Anhydrous dioxane (40 mL) was added to the flask, followed by diethyl malonate 156-2 (6 mL, 40 mmol). The mixture was stirred at 96° C. for 36 hours under argon. After cooled to room temperature, the mixture was partitioned between ethyl acetate and water. The organic portion was dried over Na$_2$SO$_4$, filtered and concentrated by rotary evaporation. The crude product was purified by flash chromatography, eluted with 20% ethyl acetate in hexanes to give diethyl 2-(6-chloro-5-methylpyridin-3-yl)malonate 156-3 as colorless oil. MS m/z 286.1 (M+1).

Step 2: To a reaction flask containing diethyl 2-(6-chloro-5-methylpyridin-3-yl)malonate 156-3 (1.00 g, 4.00 mmol), 2-methyl-4-(tributylstannyl)pyridine (1.53 g, 4.00 mmol) and Pd(PPh$_3$)$_4$ (440 mg, 0.4 mmol) under argon was added DMF (20 mL). The mixture was stirred at 120° C. for 10 hours. After the mixture was cooled down to room temperature, 1N KF aqueous solution was added to it and stirred for 15 minutes. The mixture was diluted with ethyl acetate and the two layers were separated. The organic layer was further washed with water and brine, dried over Na$_2$SO$_4$, concentrated to dryness by rotary evaporation. The crude product was purified by silica gel flash chromatography, eluted with 5% methanol in dichloromethane to give diethyl 2-(2',3-dimethyl-2,4'-bipyridin-5-yl)malonate 156-4 as colorless oil. MS m/z 343.1 (M+1)

Step 3: A mixture of diethyl 2-(2',3-dimethyl-2,4'-bipyridin-5-yl)malonate 156-4 (935 mg, 3 mmol) and NaOH (480 mg, 12 mmol) in THF (1.8 mL) and water (1.8 mL) was stirred at 65° C. for 3 hours. After cooled down to room temperature, the mixture was treated with 3N HCl aqueous solution to adjust the pH around 3, and then stirred for 15 minutes. The resulting solution was evaporated to dryness and the remaining solid was extracted with 20% methanol in ethyl acetate. The organic extraction was concentrated to give 2-(2',3-dimethyl-2,4'-bipyridin-5-yl)acetic acid 156-5 as white solid. MS m/z 243.1 (M+1).

Step 4: To a solution of 2-(2',3-dimethyl-2,4'-bipyridin-5-yl)acetic acid 156-5 (100 mg, 0.41 mmol) in dichloromethane (3 mL) and methanol (0.5 mL) was added mCPBA (91 mg, 0.41 mmol) in small portions at 0° C. The mixture was stirred for 3 hours at 0° C., and then was concentrated to dryness to give 4-(5-(carboxymethyl)-3-methylpyridin-2-yl)-2-methylpyridine 1-oxide 156-6 as white solid, which was used for next step without further purification. MS m/z 259.1 (M+1).

Step 5: A mixture of 4-(5-(carboxymethyl)-3-methylpyridin-2-yl)-2-methylpyridine 1-oxide 156-6 from Step 4 (0.41 mmol), 5-(pyrazin-2-yl)pyridin-2-amine 86-3 (141 mg, 0.82 mmol), 1,3-dicyclohexylcarbodiimide (188 mg, 0.90 mmol) and 4-(dimethylamino)pyridine (16 mg, 0.16 mmol) in DMF (2 mL) was stirred at room temperature for 10 hours. The crude product was filtered to remove the insoluble and the filtrate was purified by reverse phase HPLC to give 2-methyl-4-(3-methyl-5-(2-oxo-2-(5-(pyrazin-2-yl)pyridin-2-ylamino)ethyl)pyridin-2-yl)pyridine 1-oxide 156 as white solid. MS m/z 413.2 (M+1); $^1$H NMR 400 MHz (DMSO-d$_6$) δ 11.12 (s, 1H), 9.31 (d, 1H), 9.11 (d, 1H), 8.72 (m, 1H), 8.62 (d, 1H), 8.52 (dd, 1H), 8.48 (d, 1H), 8.31 (d, 1H), 8.21 (d, 1H), 7.73 (m, 2H), 7.52 (dd, 1H), 3.86 (s, 2H), 2.41 (s, 3H), 2.40 (s, 3H).

EXAMPLE 25

N-(5-(4-acetylpiperazin-1-yl)pyridin-2-yl)-2-(3-methyl-4-(2-methylpyridin-4-yl)phenyl)acetamide (159)

24-5

159-1

159-2

Compound 159

Step 1: To a mixture of 2-(4-bromo-3-methylphenyl)acetic acid 24-5 (100 mg, 0.44 mmol), 1-(4-(6-aminopyridin-3-yl)piperazin-1-yl)ethanone 111-4 (96 mg, 0.44 mmol) and HATU (200 mg, 0.53 mmol) in DMF (2 mL) was added DIEA (230 uL, 1.32 mmol) and the mixture was stirred at room temperature overnight. The reaction mixture was partitioned between ethyl acetate and water. The organic phase was washed with brine and dried over Na$_2$SO$_4$ and the solvent was evaporated. The residue was subject to silica gel flash chromatography to give N-(5-(4-acetylpiperazin-1-yl)pyridin-2-yl)-2-(4-bromo-3-methylphenyl)acetamide 159-1. MS m/z 431.1 (M+1).

Step 2: To the mixture of N-(5-(4-acetylpiperazin-1-yl)pyridin-2-yl)-2-(4-bromo-3-methylphenyl)acetamide 159-1 (65 mg, 0.15 mmol) and 2-methyl-4-(tributylstannyl)pyridine 159-2 (58 mg, 0.15 mmol) in DMF (0.8 mL) was added [1,1'-Bis(diphenylphosphino)ferrocene]dichloropalladium (II) (30 mg, 0.036 mmol). The reaction was stirred at 110° C. for 20 hours. After cooling down to room temperature, the reaction mixture was diluted into DMSO and purified by reverse-phase HPLC to give N-(5-(4-acetylpiperazin-1-yl) pyridin-2-yl)-2-(3-methyl-4-(2-methylpyridin-4-yl)phenyl) acetamide 159 as off-white solid. MS m/z 444.2 (M+1); $^1$H NMR 400 MHz (DMSO-$d_6$) δ10.47 (s, 1H), 8.41 (d, 1H), 7.97 (d, 1H), 7.88 (d, 1H), 7.37 (dd, 1H), 7.21-7.18 (m, 2H), 7.16 (s, 1H), 7.12-7.09 (m, 2H), 3.61 (s, 2H), 3.52 (m, 4H), 3.08 (t, 2H), 3.02 (t, 2H), 2.17 (s, 3H), 1.97 (s, 3H).

EXAMPLE 26

N-(5-(4-acetylpiperazin-1-yl)pyridin-2-yl)-2-(3-fluoro-4-(2-methylpyridin-4-yl)phenyl)acetamide (168)

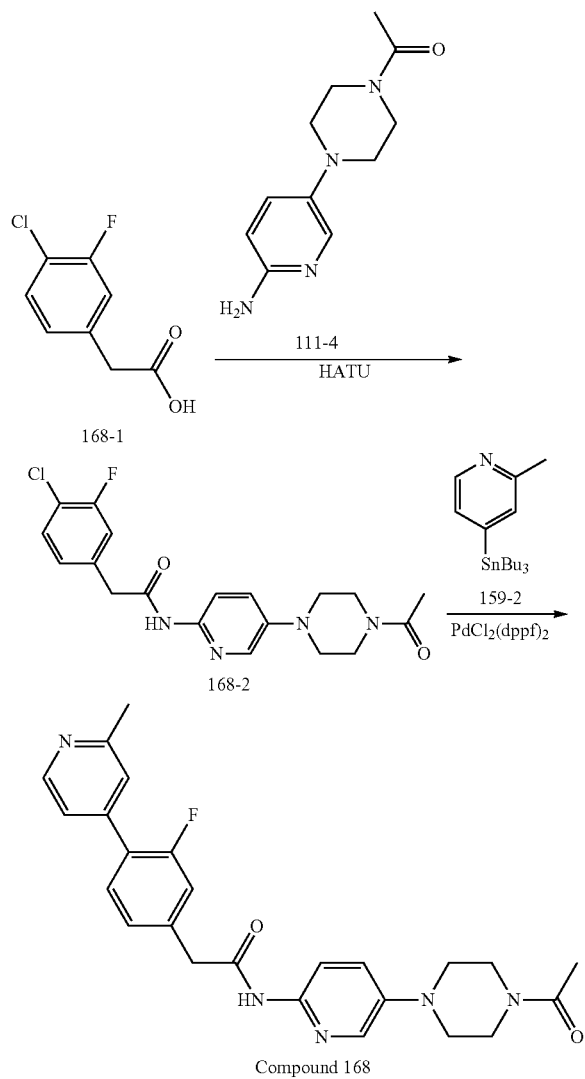

Compound 168

Step 1: To a mixture of 2-(4-chloro-3-fluorophenyl)acetic acid 168-1 (188 mg, 1.0 mmol), 1-(4-(6-aminopyridin-3-yl) piperazin-1-yl)ethanone 111-4 (220 mg, 1.0 mmol) and HATU (400 mg, 1.05 mmol) in DMF (4 mL) was added DIEA (521 uL, 3.0 mmol) and the mixture was stirred at room temperature over night. The reaction mixture was partitioned between ethyl acetate and water. The organic phase was washed with brine and dried over $Na_2SO_4$ and the solvent was evaporated. The residue was subject to silica gel flash chromatography to give N-(5-(4-acetylpiperazin-1-yl)pyridin-2-yl)-2-(4-chloro-3-fluorophenyl)acetamide 168-2. MS m/z 391.1 (M+1).

Step 2: To the mixture of N-(5-(4-acetylpiperazin-1-yl) pyridin-2-yl)-2-(4-chloro-3-fluorophenyl)acetamide 168-2 (80 mg, 0.2 mmol) and 2-methyl-4-(tributylstannyl)pyridine (78 mg, 0.2 mmol) in DMF (0.6 mL) was added [1,1'-Bis (diphenylphosphino)ferrocene]dichloropalladium(II) (33 mg, 0.04 mmol). The reaction was stirred at 110° C. for 20 hours. After cooling down to room temperature, the reaction mixture was diluted into DMSO and purified by reverse-phase HPLC to give N-(5-(4-acetylpiperazin-1-yl)pyridin-2-yl)-2-(3-fluoro-4-(2-methylpyridin-4-yl)phenyl)acetamide 168 as white solid. MS m/z 448.1 (M+1); $^1$H NMR 400 MHz (DMSO-$d_6$) δ10.57 (s, 1H), 8.52 (d, 1H), 8.04 (s, 1H), 7.93 (d, 1H), 7.59 (m, 1H), 7.44-7.29 (m, 5H), 3.77 (s, 2H), 3.58 (b, 2H), 3.14 (b, 2H), 3.08 (b, 2H), 2.55 (s, 2H), 2.51 (s, 3H), 2.04 (s, 3H).

EXAMPLE 27

N-(5-(4-acetylpiperazin-1-yl)pyridin-2-yl)-2-(4-(2-methylpyridin-4-yl)-3-(trifluoromethyl)phenyl)acetamide (172)

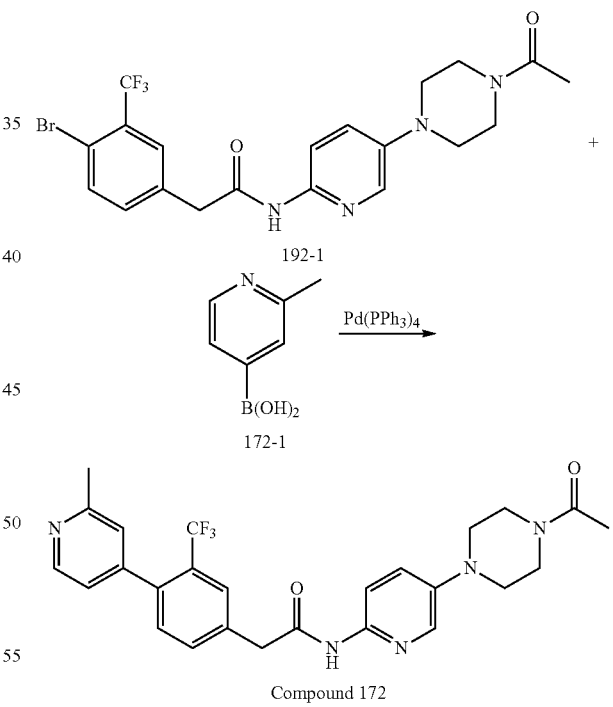

Compound 172

To a reaction vessel charged with N-(5-(4-acetylpiperazin-1-yl)pyridin-2-yl)-2-(4-bromo-3-(trifluoromethyl)phenyl) acetamide 192-1 (300 mg, 0.62 mmol), 2-methylpyridin-4-ylboronic acid 172-1 (127 mg, 0.93 mmol) and Pd(PPh$_3$)$_4$ (36 m g, 0.03 mmol) was added toluene (6 mL), ethanol (2 mL) and saturated sodium carbonate (2 mL). The reaction mixture was flushed with nitrogen and heated to 110° C. for 10 hours. After the reaction was cooled down to room temperature, it was partitioned between ethyl acetate and saturated NaHCO$_3$ and the organic phase was washed with brine and dried over Na₂SO₄. The solvent was removed by rotary evaporation and the residue was purified by reverse phase HPLC to give N-(5-(4-acetylpiperazin-1-yl)pyridin-2-yl)-2-(4-(2-methylpyridin-4-yl)-3-(trifluoromethyl)phenyl)acetamide 172. MS m/z 498.2 (M+1). ¹H NMR 400 MHz (DMSO-d₆) δ10.67 (s, 1H), 8.66 (d, 1H), 8.05 (m, 1H), 7.94 (m, 2H), 7.75 (d, 1H), 7.52 (s, 1H), 7.45 (m, 3H), 3.88 (s, 2H), 3.58 (b, 4H), 3.14 (b, 2H), 3.09 (b, 2H), 2.61 (s, 3H), 2.05 (s, 3H).

EXAMPLE 28

N-(5-(4-(cyanomethyl)piperazin-1-yl)pyridin-2-yl)-2-(4-(2-methylpyridin-4-yl)phenyl)acetamide (175)

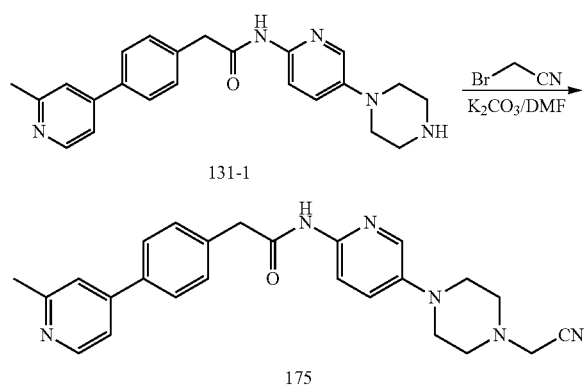

Step 1: A mixture of 2-(4-(2-methylpyridin-4-yl)phenyl)-N-(5-(piperazin-1-yl)pyridin-2-yl)acetamide 131-1 (39 mg, 0.10 mmol), 2-bromoacetonitrile (8 uL, 0.12 mmol) and Potassium Carbonate (28 mg, 0.20 mmol) in DMF (1 mL) was stirred at room temperature overnight. The mixture was poured into water (5 ml) and extracted with ethyl acetate (5 mL×3). The combined organic phases were dried over Na₂SO₄ and concentrated. The crude product was purified by reverse phase HPLC to give N-(5-(4-(cyanomethyl)piperazin-1-yl)pyridin-2-yl)-2-(4-(2-methylpyridin-4-yl)phenyl)acetamide 175. MS m/z 427.2 (M+1); ¹H NMR 400 MHz (MeOD) δ 8.37(d, 1H), 7.94(s, 1H), 7.87(d, 1H), 7.68(d, 2H), 7.55(s, 1H), 7.48-7.44(m, 3H), 7.36(dd, 1H), 3.74(s, 2H), 3.67(s, 2H), 3.17(t, 4H), 2.69(t, 4H), 2.54(s, 3H).

EXAMPLE 29

N-(5-(4-cyanopiperazin-1-yl)pyridin-2-yl)-2-(4-(2-methylpyridin-4-yl)phenyl)acetamide(176)

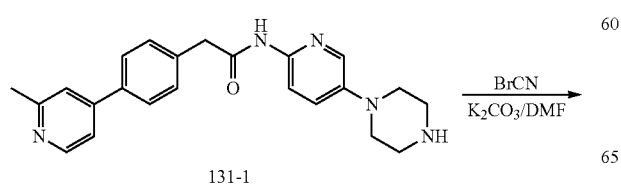

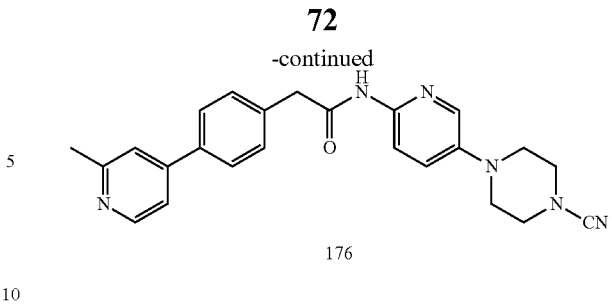

Step 1: A mixture of 2-(4-(2-methylpyridin-4-yl)phenyl)-N-(5-(piperazin-1-yl)pyridin-2-yl)acetamide 131-1 (39 mg, 0.10 mmol), Cyanogen Bromide (13 mg, 0.12 mmol) and Potassium Carbonate (28 mg, 0.20 mmol) in DMF (1 mL) was stirred at room temperature overnight. The mixture was poured into water (5 ml) and extracted with ethyl acetate (5 mL×3). The combined organic phases were dried over Na₂SO₄, and concentrated. The crude product was purified by reverse phase HPLC to give N-(5-(4-cyanopiperazin-1-yl)pyridin-2-yl)-2-(4-(2-methylpyridin-4-yl)phenyl)acetamide 176. MS m/z 413.2 (M+1); ¹H NMR 400 MHz (MeOD) δ 8.39(d, 1 Hz), 7.96(s, 1H), 7.89(d, 1H),7.68(d, 2H), 7.58(s, 1H), 7.50(d, 1H), 7.46(d, 2H), 7.37(dd, 1H), 3.74(s, 2H), 3.35(t, 4H), 3.18(t, 4H),2.55(s, 3H).

EXAMPLE 30

N-(5-(4-acetylpiperazin-1-yl)pyridin-2-yl)-2-(4-(2-chloropyridin-4-yl)phenyl)acetamide (177)

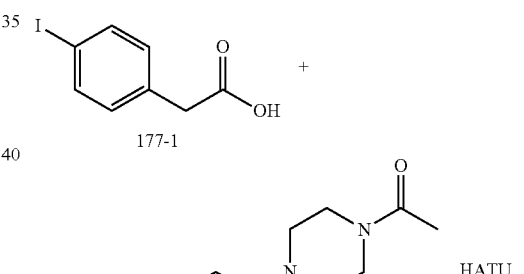

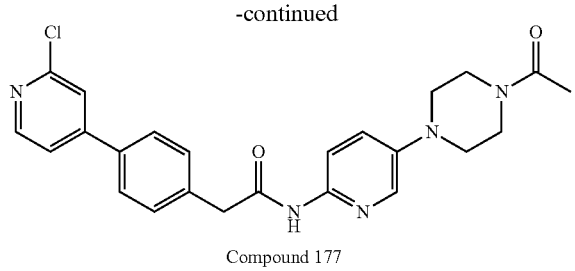

Compound 177

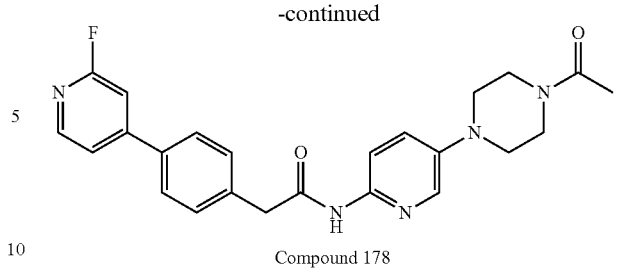

Compound 178

Step 1: To a mixture of 2-(4-iodophenyl)acetic acid 177-1 (524 mg, 2.0 mmol), 1-(4-(6-aminopyridin-3-yl)piperazin-1-yl)ethanone 111-4 (440 mg, 2.0 mmol) and O-(7-azabenzotriazol-1-yl)-N,N,N',N'-tetramethyluroniumhexafluorophosphate (HATU) (798 mg, 2.1 mmol) in DMF (10 mL) was added DIEA (1.04 mL, 6.0 mmol) at room temperature. The mixture was stirred at room temperature for 2 hours. The reaction mixture was diluted into ethyl acetate, washed with saturated NaHCO₃ then brine, dried over Na₂SO₄. The solvent was removed by rotary evaporation to give N-(5-(4-acetylpiperazin-1-yflpyridin-2-yl)-2-(4-iodophenyl)acetamide 177-2 as tan solid. MS m/z 465.2 (M+1).

Step 2: To a sealed tube was added N-(5-(4-acetylpiperazin-1-yflpyridin-2-yl)-2-(4-iodophenyl)acetamide 177-2 (100 mg, 0.22 mmol), 2-chloropyridin-4-ylboronic acid 177-3 (52 mg, 0.33 mmol), Pd(PPh₃)₄ (23 mg, 0.02 mmol), saturated Na₂CO₃ (1 mL), ethanol (1 mL) and toluene (3 mL). The reaction was heated to 110° C. and stirred for 16 hours. The reaction was cooled down to room temperature, then extracted with ethyl acetate. The crude product was purified by silica-gel flash chromatography, eluted with ethyl acetate to give N-(5-(4-acetylpiperazin-1-yflpyridin-2-yl)-2-(4-(2-fluoropyridin-4-yl)phenyl)acetamide 177 as off-white solid. MS m/z 450.1 (M+1); ¹H NMR 400 MHz (DMSO-d₆) δ10.51 (s, 1H), 8.40 (d, 1H), 7.97 (d, 1H), 7.87 (d, 1H), 7.78 (d, 1H), 7.76 (d, 2H), 7.69 (dd, 1H), 7.43 (d, 2H), 7.37 (dd, 1H), 3.68 (s, 2H), 3.52 (m, 4H), 3.09 (t, 2H), 3.02 (t, 2H), 1.97 (s, 3H).

EXAMPLE 31

N-(5-(4-acetylpiperazin-1-yl)pyridin-2-yl)-2-(4-(2-fluoropyridin-4-yl)phenyl)acetamide (178)

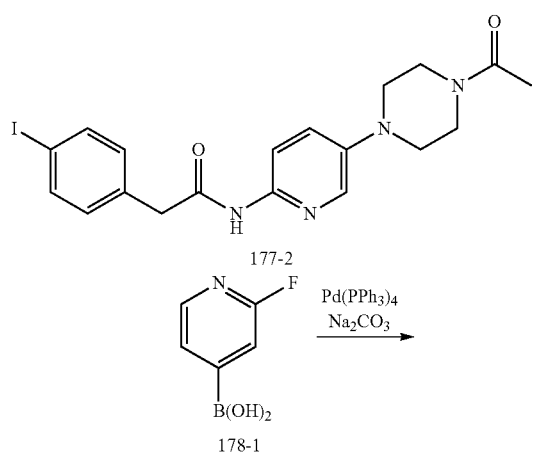

To a sealed tube was added N-(5-(4-acetylpiperazin-1-yl)pyridin-2-yl)-2-(4-iodophenyl)acetamide 177-2 (520 mg, 1.1 mmol), 2-fluoropyridin-4-ylboronic acid 178-1 (237 mg, 1.6 mmol), Pd(PPh₃)₄ (65 mg, 0.055 mmol), saturated Na₂CO₃ (5 mL), ethanol (5 mL) and toluene (15 mL). The reaction was heated to 110° C. and stirred for 16 hours. The reaction was cooled down to room temperature, then extracted with ethyl acetate. The crude product was purified by silica-gel flash chromatography, eluted with ethyl acetate to give N-(5-(4-acetylpiperazin-1-yl)pyridin-2-yl)-2-(4-(2-fluoropyridin-4-yl)phenyl)acetamide 178 as off-white solid. MS m/z 434.2 (M+1); ¹H NMR 400 MHz (DMSO-d₆) δ10.58 (s, 1H), 8.30 (d, 1H, J=5.6 Hz), 8.04 (d, 1H, J=2.8 Hz), 7.94 (d, 1H, J=9.2 Hz), 7.84-7.82 (m, 2H), 7.71-7.69 (m, 1H), 7.53-7.49 (m, 3H), 7.44 (dd, 1H, J1=9.2 Hz, J2=2.8 Hz), 3.76 (s, 2H), 3.59 (b, 4H), 3.16 (t, 2H, J=2.8 Hz), 3.09 (t, 2H, J=2.8 Hz), 2.04 (s, 3H).

EXAMPLE 32

2-(3-cyano-4-(2-methylpyridin-4-yl)phenyl)-N-(5-(pyridazin-3-yl)pyridin-2-yl)acetamide (181)

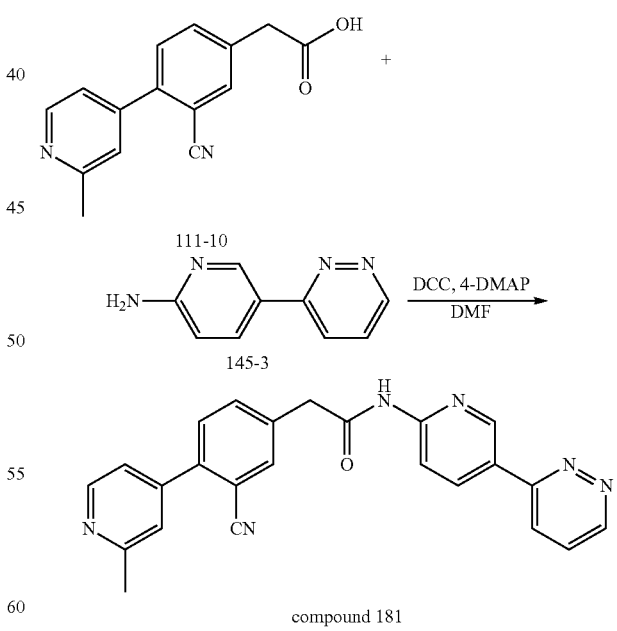

compound 181

Step 1: A mixture of 2-(3-cyano-4-(2-methylpyridin-4-yl)phenyl)acetic acid 111-10 (50 mg, 0.2 mmol), 5-(pyridazin-3-yl)pyridin-2-amine 145-3 (34 mg, 0.2 mmol), 1,3-dicyclohexylcarbodiimide (50 mg, 0.24 mmol) and 4-(dimethylamino)pyridine (4 mg, 0.04 mmol) in DMF (0.9 mL) was stirred at room temperature for 10 hours. The crude product was filtered to remove the insoluble and the filtrate was purified by reverse phase HPLC to give 2-(3-cyano-4-(2-methylpyridin-4-yl)phenyl)-N-(5-(pyridazin-3-yl)pyridin-2-yl)acetamide 181 as white solid. MS m/z 407.2 (M+1); $^1$H NMR 400 MHz (DMSO-d$_6$) δ 11.13 (s, 1H), 9.22 (dd, 1H), 9.13 (d, 1H), 8.59 (d, 1H), 8.56 (dd, 1H), 8.29 (dd, 1H), 8.23 (d, 1H), 7.98 (d, 1H), 7.83-7.79 (m, 2H), 7.67 (d, 1H), 7.48 9s, 1H), 7.42 (dd, 1H), 3.95 (s, 2H), 2.56 (s, 3H).

EXAMPLE 33

N-(5-(4-acetylpiperazin-1-yl)pyridin-2-yl)-2-(3-methoxy-4-(2-methylpyridin-4-yl)phenyl)acetamide (182)

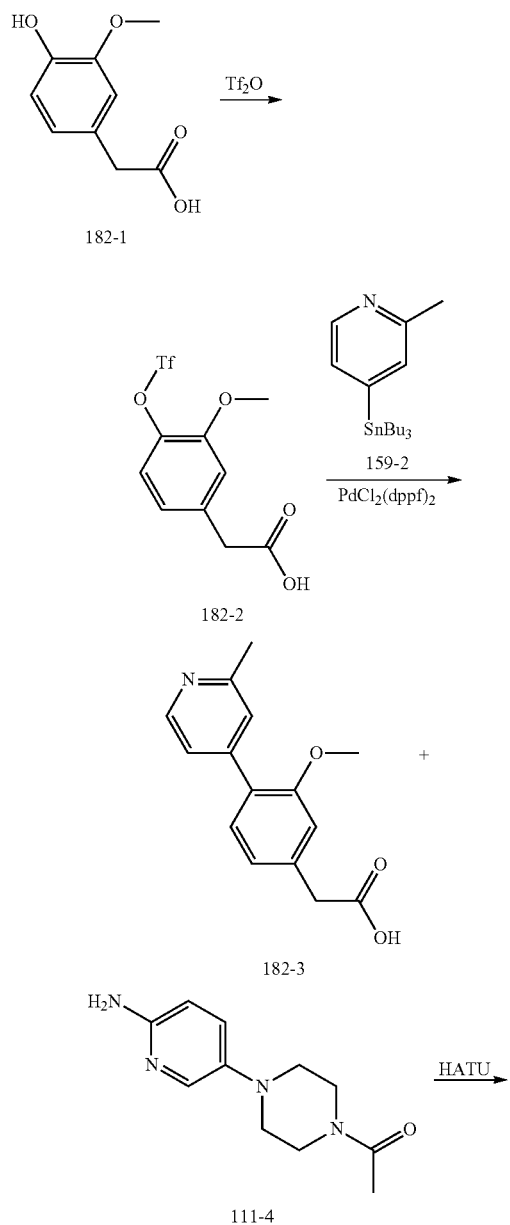

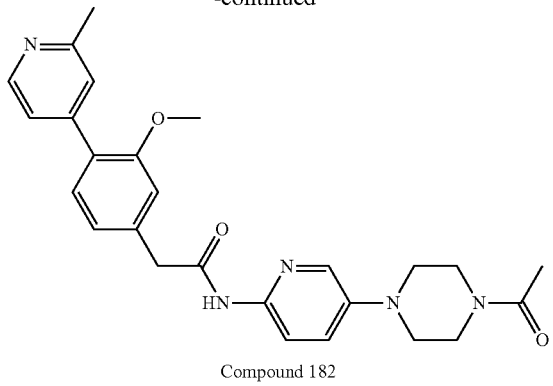

Compound 182

Step 1: To the solution of 2-(4-hydroxy-3-methoxyphenyl)acetic acid 182-1 (364 mg, 2 mmol) and TEA (404 mg, 4 mmol) in DCM (40 mL) was added triflic anhydride (564 mg, 2 mmol) slowly at 0° C. The reaction was warmed up to room temperature after addition and stirred for 1 hour at room temperature. The reaction mixture was then partitioned between DCM and water. The organic phase was washed with brine and dried over Na$_2$SO$_4$. The solvent was removed by rotary evaporation to give 2-(3-methoxy-4-(trifluoromethylsulfonyloxy)phenyl)acetic acid 182-2 (590 mg, 95%).

Step 2: To the mixture of 2-(3-methoxy-4-(trifluoromethylsulfonyloxy)phenyl)acetic acid 182-2 (590 mg, 1.9 mmol) and 2-methyl-4-(tributylstannyl)pyridine (730 mg, 1.9 mmol) in DMF (2.0 mL) was added [1,1'-Bis(diphenylphosphino)ferrocene]dichloropalladium(II) (33 mg, 0.04 mmol). The reaction was stirred at 110° C. for 20 hours. After cooling down to room temperature, the reaction mixture was diluted into DMSO and purified by reverse-phase HPLC to give 2-(3-methoxy-4-(2-methylpyridin-4-yl)phenyl)acetic acid 182-3. MS m/z 258.1 (M+1).

Step 3: To a mixture of 2-(3-methoxy-4-(2-methylpyridin-4-yl)phenyl)acetic acid 182-3 (26 mg, 0.1 mmol), 1-(4-(6-aminopyridin-3-yl)piperazin-1-yl)ethanone 111-4 (22 mg, 0.1 mmol) and HATU (38 mg, 0.1 mmol) in DMF (0.6 mL) was added DIEA (52 uL, 0.3 mmol) and the mixture was stirred at room temperature over night. The reaction mixture was diluted into DMSO and purified by reverse phase HPLC to give N-(5-(4-acetylpiperazin-1-yl)pyridin-2-yl)-2-(3-methoxy-4-(2-methylpyridin-4-yl)phenyl)acetamide 182. MS m/z 460.2 (M+1). $^1$H NMR 400 MHz (DMSO-d$_6$) δ 10.52 (s, 1H), 8.43 (d, 1H), 8.03 (s, 1H), 7.94 (d, 1H), 7.43-7.30 (m, 3H), 7.15 (s, 1H), 7.04 (d, 1H), 3.79 (s, 2H), 3.72 (b, 2H), 3.57 (b, 2H), 3.14 (b, 2H), 3.07 (b, 2H), 2.49 (s, 3H), 2.04 (s, 3H), 1.23 (s, 3H).

EXAMPLE 34

N-(5-(4-acetylpiperazin-1-yl)pyridin-2-yl)-2-(4-(2-methylpyridin-4-yl)phenyl)acetamide (183)

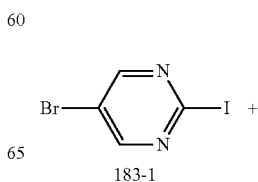

183-1

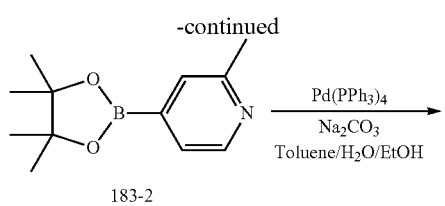

183-2

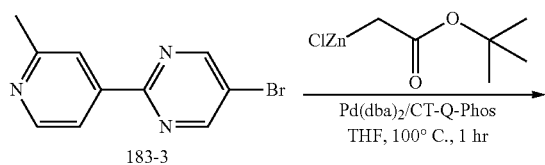

183-3

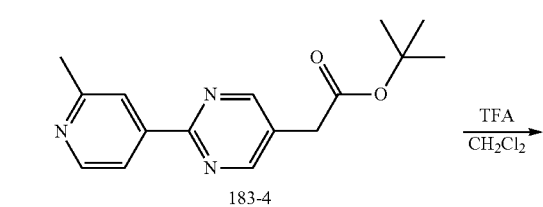

183-4

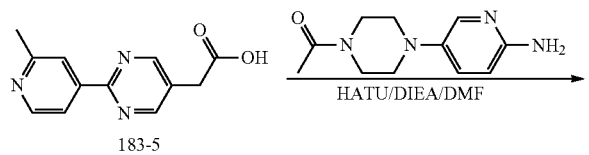

183-5

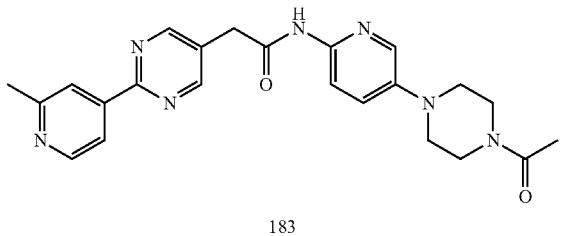

183

Step 1: To a sealed tube were added 5-bromo-2-iodopyrimidine 183-1 (114 mg, 0.4 mmol), 2-methyl-4-(4,4,5,5-tetramethyl-1,3,2-dioxaborolan-2-yl)pyridine 183-2 (88 mg, 0.4 mmol), Pd(PPh$_3$)$_4$ (23 mg, 0.02 mmol), Na$_2$CO$_3$ (170 mg, 1.6 mmol), toluene (0.4 mL), H$_2$O (0.4 mL) and ethanol (0.1 mL). The reaction mixture was stirred at 100° C. for 10 hours. After cooling to room temperature, the solvents were evaporated and the residue was redissolved in water (3 ml) and extracted with ethyl acetate (5 mL×3). The combined organic phases were dried over Na$_2$SO$_4$ and concentrated. The residue was purified by silica gel flash chromatography and eluted with 20% ethyl acetate in hexane to give 5-bromo-2-(2-methylpyridin-4-yl)pyrimidine 183-3. MS m/z 250.0 (M+1).

Step 2: To a sealed tube were added 5-bromo-2-(2-methylpyridin-4-yl)pyrimidine 183-3 (50 mg, 0.20 mmol), 0.5 M (2-tert-butoxy-2-oxoethyl) zinc(II) chloride in ether (0.60 mL, 0.30 mmol), Pd(dba)$_2$ (6 mg, 0.01 mmol), Q-phos (14 mg, 0.02 mmol) and THF (1.5 mL). The reaction mixture was bubbled with nitrogen for 1 minute and stirred at 100° C. for 1 hour. After cooling to room temperature, all the solvents were evaporated and the residue was redissolved in ethyl acetate, washed with water and brine, dried over Na$_2$SO$_4$ and concentrated to dryness by rotary evaporation. The crude product was purified by silica gel flash chromatography and eluted with 25% ethyl acetate in hexane to give tert-butyl 2-(2-(2-methylpyridin-4-yl)pyrimidin-5-yl)acetate 183-4. MS m/z 286.2 (M+1).

Step 3: A mixture of tert-butyl 2-(2-(2-methylpyridin-4-yl)pyrimidin-5-yl)acetate 183-4 (35 mg, 0.12 mmol) and TFA (0.5 mL) in DCM (3 mL) was stirred at room temperature for 2 hours. The solvents were evaporated to dryness under high vacuum. The crude product, 2-(2-(2-methylpyridin-4-yl)pyrimidin-5-yl)acetic acid 183-5, was dissolved in DMF (2 mL). 1-(4-(6-aminopyridin-3-yl)piperazin-1-yl)ethanone (35 mg, 0.16 mmol) and DIEA (107 uL, 0.61 mmol) were added to the solution before O-(7-azabenzotriazol-1-yl)-N,N,N',N'-tetramethyluroniumhexafluorophosphate (70 mg, 0.18 mmol). The mixture was stirred at room temperature overnight. The solvent was removed by rotary evaporation. The crude product was purified by reverse phase HPLC to give N-(5-(4-acetylpiperazin-1-yl)pyridin-2-yl)-2-(2-(2-methylpyridin-4-yl)pyrimidin-5-yl)acetamide 183. MS m/z 433.2 (M+1); $^1$H NMR 400 MHz (MeOD) δ 8.47(s, 2H), 8.50(d, 1H), 8.22(s, 1H), 8.14(d, 1H), 7.97(d, 1H), 7.87(d, 1H), 7.38 (dd, 1H), 3.83(s, 2H), 3.68(t, 2H), 3.64(t, 2H), 3.15(t, 2H), 3.09(t, 2H), 2.58(s, 3H), 2.09(s, 3H).

EXAMPLE 35

N-(5-(4-acetylpiperazin-1-yl)pyridin-2-yl)-2-(3-chloro-2'-methyl-2,4'-bipyridin-5-yl)acetamide (184)

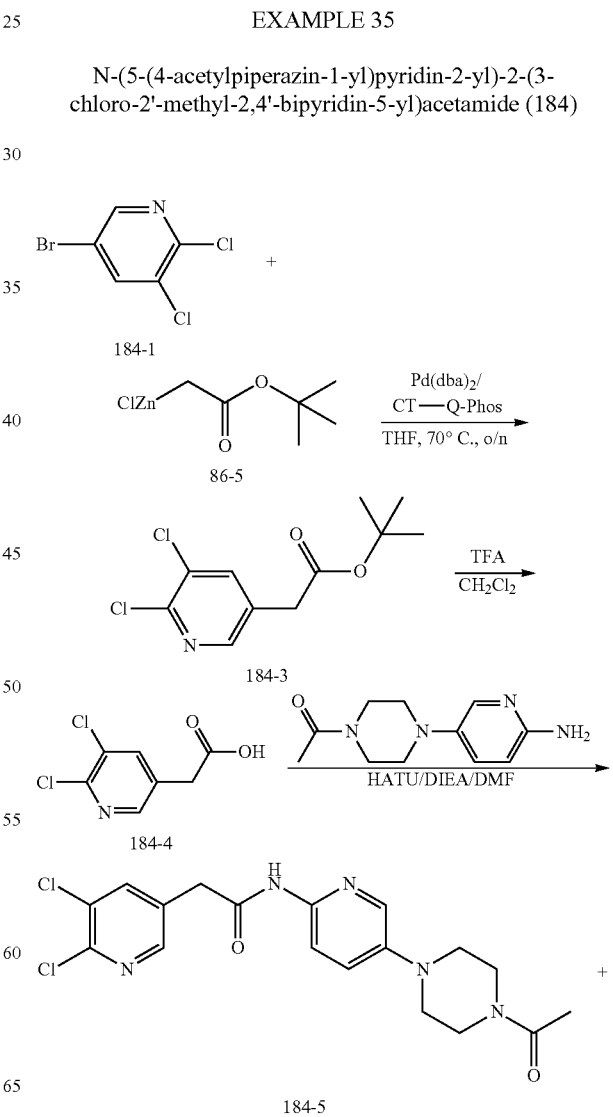

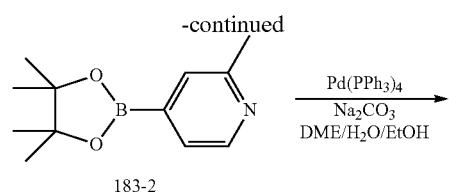

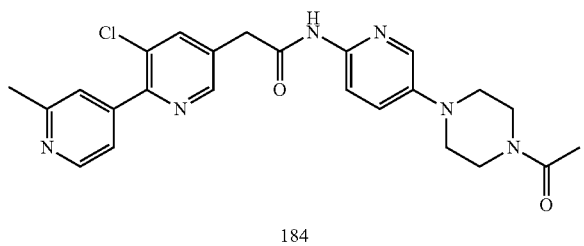

Step 1: To a sealed tube were added 5-bromo-2,3-dichloropyridine-184-1 (113 mg, 0.50 mmol), 0.5 M (2-tert-butoxy-2-oxoethyl) zinc(II) chloride 86-5 in ether (1.2 mL, 0.60 mmol), Pd(dba)$_2$ (14 mg, 0.025 mmol), Q-phos (36 mg, 0.05 mmol) and THF (1.5 mL). The reaction mixture was bubbled with nitrogen for 1 minute and stirred at 70° C. overnight. After cooling to room temperature, all the solvents were evaporated and the residue was redissolved in ethyl acetate, washed with water and brine, dried over Na$_2$SO$_4$ and concentrated to dryness by rotary evaporation. The crude product was purified by silica gel flash chromatography and eluted with 20% ethyl acetate in hexane to give tert-butyl 2-(5,6-dichloropyridin-3-yl)acetate 184-3. MS m/z 262.1 (M+1).

Step 2: A mixture of tert-butyl 2-(5,6-dichloropyridin-3-yl)acetate 184-3 (130 mg, 0.49 mmol) and TFA (0.5 mL) in DCM (3 mL) was stirred at room temperature for 2 hours. The solvents were evaporated to dryness under high vacuum. The crude product, 2-(5,6-dichloropyridin-3-yl)acetic acid 184-4, was dissolved in DMF (3 mL). 1-(4-(6-aminopyridin-3-yl)piperazin-1-yl)ethanone (128 mg, 0.58 mmol) and DIEA (435 uL, 2.5 mmol) were added to the solution before O-(7-azabenzotriazol-1-yl)-N,N,N',N'-tetramethyluronium-hexafluorophosphate (277 mg, 0.73 mmol). The mixture was stirred at room temperature overnight. The solvent was removed by rotary evaporation. The residue was purified by silica gel flash chromatography and eluted with 5% MeOH in CH$_2$Cl$_2$ to give N-(5-(4-acetylpiperazin-1-yl)pyridin-2-yl)-2-(5,6-dichloropyridin-3-yl)acetamide 184-5. MS m/z 408.1 (M+1).

Step 3: To a sealed tube were added N-(5-(4-acetylpiperazin-1-yl)pyridin-2-yl)-2-(5,6-dichloropyridin-3-yl)acetamide 184-5 (65 mg, 0.16 mmol), 2-methyl-4-(4,4,5,5-tetramethyl-1,3,2-dioxaborolan-2-yl)pyridine 183-2 (42 mg, 0.19 mmol), Pd(PPh$_3$)$_4$ (9 mg, 0.08 mmol), Na$_2$CO$_3$ (84 mg, 0.79 mmol), DME (0.5 mL), H$_2$O (0.5 mL) and ethanol (0.1 mL). The reaction mixture was stirred at 100° C. overnight. After cooling to room temperature, the solvents were removed by rotary evaporation. The crude product was purified by reverse phase HPLC to give N-(5-(4-acetylpiperazin-1-yl)pyridin-2-yl)-2-(2-(2-methylpyridin-4-yl)pyrimidin-5-yl)acetamide 184. MS m/z 465.2 (M+1); $^1$H NMR 400 MHz (MeOD) δ 8.52(d, 2H), 8.46(d, 1H), 7.98-7.95(m, 2H), 7.87(d, 1H), 7.53(s, 1H), 7.49-7.46(m, 1 Hz), 7.36(dd, 1H), 3.81(s, 2H), 3.67(t, 2H), 3.62(t, 2H), 3.13(t, 2H), 3.08(t, 2H), 2.56(s, 3H), 2.08(s, 3H).

EXAMPLE 36

N-(5-(4-acetylpiperazin-1-yl)pyridin-2-yl)-2-(3-cyano-2'-methyl-2,4'-bipyridin-5-yl)acetamide (188)

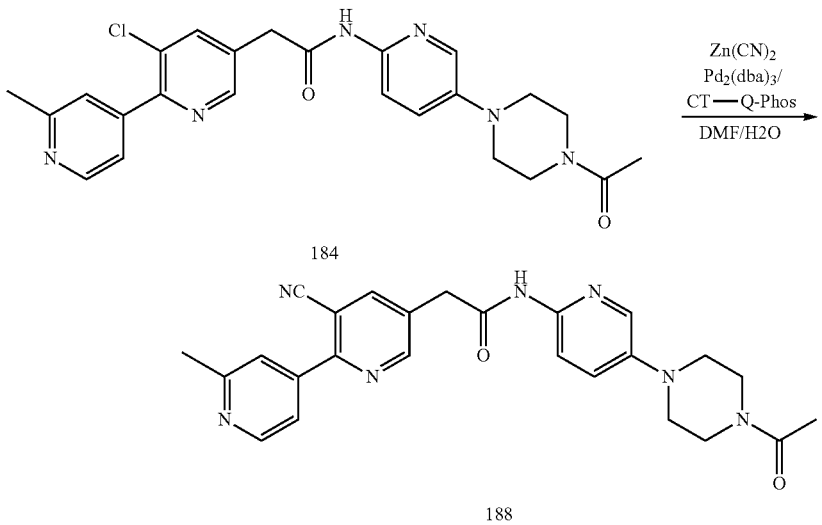

Step 1: To a sealed tube were added N-(5-(4-acetylpiperazin-1-yl)pyridin-2-yl)-2-(3-chloro-2'-methyl-2,4'-bipyridin-5-yl)acetamide 184 (46 mg, 0.10 mmol), zinc cyanide (14 mg, 0.12 mmol), Pd$_2$(dba)$_3$ (9 mg, 0.010 mmol), Q-phos (9 mg, 0.022 mmol) and 1 ml DMF/H$_2$O (99/1, v/v). The reaction mixture was bubbled with nitrogen for 1 minute and stirred at 130° C. overnight. After cooling to room temperature, the solvents were evaporated and the crude product was purified by reverse phase HPLC to give N-(5-(4-acetylpiperazin-1-yl)pyridin-2-yl)-2-(3-cyano-2'-methyl-2,4'-bipyridin-5-yl)acetamide 188. MS m/z 456.2 (M+1); $^1$H NMR 400 MHz (MeOD) δ 8.85(d, 1H), 8.56(d, 1H), 8.28(d, 1H), 7.98(s, 1 Hz), 7.88(d, 1H), 7.78(s, 1H), 7.73-7.70(m, 1 Hz), 7.39(dd, 1H), 3.89(s, 2H), 3.69(t, 2H), 3.65(t, 2H), 3.16(t, 2H), 3.11(t, 2H), 2.61(s, 3H), 2.09(s, 3H).

EXAMPLE 37

N-(5-(4-acetylpiperazin-1-yl)pyridin-2-yl)-2-(2'-methyl-3-(trifluoromethyl)-2,4'-bipyridin-5-yl)acetamide (189)

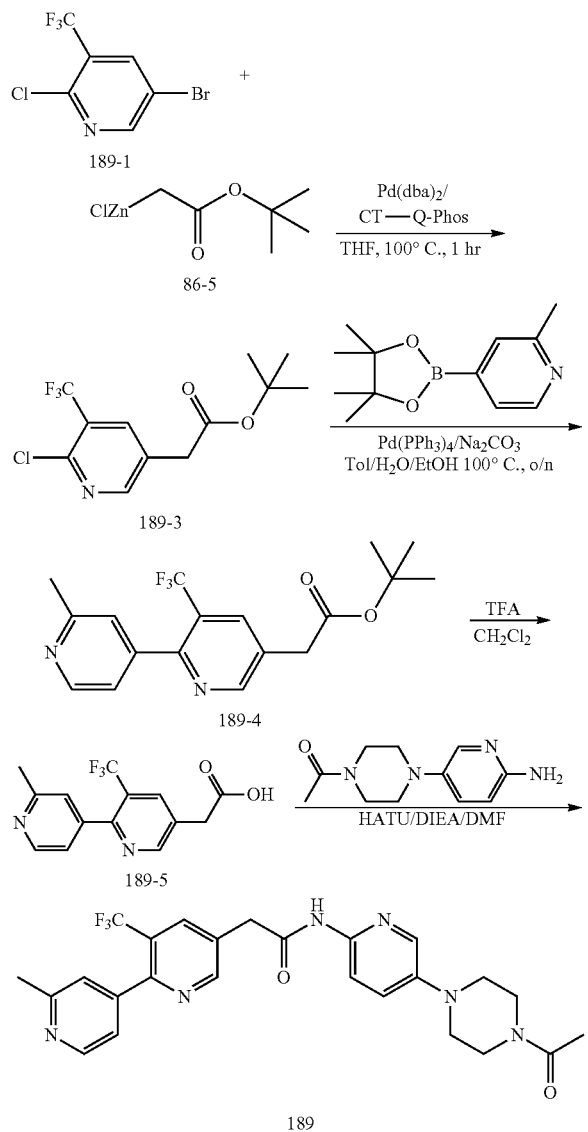

Step 1: To a sealed tube were added 5-bromo-2-chloro-3-(trifluoromethyl)pyridine 189-1 (170 mg, 0.65 mmol), 0.5 M (2-tert-butoxy-2-oxoethyl) zinc(II) chloride 86-5 in ether (1.57 mL, 0.78 mmol), Pd(dba)$_2$ (19 mg, 0.03 mmol), Q-phos (46 mg, 0.06 mmol) and THF (3 mL). The reaction mixture was bubbled with nitrogen for 1 minute and stirred at 100° C. for 1 hour. After cooling to room temperature, all the solvents were evaporated and the residue was redissolved in ethyl acetate, washed with water and brine, dried over Na$_2$SO$_4$ and concentrated to dryness by rotary evaporation. The crude product was purified by silica gel flash chromatography and eluted with 20% ethyl acetate in hexane to give tert-butyl 2-(6-chloro-5-(trifluoromethyl)pyridin-3-yl)acetate 189-3. MS m/z 296.1 (M+1).

Step 2: To a sealed tube were added tert-butyl 2-(6-chloro-5-(trifluoromethyl) pyridin-3-yl)acetate 189-3 (318 mg, 1.08 mmol), 2-methyl-4-(4,4,5,5-tetramethyl-1,3,2-dioxaborolan-2-yl)pyridine (283 mg, 1.29 mmol), Pd(PPh$_3$)$_4$ (62 mg, 0.05 mmol), Na$_2$CO$_3$ (342 mg, 3.22 mmol), Toluene (3 mL), H$_2$O (3 mL) and ethanol (0.75 mL). The reaction mixture was stirred at 100° C. overnight. After cooling to room temperature, the solvents were evaporated and the residue was redissolved in water (10 ml) and extracted with ethyl acetate (10 mL×3). The combined organic phases were dried over Na$_2$SO$_4$, and concentrated. The residue was purified by silica gel flash chromatography and eluted with 30% ethyl acetate in hexane to tert-butyl 2-(2'-methyl-3-(trifluoromethyl)-2,4'-bipyridin-5-yl)acetate 189-4. MS m/z 35.2 (M+1).

Step 3: A mixture of tert-butyl 2-(2'-methyl-3-(trifluoromethyl)-2,4'-bipyridin-5-yl)acetate 189-4 (230 mg, 0.65 mmol) and TFA (1 mL) in DCM (5 mL) was stirred at room temperature for 5 hours. The solvents were evaporated to dryness under high vacuum. The crude product, 2-(2'-methyl-3-(trifluoromethyl)-2,4'-bipyridin-5-yl)acetic acid 189-5, was dissolved in DMF (4 mL). 1-(4-(6-aminopyridin-3-yl)piperazin-1-yl)ethanone (173 mg, 0.78 mmol) and DIEA (910 uL, 5.22 mmol) were added to the solution before O-(7-azabenzotriazol-1-yl)-N,N,N',N'-tetramethyluroniumhexafluorophosphate (372 mg, 0.98 mmol). The mixture was stirred at room temperature overnight. The solvent was removed by rotary evaporation. The crude product was purified by reverse phase HPLC to give N-(5-(4-acetylpiperazin-1-yl)pyridin-2-yl)-2-(2'-methyl-3-(trifluoromethyl)-2,4'-bipyridin-5-yl)acetamide 189. MS m/z 499.2 (M+1); $^1$H NMR 400 MHz (MeOD) δ 8.78(s, 1H), 8.48(d, 1H), 8.26(s, 1H), 7.99(s, 1H), 7.88(d, 1H), 7.42-7.36(m, 2H), 7.31(d, 1H), 3.92(s, 2H), 3.69(t, 2H), 3.65(t, 2H), 3.16(t, 2H), 3.11(t, 2H), 2.57(s, 3H), 2.09(s, 3H).

EXAMPLE 38

N-(5-(4-acetylpiperazin-1-yl)pyridin-2-yl)-2-(3-fluoro-2'-methyl-2,4'-bipyridin-5-yl)acetamide (190)

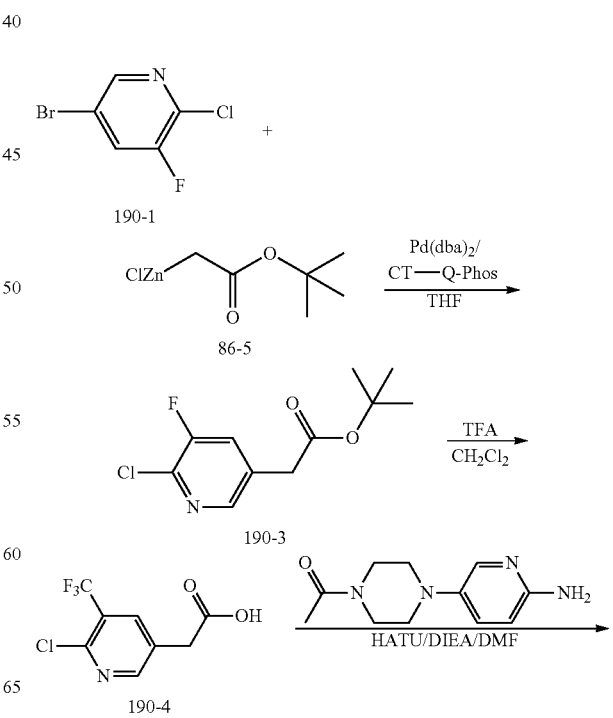

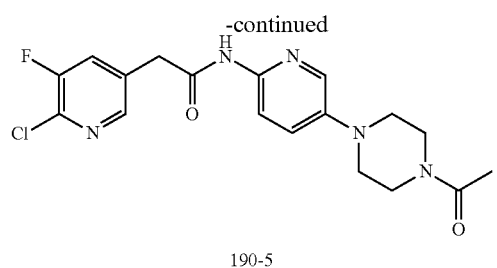

190-5

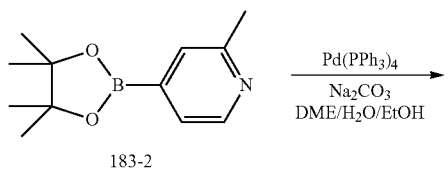

183-2

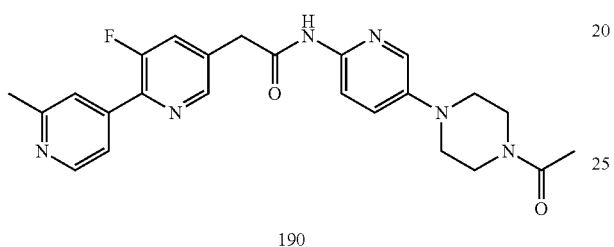

190

Step 1: To a sealed tube were added 5-bromo-2-chloro-3-fluoropyridine 190-1 (210 mg, 1.0 mmol), 0.5 M (2-tert-butoxy-2-oxoethyl) zinc(II) chloride 86-5 in ether (2.4 mL, 1.2 mmol), Pd(dba)$_2$ (29 mg, 0.005 mmol), Q-phos (71 mg, 0.10 mmol) and THF (3 mL). The reaction mixture was bubbled with nitrogen for 1 minute and stirred at 100° C. for 1 hour. After cooling to room temperature, all the solvents were evaporated and the residue was redissolved in ethyl acetate, washed with water and brine, dried over Na$_2$SO$_4$ and concentrated to dryness by rotary evaporation. The crude product was purified by silica gel flash chromatography and eluted with 20% ethyl acetate in hexane to give tert-butyl 2-(6-chloro-5-fluoropyridin-3-yl)acetate 190-3. MS m/z 246.1 (M+1).

Step 2: A mixture of tert-butyl 2-(6-chloro-5-fluoropyridin-3-yl)acetate 190-3 (123 mg, 0.50 mmol) and TFA (0.5 mL) in DCM (3 mL) was stirred at room temperature for 2 hours. The solvents were evaporated to dryness under high vacuum. The crude product, 2-(6-chloro-5-fluoropyridin-3-yl)acetic acid 190-4, was dissolved in DMF (3 mL). 1-(4-(6-aminopyridin-3-yl)piperazin-1-yl)ethanone (110 mg, 0.50 mmol) and DIEA (500 uL, 2.87 mmol) were added to the solution before O-(7-azabenzotriazol-1-yl)-N,N,N',N'-tetramethyluroniumhexafluorophosphate (285 mg, 0.75 mmol). The mixture was stirred at room temperature overnight. The solvent was removed by rotary evaporation. The residue was purified by silica gel flash chromatography and eluted with 5% MeOH in CH$_2$Cl$_2$ to give N-(5-(4-acetylpiperazin-1-yl)pyridin-2-yl)-2-(6-chloro-5-fluoropyridin-3-yl)acetamide 190-5. MS m/z 392.2 (M+1).

Step 3: To a sealed tube were added N-(5-(4-acetylpiperazin-1-yl)pyridin-2-yl)-2-(6-chloro-5-fluoropyridin-3-yl)acetamide 190-5 (59 mg, 0.15 mmol), 2-methyl-4-(4,4,5,5-tetramethyl-1,3,2-dioxaborolan-2-yl)pyridine 183-2 (49 mg, 0.23 mmol), Pd(PPh$_3$)$_4$ (9 mg, 0.08 mmol), Na$_2$CO$_3$ (79 mg, 0.75 mmol), Toluene (0.8 mL), H$_2$O (0.8 mL) and ethanol (0.2 mL). The reaction mixture was stirred at 100° C. overnight. After cooling to room temperature, the solvents were removed by rotary evaporation. The crude product was purified by reverse phase HPLC to give N-(5-(4-acetylpiperazin-1-yl)pyridin-2-yl)-2-(3-fluoro-2'-methyl-2,4'-bipyridin-5-yl)acetamide 190. MS m/z 449.2 (M+1); $^1$H NMR 400 MHz (MeOD) δ 8.48-8.46(m, 2H), 7.96(s, 1H), 7.87(d, 1H), 7.81 (s, 1H), 7.75-7.69(m, 2 Hz), 7.36(dd, 1H), 3.84(s, 2H), 3.67(t, 2H), 3.62(t, 2H), 3.13(t, 2H), 3.08(t, 2H), 2.56(s, 3H), 2.08(s, 3H).

EXAMPLE 39

N-(5-(4-acetylpiperazin-1-yl)pyridin-2-yl)-2-(2-fluoro-5-methyl-4-(2-methylpyridin-4-yl)phenyl)acetamide (191)

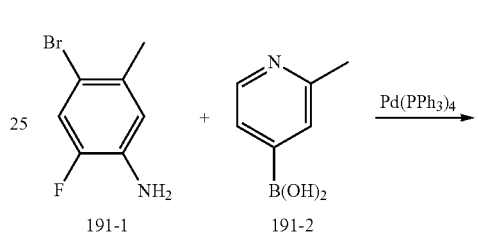

191-1      191-2

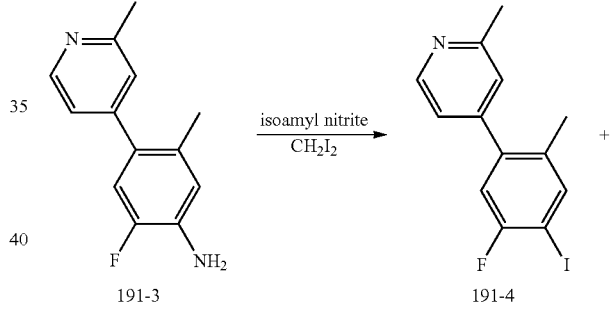

191-3      191-4

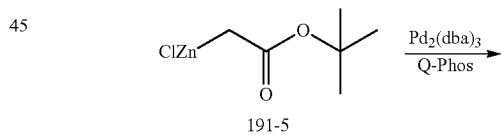

191-5

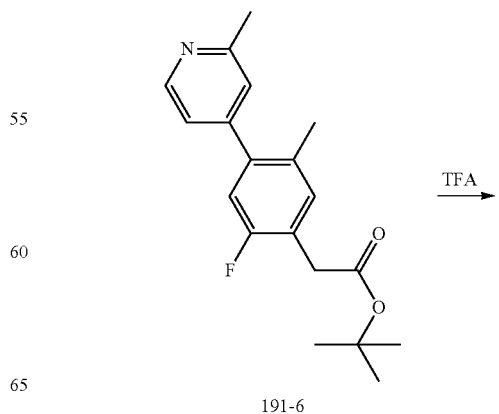

191-6

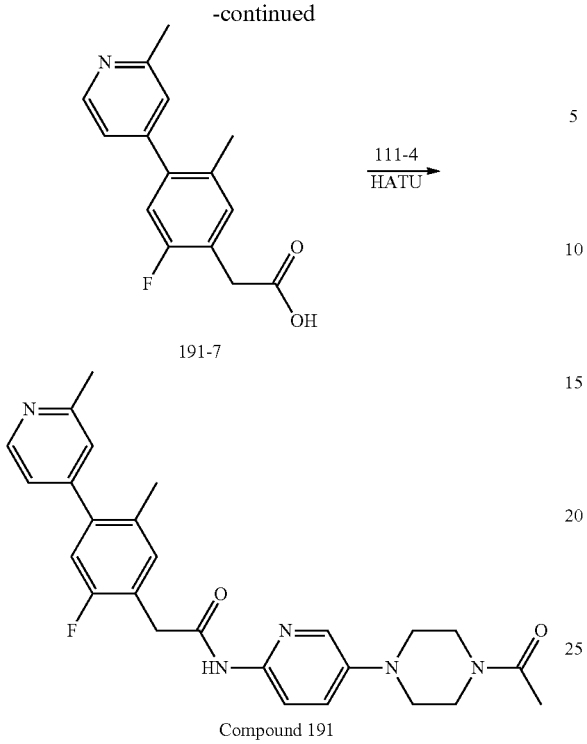

Step 1: To a round bottom flask charged with 4-bromo-2-fluoro-5-methylaniline 191-1 (2.04 g, 10 mmol), 2-methylpyridin-4-ylboronic acid 191-2 (1.37 g, 10 mmol) and Pd(PPh₃)₄ (0.4 g, 0.35 mmol) was added toluene (30 mL), ethanol (10 mL) and saturated sodium carbonate (10 mL). The flask was flushed with nitrogen and the reaction was heated to reflux for 10 hours. After the reaction was cooled down to room temperature, it was partitioned between ethyl acetate and saturated NaHCO₃ and the organic phase was washed with brine and dried over Na₂SO₄. The solvent was removed by rotary evaporation and the residue was purified by silica gel flash chromatography, eluted with 50% ethyl acetate in hexane to give 2-fluoro-5-methyl-4-(2-methylpyridin-4-yl)aniline 191-3. MS m/z 217.1 (M+1).

Step 2: To the solution of 2-fluoro-5-methyl-4-(2-methylpyridin-4-yl)aniline 191-3 (1.02 g, 4.7 mmol) in CH₂I₂ (16 mL) was added isoamyl nitrite (6 mL) slowly at −10° C. After 20 minutes, the reaction was heated to 100° C. for 2 hours. The solvent was removed by rotary evaporation and the residue was dissolved in ethyl acetate and washed with Na2S2O5, brine and taken to dryness by rotary evaporation. The residue was purified by silica gel flash chromatography, eluted with 40% ethyl acetate in hexane to give 4-(5-fluoro-4-iodo-2-methylphenyl)-2-methylpyridine 191-4. MS m/z 328.10 (M+1).

Step 3: To a seal tube charged with 4-(5-fluoro-4-iodo-2-methylphenyl)-2-methylpyridine 191-4 (200 mg, 0.6 mmol), Pd2(dba)₃ (28 mg, 0.03 mmol), and Q-Phos (21 mg, 0.03 mmol) was added anhydrous THF (2.5 mL). The reaction vessel was flushed with nitrogen and (2-tert-butoxy-2-oxoethyl)zinc(II) chloride (0.5 M in ether, 1.34 mL, 0.67 mmol) was added subsequently. The reaction was heated to 70° C. for 12 hours. The solvent was removed by rotary evaporation and the residue was purified by silica gel flash chromatography, eluted with 50% ethyl acetate in hexane to give tert-butyl 2-(2-fluoro-5-methyl-4-(2-methylpyridin-4-yl)phenyl)acetate 191-5. MS m/z 316.10 (M+1).

Step 4: To the solution of tert-butyl 2-(2-fluoro-5-methyl-4-(2-methylpyridin-4-yl)phenyl)acetate 191-5 (80 mg, 0.37 mmol) in DCM (2 mL) was added TFA (2 mL). The reaction was stirred at room temperature for 2 hours. The solvent and TFA was removed by rotary evaporation to give 2-(2-fluoro-5-methyl-4-(2-methylpyridin-4-yl)phenyl)acetic acid 191-6. The product was used for next step without further purification.

Step 5: To a mixture of 2-(2-fluoro-5-methyl-4-(2-methylpyridin-4-yl)phenyl)acetic acid 191-6 (35 mg, 0.13 mmol), 1-(4-(6-aminopyridin-3-yl)piperazin-1-yl)ethanone 111-4 (30 mg, 0.13 mmol) and HATU (50 mg, 0.13 mmol) in DMF (1.0 mL) was added DIEA (67 uL, 0.4 mmol) and the mixture was stirred at room temperature over night. The reaction mixture was diluted into DMSO and purified by reverse phase HPLC to give N-(5-(4-acetylpiperazin-1-yl)pyridin-2-yl)-2-(2-fluoro-5-methyl-4-(2-methylpyridin-4-yl)phenyl)acetamide 191. MS m/z 462.2 (M+1). ¹H NMR 400 MHz (DMSO-d₆) δ10.51 (s, 1H), 8.49 (d, 1H), 8.03 (s, 1H), 7.91 (d, 1H), 7.43 (m, 1H), 7.32 (d, 1H), 7.28 (s, 1H), 7.21 (d, 1H), 7.08 (d, 1H), 3.77 (s, 2H), 3.53 (b, 4H), 3.14 (b, 2H), 3.07 (b, 2H), 2.55 (s, 3H), 2.20 (s, 3H), 2.04 (s, 3H).

EXAMPLE 40

N-(5-(4-acetylpiperazin-1-yl)pyridin-2-yl)-2-(4-(2-methylpyrimidin-4-yl)-3-(trifluoromethyl)phenyl) acetamide (192)

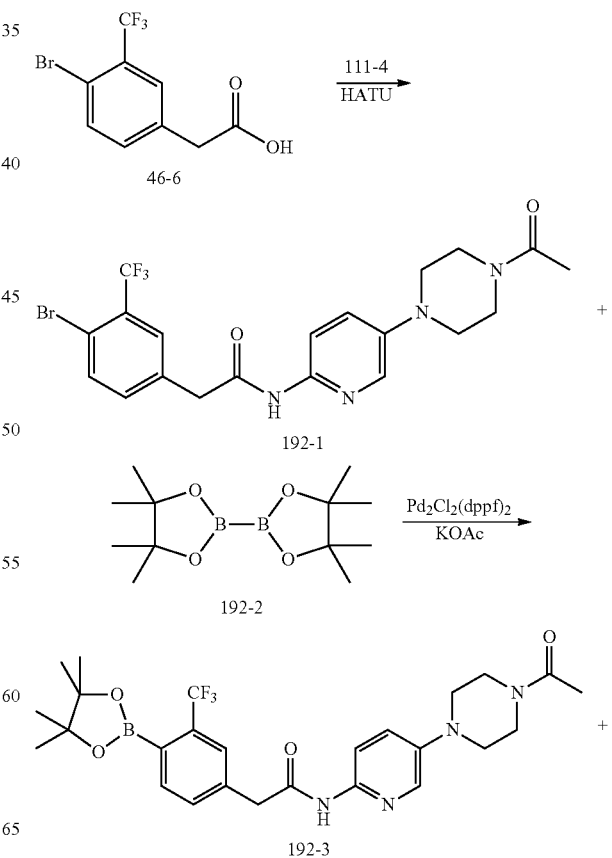

EXAMPLE 41

N-(5-(4-acetylpiperazin-1-yl)pyridin-2-yl)-2-(2'-fluoro-3-methyl-2,4'-bipyridin-5-yl)acetamide (193)

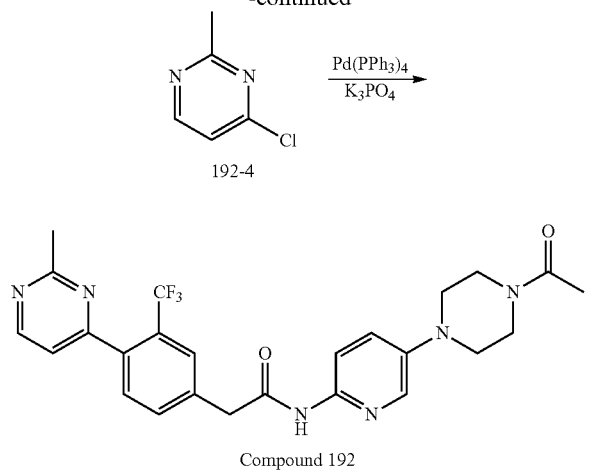

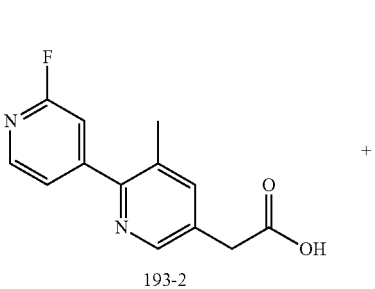

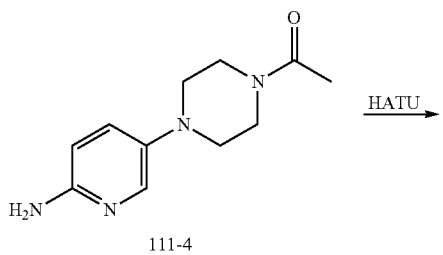

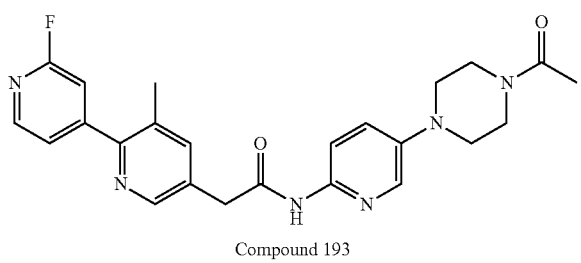

Compound 193

Step 1: To a mixture of 2-(4-bromo-3-(trifluoromethyl)phenyl)acetic acid 46-6 (564 mg, 2.0 mmol), 1-(4-(6-aminopyridin-3-yl)piperazin-1-yl)ethanone 111-4 (440 mg, 2.0 mmol) and HATU (798 mg, 2.1 mmol) in DMF (6 mL) was added DIEA (1.04 mL, 6.0 mmol) and the mixture was stirred at room temperature over night. The reaction mixture was partitioned between ethyl acetate and water. The organic phase was washed with brine and dried over $Na_2SO_4$ and the solvent was evaporated. The residue was subject to silica gel flash chromatography to give N-(5-(4-acetylpiperazin-1-yl)pyridin-2-yl)-2-(4-bromo-3-(trifluoromethyl)phenyl)acetamide 192-1 (920 mg, 95%). MS m/z 485.1 (M+1).

Step 2: A mixture of N-(5-(4-acetylpiperazin-1-yl)pyridin-2-yl)-2-(4-bromo-3-(trifluoromethyl)phenyl)acetamide 192-1 (0.48 g, 1 mmol), 4,4,4',4',5,5,5',5'-octamethyl-2,2'-bi(1,3,2-dioxaborolane) 192-2 (0.51 g, 2 mmol), KOAc (0.29 g, 3 mmol) $PdCl_2(dppf)_2 \cdot CH_2Cl_2$ (82 mg, 0.1 mmol) in DMSO (5 mL) was flushed with nitrogen and heated to 100° C. for 2 hours. The reaction mixture was partitioned between ethyl acetate and water. The organic phase was washed with brine and dried over $Na_2SO_4$. The solvent was evaporated and the residue was subject to silica gel flash chromatography to give N-(5-(4-acetylpiperazin-1-yl)pyridin-2-yl)-2-(4-(4,4,5,5-tetramethyl-1,3,2-dioxaborolan-2-yl)-3-(trifluoromethyl)phenyl)acetamide 192-3. MS m/z 533.2 (M+1).

Step 3: A mixture of N-(5-(4-acetylpiperazin-1-yl)pyridin-2-yl)-2-(4-(4,4,5,5-tetramethyl-1,3,2-dioxaborolan-2-yl)-3-(trifluoromethyl)phenyl)acetamide 192-3 (53 mg, 0.1 mmol), 4-chloro-2-methylpyrimidine 192-4 (18 mg, 0.14 mmol) $Pd(PPh_3)_4$ (11 mg, 0.01 mmol) and $K_3PO_4$ (42 mg, 0.2 mmol) in dioaxane (1.0 mL) was flushed with nitrogen and heated to 100° C. for 2 hours. The salt was removed by filtration and the filtrate was taken to dryness by rotary evaporation. The residue was purified by reverse phase HPLC to give N-(5-(4-acetylpiperazin-1-yl)pyridin-2-yl)-2-(4-(2-methylpyrimidin-4-yl)-3-(trifluoromethyl)phenyl)acetamide 192. MS m/z 499.2 (M+1). $^1$H NMR 400 MHz (DMSO-$d_6$) δ0.58 (s, 1H), 8.77 (d, 1H), 8.02 (s, 1H), 7.89 (m, 2H), 7.73 (d, 1H), 7.54 (d, 1H), 7.42 (m, 2H), 3.76 (s, 2H), 3.66 (b, 4H), 3.14 (b, 2H), 3.07 (b, 2H), 2.64 (s, 3H), 2.03 (s, 3H).

Step 1: To a reaction vial was added 2-(6-chloro-5-methylpyridin-3-yl)acetic acid 74-4 (185 mg, 1 mmol), 2-fluoropyridin-4-ylboronic acid 193-1 (220 mg, 1.5 mmol), $Pd(OAc)_2$ (12 mg, 0.05 mmol), S-Phos (41 mg, 0.1 mmol) and $K_3PO_4$ (636 mg, 3 mmol) in 1 mL 2-butanol. The reaction was heated to 100° C. and stirred for 2 hours. The reaction was cooled down to room temperature and then diluted to DMSO. The reaction mixture was filtered and the filtrate was purified by reverse-phase HPLC to give 2-(2'-fluoro-3-methyl-2,4'-bipyridin-5-yl)acetic acid 193-2 as white solid. MS m/z 247.2 (M+1).

Step 2: To a reaction vial was added 2-(2'-fluoro-3-methyl-2,4'-bipyridin-5-yl)acetic acid 193-2 (60 mg, 0.17 mmol), 1-(4-(6-aminopyridin-3-yl)piperazin-1-yl)ethanone 111-4 (50 mg, 0.22 mmol), O-(7-azabenzotriazol-1-yl)-N,N,N',N'-tetramethyluroniumhexafluorophosphate (HATU) (115 mg, 0.3 mmol) and DIEA (104 μL, 0.58 mmol) in DMF (1 mL) at room temperature. The mixture was stirred at room temperature for 2 hours. The reaction was diluted with DMSO and then purified by reverse-phase HPLC to give N-(5-(4-acetylpiperazin-1-yl)pyridin-2-yl)-2-(2'-fluoro-3-methyl-2,4'-bipyridin-5-yl)acetamide 193 as white solid. MS m/z 449.2 (M+1); $^1$H NMR 400 MHz (DMSO-$d_6$) δ10.58 (s, 1H), 8.42 (d, 1H, J=1.6 Hz), 8.28 (d, 1H, J=5.2 Hz), 7.98 (d, 1H, J=2.8 Hz), 7.87 (d, 1H, J=9.2 Hz), 7.67 (d, 1H, J=1.6 Hz), 7.50-7.48 (m, 1H), 7.37 (dd, 1H, J1=9.2 Hz, J2=3.2 Hz), 7.30 (s, 1H), 3.71 (s, 2H), 3.50 (b, 4H), 3.09 (t, 2H, J=5.2 Hz), 3.02 (t, 2H, J=5.2 Hz), 2.30 (s, 3H), 1.97 (s, 3H).

EXAMPLE 42

N-(5-(4-acetylpiperazin-1-yl)pyridin-2-yl)-2-(2',3-difluoro-2,4'-bipyridin-5-yl)acetamide (194)

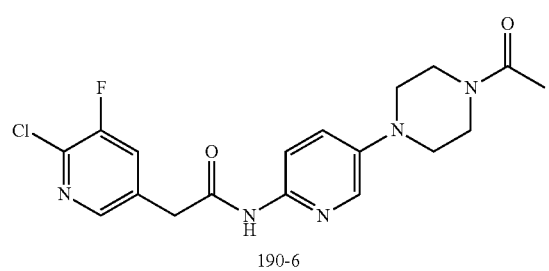

190-6

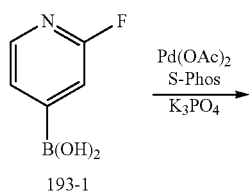

193-1

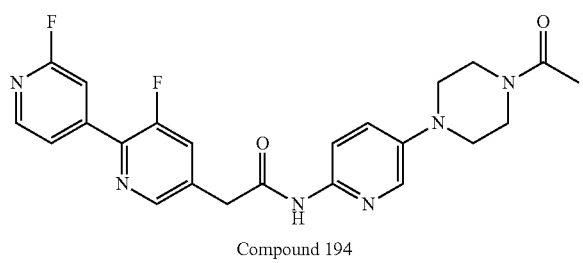

Compound 194

To a reaction vial was added N-(5-(4-acetylpiperazin-1-yl)pyridin-2-yl)-2-(6-chloro-5-fluoropyridin-3-yl)acetamide 190-6 (66 mg, 0.17 mmol), 2-fluoropyridin-4-ylboronic acid 193-1 (35 mg, 0.25 mmol), Pd(OAc)$_2$ (2 mg, 0.009 mmol), S-Phos (7 mg, 0.017 mmol) and K$_3$PO$_4$ (108 mg, 0.51 mmol) in 2-butanol (0.3 mL). The reaction was heated to 100° C. and stirred for 2 hours. The reaction was cooled down to room temperature and then diluted to DMSO. The reaction mixture was filtered and the filtrate was purified by reverse-phase HPLC to give N-(5-(4-acetylpiperazin-1-yl)pyridin-2-yl)-2-(2',3-difluoro-2,4'-bipyridin-5-yl)acetamide 194. MS m/z 453.1 (M+1).

EXAMPLE 43

N-(5-(4-acetylpiperazin-1-yl)pyridin-2-yl)-2-(4-(5-fluoropyrimidin-4-yl)phenyl)acetamide (196)

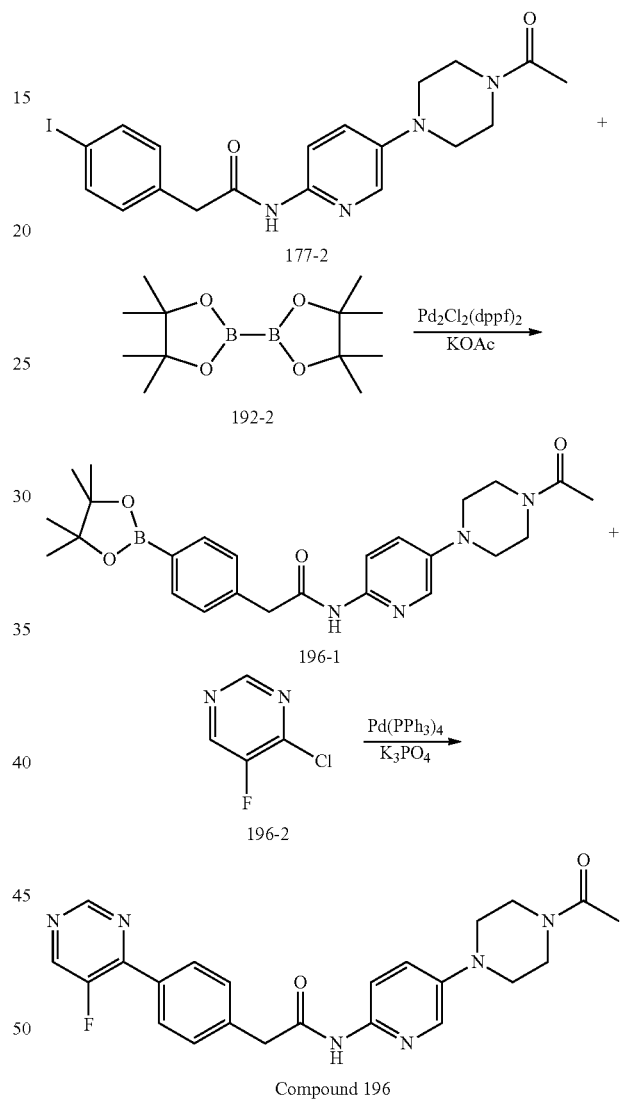

Step 1: A mixture of N-(5-(4-acetylpiperazin-1-yl)pyridin-2-yl)-2-(4-iodophenyl)acetamide 177-2 (398 mg, 0.86 mmol), 4,4,4',4',5,5,5',5'-octamethyl-2,2'-bi(1,3,2-dioxaborolane) 192-2 (380 mg, 1.5 mmol), KOAc (270 mg, 2.7 mmol) PdCl$_2$(dppf$_2$.CH$_2$Cl$_2$ (70 mg, 0.086 mmol) in DMSO (5 mL) was flushed with nitrogen and heated to 90° C. for 2 hours. The reaction mixture was partitioned between ethyl acetate and water. The organic phase was washed with brine and dried over Na$_2$SO$_4$. The solvent was evaporated and the residue was subject to silica gel flash chromatography to give N-(5-(4-acetylpiperazin-1-yl)pyridin-2-yl)-2-(4-(4,4,5,5-tetramethyl-1,3,2-dioxaborolan-2-yl)phenyl)acetamide 196-1. MS m/z 465.2 (M+1).

Step 2: A mixture of N-(5-(4-acetylpiperazin-1-yl)pyridin-2-yl)-2-(4-(4,4,5,5-tetramethyl-1,3,2-dioxaborolan-2-yl)phenyl)acetamide 196-1 (30 mg, 0.065 mmol), 4-chloro-5-fluoropyrimidine 196-2 (28 mg, 0.21 mmol) Pd(PPh$_3$)$_4$ (12 mg, 0.01 mmol) and K$_3$PO$_4$ (90 mg, 0.424 mmol) in dioaxane (0.6 mL) was flushed with nitrogen and heated to 110° C. for 2 hours. The salt was removed by filtration and the filtrate was taken to dryness by rotary evaporation. The residue was purified by reverse phase HPLC to give N-(5-(4-acetylpiperazin-1-yl)pyridin-2-yl)-2-(4-(5-fluoropyrimidin-4-yl)phenyl)acetamide 196. MS m/z 435.10 (M+1). $^1$H NMR 400 MHz (DMSO-d$_6$) δ10.54 (s, 1H), 9.06 (d, 1H), 8.90 (d, 1H), 7.98 (m, 3H), 7.86 (d, 1H), 7.49 (d, 2H), 7.37 (m, 1H), 3.73 (s, 2H), 3.50 (m, 4H), 3.09 (t, 2H), 3.02 (t, 2H), 1.97 (s, 3H).

EXAMPLE 44

N-(5-(4-acetylpiperazin-1-yl)pyridin-2-yl)-2-(2'-methyl-3-(methylsulfonyl)-2,4'-bipyridin-5-yl)acetamide (197)

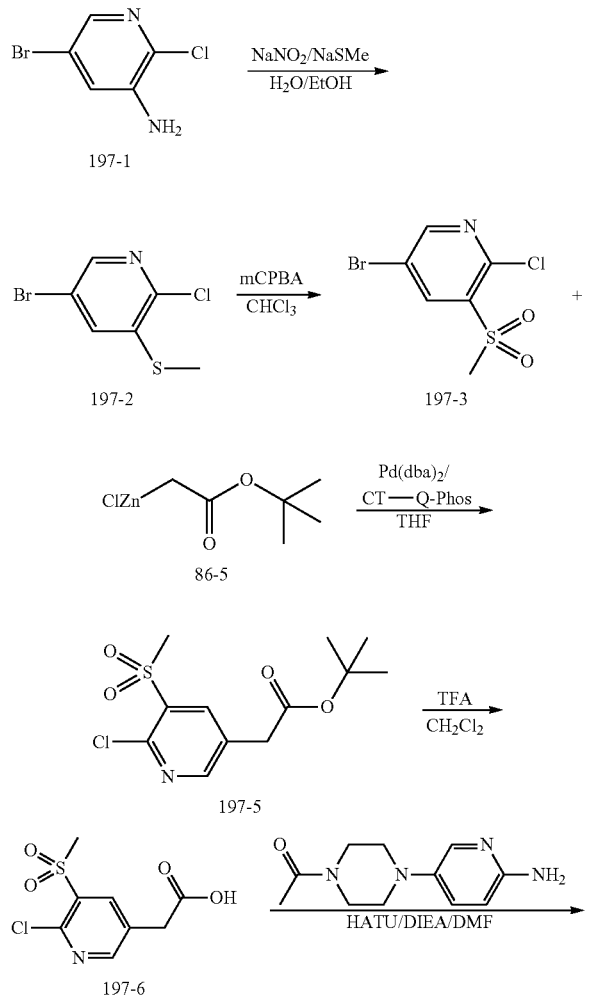

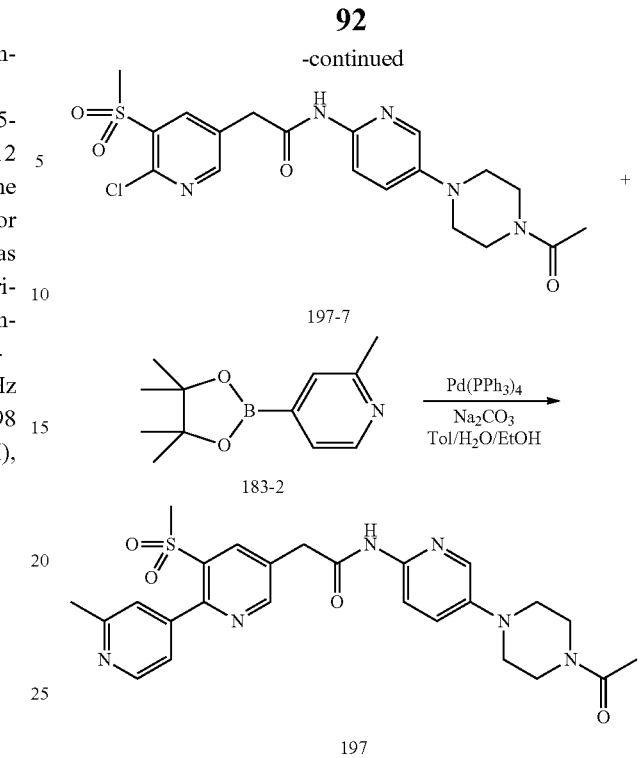

Step 1: 5-bromo-2-chloro-3-(methylsulfonyl)pyridine 197-3 was synthesized according to the literature procedure from 5-bromo-2-chloropyridin-3-amine 197-1.

Step 2: To a sealed tube were added 5-bromo-2-chloro-3-(methylsulfonyl)pyridine 197-3 (60 mg, 0.22 mmol), 0.5 M (2-tert-butoxy-2-oxoethyl) zinc(II) chloride 86-5 in ether (0.54 mL, 0.27 mmol), Pd(dba)$_2$ (6.4 mg, 0.001 mmol), Q-phos (16 mg, 0.02 mmol) and THF (1 mL). The reaction mixture was bubbled with nitrogen for 1 minute and stirred at 100° C. for 1 hour. After cooling to room temperature, all the solvents were evaporated and the residue was redissolved in ethyl acetate, washed with water and brine, dried over Na$_2$SO$_4$ and concentrated to dryness by rotary evaporation. The crude product was purified by silica gel flash chromatography and eluted with 20% ethyl acetate in hexane to give tert-butyl 2-(6-chloro-5-(methylsulfonyl)pyridin-3-yl)acetate 197-5. MS m/z 306.1 (M+1).

Step 3: A mixture of tert-butyl 2-(6-chloro-5-(methylsulfonyl)pyridin-3-yl)acetate 197-5 (40 mg, 0.13 mmol) and TFA (0.5 mL) in DCM (3 mL) was stirred at room temperature for 2 hours. The solvents were evaporated to dryness under high vacuum. The crude product, 2-(6-chloro-5-(methylsulfonyl)pyridin-3-yl)acetic acid 197-6, was dissolved in DMF (2 mL). 1-(4-(6-aminopyridin-3-yl)piperazin-1-yl) ethanone (35 mg, 0.16 mmol) and DIEA (114 uL, 0.65 mmol) were added to the solution before O-(7-azabenzotriazol-1-yl)-N,N,N',N'-tetramethyluroniumhexafluorophosphate (75 mg, 0.20 mmol). The mixture was stirred at room temperature overnight. The solvent was removed by rotary evaporation. The residue was purified by silica gel flash chromatography and eluted with 5% MeOH in CH$_2$Cl$_2$ to give N-(5-(4-acetylpiperazin-1-yl)pyridin-2-yl)-2-(6-chloro-5-(methylsulfonyl)pyridin-3-yl)acetamide 197-7. MS m/z 452.1 (M+1).

Step 4: To a sealed tube were added N-(5-(4-acetylpiperazin-1-yl)pyridin-2-yl)-2-(6-chloro-5-(methylsulfonyl)pyridin-3-yl)acetamide 197-7 (30 mg, 0.07 mmol), 2-methyl-4-(4,4,5,5-tetramethyl-1,3,2-dioxaborolan-2-yl)pyridine 183-2

(22 mg, 0.10 mmol), Pd(PPh$_3$)$_4$ (4 mg, 0.003 mmol), Na$_2$CO$_3$ (22 mg, 0.20 mmol), Toluene (0.4 mL), H$_2$O (0.4 mL) and ethanol (0.1 mL). The reaction mixture was stirred at 100° C. overnight. After cooling to room temperature, the solvents were removed by rotary evaporation. The crude product was purified by reverse phase HPLC to give N-(5-(4-acetylpiperazin-1-yl)pyridin-2-yl)-2-(2'-methyl-3-(methylsulfonyl)-2,4'-bipyridin-5-yl)acetamide 197. MS m/z 509.2 (M+1); $^1$H NMR 400 MHz (MeOD) δ 8.81(d, 1H), 8.52(d, 1H), 8.49(d, 1H), 7.97(s, 1H), 7.87(d, 1H), 7.47(s, 1H) 7.41(dd, 1H), 7.37 (dd, 1H), 3.95(s, 2H), 3.68(t, 2H), 3.63(t, 2H), 3.15(t, 2H), 3.09(t, 2H), 2.92(s, 3H), 2.57(s, 3H), 2.09(s, 3H).

EXAMPLE 45

N-(5-(4-acetylpiperazin-1-yl)pyridin-2-yl)-2-(4-(6-methylpyrimidin-4-yl)phenyl)acetamide (198)

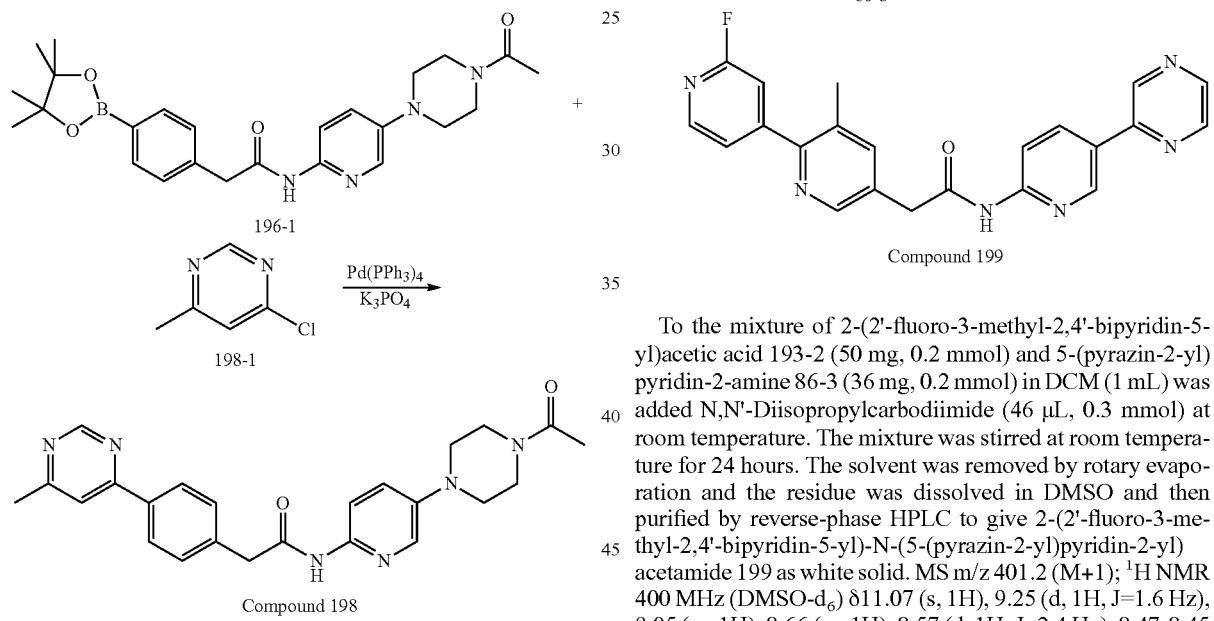

A mixture of N-(5-(4-acetylpiperazin-1-yl)pyridin-2-yl)-2-(4-(4,4,5,5-tetramethyl-1,3,2-dioxaborolan-2-yl)phenyl)acetamide 196-1 (20 mg, 0.04 mmol), 4-chloro-6-methylpyrimidine 198-1 (8 mg, 0.06 mmol) Pd(PPh$_3$)$_4$ (2 mg, 0.002 mmol) and K$_3$PO$_4$ (25 mg, 0.12 mmol) in dioxaane (0.6 mL) was flushed with nitrogen and heated to 110° C. for 2 hours. The salt was removed by filtration and the filtrate was taken to dryness by rotary evaporation. The residue was purified by reverse phase HPLC to give N-(5-(4-acetylpiperazin-1-yl)pyridin-2-yl)-2-(4-(6-methylpyrimidin-4-yl)phenyl)acetamide 198. MS m/z 431.20 (M+1). $^1$H NMR 400 MHz (DMSO-d$_6$) δ10.59 (s, 1H), 8.16 (d, 2H), 8.04 (d, 1H), 7.98 (s, 1H), 7.92 (m, 1H), 7.51 (d, 2H), 7.45-7.40 (m, 2H), 3.77 (s, 2H), 3.58 (b, 2H), 3.15 (b, 2H), 3.08 (b, 2H), 2.55 (s, 3H), 2.53 (s, 2H), 2.04 (s, 3H).

EXAMPLE 46

2-(2'-fluoro-3-methyl-2,4'-bipyridin-5-yl)-N-(5-(pyrazin-2-yl)pyridin-2-yl)acetamide (199)

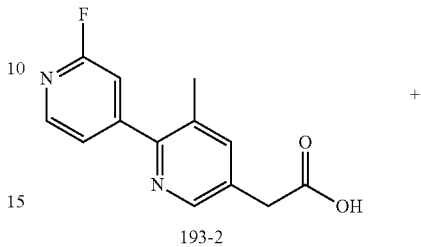

To the mixture of 2-(2'-fluoro-3-methyl-2,4'-bipyridin-5-yl)acetic acid 193-2 (50 mg, 0.2 mmol) and 5-(pyrazin-2-yl)pyridin-2-amine 86-3 (36 mg, 0.2 mmol) in DCM (1 mL) was added N,N'-Diisopropylcarbodiimide (46 µL, 0.3 mmol) at room temperature. The mixture was stirred at room temperature for 24 hours. The solvent was removed by rotary evaporation and the residue was dissolved in DMSO and then purified by reverse-phase HPLC to give 2-(2'-fluoro-3-methyl-2,4'-bipyridin-5-yl)-N-(5-(pyrazin-2-yl)pyridin-2-yl)acetamide 199 as white solid. MS m/z 401.2 (M+1); $^1$H NMR 400 MHz (DMSO-d$_6$) δ11.07 (s, 1H), 9.25 (d, 1H, J=1.6 Hz), 9.05 (m, 1H), 8.66 (m, 1H), 8.57 (d, 1H, J=2.4 Hz), 8.47-8.45 (m, 2H), 8.28 (d, 1H, J=5.2 Hz), 8.16 (d, 1H, J=8.8 Hz), 7.71 (d, 1H, J=1.6 Hz), 7.51-7.49 (m, 1H), 7.31 (s, 1H), 3.82 (s, 2H), 2.31 (s, 3H).

EXAMPLE 47

N-(5-(4-acetylpiperazin-1-yl)pyridin-2-yl)-2-(4-(2-(difluoromethyl)pyridin-4-yl)phenyl)acetamide (201)

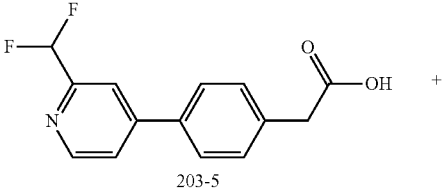

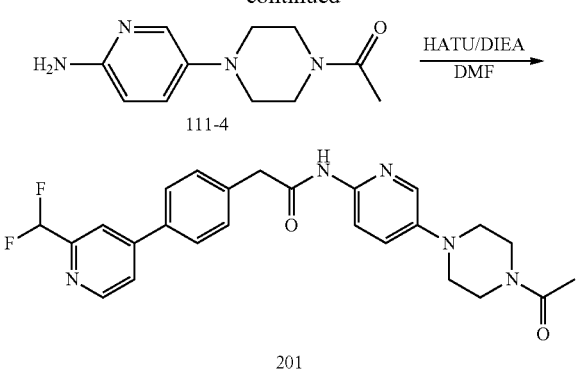

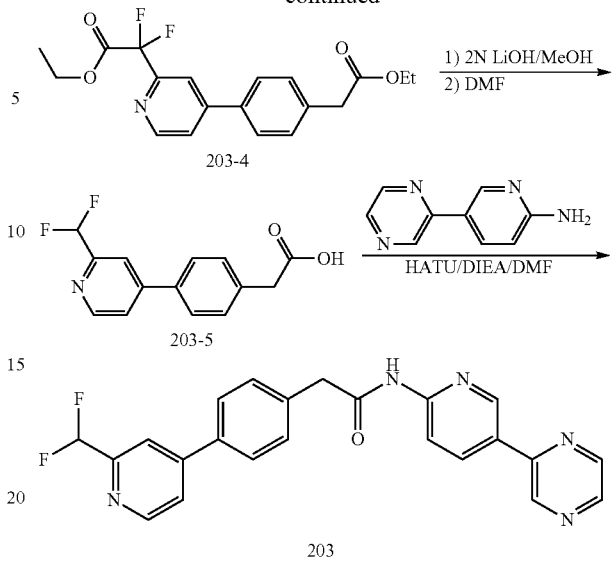

Step 1: A mixture of 2-(4-(2-(difluoromethyl)pyridin-4-yl)phenyl)acetic acid 203-5 (30 mg, 0.11 mmol), 1-(4-(6-aminopyridin-3-yl)piperazin-1-yl)ethanone 111-4 (28 mg, 0.13 mmol), N,N-diisopropylethylamine (99 μL, 0.57 mmol) and O-(7-azabenzotriazol-1-yl)-N,N,N',N'-tetramethyluronium-hexafluorophosphate (65 mg, 0.17 mmol) in DMF (2 mL) was stirred at room temperature for 3 hours. The solvent was removed by rotary evaporation. The crude product was purified by reverse phase HPLC to give 2 N-(5-(4-acetylpiperazin-1-yl)pyridin-2-yl)-2-(4-(2-(difluoromethyl)pyridin-4-yl)phenyl)acetamide 201. MS m/z 418.2 (M+1); $^1$H NMR 400 MHz (MeOD) δ 8.61(d, 1H), 8.25(d, 1H), 7.91(d, 1H), 7.80-7.72(m, 4H), 7.49(d, 2H), 6.79(d, 1H), 6.73(t, 1H), 3.70 (s, 2H), 3.66-3.58(m, 4H), 3.52-3.47(m, 2H), 3.45-3.40(m, 2H), 2.09(s, 3H).

EXAMPLE 48

2-(4-(2-(difluoromethyl)pyridin-4-yl)phenyl)-N-(5-(pyrazin-2-yl)pyridin-2-yl)acetamide (203)

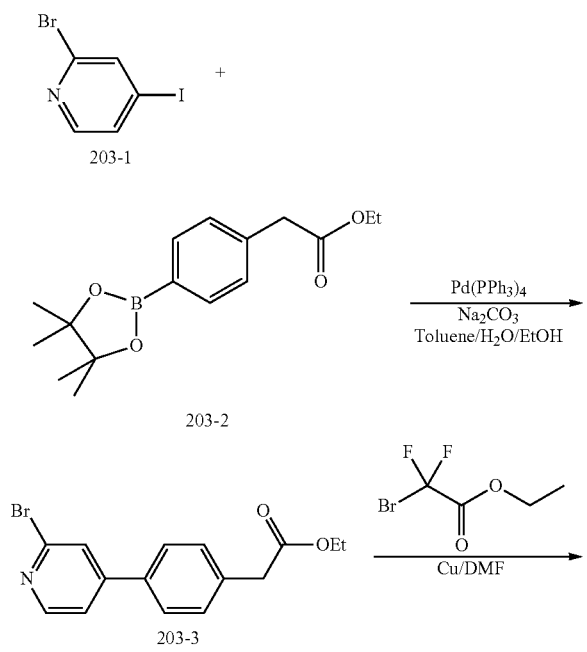

Step 1: To a sealed tube were added 2-bromo-4-iodopyridine 203-1 (568 mg, 2.0 mmol), ethyl 2-(4-(4,4,5,5-tetramethyl-1,3,2-dioxaborolan-2-yl)phenyl)acetate 203-2 (580 mg, 2.0 mmol), Pd(PPh$_3$)$_4$ (116 mg, 0.1 mmol), Na$_2$CO$_3$ (636 mg, 6.0 mmol), toluene (4 mL), H$_2$O (4 mL) and ethanol (1 mL). The reaction mixture was bubbled with nitrogen for 2 minutes and stirred at 80° C. for 10 hours. After cooling to room temperature, the solvents were evaporated and the residue was redissolved in water (5 ml) and extracted with ethyl acetate (5 mL×3). The combined organic phases were dried over Na$_2$SO$_4$, and concentrated. The residue was purified by silica gel flash chromatography and eluted with 15% ethyl acetate in hexane to give ethyl 2-(4-(2-bromopyridin-4-yl)phenyl)acetate 203-3. MS m/z 320.1 (M+1).

Step 2: To a sealed tube were added ethyl 2-(4-(2-bromopyridin-4-yl)phenyl)acetate 203-3 (440 mg, 1.37 mmol), ethyl 2-bromo-2,2-difluoroacetate (1.7 mL, 13.7 mmol), Cu (1.3 g, 20.6 mmol) and DMF (5 mL). The reaction mixture was bubbled with nitrogen for 1 minute and stirred at 80° C. for 1 hour. After cooling to room temperature, the mixture was filtered through a layer of Celite and concentrated. The residue was purified by silica gel flash chromatography and eluted with 20% ethyl acetate in hexane to give ethyl 2-(4-(4-(2-ethoxy-2-oxoethyl)phenyl)pyridin-2-yl)-2,2-difluoroacetate 203-4. MS m/z 364.2 (M+1).

Step 3: Ethyl 2-(4-(4-(2-ethoxy-2-oxoethyl)phenyl)pyridin-2-yl)-2,2-difluoroacetate 203-4 (476 mg, 1.3 mmol) was dissolved in 5 mL MeOH and 2 mL 2N LiOH. The reaction mixture was stirred at 55° C. for 12 hrs. After cooling to room temperature, the mixture was redissolved in 5 mL DMF and 1.5 mL concentrated HCl. The solution was stirred at 130° C. for 3 hrs. After cooling to room temperature, the solution was poured into 5 ml water and extracted with ethyl acetate (5 mL×3). The combined organic phases were dried over Na$_2$SO$_4$, and concentrated. The residue was purified by silica gel flash chromatography and eluted with 5% MeOH in CH$_2$Cl$_2$ to give 2-(4-(2-(difluoromethyl)pyridin-4-yl)phenyl)acetic acid 203-5. MS m/z 264.1 (M+1).

Step 4: A mixture of 2-(4-(2-(difluoromethyl)pyridin-4-yl)phenyl)acetic acid 203-5 (70 mg, 0.27 mmol), 5-(pyrazin-2-yl)pyridin-2-amine (55 mg, 0.32 mmol), N,N-diisopropylethylamine (139 μL, 0.80 mmol) and O-(7-azabenzotriazol-1-yl)-N,N,N',N'-tetramethyluroniumhexafluorophosphate (152 mg, 0.40 mmol) in DMF (2 mL) was stirred at room temperature overnight. The solvent was removed by rotary evaporation. The crude product was purified by reverse phase HPLC to give 2-(4-(2-(difluoromethyl)pyridin-4-yl)phenyl)-N-(5-(pyrazin-2-yl)pyridin-2-yl)acetamide 203. MS m/z 418.2 (M+1); $^1$H NMR 400 MHz (CDCl$_3$) δ 8.99(d, 1H), 8.90(dd, 1H), 8.70(d, 1H), 8.63(dd, 1H), 8.53(d, 1H), 8.40-8.33(m, 2H), 8.30(s, 1H), 7.84(s, 1H), 7.70-7.68(m, 2H), 7.62-7.60(m, 1H), 7.50-7.49(m, 2H), 6.70(t, 1H), 3.87(s, 2H).

EXAMPLE 49

2-(2',3-difluoro-2,4'-bipyridin-5-yl)-N-(5-(pyrazin-2-yl)pyridin-2-yl)acetamide (205)

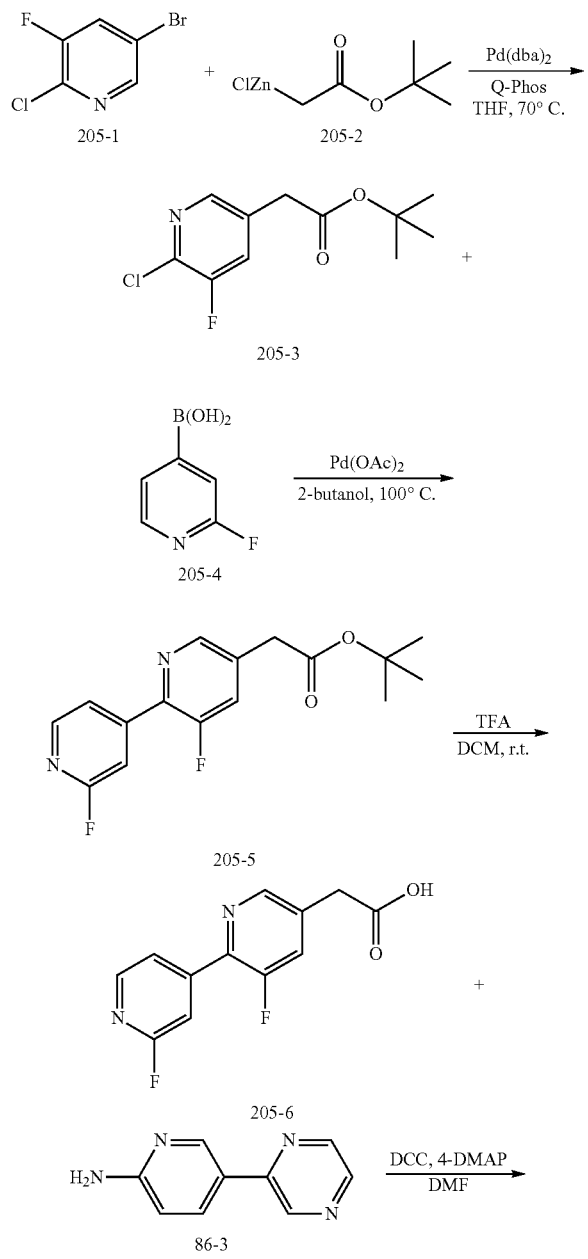

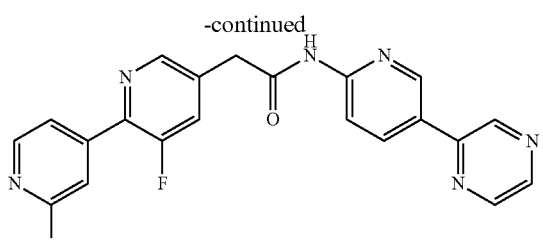

Compound 205

Step 1: In a sealed tube, a mixture of 5-bromo-2-chloro-3-fluoropyridine 205-1 (631 mg, 3 mmol), 0.5 M (2-tert-butoxy-2-oxoethyl) zinc(II) chloride 205-2 in ether (6.6 mL, 3.3 mmol), Pd(dba)$_2$ (87 mg, 0.15 mmol), 1,2,3,4,5-pentaphenyl-1'-(di-t-butylphosphino)ferrocene (Q-phos, 107 mg, 0.15 mmol), and THF (12 mL) under argon was stirred at 70° C. for 18 hours. After cooled to room temperature, the solvents were evaporated and the residue was redissolved in ethyl acetate, washed with water and brine, dried over Na$_2$SO$_4$ and concentrated to dryness by rotary evaporation. The crude product was purified by silica gel flash chromatography, eluted with 30% ethyl acetate in hexane to give tert-butyl 2-(6-chloro-5-fluoropyridin-3-yl)acetate 205-3 as a brown oil. MS m/z 246.1 (M+1).

Step 2: To a flask containing tert-butyl 2-(6-chloro-5-fluoropyridin-3-yl)acetate 205-3 (370 mg, 1.5 mmol), 2-fluoropyridin-4-ylboronic acid 205-4 (318 mg, 2.25 mmol), Pd(OAc)$_2$ (17 mg, 0.075 mmol.), 2-dicyclohexylphosphino-2',6'-dimethoxyybiphenyl (62 mg, 0.15 mmol), K$_3$PO$_4$ (800 mg, 9 mmol) under argon was added 2-butanol (1.5 mL). The reaction mixture was stirred at 100° C. for 10 hours. After cooled to room temperature, the mixture was diluted with ethyl acetate, washed with water and brine, dried over Na$_2$SO$_4$, and concentrated to dryness by rotary evaporation. The crude was purified by silica gel flash chromatography, eluted with 20% ethyl acetate in dichloromethane to give tert-butyl 2-(2',3-difluoro-2,4'-bipyridin-5-yl)acetate 205-5 as a yellow oil. MS m/z 307.1 (M+1).

Step 3: A mixture of tert-butyl 2-(2',3-difluoro-2,4'-bipyridin-5-yl)acetate 205-5 (248 mg, 0.81 mmol) and TFA (0.8 mL) in DCM (0.8 mL) was stirred at room temperature for 3 hours. The solution was adjusted to pH around 12 by Na$_2$CO$_3$ and extracted with dichloromethane. The aqueous phase was acidified to pH 3 by 1N HCl aqueous solution and stirred for 15 minutes. The solvents were evaporated and the remaining solid was extracted with 20% methanol in ethyl acetate and filtered to remove the insoluble. The filtrate was concentrated to dryness by rotary evaporation to give 2-(2',3-difluoro-2,4'-bipyridin-5-yl)acetic acid 205-6, which was used directly for next step. MS m/z 251.1 (M+1).

Step 4: A mixture of 2-(2',3-difluoro-2,4'-bipyridin-5-yl) acetic acid 205-6 (50 mg, 0.2 mmol), 5-(pyrazin-2-yl)pyridin-2-amine 86-3 (34 mg, 0.2 mmol), 1,3-dicyclohexylcarbodiimide (50 mg, 0.24 mmol) and 4-(dimethylamino) pyridine (4 mg, 0.04 mmol) in DMF (0.9 mL) was stirred at room temperature for 10 hours. The crude product was filtered and the filtrate was subjected directly for reverse phase HPLC to give 2-(2',3-difluoro-2,4'-bipyridin-5-yl)-N-(5-(pyrazin-2-yl)pyridin-2-yl)acetamide 205 as white solid. MS m/z 405.2 (M+1); $^1$H NMR 400 MHz (DMSO-d$_6$) δ 11.16 (s, 1H), 9.31 (d, 1H), 9.12 (d, 1H), 8.72 (dd, 1H), 8.63 (d, 1H), 8.61-8.60 (m, 1H), 8.52 (dd, 1H), 8.41 (d, 1H), 8.21 (d, 1H), 7.94 (dd, 1H), 7.88 (dd, 1H), 7.64 (s, 1H), 4.01 (s, 2H).

EXAMPLE 50

N-(5-(4-acetylpiperazin-1-yl)pyridin-2-yl)-2-(3-cyano-4-(2-fluoropyridin-4-yl)phenyl)acetamide (206)

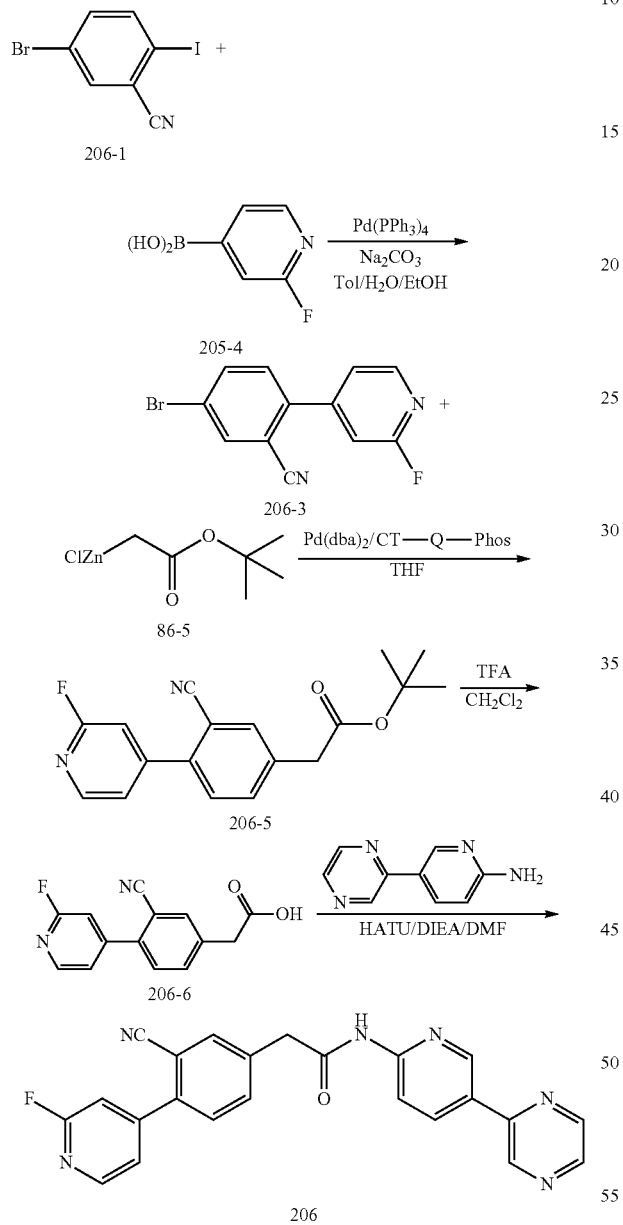

Step 1: To a sealed tube were added 5-bromo-2-iodobenzonitrile 206-1 (500 mg, 1.6 mmol), 2-fluoropyridin-4-ylboronic acid 205-4 (229 mg, 1.6 mmol), Pd(PPh$_3$)$_4$ (94 mg, 0.08 mmol), Na$_2$CO$_3$ (516 mg, 4.9 mmol), toluene (2 mL), H$_2$O (2 mL) and ethanol (0.5 mL). The reaction mixture was stirred at 120° C. overnight. After cooling to room temperature, the solvents were evaporated and the residue was redissolved in water (5 ml) and extracted with ethyl acetate (8 mL×3). The combined organic phases were dried over Na$_2$SO$_4$, and concentrated. The residue was purified by silica gel flash chromatography and eluted with 15% ethyl acetate in hexane to give 5-bromo-2-(2-fluoropyridin-4-yl)benzonitrile 206-3. MS m/z 277.1 (M+1).

Step 2: To a sealed tube were added 5-bromo-2-(2-fluoropyridin-4-yl)benzonitrile 206-3 (42 mg, 0.16 mmol), 0.5 M (2-tert-butoxy-2-oxoethyl) zinc(II) chloride 86-5 in ether (0.46 mL, 0.23 mmol), Pd(dba)$_2$ (4.4 mg, 0.008 mmol), Q-phos (10.8 mg, 0.015 mmol) and THF (1 mL). The reaction mixture was bubbled with nitrogen for 1 minute and stirred at 100° C. for 1 hour. After cooling to room temperature, all the solvents were evaporated and the residue was redissolved in ethyl acetate, washed with water and brine, dried over Na$_2$SO$_4$ and concentrated to dryness by rotary evaporation. The crude product was purified by silica gel flash chromatography and eluted with 20% ethyl acetate in hexane to give tert-butyl 2-(3-cyano-4-(2-fluoropyridin-4-yl)phenyl)acetate 206-5. MS m/z 313.2 (M+1).

Step 3: A mixture of tert-butyl 2-(3-cyano-4-(2-fluoropyridin-4-yl)phenyl)acetate 206-5 (35 mg, 0.11 mmol) and TFA (0.5 mL) in DCM (3 mL) was stirred at room temperature for 5 hours. The solvents were evaporated to dryness under high vacuum. The crude product, 2-(3-cyano-4-(2-fluoropyridin-4-yl)phenyl)acetic acid 206-6, was dissolved in DMF (2 mL). 5-(pyrazin-2-yl)pyridin-2-amine (23 mg, 0.13 mmol) and DIEA (98 uL, 0.56 mmol) were added to the solution before O-(7-azabenzotriazol-1-yl)-N,N,N',N'-tetramethyluronium-hexafluorophosphate (64 mg, 0.17 mmol). The mixture was stirred at room temperature overnight. The mixture was stirred at room temperature overnight. The solvent was removed by rotary evaporation. The crude product was purified by reverse phase HPLC to give N-(5-(4-acetylpiperazin-1-yl)pyridin-2-yl)-2-(3-cyano-4-(2-fluoropyridin-4-yl)phenyl)acetamide 206. MS m/z 411.2 (M+1); $^1$H NMR 400 MHz (MeOD) δ 9.09 (s, 1H), 9.01 (s, 1H), 8.66 (dd, 1H), 8.52 (d, 1H), 8.42 (dd, 1H), 8.32 (d, 1H), 8.25 (d, 1H), 7.92 (d, 1H), 7.81 (dd, 1H), 7.64 (d, 1H), 7.52 (dt, 1H), 7.28 (s, 1H), 3.93 (s, 2H).

EXAMPLE 51

N-(5-(4-acetylpiperazin-1-yl)pyridin-2-yl)-2-(3-fluoro-4-(2-fluoropyridin-4-yl)phenyl)acetamide (207)

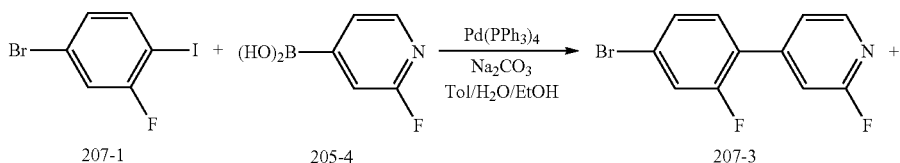

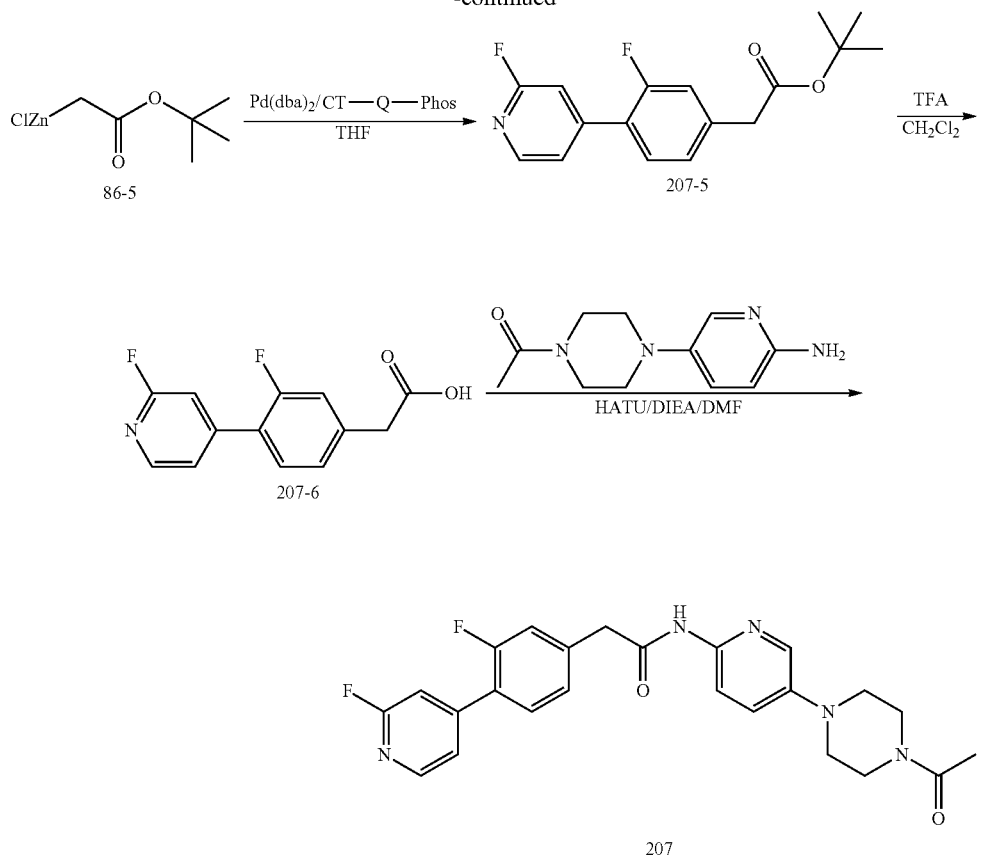

Step 1: To a sealed tube were added 4-bromo-2-fluoro-1-iodobenzene 207-1 (600 mg, 2.0 mmol), 2-fluoropyridin-4-ylboronic acid 205-4 (282 mg, 2.0 mmol), Pd(PPh$_3$)$_4$ (116 mg, 0.1 mmol), Na$_2$CO$_3$ (636 mg, 6.0 mmol), toluene (2 mL), H$_2$O (2 mL) and ethanol (0.5 mL). The reaction mixture was stirred at 120° C. overnight. After cooling to room temperature, the solvents were evaporated and the residue was redissolved in water (5 ml) and extracted with ethyl acetate (8 mL×3). The combined organic phases were dried over Na$_2$SO$_4$, and concentrated. The residue was purified by silica gel flash chromatography and eluted with 15% ethyl acetate in hexane to give 4-(4-bromo-2-fluorophenyl)-2-fluoropyridine 207-3. MS m/z 270.1 (M+1).

Step 2: To a sealed tube were added 4-(4-bromo-2-fluorophenyl)-2-fluoropyridine 207-3 (210 mg, 0.76 mmol), 0.5 M (2-tert-butoxy-2-oxoethyl) zinc(II) chloride 86-5 in ether (2.3 mL, 1.14 mmol), Pd(dba)$_2$ (22 mg, 0.04 mmol), Q-phos (54 mg, 0.07 mmol) and THF (5 mL). The reaction mixture was bubbled with nitrogen for 1 minute and stirred at 100° C. for 1 hour. After cooling to room temperature, all the solvents were evaporated and the residue was redissolved in ethyl acetate, washed with water and brine, dried over Na$_2$SO$_4$ and concentrated to dryness by rotary evaporation. The crude product was purified by silica gel flash chromatography and eluted with 20% ethyl acetate in hexane to give tert-butyl 2-(3-fluoro-4-(2-fluoropyridin-4-yl)phenyl)acetate 207-5. MS m/z 306.2 (M+1).

Step 3: A mixture of tert-butyl 2-(3-fluoro-4-(2-fluoropyridin-4-yl)phenyl)acetate 207-5 (100 mg, 0.33 mmol) and TFA (0.5 mL) in DCM (3 mL) was stirred at room temperature for 5 hours. The solvents were evaporated to dryness under high vacuum. The crude product, 2-(3-fluoro-4-(2-fluoropyridin-4-yl)phenyl)acetic acid 207-6 (50 mg, 0.20 mmol), was dissolved in DMF (2 mL), 1-(4-(6-aminopyridin-3-yl)piperazin-1-yl)ethanone (53 mg, 0.24 mmol) and DIEA (174 uL, 1.0 mmol) were added to the solution before O-(7-azabenzotriazol-1-yl)-N,N,N',N'-tetramethyluronium-hexafluorophosphate (114 mg, 0.30 mmol). The mixture was stirred at room temperature overnight. The solvent was removed by rotary evaporation. The crude product was purified by reverse phase HPLC to give N-(5-(4-acetylpiperazin-1-yl)pyridin-2-yl)-2-(3-fluoro-4-(2-fluoropyridin-4-yl)phenyl)acetamide 207. MS m/z 452.2 (M+1); $^1$H NMR 400 MHz (MeOD) δ 8.21 (d, 1H), 7.96 (d, 1H), 7.88 (d, 1H), 7.57-7.51 (m, 1H), 7.48-7.45 (m, 1H), 7.37 (dd, 1H), 7.30-7.21 (m, 3H), 3.75 (s, 2H), 3.68 (t, 2H), 3.63 (t, 2H), 3.14 (t, 2H), 3.09 (t, 2H, J=5.2 Hz), 2.09 (s, 3H).

EXAMPLE 52

2-(2'-fluoro-2,4'-bipyridin-5-yl)-N-(5-(pyrazin-2-yl)pyridin-2-yl)acetamide (208)

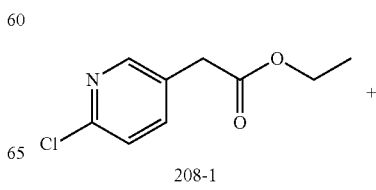

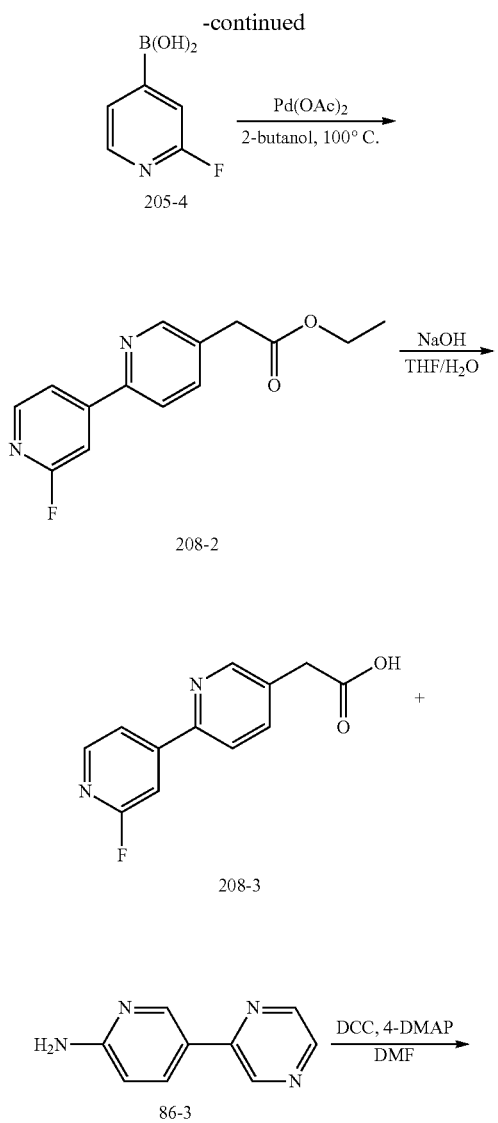

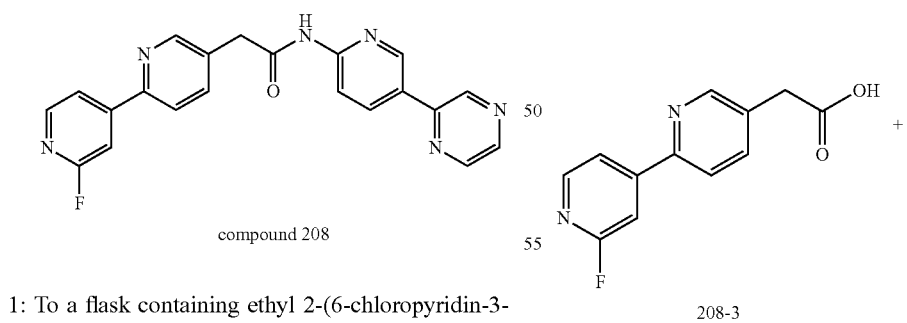

Step 1: To a flask containing ethyl 2-(6-chloropyridin-3-yl)acetate 208-1 (300 mg, 1.5 mmol), 2-fluoropyridin-4-yl-boronic acid 205-4 (318 mg, 2.25 mmol), Pd(OAc)$_2$ (17 mg, 0.075 mmol.), 2-dicyclohexylphosphino-2',6'-dimethoxyy-biphenyl (62 mg, 0.15 mmol), K$_3$PO$_4$ (800 mg, 9 mmol) under argon was added 2-butanol (1.5 mL). The reaction mixture was stirred at 100° C. for 10 hours. After cooled to room temperature, the mixture was diluted with ethyl acetate, washed with water and brine, dried over Na$_2$SO$_4$, and concentrated to dryness by rotary evaporation. The crude was purified by silica gel flash chromatography, eluted with 40% ethyl acetate in dichloromethane to give ethyl 2-(2'-fluoro-2,4'-bipyridin-5-yl)acetate 208-2 as a yellow solid. MS m/z 261.1 (M+1).

Step 2: A mixture of ethyl 2-(2'-fluoro-2,4'-bipyridin-5-yl)acetate 208-2 (93 mg, 0.36 mmol) and NaOH (57 mg, 1.43 mmol) in THF (0.5 mL) and water (0.5 mL) was stirred at 65° C. for 3 hours. After cooled down to room temperature, the mixture was treated with 3N HCl aqueous solution to adjust the pH around 3, and then stirred for 15 minutes. The resulting solution was evaporated to dryness and the remaining solid was extracted with 20% methanol in ethyl acetate. The organic portion was concentrated to give 2-(2'-fluoro-2,4'-bipyridin-5-yl)acetic acid 208-3 as pale white solid. MS m/z 233.1 (M+1).

Step 3: A mixture of 2-(2'-fluoro-2,4'-bipyridin-5-yl)acetic acid 208-3 (42 mg, 0.18 mmol), 5-(pyrazin-2-yl)pyridin-2-amine 86-3 (31 mg, 0.18 mmol), 1,3-dicyclohexylcarbodiimide (45 mg, 0.22 mmol) and 4-(dimethylamino)pyridine (4 mg, 0.036 mmol) in DMF (0.9 mL) was stirred at room temperature for 10 hours. The crude product was filtered and the filtrate was purified by reverse phase HPLC to give 2-(2'-fluoro-2,4'-bipyridin-5-yl)-N-(5-(pyrazin-2-yl)pyridin-2-yl)acetamide 208 as white solid. MS m/z 387.1 (M+1); $^1$H NMR 400 MHz (DMSO-d$_6$) δ 11.14 (s, 1H), 9.31 (d, 1H), 9.11 (d, 1H), 8.73-8.71 (m, 2H), 8.62 (d, 1H), 8.52 (dd, 1H), 8.36 (d, 1H), 8.23-8.17 (m, 2H), 8.06-8.02 (m, 1H), 7.95 (dd, 1H), 7.82 (s, 1H), 7.64 (s, 1H), 3.94 (s, 2H).

EXAMPLE 53

N-(5-(4-acetylpiperazin-1-yl)pyridin-2-yl)-2-(2'-fluoro-2,4'-bipyridin-5-yl)acetamide (209)

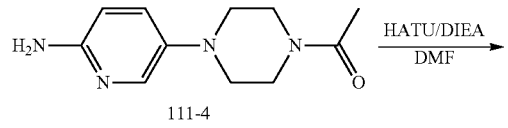

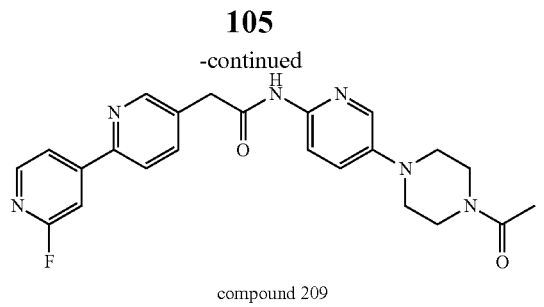

compound 209

Step 1: To a mixture of 2-(2'-fluoro-2,4'-bipyridin-5-yl)acetic acid 208-3 (42 mg, 0.18 mmol), 1-(4-(6-aminopyridin-3-yl)piperazin-1-yl)ethanone 111-4 (40 mg, 0.18 mmol), o-(7-azabenzotriazol-1-yl)-N,N,N',N'-tetramethyluronium hexafluorophosphate (HATU, 68 mg, 0.18 mmol) were added DMF (1 mL) and diisopropylethyl amine (DIEA, 0.15 mL, 0.9 mmol) and the mixture was stirred at room temperature overnight. The crude product, a clear DMF solution, was subjected directly for reverse phase HPLC to give N-(5-(4-acetylpiperazin-1-yl)pyridin-2-yl)-2-(2'-fluoro-2,4'-bipyridin-5-yl)acetamide 209 as white solid. MS m/z 435.2 (M+1); $^1$H NMR 400 MHz (DMSO-$d_6$) δ 10.65 (s, 1H), 8.69 (d, 1H), 8.36 (d, 1H), 8.15 (d, 1H), 8.05-8.02 (m, 2H), 7.94-7.90 (m, 2H), 7.81 (s, 1H), 7.42 (dd, 1H), 3.83 (s, 2H), 3.57-3.54 (m, 4H), 3.15-3.13 (m, 2H), 3.09-3.06 (m, 2H), 2.03 (s, 3H).

EXAMPLE 54

2-(2',3-difluoro-2,4'-bipyridin-5-yl)-N-(5-(pyridazin-3-yl)pyridin-2-yl)acetamide (210)

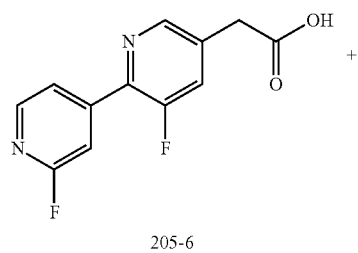

205-6

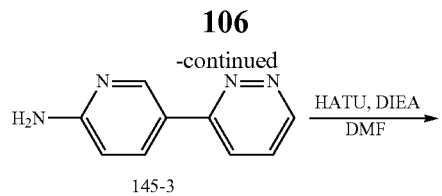

145-3

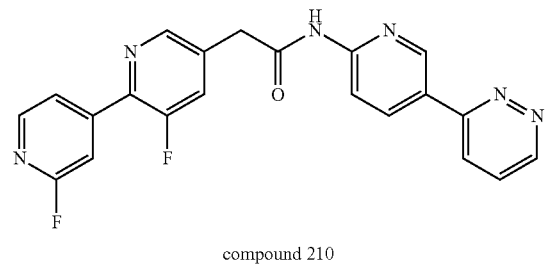

compound 210

Step 1: To a mixture of 2-(2',3-difluoro-2,4'-bipyridin-5-yl)acetic acid 205-6 (25 mg, 0.1 mmol), 5-(pyridazin-3-yl)pyridin-2-amine 145-3 (17 mg, 0.1 mmol), o-(7-azabenzotriazol-1-yl)-N,N,N',N'-tetramethyluronium hexafluorophosphate (HATU, 38 mg, 0.1 mmol) were added DMF (0.5 mL) and diisopropylethyl amine (DIEA, 0.05 mL, 0.3 mmol) and the mixture was stirred at room temperature overnight. The crude DMF solution was directly purified by reverse phase HPLC to give 2-(2',3-difluoro-2,4'-bipyridin-5-yl)-N-(5-(pyridazin-3-yl)pyridin-2-yl)acetamide 210 as white solid. MS m/z 405.1 (M+1); $^1$H NMR 400 MHz (DMSO-$d_6$) δ 11.18 (s, 1H), 9.23 (d, 1H), 9.14 (d, 1H), 8.61 (m, 1H), 8.56 (dd, 1H), 8.41 (d, 1H), 8.29 (dd, 1H), 8.23 (d, 1H), 7.95 (dd, 1H), 7.91-7.86 (m, 1H), 7.81 (dd, 1H), 7.65 (s, 1H), 4.02 (s, 2H).

EXAMPLE 55

N-(5-(4-acetylpiperazin-1-yl)pyridin-2-yl)-2-(3-cyano-4-(2-fluoropyridin-4-yl)phenyl)acetamide (211)

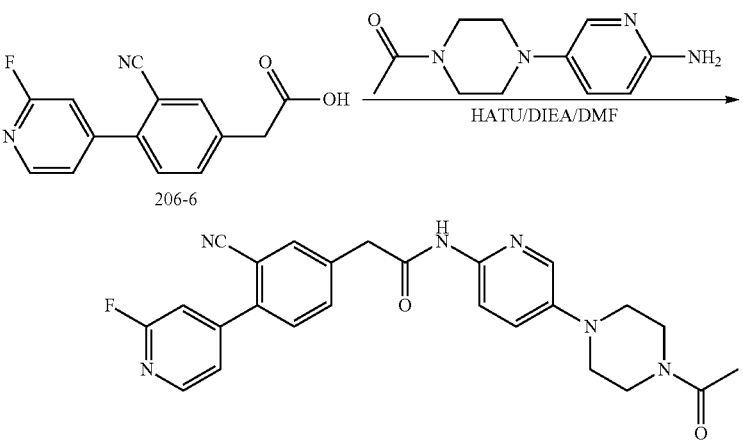

211

Step 1: 2-(3-cyano-4-(2-fluoropyridin-4-yl)phenyl)acetic acid 206-6 (50 mg, 0.20 mmol) was dissolved in DMF (2 mL). 1-(4-(6-aminopyridin-3-yl)piperazin-1-yl)ethanone (52 mg, 0.23 mmol) and DIEA (170 uL, 0.98 mmol) were added to the solution before O-(7-azabenzotriazol-1-yl)-N,N,N',N'-tetramethyluroniumhexafluorophosphate (111 mg, 0.29 mmol). The mixture was stirred at room temperature overnight. The solvent was removed by rotary evaporation. The crude product was purified by reverse phase HPLC to give N-(5-(4-acetylpiperazin-1-yl)pyridin-2-yl)-2-(3-cyano-4-(2-fluoropyridin-4-yl)phenyl)acetamide 211. MS m/z 459.2 (M+1)); ¹H NMR 400 MHz (DMSO-d₆) δ 10.64 (s, 1H), 8.41 (d, 1H), 8.05 (d, 1H), 7.98 (d, 1H), 7.91 (d, 1H), 7.81 (dd, 1H), 7.71 (d, 1H), 7.62 (dt, 1H), 7.49 (s, 1H), 7.42 (dd, 1H), 3.85 (s, 2H), 3.59-3.54 (m, 4H), 3.15 (t, 2H), 3.08 (t, 2H), 2.04 (s, 3H).

EXAMPLE 56

2-(3-fluoro-4-(2-fluoropyridin-4-yl)phenyl)-N-(5-(pyrazin-2-yl)pyridin-2-yl)acetamide (212)

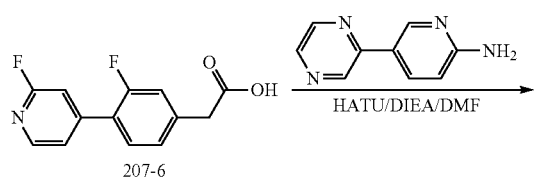

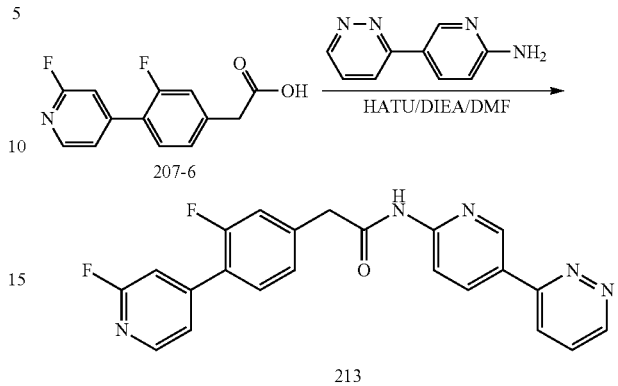

Step 1: 2-(3-fluoro-4-(2-fluoropyridin-4-yl)phenyl)acetic acid 207-6 (50 mg, 0.20 mmol), was dissolved in DMF (2 mL), 5-(pyrazin-2-yl)pyridin-2-amine (41 mg, 0.24 mmol) and DIEA (174 uL, 1.0 mmol) were added to the solution before O-(7-azabenzotriazol-1-yl)-N,N,N',N'-tetramethyluroniumhexafluorophosphate (114 mg, 0.30 mmol). The mixture was stirred at room temperature overnight. The solvent was removed by rotary evaporation. The crude product was purified by reverse phase HPLC to give 2-(3-fluoro-4-(2-fluoropyridin-4-yl)phenyl)-N-(5-(pyrazin-2-yl)pyridin-2-yl)acetamide 212. MS m/z 404.1 (M+1); ¹H NMR 400 MHz (DMSO-d₆) δ 11.10 (s, 1H), 9.31 (d, 1H), 9.11 (dd, 1H), 8.73-8.71 (m, 1H), 8.63 (d, 1H), 8.52 (dd, 1H), 8.34 (d, 1H), 8.21 (d, 1H), 7.70-7.52 (m, 2H), 7.43-7.34 (m, 3H), 3.89 (s, 2H).

EXAMPLE 57

2-(3-fluoro-4-(2-fluoropyridin-4-yl)phenyl)-N-(5-(pyridazin-3-yl)pyridin-2-yl)acetamide (213)

Step 1: 2-(3-fluoro-4-(2-fluoropyridin-4-yl)phenyl)acetic acid 207-6 (37 mg, 0.15 mmol), was dissolved in DMF (2 mL), 5-(pyridazin-3-yl)pyridin-2-amine (31 mg, 0.18 mmol) and DIEA (131 uL, 0.75 mmol) were added to the solution before O-(7-azabenzotriazol-1-yl)-N,N,N',N'-tetramethyluroniumhexafluorophosphate (86 mg, 0.23 mmol). The mixture was stirred at room temperature overnight. The solvent was removed by rotary evaporation. The crude product was purified by reverse phase HPLC to give 2-(3-fluoro-4-(2-fluoropyridin-4-yl)phenyl)-N-(5-(pyridazin-3-yl)pyridin-2-yl)acetamide 213. MS m/z 404.2 (M+1); ¹H NMR 400 MHz (DMSO-d₆) δ 11.11 (s, 1H), 9.22 (dd, 1H), 9.13 (dd, 1H), 8.55 (dd, 1H), 8.34 (d, 1H), 8.29 (dd, 1H), 8.23 (d, 1H), 8.02 (d, 1H), 7.83-7.78 (m, 1H), 7.71-7.65 (m, 1H), 7.60-7.57 (m, 1H), 7.44-7.35 (m, 3H), 3.90 (s, 2H).

EXAMPLE 58

2-(3-cyano-4-(2-fluoropyridin-4-yl)phenyl)-N-(5-(pyridazin-3-yl)pyridin-2-yl)acetamide (214)

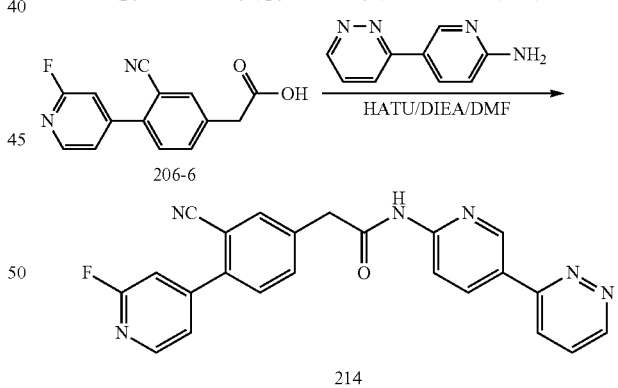

Step 1: 2-(3-cyano-4-(2-fluoropyridin-4-yl)phenyl)acetic acid 206-6 (38 mg, 0.15 mmol), was dissolved in DMF (2 mL), 5-(pyridazin-3-yl)pyridin-2-amine (31 mg, 0.18 mmol) and DIEA (131 uL, 0.75 mmol) were added to the solution before O-(7-azabenzotriazol-1-yl)-N,N,N',N'-tetramethyluroniumhexafluorophosphate (86 mg, 0.23 mmol). The mixture was stirred at room temperature overnight. The solvent was removed by rotary evaporation. The crude product was purified by reverse phase HPLC to give 2-(3-cyano-4-(2-fluoropyridin-4-yl)phenyl)-N-(5-(pyridazin-3-yl)pyridin-2-yl)acetamide 214. MS m/z 411.2 (M+1); ¹H NMR 400 MHz (DMSO-d₆) δ 11.14 (s, 1H), 9.23 (dd, 1H), 9.13 (d, 1H), 8.56

(dd, 1H), 8.42 (d, 1H), 8.30 (dd, 1H), 8.23 (d, 1H), 8.02 (d, 1H), 7.86-7.78 (m, 2H), 7.74 (d, 1H), 7.63 (dt, 1H), 7.50 (s, 1H), 3.97 (s, 2H).

EXAMPLE 59

N-(6-(3-fluorophenyl)pyridin-3-yl)-2-(S,S-dioxo-6-thiomorpholinopyridin-3-yl)acetamide (219)

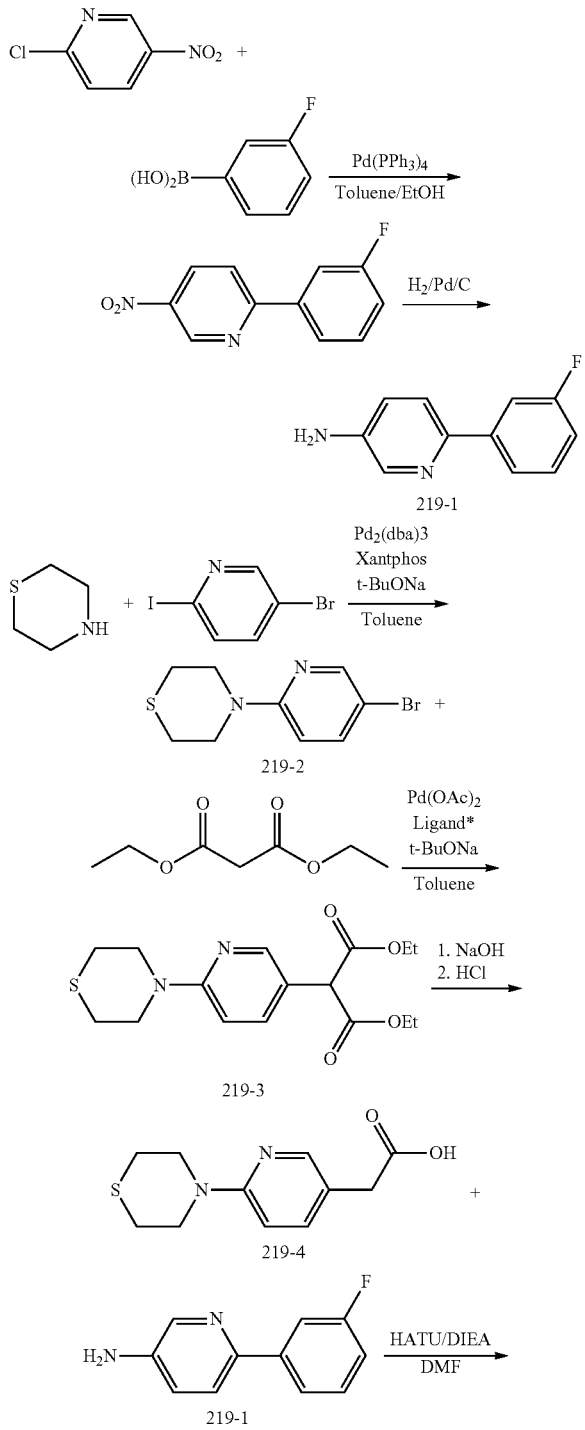

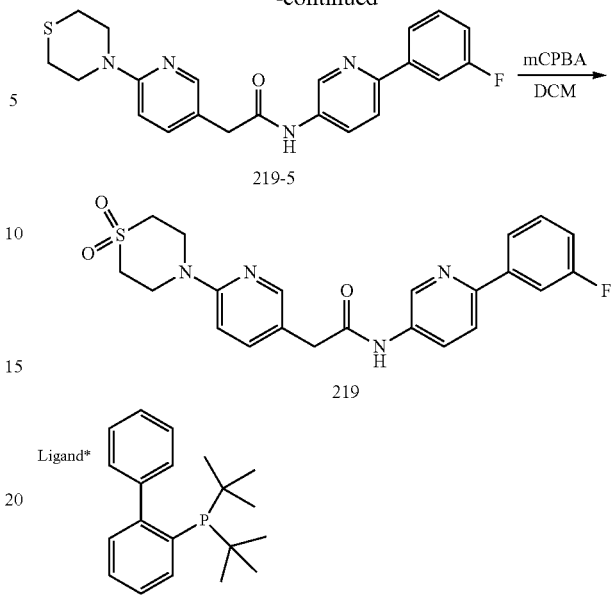

Step 1. To a round bottom flask were added 2-chloro-5-nitropyridine (3.2 g, 20 mmol), (3-fluorophenyl) boronic acid (2.8 g, 20 mmol), Pd(PPh₃)₄ (0.46 g, 0.4 mmol), toluene (60 mL), ethanol (20 mL) and Na₂CO₃ (2 M, 20 mL). The reaction mixture was bubbled with nitrogen for 2 minutes and refluxed at 110° C. for 2 hours. After cooled down to room temperature, the reaction mixture was diluted with ethyl acetate (500 mL) and washed with saturated NaHCO₃ aqueous solution and brine. The organic phase was dried over Na₂SO₄ and concentrated to dryness by rotary evaporation. The crude product was purified by silica gel flash chromatography, eluted with 50% to 100% ethyl acetate in hexane 2-(3-fluorophenyl)-5-nitropyridine as yellow solid. MS m/z 219.1 (M+1).

Step 2. To a round-bottom flask was added 2-(3-fluorophenyl)-5-nitropyridine (3.8 g, 17 mmol), Pd/C (0.5 g) and methanol (100 mL). The reaction was stirred for 4 hours under hydrogen atmosphere by attaching a hydrogen balloon. The reaction was flushed with nitrogen and the solid was removed by filtration. The solvent was removed by rotary evaporation to give 6-(3-fluorophenyl)pyridin-3-amine 219-1 as brown solid. MS m/z 189.1 (M+1).

Step 3. A mixture of thiomorpholine (1.03 g, 10.0 mmol), 5-bromo-2-iodopyridine (3.69 g, 13 mmol), Pd₂(dba)₃ (200 mg, 0.2 mmol), xantphos (510 mg, 0.6 mmol) and t-BuONa (1.44 g, 15 mmol) in toluene (50 ml) was stirred under argon at 98° C. for 3 hours. After cooled to room temperature, the mixture was filtered through celite and washed with ethyl acetate. The filtrate was evaporated and the residue was subjected to silica gel column chromatography with 0-5% ethyl acetate in hexanes as eluent to give 4-(5-bromopyridin-2-yl)thiomorpholine 219-2 as solid.

Step 4. A mixture of 4-(5-bromopyridin-2-yl)thiomorpholine 219-2 (2.37 g, 9.15 mmol), diethyl malonate (2.04 g, 12.8 mmol), Pd(OAc)₂ (102 mg, 0.46 mmol), biphenyl-2-yl-di-tert-butylphosphine (270 mg, 0.9 mmol) and t-BuONa (1.76 g, 18.3 mmol) in toluene (45 ml) was stirred under argon at 98° C. for 1 hour. After cooled to room temperature, the mixture was filtered through celite and washed with ethyl acetate. The filtrate was evaporated and the residue was subjected to silica gel column chromatography to give diethyl 2-(6-thiomorpholinopyridin-3-yl)malonate 219-3.

Step 5. 2-(6-Thiomorpholinopyridin-3-yl)malonate 219-3 (564 mg, 1.67 mmol) was stirred with NaOH (334 mg, 8.35 mmol) in dioxane (5 ml) and water (5 ml) for 4 hours. HCl solution was added to adjust the pH around 1 and the reaction mixture heated at 88° C. for 1 hour. Then $Na_2CO_3$ was used to adjust the pH to around 4 before the solvents were evaporated. The residue was extracted with ethyl acetate and the organic extraction dried over $Na_2SO_4$ and concentrated by rotary evaporation. Purification with reverse phase HPLC afforded 2-(6-thiomorpholinopyridin-3-yl)acetic acid 219-4.

Step 6. A mixture of 2-(6-thiomorpholinopyridin-3-yl)acetic acid 219-4 (92 mg, 0.39 mmol), 6-(3-fluorophenyl)pyridin-3-amine 219-1 (73 mg, 0.39 mmol), HATU (162 mg, 0.43 mmol) and DIEA (104 µl, 0.6 mmol) in DMF (1.0 ml) was stirred at room temperature overnight. Then it was redistributed between water (30 ml) and ethyl acetate (40 ml). The organic phase was dried over $Na_2SO_4$ and concentrated by rotary evaporation. Silica gel column chromatography (with ethyl acetate/hexanes from 1:10 to 2:1 as eluent) gave N-(6-(3-fluorophenyl)pyridin-3-yl)-2-(6-thiomorpholinopyridin-3-yl)acetamide 219-5 as solid. Step 7. N-(6-(3-fluorophenyl)pyridin-3-yl)-2-(6-thiomorpholinopyridin-3-yl)acetamide 219-5 (114 mg, 0.28 mmol) was treated with mCPBA in DCM (2 ml) at 0° C. The mixture was stirred at room temperature overnight. The mixture was diluted with ethyl acetate (30 mL), washed with 5% $Na_2CO_3$ solution, dried over $Na_2SO_4$ and concentrated by rotary evaporation. The residue was subjected to reverse phase HPLC purification and gave N-(6-(3-fluorophenyl)pyridin-3-yl)-2-(S,S-dioxo-6-thiomorpholinopyridin-3-yl)acetamide 219 as solid. MS m/z 396.3 (M+1); $^1$H NMR 400 MHz (DMSO-$d_6$) δ 10.53 (s, 1 H), 8.82 (d, 1 H), 8.16 (dd, 1 H), 8.11 (d, 1 H), 7.99 (d, 1 H), 7.92-7.80 (m, 2 H), 7.60 (dd, 1 H), 7.50 (m, 1 H), 7.22 (m, 1 H), 7.02 (d, 1 H), 4.06-4.01 (m, 4 H), 3.61 (s, 2 H), 3.10-3.05 (m, 4 H).

EXAMPLE 60

2-(2'-fluoro-3-methyl-2,4'-bipyridin-5-yl)-N-(5-(pyridazin-3-yl)pyridin-2-yl)acetamide (221)

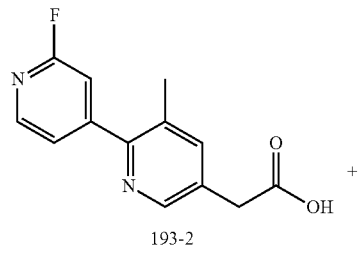

193-2

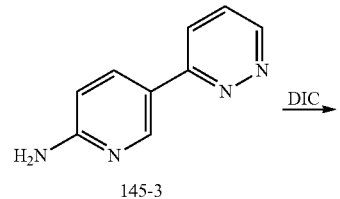

145-3

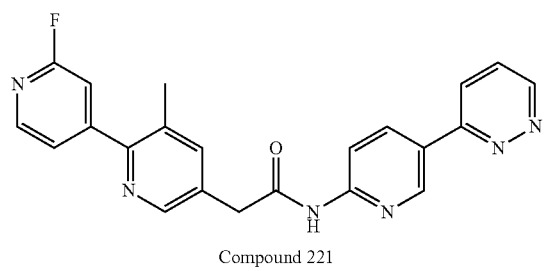

Compound 221

To the mixture of 2-(2'-fluoro-3-methyl-2,4'-bipyridin-5-yl)acetic acid 193-2 (25 mg, 0.1 mmol) and 5-(pyridazin-3-yl)pyridin-2-amine 145-3 (17 mg, 0.1 mmol) in DCM (1 mL) was added N,N'-Diisopropylcarbodiimide (22 µL, 0.15 mmol) at room temperature. The mixture was stirred at room temperature for 24 hours. The solvent was removed by rotary evaporation and the residue was dissolved in DMSO and then purified by reverse-phase HPLC to give 2-(2'-fluoro-3-methyl-2,4'-bipyridin-5-yl)-N-(5-(pyrazin-2-yl)pyridin-2-yl)acetamide 221 as white solid. MS m/z 401.1 (M+1); $^1$H NMR 400 MHz (DMSO-$d_6$) δ 11.09 (s, 1H), 9.17 (dd, 1H), 9.07 (d, 1H), 8.51 (dd, 1H), 8.46 (d, 1H), 8.28 (d, 1H), 8.25 (dd, 1H), 8.18 (d, 1H), 7.76 (m, 1H), 7.71 (d, 1H), 7.51 (m, 1H), 7.31 (s, 1H), 3.83 (s, 2H), 2.31 (s, 3H).

EXAMPLE 61

N-(5-(4-acetylpiperazin-1-yl)pyridin-2-yl)-2-(3-methyl-2'-(trifluoromethyl)-2,4'-bipyridin-5-yl)acetamide (222)

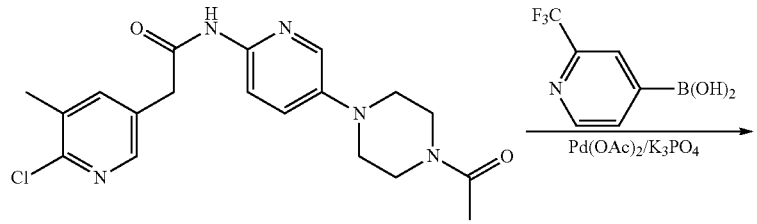

148-1

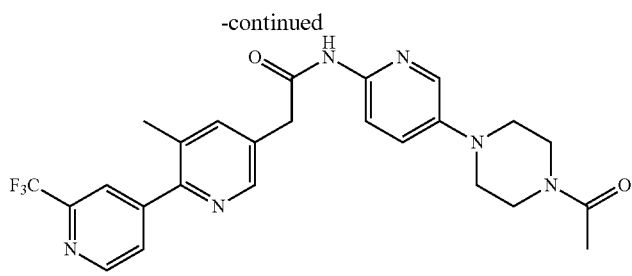

222

To a sealed tube were added N-(5-(4-acetylpiperazin-1-yl)pyridin-2-yl)-2-(6-chloro-5-methylpyridin-3-yl)acetamide 148-1 (123 mg, 0.32 mmol), 2-(trifluoromethyl)pyridin-4-ylboronic acid (61 mg, 0.32 mmol), Pd(OAc)$_2$ (3.6 mg, 0.016 mmol), 2,6-Dimethoxy-1,1'-biphenyl-2-yl)dicyclohexylphosphine (13.0 mg, 0.032 mmol) and K$_3$PO$_4$ (202 mg, 0.95 mmol). The tube and its contents were then purged with nitrogen. After degassed toluene (1.0 mL) was added, the mixture was stirred at 120° C. overnight. After cooling to room temperature, the mixture was poured into water and extracted with ethyl acetate (8 mL×3). The combined organic phases were dried over Na$_2$SO$_4$, and concentrated. The residue was purified by reverse phase HPLC to give to give N-(5-(4-acetylpiperazin-1-yl)pyridin-2-yl)-2-(3-methyl-2'-(trifluoromethyl)-2,4'-bipyridin-5-yl)acetamide 222. MS m/z 498.8 (M+1); $^1$H NMR 400 MHz (CDCl$_3$) δ 8.81 (d, 1H), 8.51 (d, 1H), 8.35 (s, 1H), 8.11 (d, 1H), 7.91 (s, 1H), 7.89 (s, 1H), 7.68-7.64 (m, 2H), 7.30 (dd, 1H), 3.80-3.75 (m, 4H), 3.63 (t, 2H), 3.14 (t, 2H), 3.11 (t, 2H), 2.39 (s, 3H), 2.14 (s, 3H).

EXAMPLE 62

2-(3-methyl-2'-(trifluoromethyl)-2,4'-bipyridin-5-yl)-N-(5-(pyrazin-2-yl)pyridin-2-yl)acetamide (223)

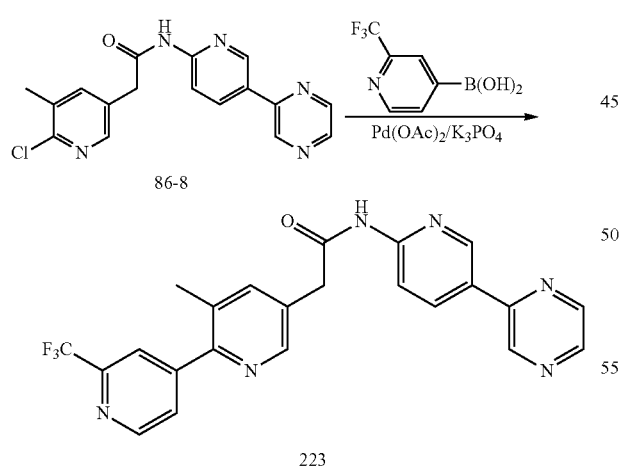

To a sealed tube were added 2-(6-chloro-5-methylpyridin-3-yl)-N-(5-(pyrazin-2-yl)pyridin-2-yl)acetamide 86-8 (85 mg, 0.25 mmol), 2-(trifluoromethyl)pyridin-4-ylboronic acid (48 mg, 0.25 mmol), Pd(OAc)$_2$ (2.8 mg, 0.013 mmol), 2,6-Dimethoxy-1,1'-biphenyl-2-yl)dicyclohexylphosphine (10.2 mg, 0.025 mmol) and K$_3$PO$_4$ (159 mg, 0.75 mmol). The tube and its contents were then purged with nitrogen. After degassed toluene (1.0 mL) was added, the mixture was stirred at 100° C. for 2 hours. After cooling to room temperature, the mixture was poured into water and extracted with ethyl acetate (8 mL×3). The combined organic phases were dried over Na$_2$SO$_4$, and concentrated. The residue was purified by reverse phase HPLC to give to give 2-(3-methyl-2'-(trifluoromethyl)-2,4'-bipyridin-5-yl)-N-(5-(pyrazin-2-yl)pyridin-2-yl)acetamide 223. MS m/z 450.8 (M+1); $^1$H NMR 400 MHz (CDCl$_3$) δ 9.01 (d, 1H), 8.95 (s, 1H), 8.81 (d, 1H), 8.76 (s, 1H), 8.63 (dd, 1H), 8.56-8.51 (m, 2H), 8.37 (s, 2H), 7.89 (s, 1H), 7.69-7.65 (m, 2H), 3.84 (s, 2H), 2.40 (s, 3H).

EXAMPLE 63

N-(5-(4-acetylpiperazin-1-yl)pyridin-2-yl)-2-(4-cyano-3-(2-methylpyridin-4-yl)phenyl)acetamide (237)

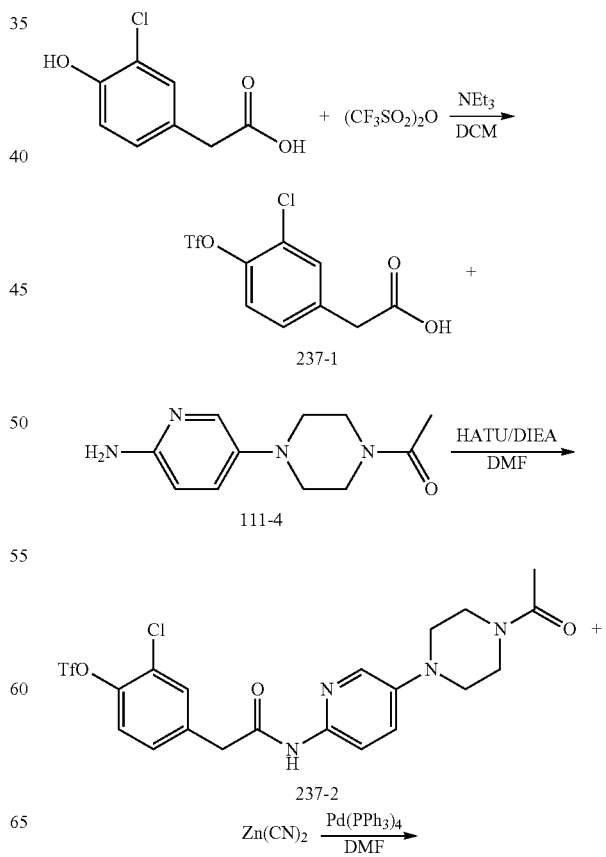

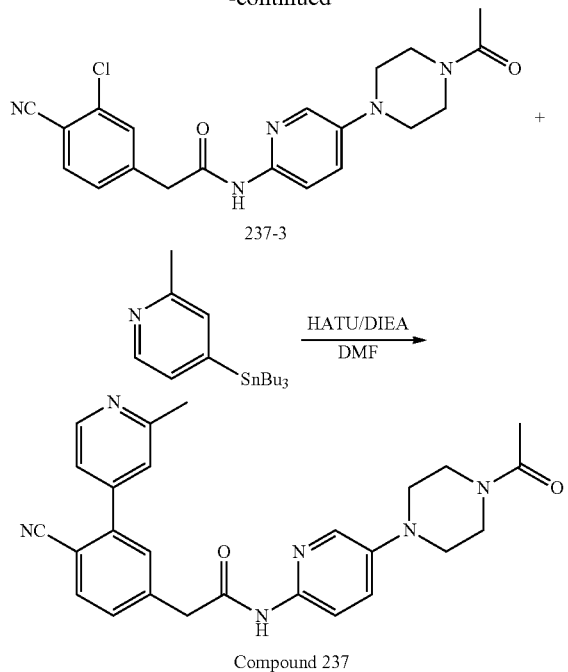

Compound 237

Step 1. To a mixture of 2-(3-chloro-4-hydroxyphenyl)acetic acid (560 mg, 3.00 mmol), trifluoromethanesulfonic anhydride (888 mg, 3.15 mmol) in DCM (30 ml) was added triethylamine (1.1 ml, 8.06 mmol) and the mixture stirred 2 hours at room temperature. Then it was washed with HCl solution (1N, 30 ml×2), dried over $Na_2SO_4$ and concentrated by rotary evaporation to give 2-(3-chloro-4-(trifluoromethylsulfonyloxy)phenyl)acetic acid 237-1 (749 mg, crude) which was used directly for reaction without further purification.

Step 2. A solution of 2-(3-chloro-4-(trifluoromethylsulfonyloxy)phenyl)acetic acid 237-1, 1-(4-(6-aminopyridin-3-yl)piperazin-1-yl)ethanone 111-4 (112 mg, 0.51 mmol), HATU (232 mg, 0.61 mmol) and DIEA (0.26 ml, 1.49 mmol) in DMF (2.0 ml) was stirred at room temperature overnight. The solution was subjected directly to reverse phase HPLC to give 4-(2-(5-(4-acetylpiperazin-1-yl)pyridin-2-ylamino)-2-oxoethyl)-2-chlorophenyl trifluoromethanesulfonate 237-2.

Step 3. A mixture of 4-(2-(5-(4-acetylpiperazin-1-yl)pyridin-2-ylamino)-2-oxoethyl)-2-chlorophenyl trifluoromethanesulfonate 237-2 (65 mg, 0.125 mmol), $Zn(CN)_2$ (30 mg, 0.255 mmol), $Pd(PPh_3)_4$ (14 mg, 0.012 mmol) in DMF (0.6 ml) was stirred at 80° C. under argon for 96 hours. After cooled to room temperature, it was filtered through celite, washed with ethyl acetate, and concentrated by evaporation of solvents. The residue was subjected to reverse phase HPLC purification to give N-(5-(4-acetylpiperazin-1-yl)pyridin-2-yl)-2-(3-chloro-4-cyanophenyl)acetamide as solid 237-3.

Step 4. A mixture of N-(5-(4-acetylpiperazin-1-yl)pyridin-2-yl)-2-(3-chloro-4-cyanophenyl)acetamide as solid 237-3 (17 mg, 0.043 mmol), 2-methyl-4-(tributylstannyl)pyridine (24.5 mg, 0.064 mmol), $Pd(PPh_3)_4$ (5 mg, 0.0043 mmol) in DMF (0.6 ml) was stirred at 118° C. under argon overnight. After cooled to room temperature, it was filtered through celite while washed and diluted with ethyl acetate (30 ml). Then it was washed with water (40 ml) and extected with 0.5 N HCl (30 ml). After the aqueous extraction was treated with $Na_2CO_3$ to have the pH adjusted to around 9, the aqueous phase was extracted with ethyl acetate (30 ml×2). The combined organic phases were dried over $Na_2SO_4$, concentrated by rotary evaporation and the residue subjected to silica gel column chromatography with MeOH in ethyl acetate (0 to 5%) as eluent to give N-(5-(4-acetylpiperazin-1-yl)pyridin-2-yl)-2-(4-cyano-3-(2-methylpyridin-4-yl)phenyl)acetamide as solid 237. MS m/z 455.2 (M+1); $^1$H NMR 400 MHz ($CDCl_3$) δ 8.62 (d, 1 H), 8.08 (d, 1 H), 8.02 (bs, 1 H), 7.91 (d, 1 H), 7.79 (d, 1 H), 7.53-7.47 (m, 2 H), 7.34 (bs, 1 H), 7.31-7.26 (m, 2 H), 3.82 (s, 2 H), 3.80-3.75 (m, 2 H), 3.65-3.60 (m, 2 H), 3.16-3.08 (m, 4 H), 2.64 (s, 3 H), 2.14 (s, 3 H).

EXAMPLE 64

2-(2'-methyl-2,4'-bipyridin-4-yl)-N-(5-(pyrazin-2-yl)pyridin-2-yl)acetamide (238)

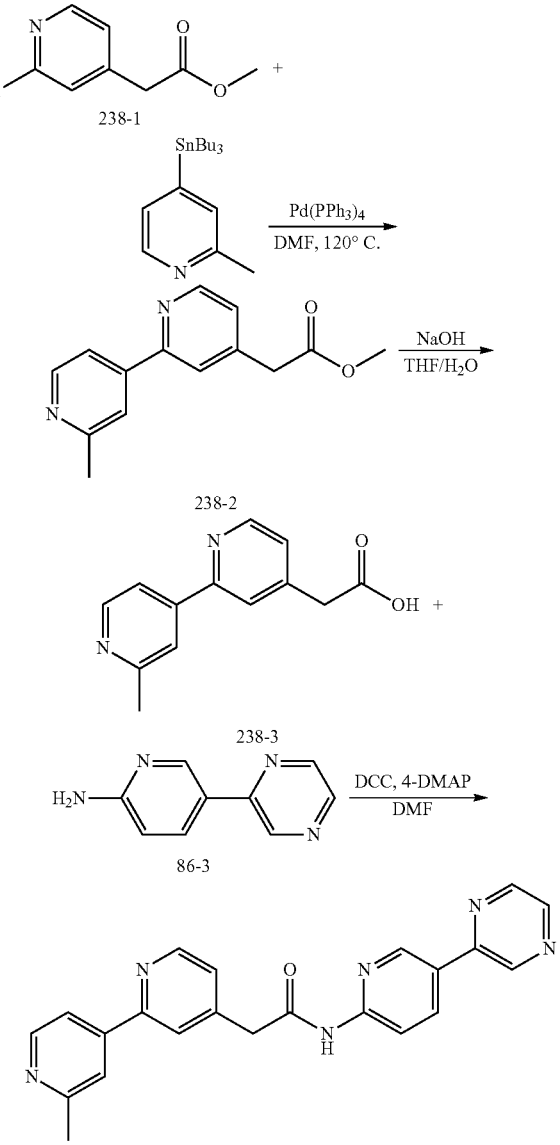

compound 238

Step 1: To a flask containing methyl 2-(2-chloropyridin-4-yl)acetate 238-1 (1.00 g, 5.38 mmol), 2-methyl-4-(tributylstannyl)pyridine (2.06 g, 5.38 mmol), $Pd(PPh_3)_4$ (594 mg, 0.54 mmol.) under argon was added DMF (15 mL). The reaction mixture was stirred at 120° C. for 10 hours. After cooled to room temperature, the mixture was diluted with ethyl acetate, washed with water and brine, dried over Na$_2$SO$_4$, and concentrated to dryness by rotary evaporation. The crude was purified by silica gel flash chromatography, eluted with 5% methano in dichloromethane to give methyl 2-(2'-methyl-2,4'-bipyridin-4-yl)acetate 238-2 as dark orange oil. MS m/z 243.1 (M+1).

Step 2: A mixture of methyl 2-(2'-methyl-2,4'-bipyridin-4-yl)acetate 238-2 (621 mg, 2.56 mmol) and NaOH (409 mg, 10.24 mmol) in 1,4-dioxane (6 mL) and water (6 mL) was stirred at 80° C. for 3 hours. After cooled down to room temperature, the mixture was treated with 3N HCl aqueous solution to adjust the pH to around 4, and then stirred for 15 minutes. The resulting solution was evaporated to dryness and the remaining solid was extracted with 20% methanol in ethyl acetate. The organic extraction was concentrated to give 2-(2'-methyl-2,4'-bipyridin-4-yl)acetic acid 238-3 as pale white solid. MS m/z 229.1 (M+1).

Step 3: A mixture of 2-(2'-methyl-2,4'-bipyridin-4-yl)acetic acid 238-3 (46 mg, 0.2 mmol), 5-(pyrazin-2-yl)pyridin-2-amine 86-3 (34 mg, 0.2 mmol),1,3-dicyclohexylcarbodiimide (50 mg, 0.24 mmol) and 4-(dimethylamino)pyridine (4 mg, 0.04 mmol) in DMF (0.9 mL) was stirred at room temperature for 10 hours. The crude product was filtered to remove the insoluble and the filtrate was submitted directly for reverse phase HPLC purification to give 2-(2'-methyl-2,4'-bipyridin-4-yl)-N-(5-(pyrazin-2-yl)pyridin-2-yl)acetamide 238 as white solid. MS m/z 383.1 (M+1); $^1$H NMR 400 MHz (DMSO-d$_6$) δ 11.14 (s, 1H), 9.30 (d, 1H), 9.11 (dd, 1H), 8.73-8.71 (m, 1H), 8.67 (d, 1H), 8.62 (d, 1H), 8.56 (d, 1H), 8.52 (dd, 1H), 8.21 (d, 1H), 8.09 (s, 1H), 7.93 (s, 1H), 7.84 (dd, 1H), 7.45 (dd, 1H), 3.95 (s, 2H), 2.56 (s, 3H).

The exemplified compounds of the invention are summarized in Table 1, with 1050 values measured using Wnt-Luc reporter assays.

TABLE 1

| Cpd | Structure | MS (m/z) (M + 1) | LC retention time (min) | IC$_{50}$ (nM) |
|---|---|---|---|---|
| 1 | 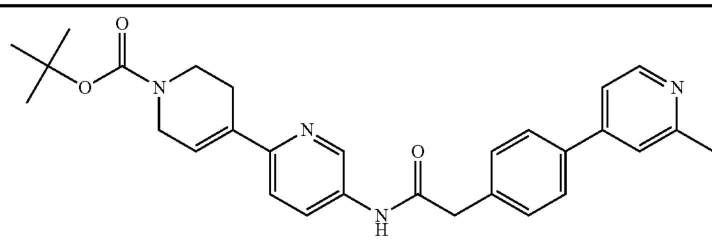 | 485.30 | 1.465 | 1.5 |
| 2 | 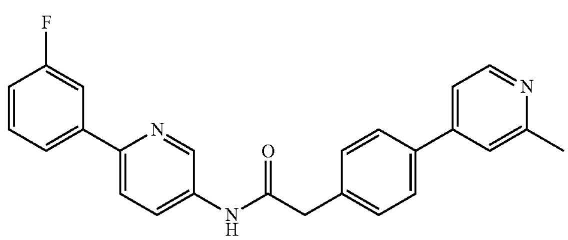 | 398.2 | 1.48 | |
| 3 | 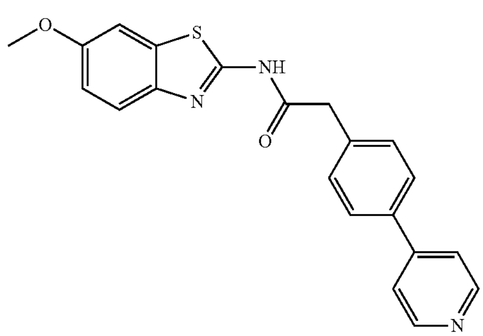 | 376.10 | 1.445 | 1.6 |
| 4 | 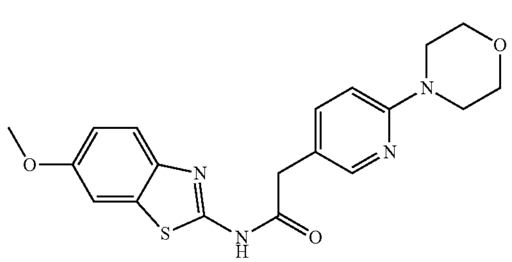 [SMILES: COc1ccc2nc(NC(=O)Cc3ccc(N4CCOCC4)nc3)sc2c1] | 385.2 | 1.342 | 774 |

TABLE 1-continued

| Cpd | Structure | MS (m/z) (M + 1) | LC retention time (min) | IC$_{50}$ (nM) |
|---|---|---|---|---|
| 5 | 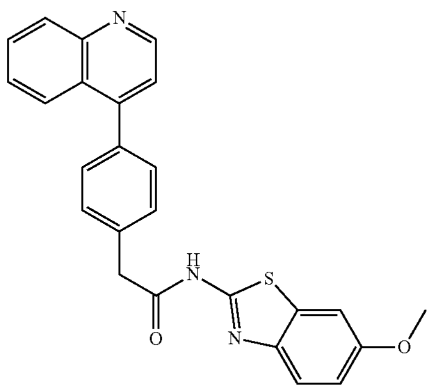 [SMILES: COc1ccc2nc(NC(=O)Cc3ccc(-c4ccnc5ccccc45)cc3)sc2c1] | 426.12 | 1.730 | 481.3 |
| 6 | 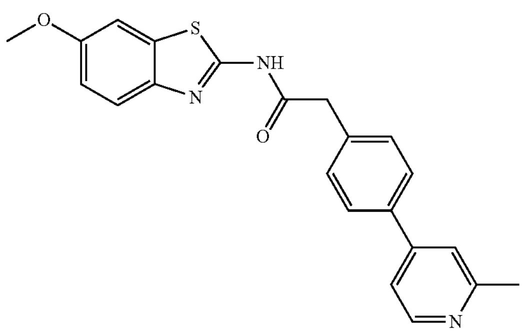 | 390.12 | 1.581 | 0.5 |
| 7 | 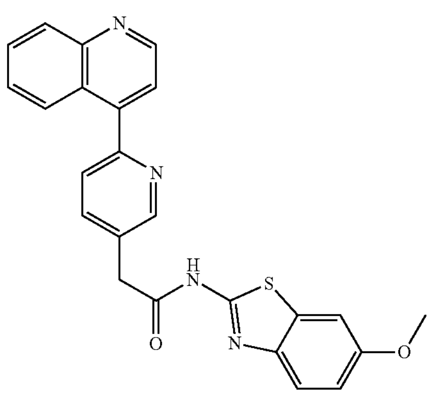 [SMILES: COc1ccc2nc(NC(=O)Cc3ccc(-c4ccnc5ccccc45)nc3)sc2c1] | 427.12 | 1.573 | 405.9 |
| 8 | 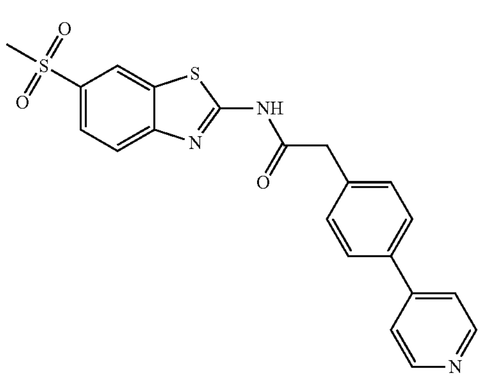 [SMILES: CS(=O)(=O)c1ccc2nc(NC(=O)Cc3ccc(-c4ccncc4)cc3)sc2c1] | 424.07 | 1.195 | 13.8 |

TABLE 1-continued

| Cpd | Structure | MS (m/z) (M + 1) | LC retention time (min) | IC$_{50}$ (nM) |
|---|---|---|---|---|
| 9 | 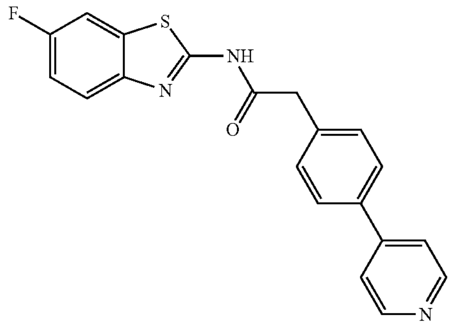 [SMILES: O=C(Cc1ccc(-c2ccncc2)cc1)Nc1nc2ccc(F)cc2s1] | 364.08 | 1.526 | 18.6 |
| 10 | 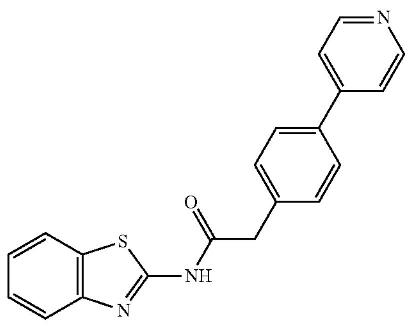 [SMILES: O=C(Cc1ccc(-c2ccncc2)cc1)Nc1nc2ccccc2s1] | 346.09 | 1.487 | 581.4 |
| 11 | 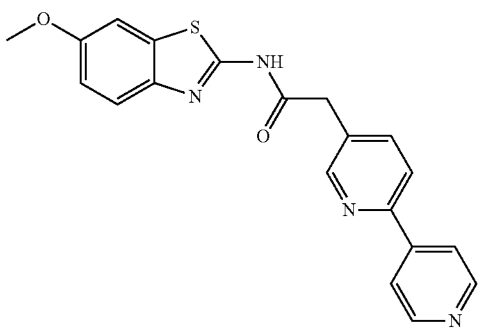 | 377.10 | 1.361 | 20.0 |
| 12 | 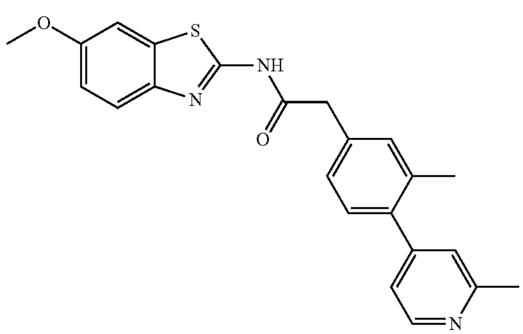 | 404.14 | 1.562 | 2.4 |

TABLE 1-continued

| Cpd | Structure | MS (m/z) (M + 1) | LC retention time (min) | IC$_{50}$ (nM) |
|---|---|---|---|---|
| 13 | 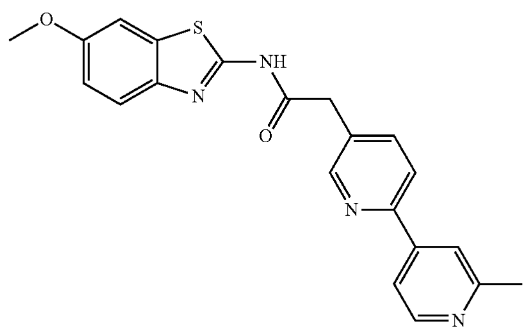 | 391.12 | 1.372 | 15.1 |
| 14 | 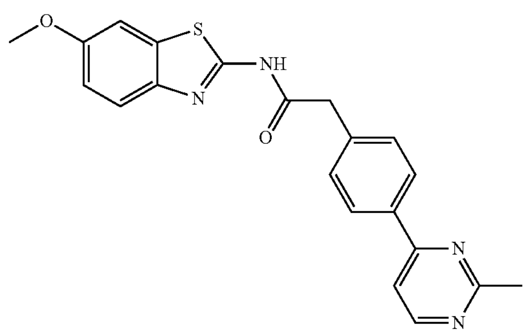 | 391.12 | 2.098 | 54.9 |
| 15 | 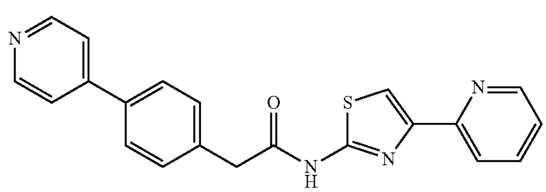 [SMILES: O=C(Cc1ccc(-c2ccncc2)cc1)Nc1nc(-c2ccccn2)cs1] | 373.10 | 0.924 | 669 |
| 16 | 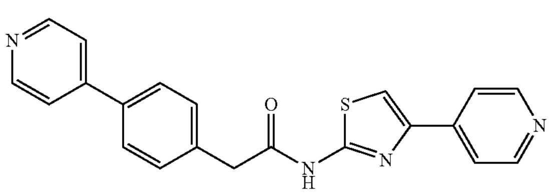 [SMILES: O=C(Cc1ccc(-c2ccncc2)cc1)Nc1nc(-c2ccncc2)cs1] | 373.10 | 1.203 | 110.6 |
| 17 | 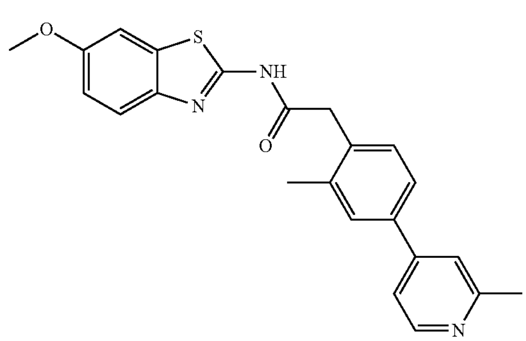 | 404.14 | 1.552 | 6.8 |

TABLE 1-continued

| Cpd | Structure | MS (m/z) (M + 1) | LC retention time (min) | IC$_{50}$ (nM) |
|---|---|---|---|---|
| 18 | 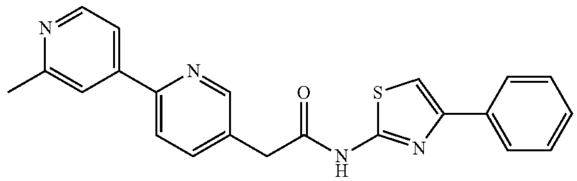 [SMILES: Cc1cc(-c2ccc(CC(=O)Nc3nc(-c4ccccc4)cs3)cn2)ccn1] | 387.12 | 1.590 | 22.2 |
| 19 | 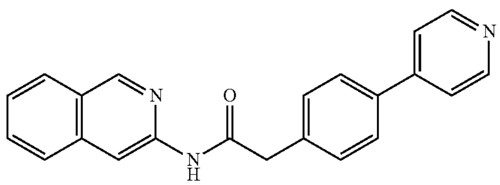 [SMILES: O=C(Cc1ccc(-c2ccncc2)cc1)Nc1cc2ccccc2cn1] | 340.14 | 1.45 | 211.1 |
| 20 | 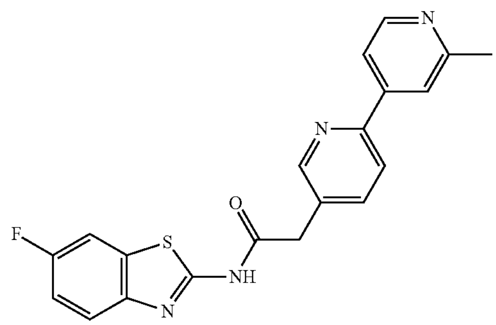 [SMILES: Cc1cc(-c2ccc(CC(=O)Nc3nc4ccc(F)cc4s3)cn2)ccn1] | 379.10 | 1.528 | 114.9 |
| 21 | 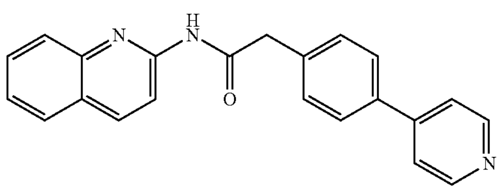 [SMILES: O=C(Cc1ccc(-c2ccncc2)cc1)Nc1ccc2ccccc2n1] | 340.14 | 1.258 | 834.8 |
| 22 | 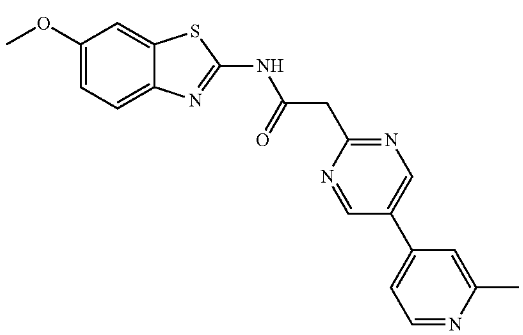 | 392.11 | 1.515 | 1243 |
| 23 | 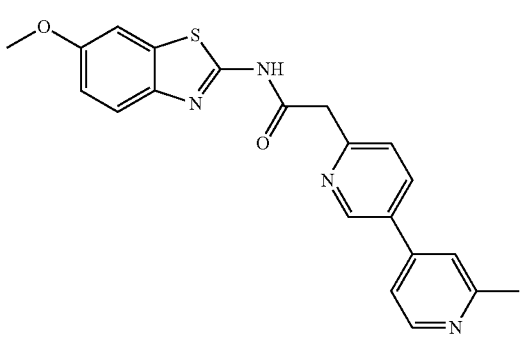 | 391.12 | 1.454 | 34.6 |

TABLE 1-continued
| Cpd | Structure | MS (m/z) (M + 1) | LC retention time (min) | IC$_{50}$ (nM) |
|---|---|---|---|---|
| 24 | 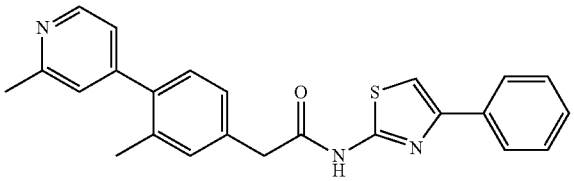 [SMILES: Cc1cc(-c2ccc(CC(=O)Nc3nc(-c4ccccc4)cs3)cc2C)ccn1] | 400.14 | 1.777 | 5.0 |
| 25 | 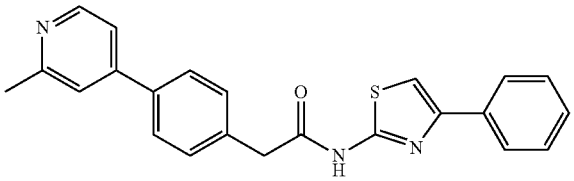 [SMILES: Cc1cc(-c2ccc(CC(=O)Nc3nc(-c4ccccc4)cs3)cc2)ccn1] | 386.12 | 1.686 | 19.5 |
| 26 | 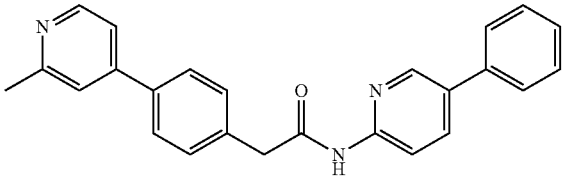 [SMILES: Cc1cc(-c2ccc(CC(=O)Nc3ccc(-c4ccccc4)cn3)cc2)ccn1] | 380.17 | 1.717 | <0.4 |
| 27 | 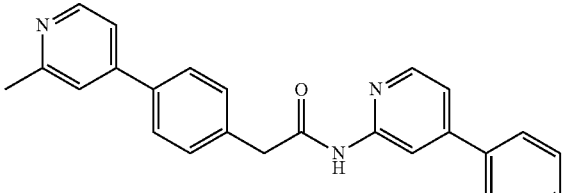 | 380.17 | 2.518 | 806.6 |
| 28 | 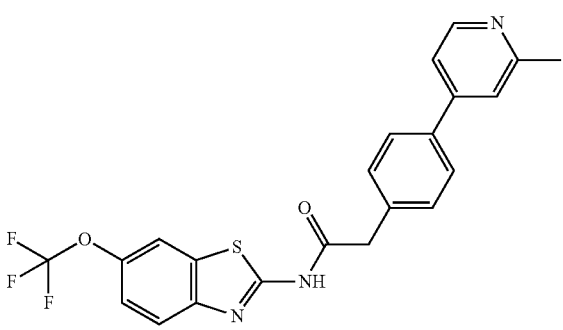 [SMILES: Cc1cc(-c2ccc(CC(=O)Nc3nc4ccc(OC(F)(F)F)cc4s3)cc2)ccn1] | 444.09 | 1.988 | 505.4 |
| 29 | 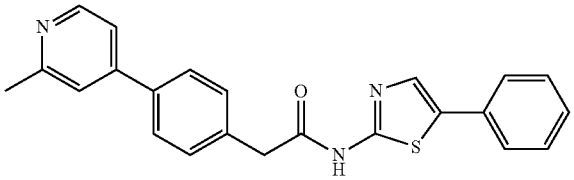 [SMILES: Cc1cc(-c2ccc(CC(=O)Nc3ncc(-c4ccccc4)s3)cc2)ccn1] | 386.12 | 1.641 | 18.9 |

TABLE 1-continued
| Cpd | Structure | MS (m/z) (M + 1) | LC retention time (min) | IC$_{50}$ (nM) |
|---|---|---|---|---|
| 30 | 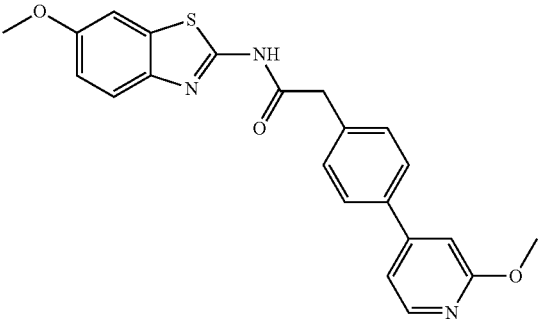 | 406.11 | 2.051 | 19.0 |
| 31 | 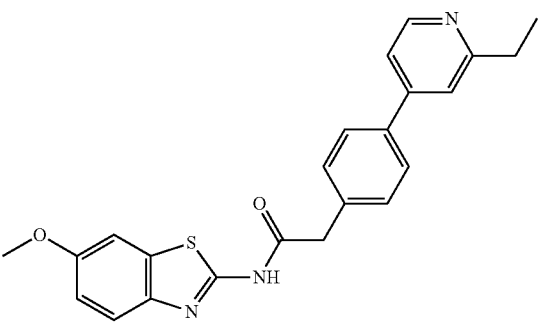 [SMILES: CCc1cc(-c2ccc(CC(=O)Nc3nc4ccc(OC)cc4s3)cc2)ccn1] | 404.14 | 1.576 | 28.0 |
| 32 | 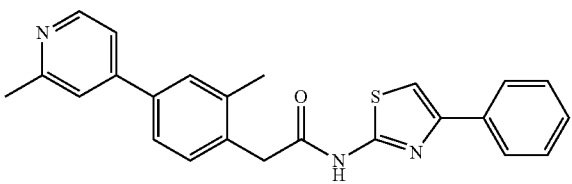 [SMILES: Cc1cc(-c2ccc(CC(=O)Nc3nc(-c4ccccc4)cs3)c(C)c2)ccn1] | 400.14 | 1.776 | 16.0 |
| 33 | 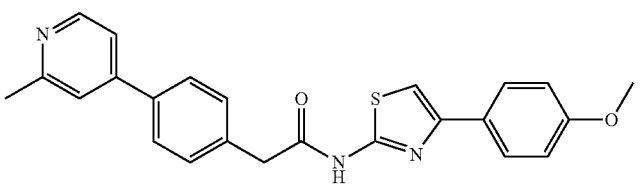 | 416.14 | 1.722 | 19.4 |
| 34 | 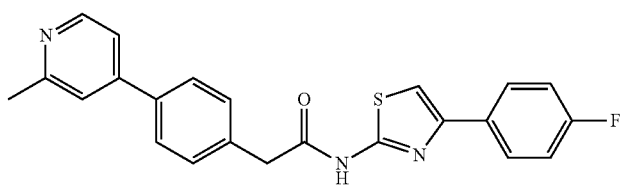 [SMILES: Cc1cc(-c2ccc(CC(=O)Nc3nc(-c4ccc(F)cc4)cs3)cc2)ccn1] | 404.12 | 1.773 | 92.3 |
| 35 | 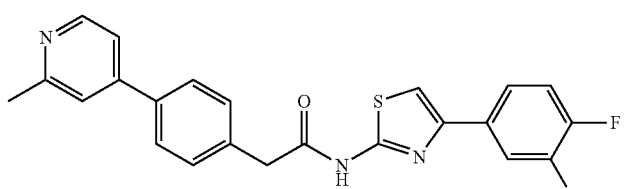 | 422.11 | 1.857 | 24.7 |

TABLE 1-continued

| Cpd | Structure | MS (m/z) (M + 1) | LC retention time (min) | IC$_{50}$ (nM) |
|---|---|---|---|---|
| 36 | 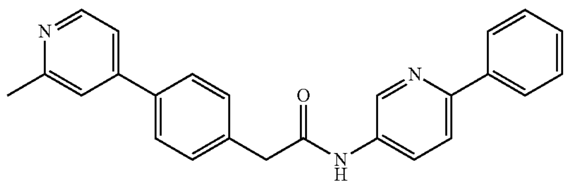 [SMILES: Cc1cc(-c2ccc(CC(=O)Nc3ccc(-c4ccccc4)nc3)cc2)ccn1] | 380.17 | 1.916 | <0.11 |
| 37 | 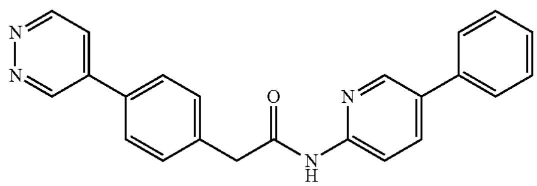 [SMILES: O=C(Cc1ccc(-c2ccnnc2)cc1)Nc1ccc(-c2ccccc2)cn1] | 367.15 | 1.934 | .28 |
| 38 | 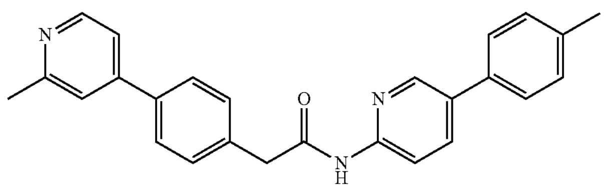 | 394.18 | 1.441 | 0.85 |
| 39 | 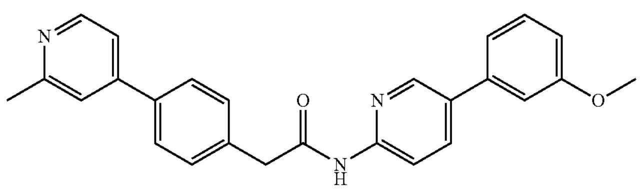 | 410.18 | 1.591 | 1.4 |
| 40 | 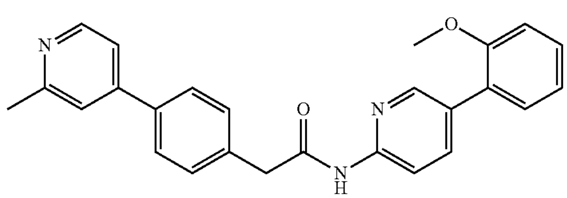 [SMILES: COc1ccccc1-c1ccc(NC(=O)Cc2ccc(-c3ccnc(C)c3)cc2)nc1] | 410.18 | 1.508 | 92.9 |
| 41 | 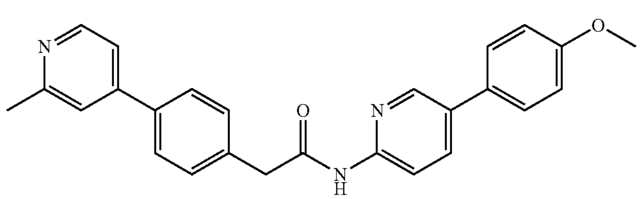 | 410.18 | 1.606 | 0.88 |
| 42 | 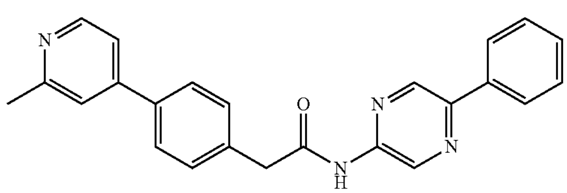 [SMILES: Cc1cc(-c2ccc(CC(=O)Nc3cnc(-c4ccccc4)cn3)cc2)ccn1] | 381.16 | 1.747 | 4.0 |
| 43 | 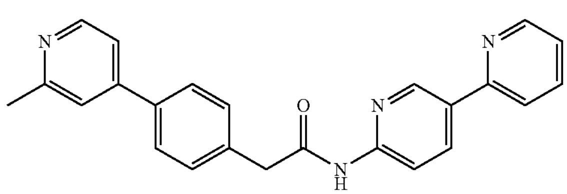 [SMILES: Cc1cc(-c2ccc(CC(=O)Nc3ccc(-c4ccccn4)cn3)cc2)ccn1] | 381.16 | 1.016 | 4.7 |

TABLE 1-continued

| Cpd | Structure | MS (m/z) (M + 1) | LC retention time (min) | IC$_{50}$ (nM) |
|---|---|---|---|---|
| 44 | 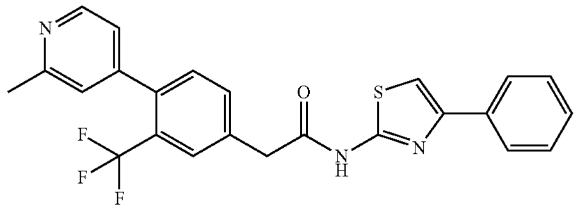 [SMILES: Cc1cc(-c2ccc(CC(=O)Nc3nc(-c4ccccc4)cs3)cc2C(F)(F)F)ccn1] | 454.11 | 2.086 | 2.5 |
| 45 | 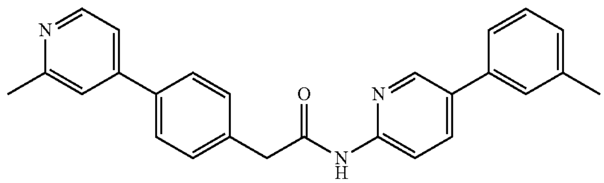 | 394.18 | 1.635 | 0.87 |
| 46 | 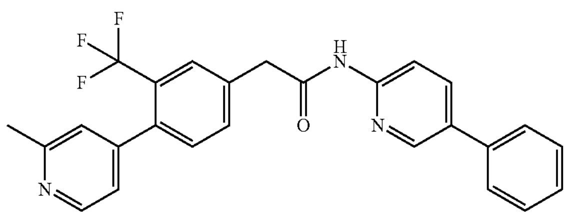 [SMILES: Cc1cc(-c2ccc(CC(=O)Nc3ccc(-c4ccccc4)cn3)cc2C(F)(F)F)ccn1] | 448.16 | 1.838 | 0.68 |
| 47 | 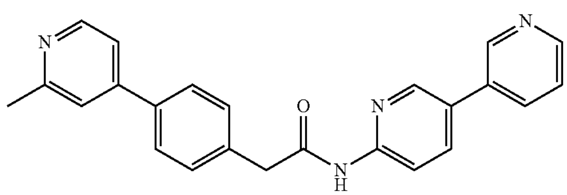 | 381.16 | 0.892 | 0.07 |
| 48 | 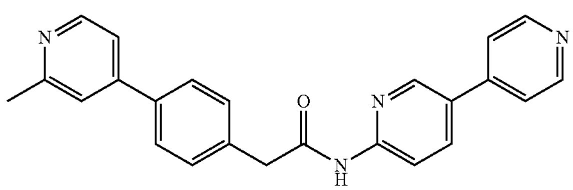 [SMILES: Cc1cc(-c2ccc(CC(=O)Nc3ccc(-c4ccncc4)cn3)cc2)ccn1] | 381.16 | 0.899 | 2.8 |
| 49 | 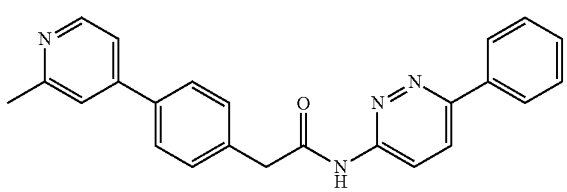 [SMILES: Cc1cc(-c2ccc(CC(=O)Nc3ccc(-c4ccccc4)nn3)cc2)ccn1] | 381.16 | 1.470 | 0.14 |
| 50 | 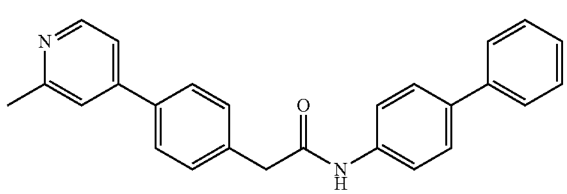 [SMILES: Cc1cc(-c2ccc(CC(=O)Nc3ccc(-c4ccccc4)cc3)cc2)ccn1] | 379.17 | 2.086 | 0.24 |

TABLE 1-continued

| Cpd | Structure | MS (m/z) (M + 1) | LC retention time (min) | IC$_{50}$ (nM) |
|---|---|---|---|---|
| 51 | 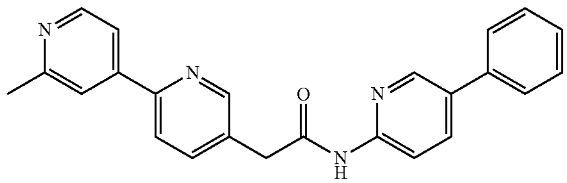 [SMILES: Cc1cc(-c2ccc(CC(=O)Nc3ccc(-c4ccccc4)cn3)cn2)ccn1] | 381.16 | 1.392 | <0.14 |
| 52 | 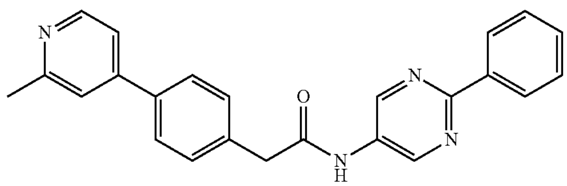 [SMILES: Cc1cc(-c2ccc(CC(=O)Nc3cnc(-c4ccccc4)nc3)cc2)ccn1] | 381.16 | 1.53 | 5.5 |
| 53 | 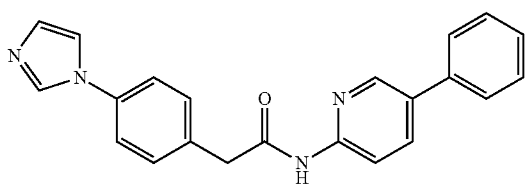 [SMILES: O=C(Cc1ccc(-n2ccnc2)cc1)Nc1ccc(-c2ccccc2)cn1] | 355.15 | 1.394 | 0.62 |
| 54 | 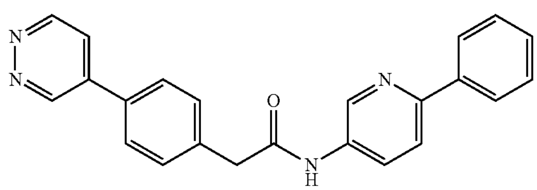 [SMILES: O=C(Cc1ccc(-c2ccnnc2)cc1)Nc1ccc(-c2ccccc2)nc1] | 367.15 | 1.296 | 1.6 |
| 55 | 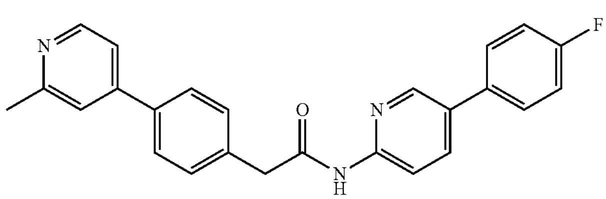 [SMILES: Cc1cc(-c2ccc(CC(=O)Nc3ccc(-c4ccc(F)cc4)cn3)cc2)ccn1] | 398.16 | 1.594 | 0.89 |
| 56 | 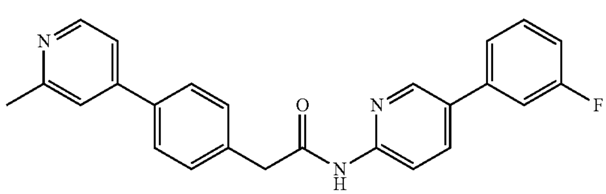 [SMILES: Cc1cc(-c2ccc(CC(=O)Nc3ccc(-c4cccc(F)c4)cn3)cc2)ccn1] | 398.16 | 1.651 | <0.09 |
| 57 | 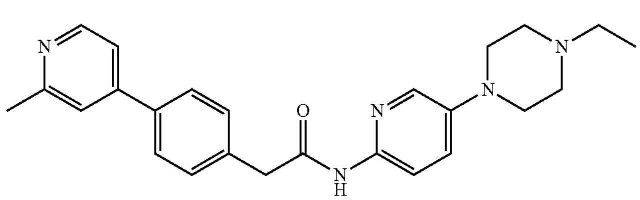 [SMILES: CCN1CCN(c2ccc(NC(=O)Cc3ccc(-c4ccnc(C)c4)cc3)nc2)CC1] | 416.24 | 0.764 | 40.3 |

TABLE 1-continued

| Cpd | Structure | MS (m/z) (M + 1) | LC retention time (min) | IC$_{50}$ (nM) |
|---|---|---|---|---|
| 58 | 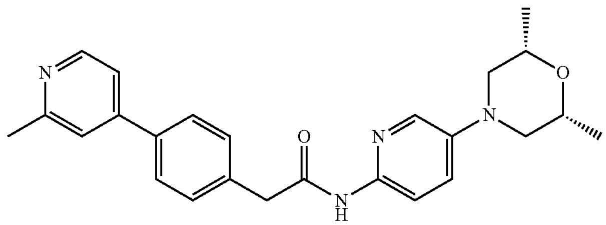 | 417.22 | 1.015 | 565.2 |
| 59 | 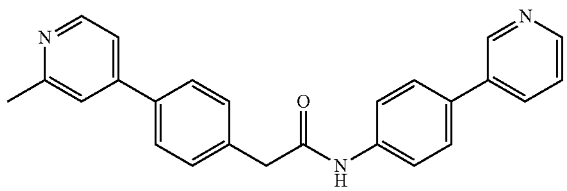 [SMILES: Cc1cc(-c2ccc(CC(=O)Nc3ccc(-c4cccnc4)cc3)cc2)ccn1] | 380.17 | 0.935 | <0.11 |
| 60 | 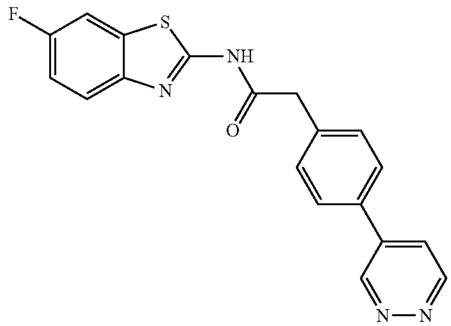 [SMILES: O=C(Cc1ccc(-c2ccnnc2)cc1)Nc1nc2ccc(F)cc2s1] | 365.08 | 1.703 | 140.8 |
| 61 | 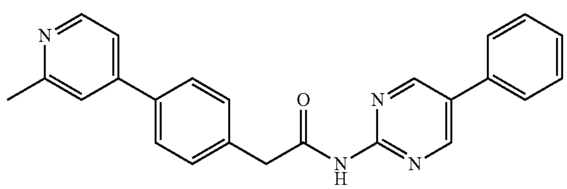 [SMILES: Cc1cc(-c2ccc(CC(=O)Nc3ncc(-c4ccccc4)cn3)cc2)ccn1] | 381.16 | 1.436 | 16.0 |
| 62 | 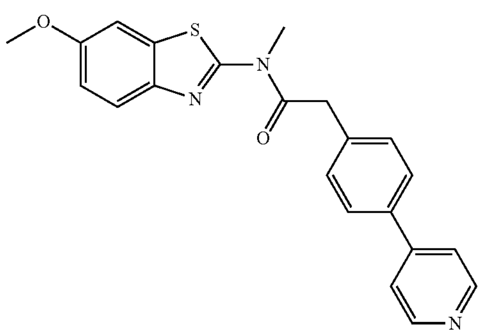 [SMILES: COc1ccc2nc(N(C)C(=O)Cc3ccc(-c4ccncc4)cc3)sc2c1] | 390.12 | 1.572 | 188.8 |
| 63 | 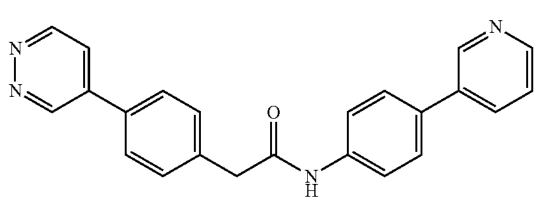 [SMILES: O=C(Cc1ccc(-c2ccnnc2)cc1)Nc1ccc(-c2cccnc2)cc1] | 367.15 | 1.004 | 0.948 |

TABLE 1-continued
| Cpd | Structure | MS (m/z) (M + 1) | LC retention time (min) | IC$_{50}$ (nM) |
|---|---|---|---|---|
| 64 | 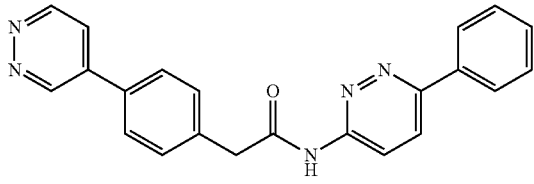 [SMILES: O=C(Cc1ccc(-c2ccnnc2)cc1)Nc1ccc(-c2ccccc2)nn1] | 368.14 | 1.708 | 0.68 |
| 65 | 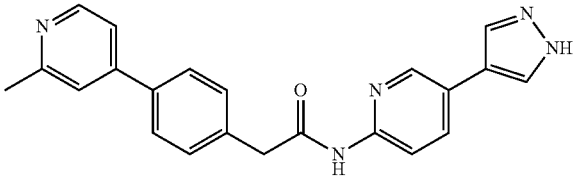 [SMILES: Cc1cc(-c2ccc(CC(=O)Nc3ccc(-c4cn[nH]c4)cn3)cc2)ccn1] | 370.16 | 1.75 | 2.0 |
| 66 | 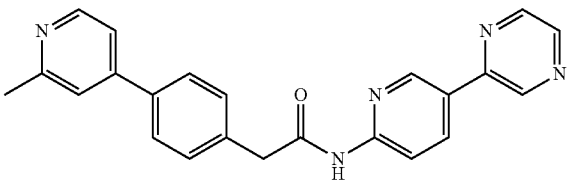 [SMILES: Cc1cc(-c2ccc(CC(=O)Nc3ccc(-c4cnccn4)cn3)cc2)ccn1] | 382.16 | 1.124 | 0.36 |
| 67 | 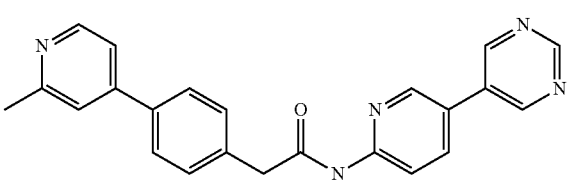 | 382.16 | 1.148 | 0.42 |
| 68 | 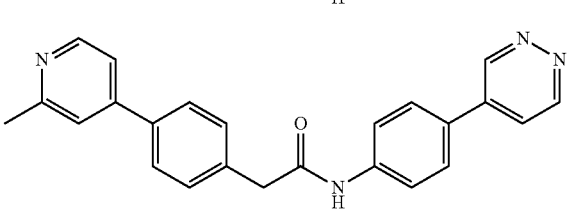 | 381.16 | 1.149 | 1.4 |
| 69 | 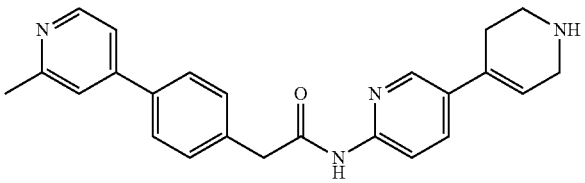 [SMILES: Cc1cc(-c2ccc(CC(=O)Nc3ccc(C4=CCNCC4)cn3)cc2)ccn1] | 385.19 | 0.806 | 41.8 |
| 70 | 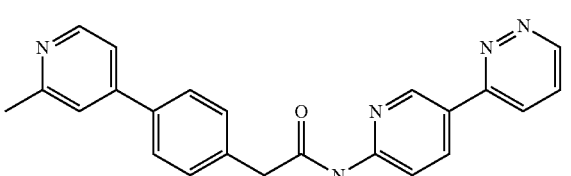 | 382.16 | 0.585 | 0.15 |
| 71 | 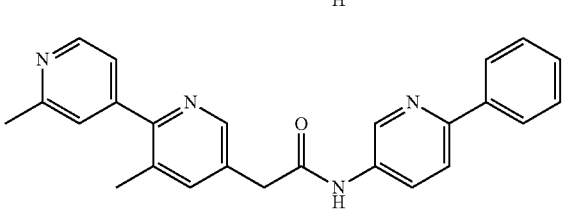 | 395.18 | 1.110 | 0.71 |

TABLE 1-continued

| Cpd | Structure | MS (m/z) (M + 1) | LC retention time (min) | IC$_{50}$ (nM) |
|---|---|---|---|---|
| 72 | 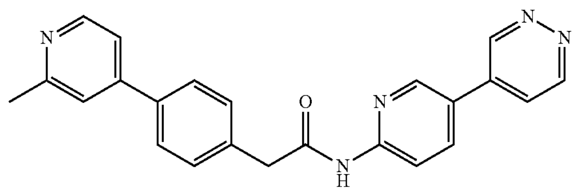 [SMILES: Cc1cc(-c2ccc(CC(=O)Nc3ccc(-c4ccnnc4)cn3)cc2)ccn1] | 382.16 | 0.431 | 1.1 |
| 73 | 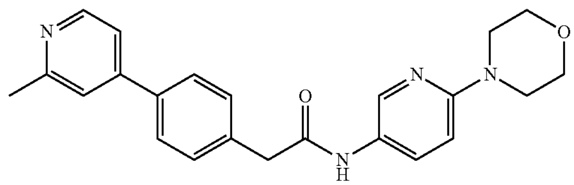 [SMILES: Cc1cc(-c2ccc(CC(=O)Nc3ccc(N4CCOCC4)nc3)cc2)ccn1] | 389.19 | 0.823 | 615.7 |
| 74 | 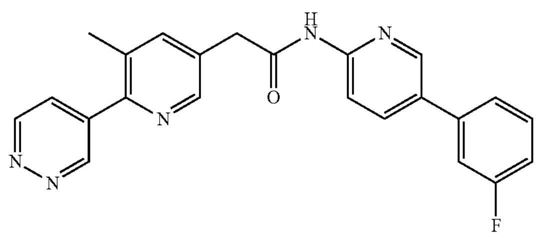 [SMILES: Cc1cc(CC(=O)Nc2ccc(-c3cccc(F)c3)cn2)cnc1-c1ccnnc1] | 400.1 | 1.655 | <0.1 |
| 75 | 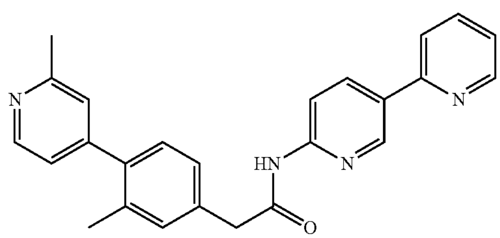 [SMILES: Cc1cc(-c2ccc(CC(=O)Nc3ccc(-c4ccccn4)cn3)cc2C)ccn1] | 395.20 | 1.068 | 0.1 |
| 76 | 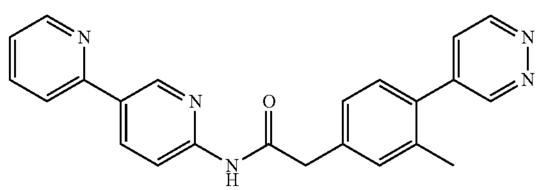 [SMILES: Cc1cc(CC(=O)Nc2ccc(-c3ccccn3)cn2)ccc1-c1ccnnc1] | 382.20 | 1.159 | 0.12 |
| 77 | 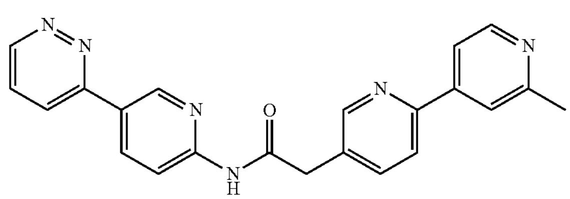 [SMILES: Cc1cc(-c2ccc(CC(=O)Nc3ccc(-c4cccnn4)cn3)cn2)ccn1] | 383.20 | 0.859 | 1.3 |
| 78 | 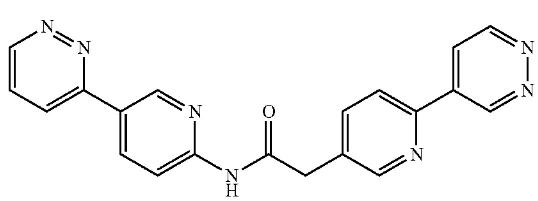 [SMILES: O=C(Cc1ccc(-c2ccnnc2)nc1)Nc1ccc(-c2cccnn2)cn1] | 370.10 | 0.878 | 9 |

TABLE 1-continued

| Cpd | Structure | MS (m/z) (M + 1) | LC retention time (min) | IC$_{50}$ (nM) |
|---|---|---|---|---|
| 79 | 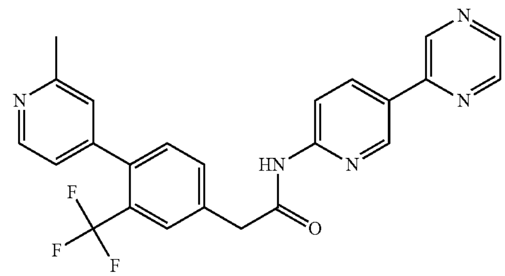 [SMILES: Cc1cc(-c2ccc(CC(=O)Nc3ccc(-c4cnccn4)cn3)cc2C(F)(F)F)ccn1] | 450.20 | 1.251 | 0.13 |
| 80 | 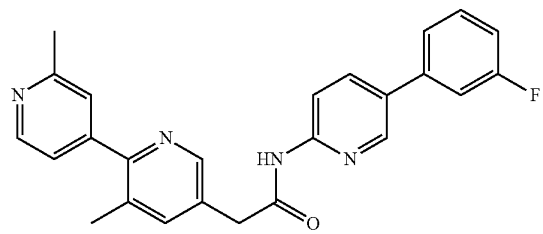 [SMILES: Cc1cc(-c2ncc(CC(=O)Nc3ccc(-c4cccc(F)c4)cn3)cc2C)ccn1] | 413.20 | 1.538 | 0.13 |
| 81 | 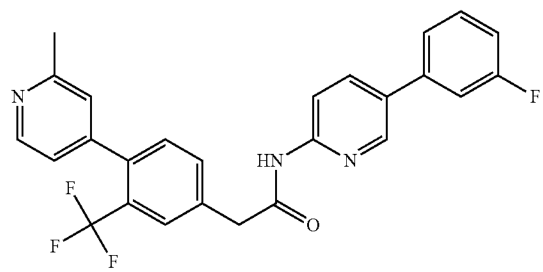 [SMILES: Cc1cc(-c2ccc(CC(=O)Nc3ccc(-c4cccc(F)c4)cn3)cc2C(F)(F)F)ccn1] | 465.20 | 1.837 | 0.2 |
| 82 | 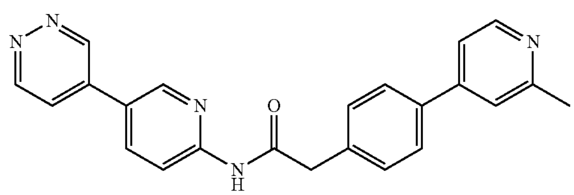 [SMILES: Cc1cc(-c2ccc(CC(=O)Nc3ccc(-c4ccnnc4)cn3)cc2)ccn1] | 382.20 | 1.016 | 0.9 |
| 83 | 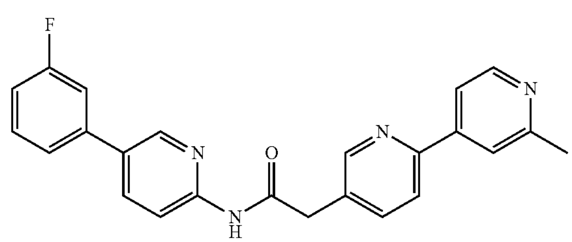 [SMILES: Cc1cc(-c2ccc(CC(=O)Nc3ccc(-c4cccc(F)c4)cn3)cn2)ccn1] | 399.20 | 1.505 | 0.06 |

$^1$H NMR 400 MHz (DMSO-d$_6$) δ 10.95 (s, 1H), 8.67 (t, 1H), 8.62 (d, 1H), 8.49 (d, 1H), 8.09 (d, 2H), 8.02 (d, 1H), 7.87 (m, 2H), 7.78 (m, 1H), 7.57-7.51 (m, 2H), 7.48-7.44 (m, 1H), 7.15 (m, 1H), 3.84 (s, 2H), 2.49 (s, 3H).

TABLE 1-continued

| Cpd | Structure | MS (m/z) (M + 1) | LC retention time (min) | IC₅₀ (nM) |
|---|---|---|---|---|
| 84 | | 399.20 | 1.456 | 128 |

¹H NMR 400 MHz (DMSO-d₆) δ 10.59 (s, 1H), 8.78 (d, 1H), 8.56 (m, 1H), 8.46 (m, 1H), 8.28 (d, 1H), 8.22 (d, 1H), 8.13 (dd, 1H), 7.95 (d, 1H), 7.84-7.81 (m, 2H), 7.77 (m, 1H), 7.70 (m, 1H), 7.47-7.42(m, 1H), 7.18-7.13 (m, 1H), 3.78 (s, 2H), 2.29 (s, 3H).

| Cpd | Structure | MS (m/z) (M + 1) | LC retention time (min) | IC₅₀ (nM) |
|---|---|---|---|---|
| 85 | 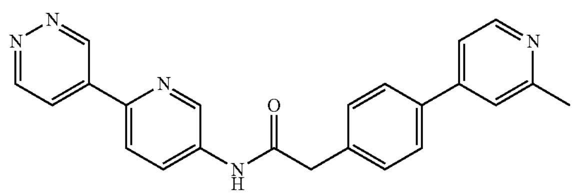 [SMILES: Cc1cc(-c2ccc(CC(=O)Nc3ccc(-c4ccnnc4)nc3)cc2)ccn1] | 382.20 | 1.022 | 37 |
| 86 | 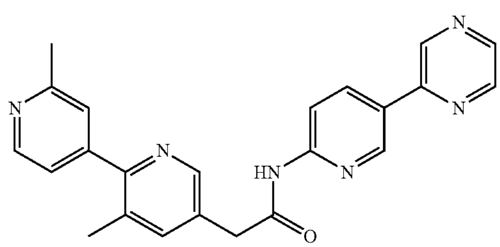 [SMILES: Cc1cc(-c2ncc(CC(=O)Nc3ccc(-c4cnccn4)cn3)cc2C)ccn1] | 397.20 | 1.074 | 0.38 |
| 87 | 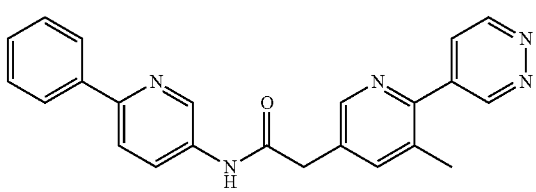 [SMILES: Cc1cc(CC(=O)Nc2ccc(-c3ccccc3)nc2)cnc1-c1ccnnc1] | 382.20 | 1.428 | 0.72 |
| 88 | 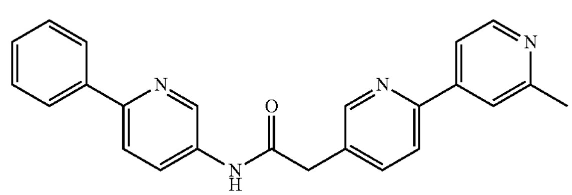 [SMILES: Cc1cc(-c2ccc(CC(=O)Nc3ccc(-c4ccccc4)nc3)cn2)ccn1] | 381.2 | 1.15 | 0.38 |
| 89 | 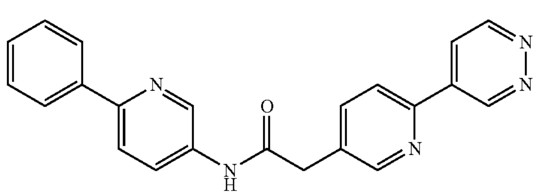 [SMILES: O=C(Cc1ccc(-c2ccnnc2)nc1)Nc1ccc(-c2ccccc2)nc1] | 368.2 | 1.19 | 2.8 |

TABLE 1-continued

| Cpd | Structure | MS (m/z) (M + 1) | LC retention time (min) | IC$_{50}$ (nM) |
|---|---|---|---|---|
| 90 | 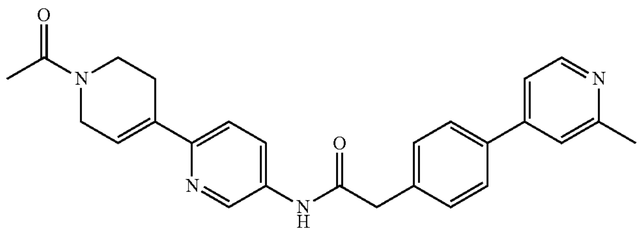 [SMILES: CC(=O)N1CC=C(c2ccc(NC(=O)Cc3ccc(-c4ccnc(C)c4)cc3)cn2)CC1] | 427.1 | 0.931 | 0.66 |
| 91 | 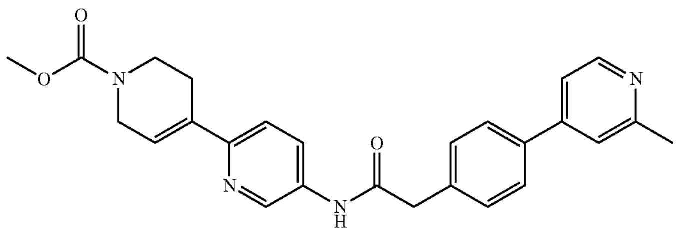 | 443.1 | 1.089 | 0.3 |
| 92 | 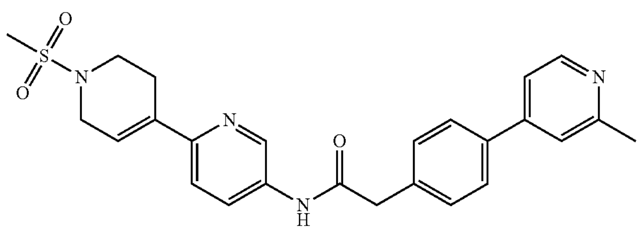 | 463.1 | 1.052 | 31 |
| 93 | 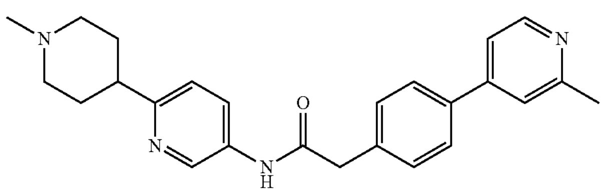 | 401.2 | 0.775 | 705 |
| 94 | 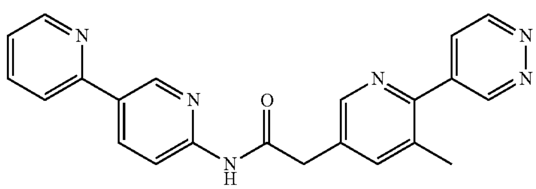 [SMILES: Cc1cc(CC(=O)Nc2ccc(-c3ccccn3)cn2)cnc1-c1ccnnc1] | 383.20 | 0.983 | 2.1 |
| 95 | 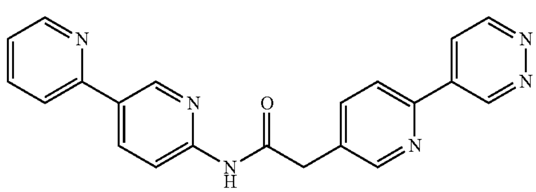 [SMILES: O=C(Cc1ccc(-c2ccnnc2)nc1)Nc1ccc(-c2ccccn2)cn1] | 369.2 | 1.23 | 1.8 |
| 96 | 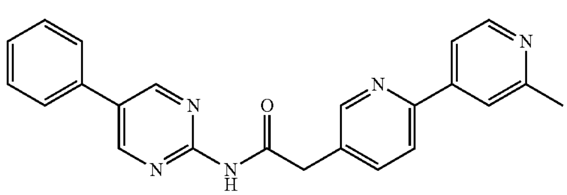 [SMILES: Cc1cc(-c2ccc(CC(=O)Nc3ncc(-c4ccccc4)cn3)cn2)ccn1] | 382.1 | 1.274 | 2.5 |

TABLE 1-continued

| Cpd | Structure | MS (m/z) (M + 1) | LC retention time (min) | IC$_{50}$ (nM) |
|---|---|---|---|---|
| 97 | 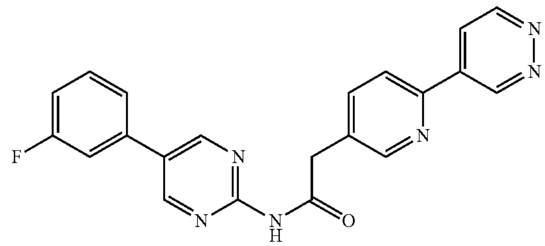 [SMILES: O=C(Cc1ccc(-c2ccnnc2)nc1)Nc1ncc(-c2cccc(F)c2)cn1] | 387.10 | 1.901 | |
| 98 | 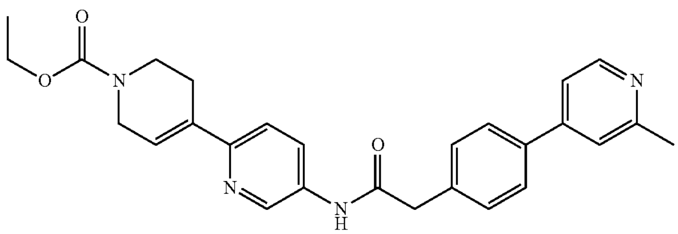 [SMILES: CCOC(=O)N1CC=C(c2ccc(NC(=O)Cc3ccc(-c4ccnc(C)c4)cc3)cn2)CC1] | 457.2 | 1.159 | |
| 99 | 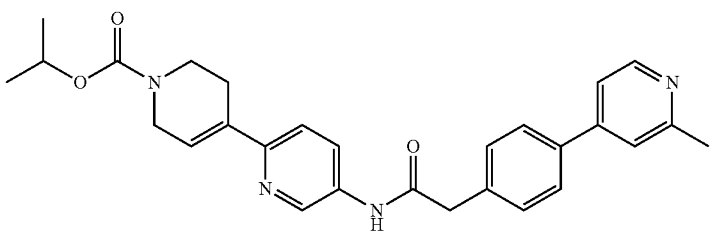 [SMILES: Cc1cc(-c2ccc(CC(=O)Nc3ccc(C4=CCN(C(=O)OC(C)C)CC4)nc3)cc2)ccn1] | 471.2 | 1.277 | |
| 100 | 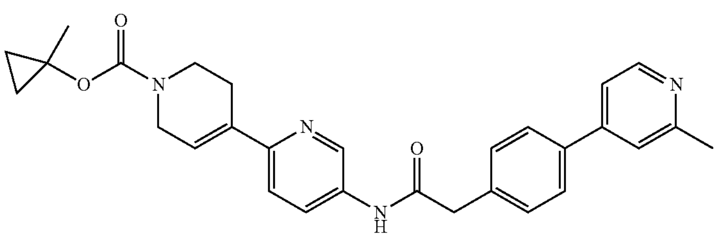 [SMILES: Cc1cc(-c2ccc(CC(=O)Nc3ccc(C4=CCN(C(=O)OC5(C)CC5)CC4)nc3)cc2)ccn1] | 483.2 | 1.280 | |
| 101 | 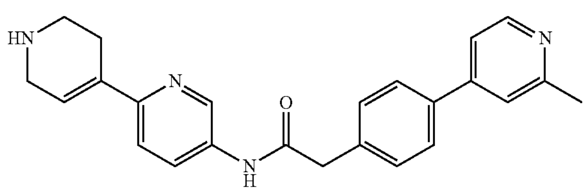 [SMILES: Cc1cc(-c2ccc(CC(=O)Nc3ccc(C4=CCNCC4)nc3)cc2)ccn1] | 385.2 | 0.791 | 66 |
| 102 | 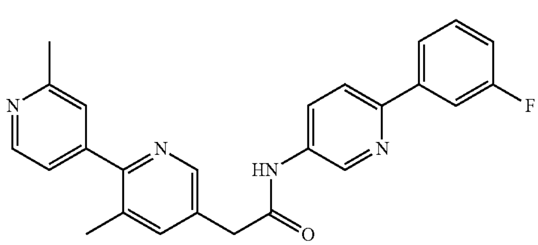 [SMILES: Cc1cc(-c2ncc(CC(=O)Nc3ccc(-c4cccc(F)c4)nc3)cc2C)ccn1] | 413.20 | 1.393 | 0.23 |

TABLE 1-continued

| Cpd | Structure | MS (m/z) (M + 1) | LC retention time (min) | IC$_{50}$ (nM) |
|---|---|---|---|---|
| 103 | 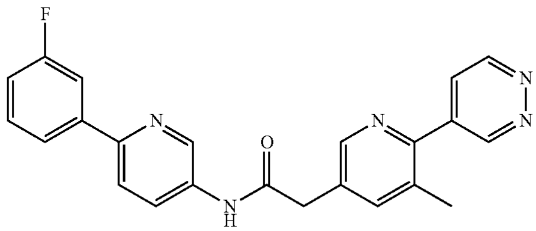 [SMILES: Cc1cc(CC(=O)Nc2ccc(-c3cccc(F)c3)nc2)cnc1-c1ccnnc1] | 400.20 | 1.496 | 0.59 |
| 104 | 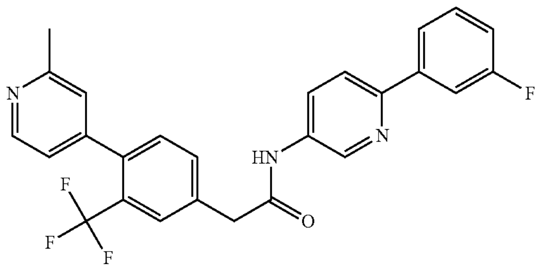 [SMILES: Cc1cc(-c2ccc(CC(=O)Nc3ccc(-c4cccc(F)c4)nc3)cc2C(F)(F)F)ccn1] | 466.20 | 1.669 | 0.29 |
| 105 | 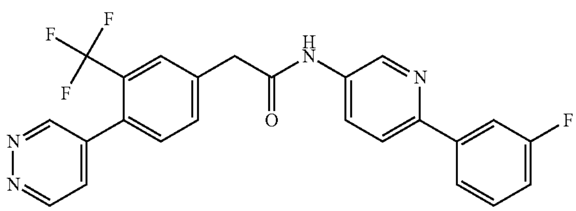 [SMILES: O=C(Cc1ccc(-c2ccnnc2)c(C(F)(F)F)c1)Nc1ccc(-c2cccc(F)c2)nc1] | 453.10 | 1.940 | 0.11 |
| 106 | 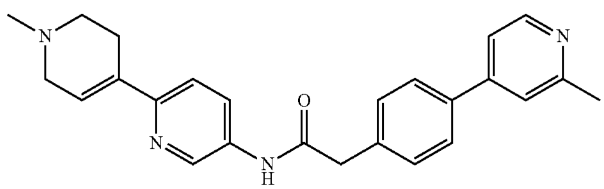 | 399.2 | 0.781 | 19 |
| 107 | 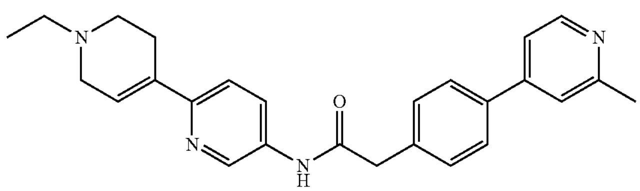 [SMILES: CCN1CC=C(c2ccc(NC(=O)Cc3ccc(-c4ccnc(C)c4)cc3)cn2)CC1] | 413.2 | 0.810 | 35 |
| 108 | 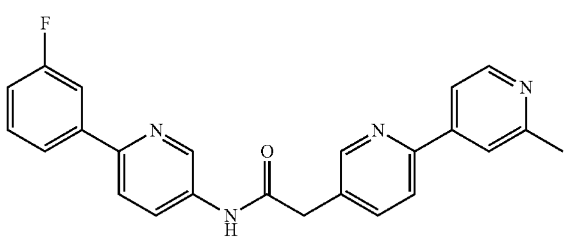 [SMILES: Cc1cc(-c2ccc(CC(=O)Nc3ccc(-c4cccc(F)c4)nc3)cn2)ccn1] | 399.2 | 1.354 | 0.2 |
| 109 | 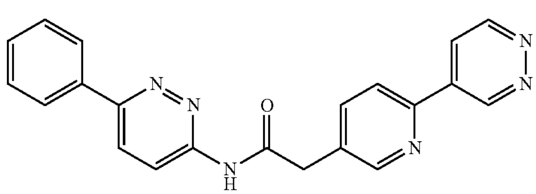 [SMILES: O=C(Cc1ccc(-c2ccnnc2)nc1)Nc1ccc(-c2ccccc2)nn1] | 369.2 | 1.74 | 1.3 |

TABLE 1-continued

| Cpd | Structure | MS (m/z) (M + 1) | LC retention time (min) | IC$_{50}$ (nM) |
|---|---|---|---|---|
| 110 | 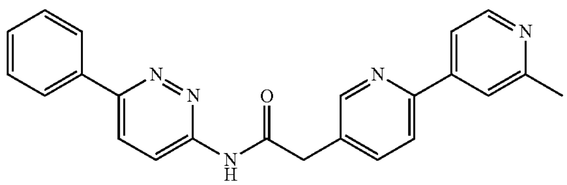 [SMILES: Cc1cc(-c2ccc(CC(=O)Nc3ccc(-c4ccccc4)nn3)cn2)ccn1] | 382.2 | 1.36 | 0.08 |
| 111 | 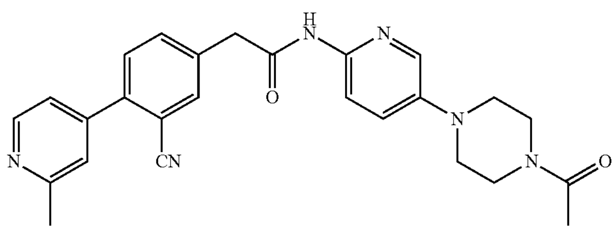 [SMILES: CC(=O)N1CCN(c2ccc(NC(=O)Cc3ccc(-c4ccnc(C)c4)c(C#N)c3)nc2)CC1] | 455.2 | | 0.11 |
| 112 | 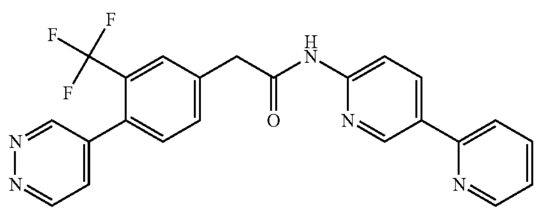 [SMILES: O=C(Cc1ccc(-c2ccnnc2)c(C(F)(F)F)c1)Nc1ccc(-c2ccccn2)cn1] | 436.10 | 1.915 | 0.1 |
| 113 | 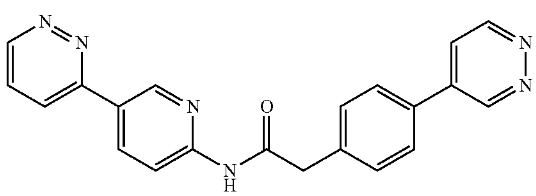 | 369.20 | 1.759 | 0.8 |
| 114 | 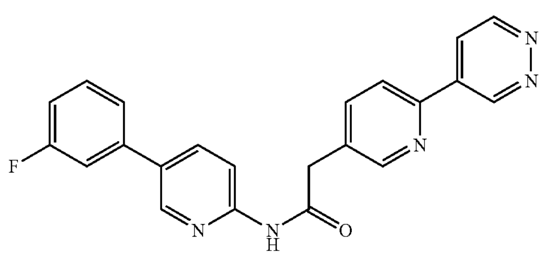 [SMILES: O=C(Cc1ccc(-c2ccnnc2)nc1)Nc1ccc(-c2cccc(F)c2)cn1] | 386.10 | 1.709 | 0.6 |
| 115 | 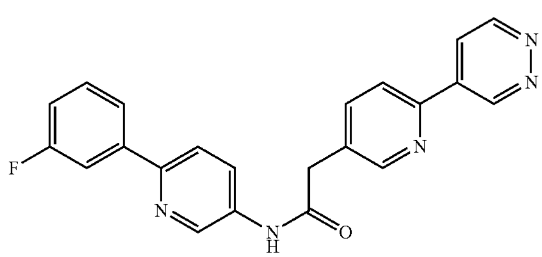 [SMILES: O=C(Cc1ccc(-c2ccnnc2)nc1)Nc1ccc(-c2cccc(F)c2)nc1] | 386.10 | 4.545 | 1.6 |

TABLE 1-continued

| Cpd | Structure | MS (m/z) (M + 1) | LC retention time (min) | IC$_{50}$ (nM) |
| --- | --- | --- | --- | --- |
| 116 | 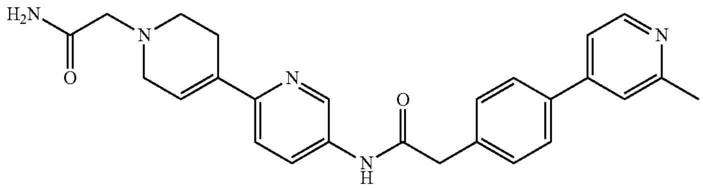 [SMILES: Cc1cc(-c2ccc(CC(=O)Nc3ccc(C4=CCN(CC(N)=O)CC4)nc3)cc2)ccn1] | 442.20 | 0.781 | 12.4 |
| 117 | 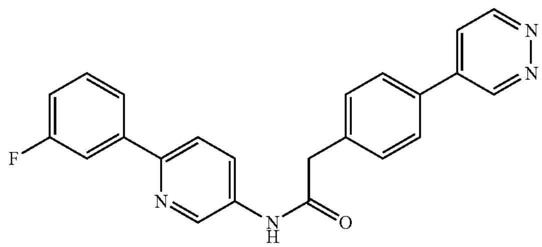 [SMILES: O=C(Cc1ccc(-c2ccnnc2)cc1)Nc1ccc(-c2cccc(F)c2)nc1] | 385.10 | 1.611 | 1.1 |
| 118 | 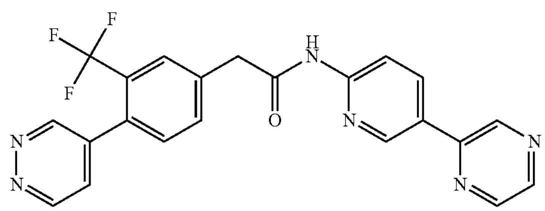 [SMILES: O=C(Cc1ccc(-c2ccnnc2)c(C(F)(F)F)c1)Nc1ccc(-c2cnccn2)cn1] | 437.10 | 1.395 | 0.1 |
| 119 | 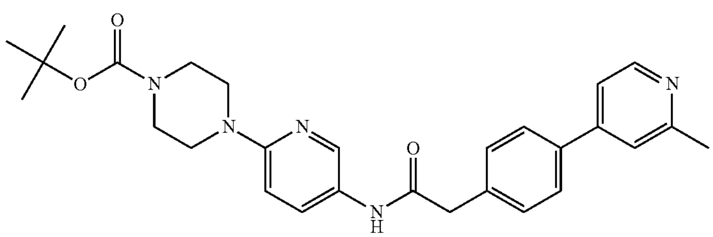 [SMILES: Cc1cc(-c2ccc(CC(=O)Nc3ccc(N4CCN(C(=O)OC(C)(C)C)CC4)nc3)cc2)ccn1] | 488.20 | 1.234 | 1.3 |
| 120 | 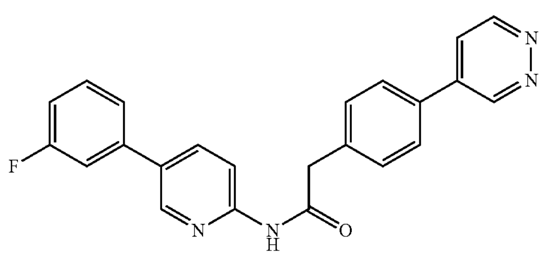 [SMILES: O=C(Cc1ccc(-c2ccnnc2)cc1)Nc1ccc(-c2cccc(F)c2)cn1] | 385.10 | 1.787 | 0.1 |
| 121 | 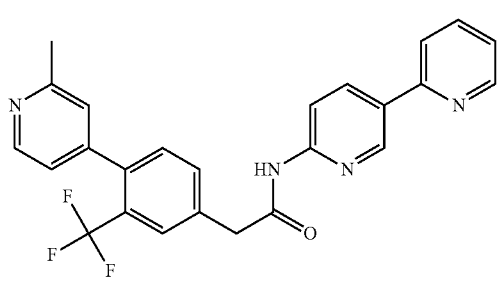 [SMILES: Cc1cc(-c2ccc(CC(=O)Nc3ccc(-c4ccccn4)cn3)cc2C(F)(F)F)ccn1] | 449.20 | 1.230 | 0.1 |

TABLE 1-continued

| Cpd | Structure | MS (m/z) (M + 1) | LC retention time (min) | IC$_{50}$ (nM) |
|---|---|---|---|---|
| 122 | 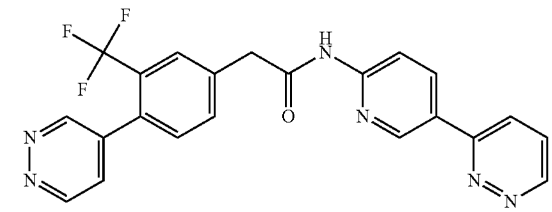 [SMILES: O=C(Cc1ccc(-c2ccnnc2)c(C(F)(F)F)c1)Nc1ccc(-c2cccnn2)cn1] | 437.10 | 1.459 | 0.2 |
| 123 | 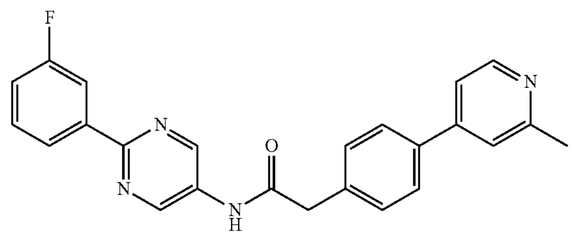 [SMILES: Cc1cc(-c2ccc(CC(=O)Nc3cnc(-c4cccc(F)c4)nc3)cc2)ccn1] | 399.10 | 1.611 | 0.9 |
| 124 | 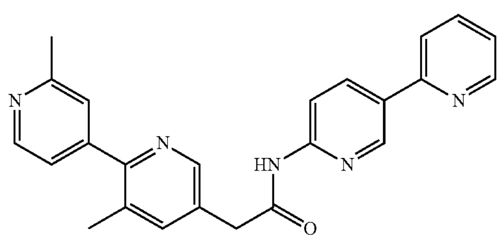 [SMILES: Cc1cc(-c2ncc(CC(=O)Nc3ccc(-c4ccccn4)cn3)cc2C)ccn1] | 396.20 | 0.949 | 0.2 |
| 125 | 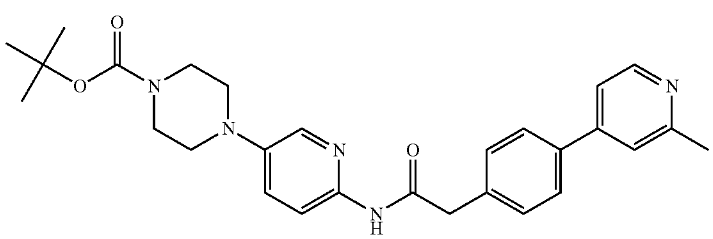 [SMILES: Cc1cc(-c2ccc(CC(=O)Nc3ccc(N4CCN(C(=O)OC(C)(C)C)CC4)cn3)cc2)ccn1] | 488.20 | 1.408 | 0.2 |
| 126 | 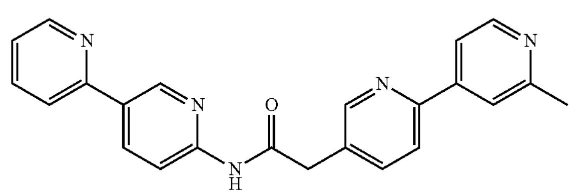 [SMILES: Cc1cc(-c2ccc(CC(=O)Nc3ccc(-c4ccccn4)cn3)cn2)ccn1] | 382.20 | 0.947 | 0.5 |
| 127 | 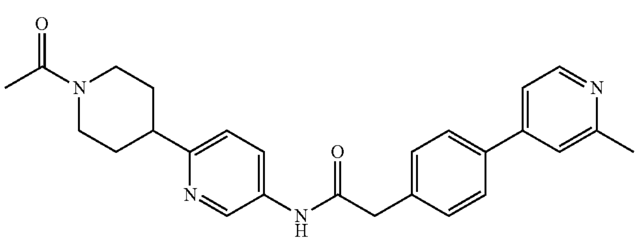 [SMILES: CC(=O)N1CCC(c2ccc(NC(=O)Cc3ccc(-c4ccnc(C)c4)cc3)cn2)CC1] | 429.20 | 0.801 | 780 |
| 128 | 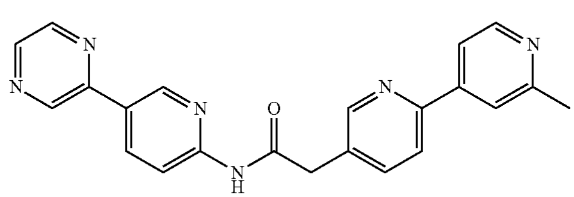 [SMILES: Cc1cc(-c2ccc(CC(=O)Nc3ccc(-c4cnccn4)cn3)cn2)ccn1] | 383.20 | 1.080 | 0.4 |

TABLE 1-continued

| Cpd | Structure | MS (m/z) (M + 1) | LC retention time (min) | IC$_{50}$ (nM) |
|---|---|---|---|---|
| 129 | 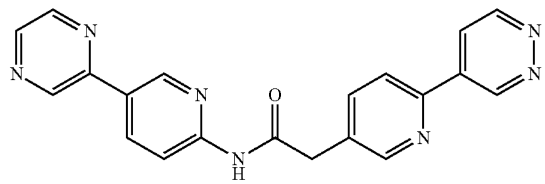 [SMILES: O=C(Cc1ccc(-c2ccnnc2)nc1)Nc1ccc(-c2cnccn2)cn1] | 370.20 | 1.173 | 7.1 |
| 130 | 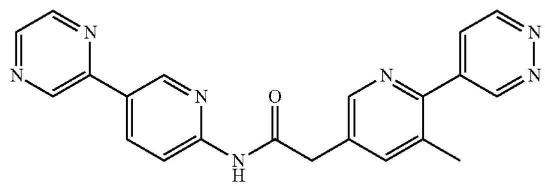 [SMILES: Cc1cc(CC(=O)Nc2ccc(-c3cnccn3)cn2)cnc1-c1ccnnc1] | 384.20 | 2.383 | 0.7 |
| 131 | 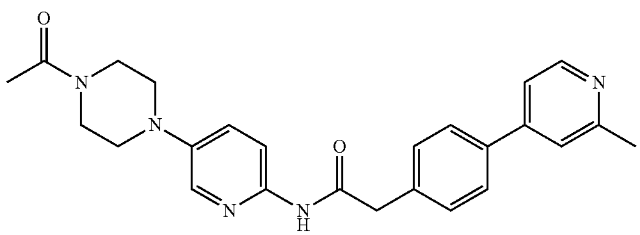 [SMILES: CC(=O)N1CCN(c2ccc(NC(=O)Cc3ccc(-c4ccnc(C)c4)cc3)nc2)CC1] | 430.20 | 0.880 | 0.3 |
| 132 | 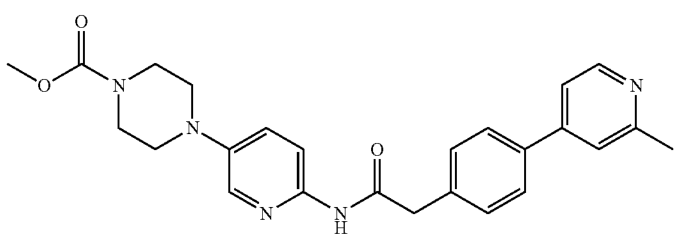 | 446.20 | 1.042 | 0.1 |
| 133 | 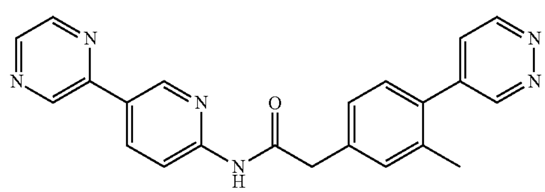 [SMILES: Cc1cc(CC(=O)Nc2ccc(-c3cnccn3)cn2)ccc1-c1ccnnc1] | 383.20 | 1.369 | 0.1 |
| 134 | 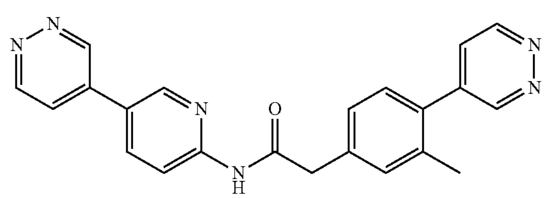 [SMILES: Cc1cc(CC(=O)Nc2ccc(-c3ccnnc3)cn2)ccc1-c1ccnnc1] | 383.20 | 0.958 | 0.8 |
| 135 | 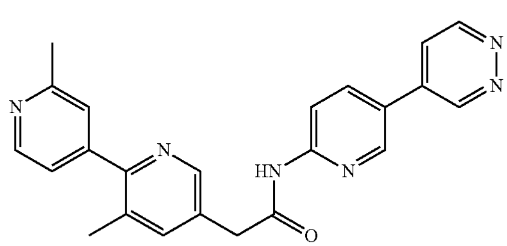 [SMILES: Cc1cc(-c2ncc(CC(=O)Nc3ccc(-c4ccnnc4)cn3)cc2C)ccn1] | 397.20 | 2.197 | 3.2 |

TABLE 1-continued

| Cpd | Structure | MS (m/z) (M + 1) | LC retention time (min) | IC$_{50}$ (nM) |
|---|---|---|---|---|
| 136 | 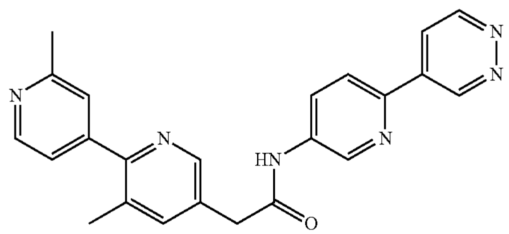 [SMILES: Cc1cc(-c2ncc(CC(=O)Nc3ccc(-c4ccnnc4)nc3)cc2C)ccn1] | 397.10 | 0.918 | 127 |
| 137 | 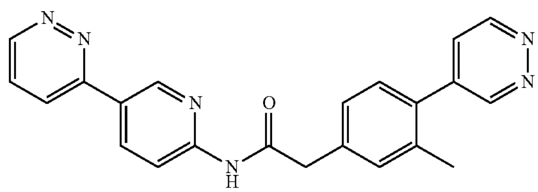 [SMILES: Cc1cc(CC(=O)Nc2ccc(-c3cccnn3)cn2)ccc1-c1ccnnc1] | 383.20 | 1.220 | 0.9 |
| 138 | 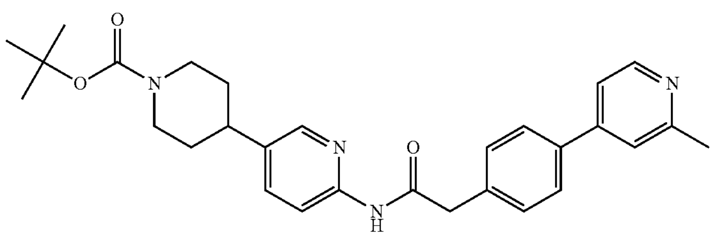 [SMILES: Cc1cc(-c2ccc(CC(=O)Nc3ccc(C4CCN(C(=O)OC(C)(C)C)CC4)cn3)cc2)ccn1] | 487.20 | 1.545 | 2.7 |
| 139 | 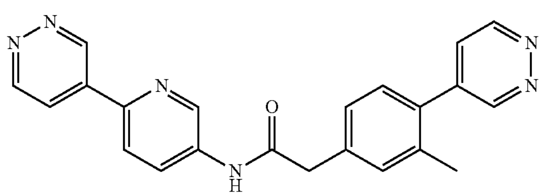 [SMILES: Cc1cc(CC(=O)Nc2ccc(-c3ccnnc3)nc2)ccc1-c1ccnnc1] | 383.20 | 1.221 | 10.3 |
| 140 | 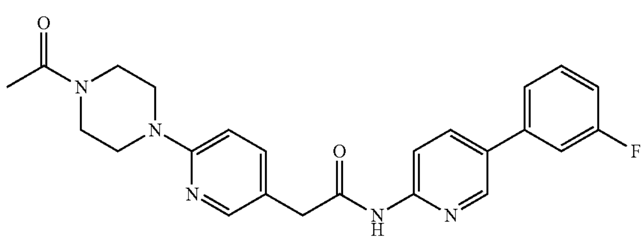 [SMILES: CC(=O)N1CCN(c2ccc(CC(=O)Nc3ccc(-c4cccc(F)c4)cn3)cn2)CC1] | 434.20 | 1.433 | 4.3 |
| 141 | 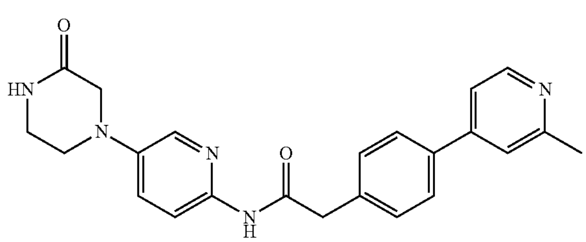 [SMILES: Cc1cc(-c2ccc(CC(=O)Nc3ccc(N4CCNC(=O)C4)cn3)cc2)ccn1] | 402.10 | 0.826 | 19.5 |

TABLE 1-continued

| Cpd | Structure | MS (m/z) (M + 1) | LC retention time (min) | IC$_{50}$ (nM) |
|---|---|---|---|---|
| 142 | 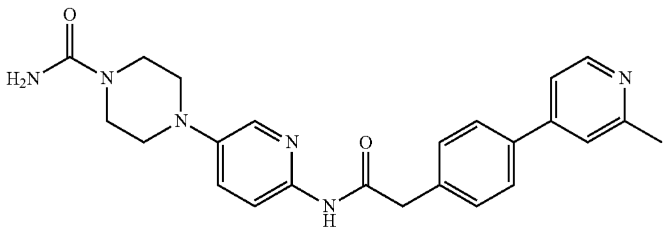 [SMILES: Cc1cc(-c2ccc(CC(=O)Nc3ccc(N4CCN(C(N)=O)CC4)cn3)cc2)ccn1] | 431.20 | 0.885 | 1.4 |
| 143 | 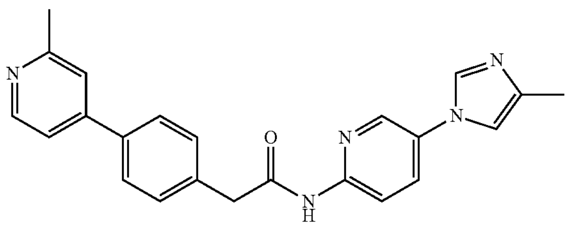 [SMILES: Cc1cc(-c2ccc(CC(=O)Nc3ccc(-n4cnc(C)c4)cn3)cc2)ccn1] | 384.10 | 0.948 | 0.6 |
| 144 | 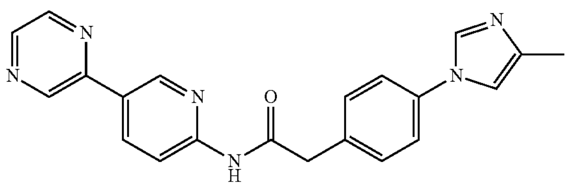 [SMILES: Cc1cn(-c2ccc(CC(=O)Nc3ccc(-c4cnccn4)cn3)cc2)cn1] | 430.20 | 0.843 | 17.4 |
| 145 | 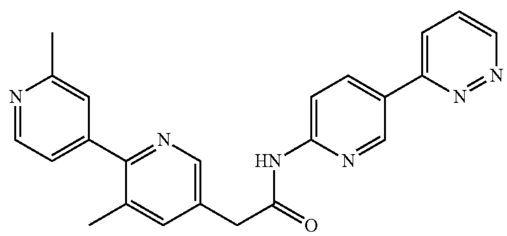 [SMILES: Cc1cc(-c2ncc(CC(=O)Nc3ccc(-c4cccnn4)cn3)cc2C)ccn1] | 397.20 | 0.950 | 1.0 |
| 146 | 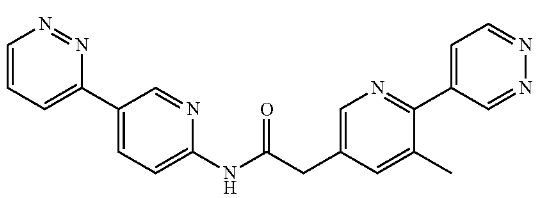 [SMILES: Cc1cc(CC(=O)Nc2ccc(-c3cccnn3)cn2)cnc1-c1ccnnc1] | 384.20 | 1.004 | 5.7 |
| 147 | 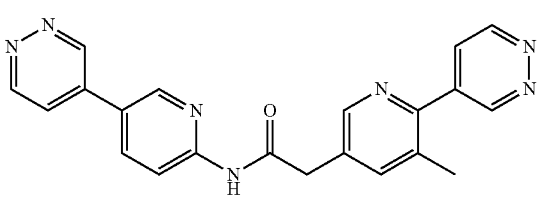 [SMILES: Cc1cc(CC(=O)Nc2ccc(-c3ccnnc3)cn2)cnc1-c1ccnnc1] | 384.20 | 0.979 | 55 |
| 148 | 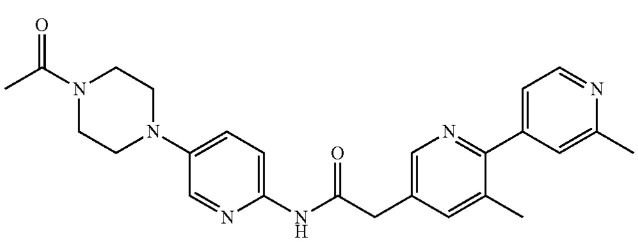 | 445.20 | 0.772 | 1.6 |

TABLE 1-continued

| Cpd | Structure | MS (m/z) (M + 1) | LC retention time (min) | IC$_{50}$ (nM) |
|---|---|---|---|---|
| 149 | 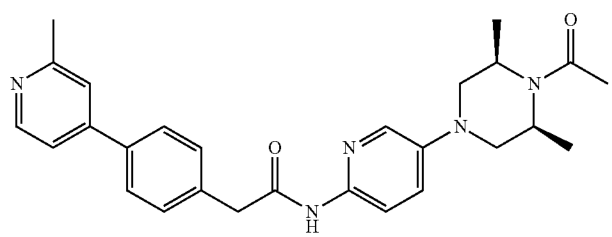 [SMILES: CC(=O)N1[C@H](C)CN(c2ccc(NC(=O)Cc3ccc(-c4ccnc(C)c4)cc3)nc2)C[C@@H]1C] | 458.20 | 0.990 | 4.2 |
| 150 | 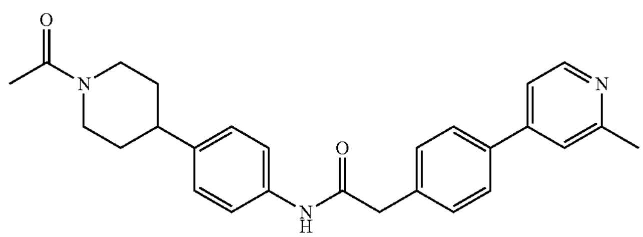 [SMILES: CC(=O)N1CCC(c2ccc(NC(=O)Cc3ccc(-c4ccnc(C)c4)cc3)cc2)CC1] | 428.20 | 1.271 | 65 |
| 151 | 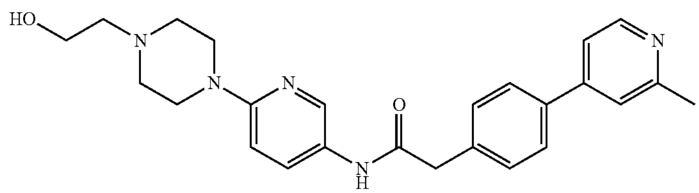 [SMILES: Cc1cc(-c2ccc(CC(=O)Nc3ccc(N4CCN(CCO)CC4)nc3)cc2)ccn1] | 432.20 | 0.750 | 163 |
| 152 | 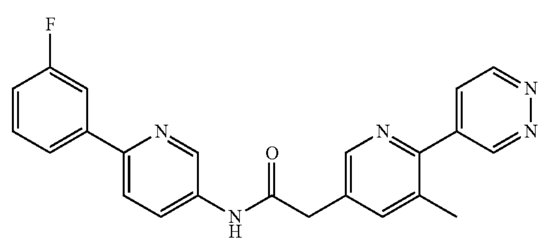 [SMILES: Cc1cc(CC(=O)Nc2ccc(-c3cccc(F)c3)nc2)cnc1-c1ccnnc1] | 400.20 | 1.459 | 0.3 |
| 153 | 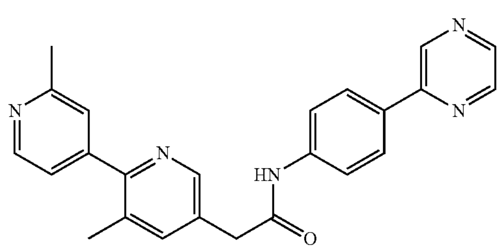 [SMILES: Cc1cc(-c2ncc(CC(=O)Nc3ccc(-c4cnccn4)cc3)cc2C)ccn1] | 396.20 | 1.160 | 0.8 |
| 154 | 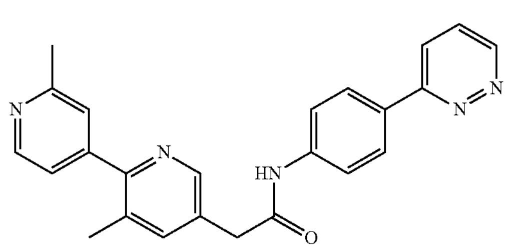 | 396.20 | 1.011 | 2.5 |

TABLE 1-continued

| Cpd | Structure | MS (m/z) (M + 1) | LC retention time (min) | IC$_{50}$ (nM) |
|---|---|---|---|---|
| 155 | 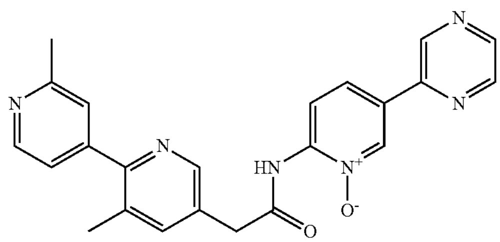 [SMILES: Cc1cc(-c2ncc(CC(=O)Nc3ccc(-c4cnccn4)c[n+]3[O-])cc2C)ccn1] | 413.20 | 0.864 | |
| 156 | 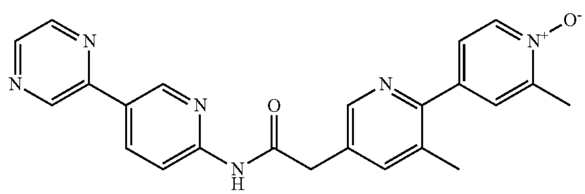 [SMILES: Cc1cc(CC(=O)Nc2ccc(-c3cnccn3)cn2)cnc1-c1cc[n+]([O-])c(C)c1] | 413.20 | 1.027 | 8.0 |
| 157 | 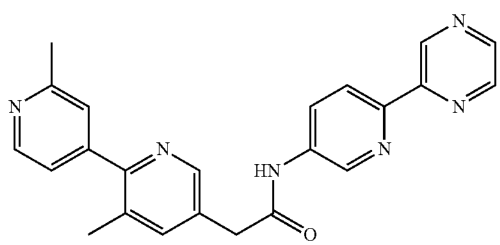 [SMILES: Cc1cc(-c2ncc(CC(=O)Nc3ccc(-c4cnccn4)nc3)cc2C)ccn1] | 397.20 | 1.040 | 1.6 |
| 158 | 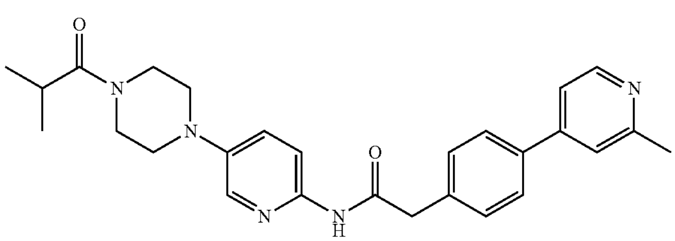 [SMILES: Cc1cc(-c2ccc(CC(=O)Nc3ccc(N4CCN(C(=O)C(C)C)CC4)cn3)cc2)ccn1] | 458.20 | 1.075 | 50.6 |
| 159 | 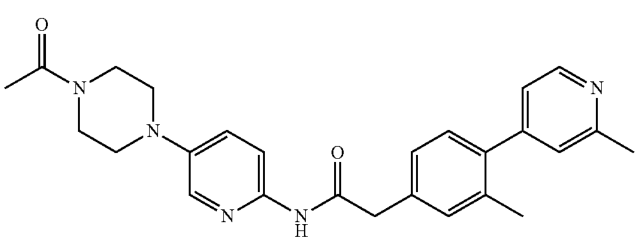 [SMILES: CC(=O)N1CCN(c2ccc(NC(=O)Cc3ccc(-c4ccnc(C)c4)c(C)c3)nc2)CC1] | 444.20 | 0.942 | 0.2 |
| 160 | 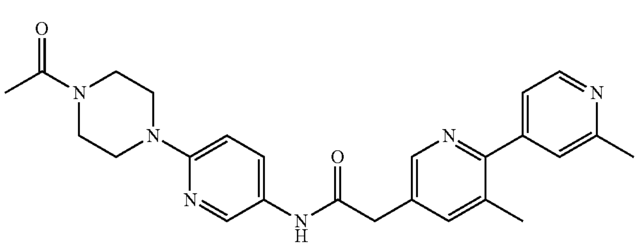 [SMILES: CC(=O)N1CCN(c2ccc(NC(=O)Cc3cnc(-c4ccnc(C)c4)c(C)c3)cn2)CC1] | 445.20 | 0.462 | 67 |

TABLE 1-continued

| Cpd | Structure | MS (m/z) (M + 1) | LC retention time (min) | IC$_{50}$ (nM) |
|---|---|---|---|---|
| 161 | 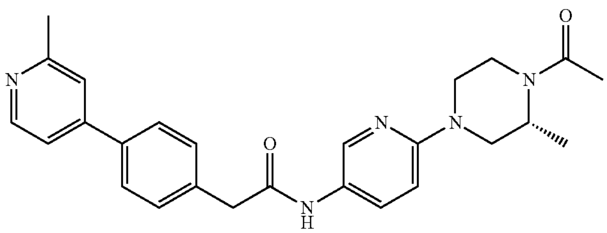 [SMILES: CC(=O)N1CCN(c2ccc(NC(=O)Cc3ccc(-c4ccnc(C)c4)cc3)cn2)C[C@H]1C] | 444.20 | 0.802 | 45 |
| 162 | 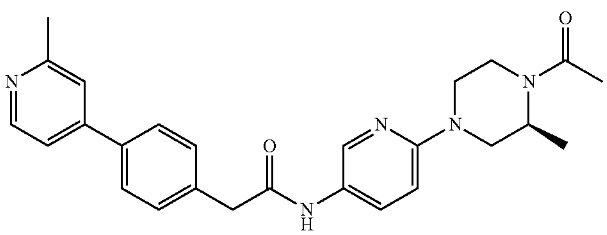 [SMILES: CC(=O)N1CCN(c2ccc(NC(=O)Cc3ccc(-c4ccnc(C)c4)cc3)cn2)C[C@@H]1C] | 444.20 | 1.070 | 10 |
| 163 | 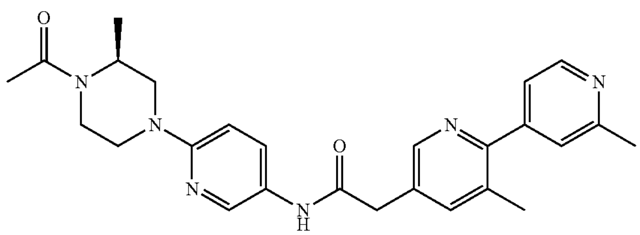 [SMILES: CC(=O)N1CCN(c2ccc(NC(=O)Cc3cnc(-c4ccnc(C)c4)c(C)c3)cn2)C[C@@H]1C] | 459.20 | 0.747 | 102 |
| 164 | 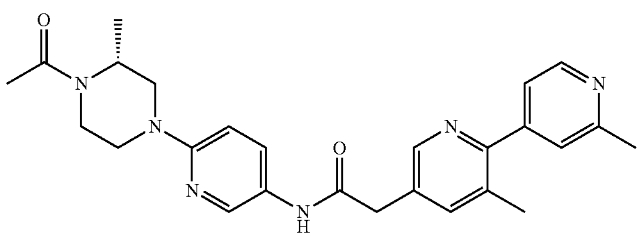 [SMILES: CC(=O)N1CCN(c2ccc(NC(=O)Cc3cnc(-c4ccnc(C)c4)c(C)c3)cn2)C[C@H]1C] | 459.20 | 0.726 | 51 |
| 165 | 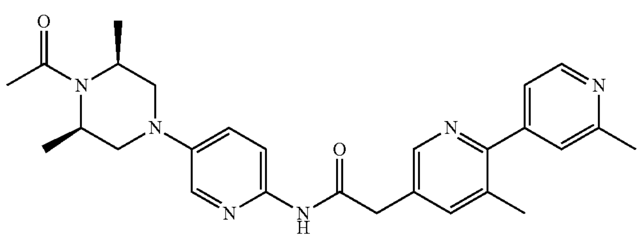 [SMILES: CC(=O)N1[C@H](C)CN(c2ccc(NC(=O)Cc3cnc(-c4ccnc(C)c4)c(C)c3)nc2)C[C@@H]1C] | 473.20 | 0.965 | 14 |
| 166 | 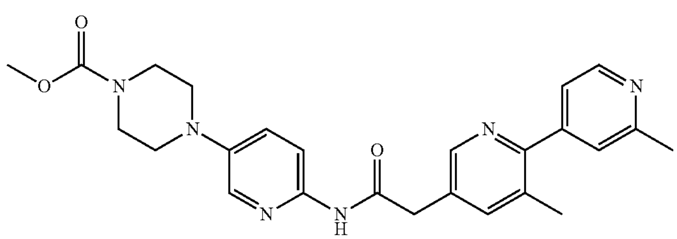 | 474.20 | 1.818 | 0.1 |

TABLE 1-continued

| Cpd | Structure | MS (m/z) (M + 1) | LC retention time (min) | IC$_{50}$ (nM) |
|---|---|---|---|---|
| 167 | 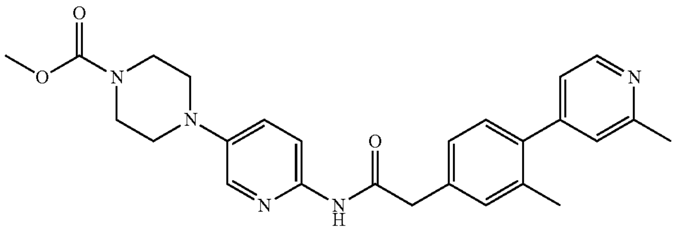 | 460.20 | 1.161 | 0.1 |
| 168 | 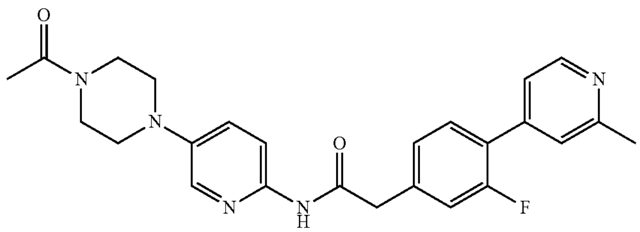 | 448.10 | 0.963 | 0.1 |
| 169 | 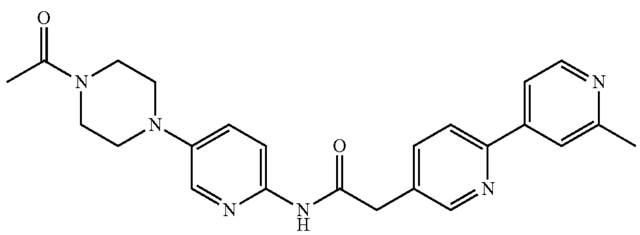 [SMILES: CC(=O)N1CCN(c2ccc(NC(=O)Cc3ccc(-c4ccnc(C)c4)nc3)nc2)CC1] | 431.20 | 0.479 | 258 |
| 170 | 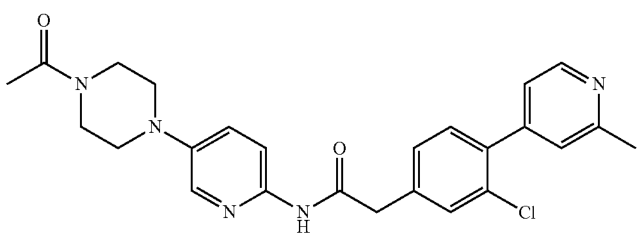 [SMILES: CC(=O)N1CCN(c2ccc(NC(=O)Cc3ccc(-c4ccnc(C)c4)c(Cl)c3)nc2)CC1] | 464.10 | 0.999 | 0.1 |
| 171 | 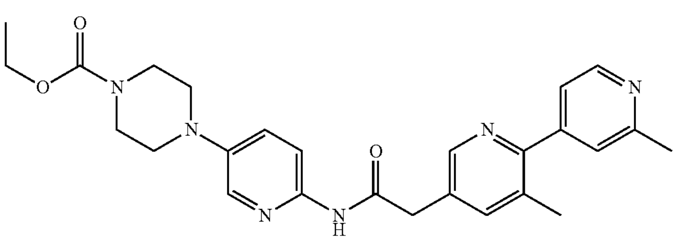 [SMILES: CCOC(=O)N1CCN(c2ccc(NC(=O)Cc3cnc(-c4ccnc(C)c4)c(C)c3)nc2)CC1] | 475.20 | 1.084 | 0.2 |
| 172 | 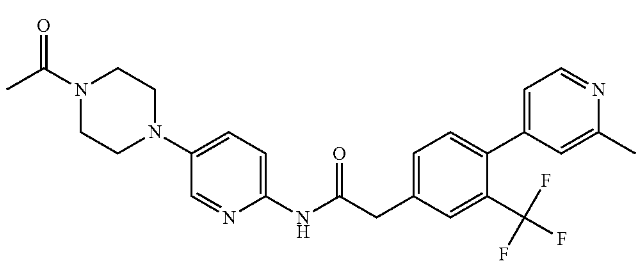 | 498.20 | 1.071 | 0.1 |

TABLE 1-continued

| Cpd | Structure | MS (m/z) (M + 1) | LC retention time (min) | IC$_{50}$ (nM) |
|---|---|---|---|---|
| 173 | 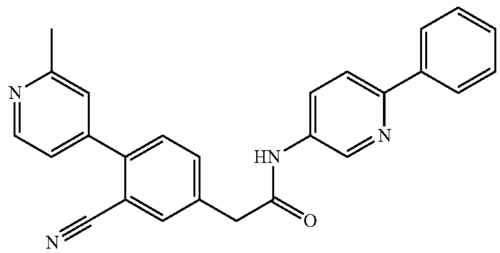 [SMILES: Cc1cc(-c2ccc(CC(=O)Nc3ccc(-c4ccccc4)nc3)cc2C#N)ccn1] | 405.20 | 1.250 | 0.1 |
| 174 | 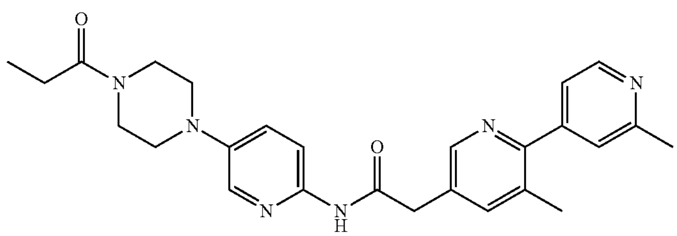 [SMILES: CCC(=O)N1CCN(c2ccc(NC(=O)Cc3cnc(-c4ccnc(C)c4)c(C)c3)nc2)CC1] | 459.20 | 0.822 | 0.5 |
| 175 | 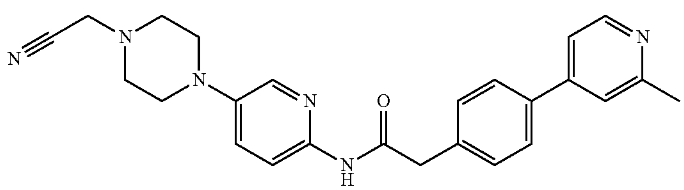 [SMILES: Cc1cc(-c2ccc(CC(=O)Nc3ccc(N4CCN(CC#N)CC4)cn3)cc2)ccn1] | 427.20 | 1.076 | 1.1 |
| 176 | 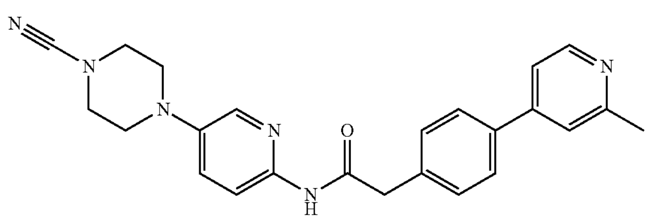 [SMILES: Cc1cc(-c2ccc(CC(=O)Nc3ccc(N4CCN(C#N)CC4)cn3)cc2)ccn1] | 413.20 | 1.097 | 0.4 |
| 177 | 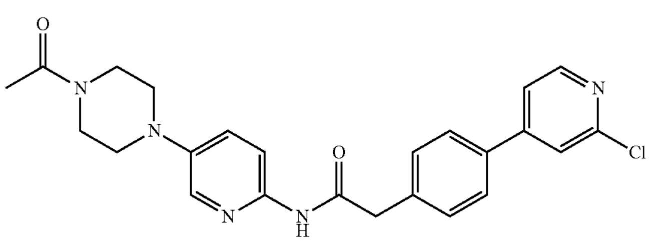 [SMILES: CC(=O)N1CCN(c2ccc(NC(=O)Cc3ccc(-c4ccnc(Cl)c4)cc3)nc2)CC1] | 450.10 | 1.433 | 0.2 |
| 178 | 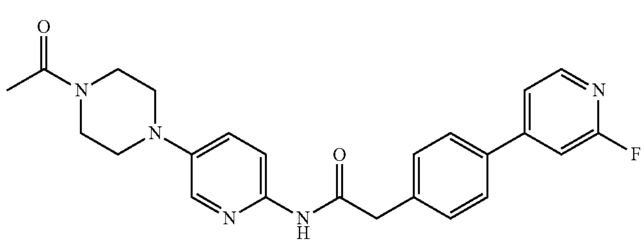 [SMILES: CC(=O)N1CCN(c2ccc(NC(=O)Cc3ccc(-c4ccnc(F)c4)cc3)nc2)CC1] | 434.20 | 1.367 | 0.1 |

TABLE 1-continued
| Cpd | Structure | MS (m/z) (M + 1) | LC retention time (min) | IC$_{50}$ (nM) |
|---|---|---|---|---|
| 179 | 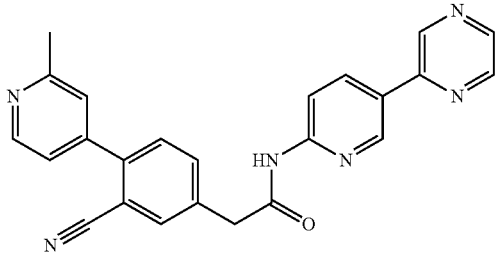 | 407.20 | 1.124 | 0.1 |
| 180 | 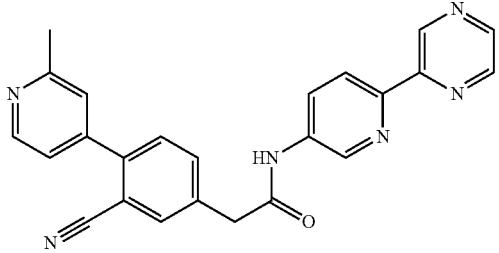 [SMILES: Cc1cc(-c2ccc(CC(=O)Nc3ccc(-c4cnccn4)nc3)cc2C#N)ccn1] | 407.20 | 1.111 | 0.1 |
| 181 | 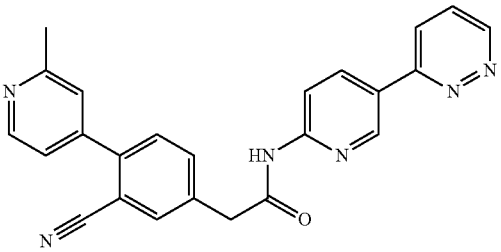 [SMILES: Cc1cc(-c2ccc(CC(=O)Nc3ccc(-c4cccnn4)cn3)cc2C#N)ccn1] | 407.20 | 1.036 | 0.1 |
| 182 | 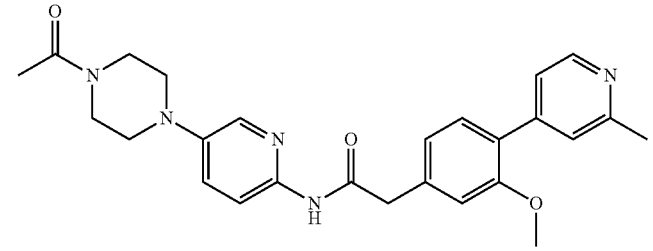 [SMILES: COc1cc(CC(=O)Nc2ccc(N3CCN(C(C)=O)CC3)cn2)ccc1-c1ccnc(C)c1] | 460.20 | 0.928 | 0.1 |
| 183 | 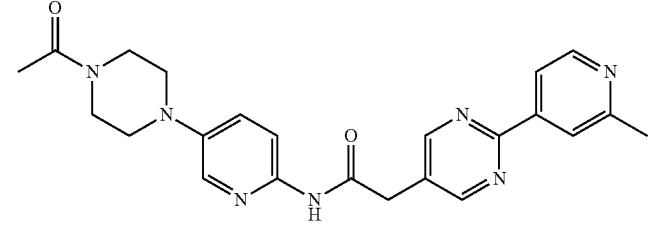 [SMILES: CC(=O)N1CCN(c2ccc(NC(=O)Cc3cnc(-c4ccnc(C)c4)nc3)nc2)CC1] | 433.20 | 0.598 | 0.3 |
| 184 | 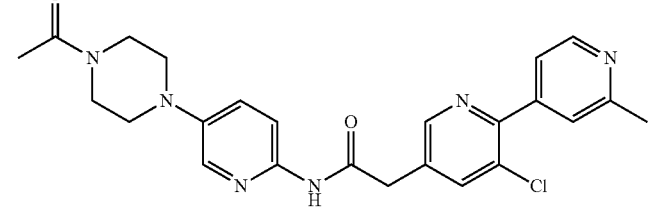 | 465.20 | 1.046 | 0.1 |

TABLE 1-continued

| Cpd | Structure | MS (m/z) (M + 1) | LC retention time (min) | IC$_{50}$ (nM) |
|---|---|---|---|---|
| 185 | 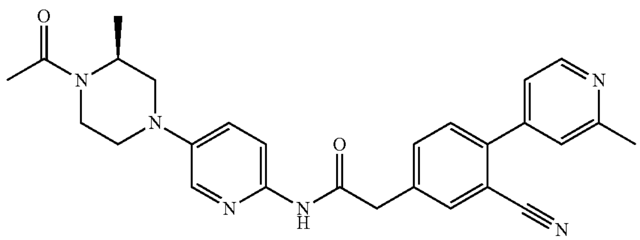 [SMILES: CC(=O)N1CCN(c2ccc(NC(=O)Cc3ccc(-c4ccnc(C)c4)c(C#N)c3)nc2)C[C@@H]1C] | 469.20 | 0.726 | 0.1 |
| 186 | 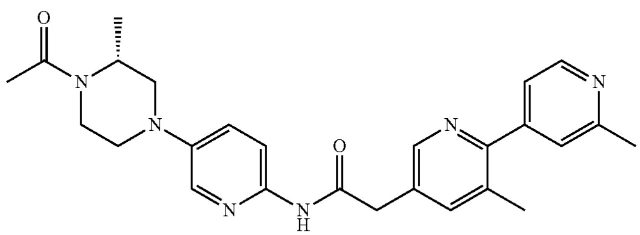 [SMILES: CC(=O)N1CCN(c2ccc(NC(=O)Cc3cnc(-c4ccnc(C)c4)c(C)c3)nc2)C[C@H]1C] | 459.20 | 0.885 | 7.6 |
| 187 | 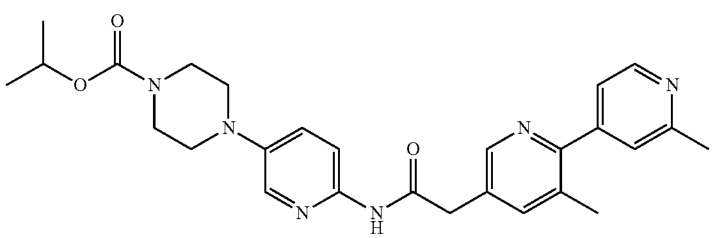 [SMILES: Cc1cc(-c2ncc(CC(=O)Nc3ccc(N4CCN(C(=O)OC(C)C)CC4)cn3)cc2C)ccn1] | 489.20 | 1.202 | 0.1 |
| 188 | 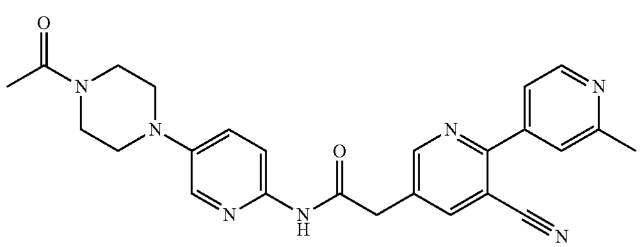 [SMILES: CC(=O)N1CCN(c2ccc(NC(=O)Cc3cnc(-c4ccnc(C)c4)c(C#N)c3)nc2)CC1] | 456.2 | 0.889 | 0.2 |
| 189 | 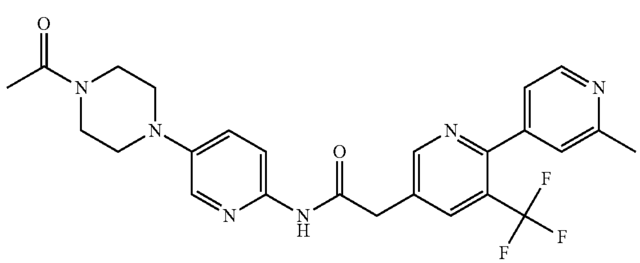 [SMILES: CC(=O)N1CCN(c2ccc(NC(=O)Cc3cnc(-c4ccnc(C)c4)c(C(F)(F)F)c3)nc2)CC1] | 499.2 | 1.084 | 0.1 |
| 190 | 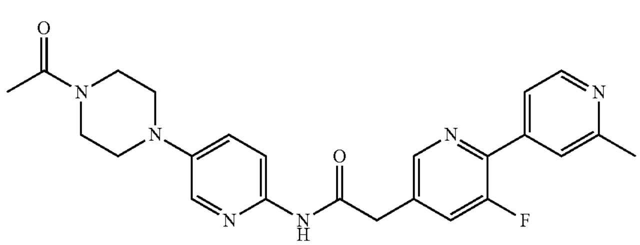 [SMILES: CC(=O)N1CCN(c2ccc(NC(=O)Cc3cnc(-c4ccnc(C)c4)c(F)c3)nc2)CC1] | 449.2 | 0.922 | 0.2 |

TABLE 1-continued

| Cpd | Structure | MS (m/z) (M + 1) | LC retention time (min) | IC$_{50}$ (nM) |
| --- | --- | --- | --- | --- |
| 191 | 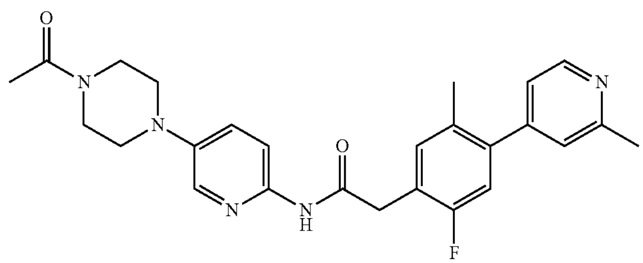 [SMILES: CC(=O)N1CCN(c2ccc(NC(=O)Cc3cc(C)c(-c4ccnc(C)c4)cc3F)nc2)CC1] | 462.20 | 0.970 | 0.04 |
| 192 | 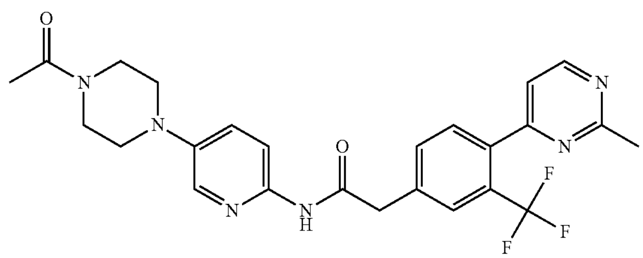 [SMILES: CC(=O)N1CCN(c2ccc(NC(=O)Cc3ccc(-c4ccnc(C)n4)c(C(F)(F)F)c3)nc2)CC1] | 499.20 | 1.319 | 0.2 |
| 193 | 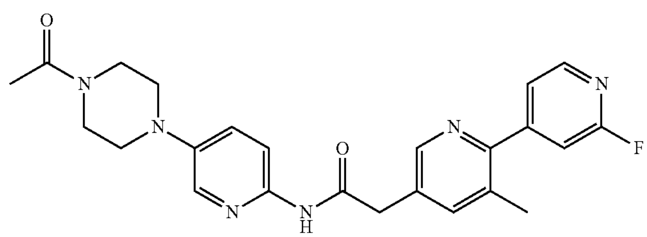 [SMILES: CC(=O)N1CCN(c2ccc(NC(=O)Cc3cnc(-c4ccnc(F)c4)c(C)c3)nc2)CC1] | 449.20 | 1.080 | 0.1 |
| 194 | 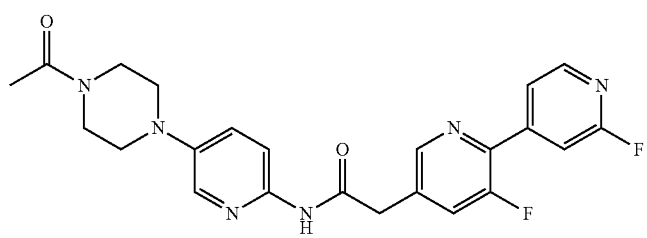 | 453.10 | 1.311 | 1.3 |
| 195 | 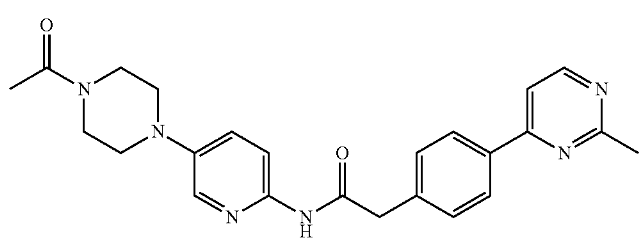 [SMILES: CC(=O)N1CCN(c2ccc(NC(=O)Cc3ccc(-c4ccnc(C)n4)cc3)nc2)CC1] | 431.20 | 1.042 | 14 |
| 196 | 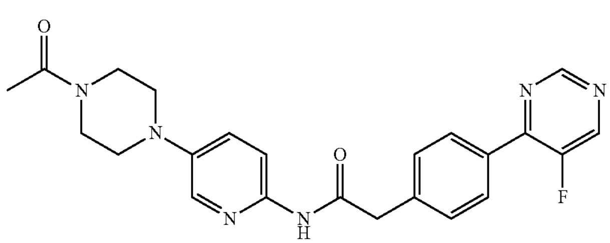 [SMILES: CC(=O)N1CCN(c2ccc(NC(=O)Cc3ccc(-c4ncncc4F)cc3)nc2)CC1] | 435.10 | 1.215 | 6.7 |

TABLE 1-continued

| Cpd | Structure | MS (m/z) (M + 1) | LC retention time (min) | IC$_{50}$ (nM) |
|---|---|---|---|---|
| 197 | 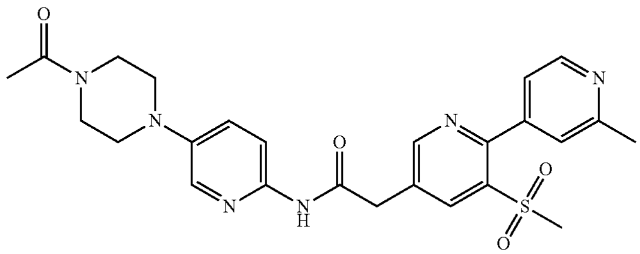 [SMILES: CC(=O)N1CCN(c2ccc(NC(=O)Cc3cnc(-c4ccnc(C)c4)c(S(C)(=O)=O)c3)nc2)CC1] | 509.2 | 0.742 | 71 |
| 198 | 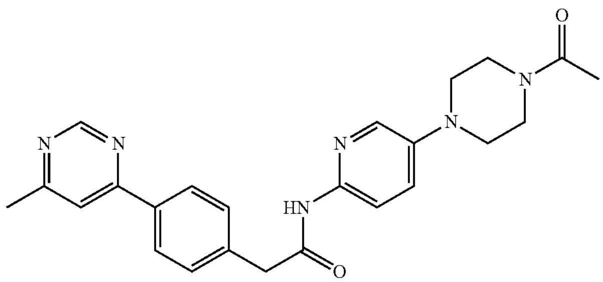 [SMILES: CC(=O)N1CCN(c2ccc(NC(=O)Cc3ccc(-c4cc(C)ncn4)cc3)nc2)CC1] | 431.20 | 1.289 | 63 |
| 199 | 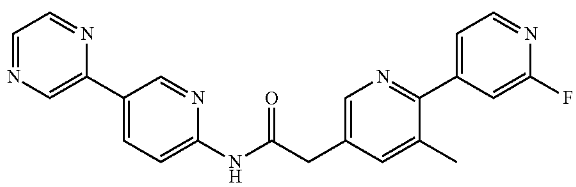 [SMILES: Cc1cc(CC(=O)Nc2ccc(-c3cnccn3)cn2)cnc1-c1ccnc(F)c1] | 401.10 | 1.388 | 0.2 |
| 200 | 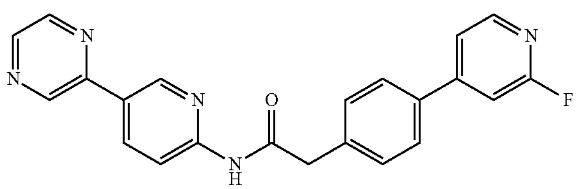 [SMILES: O=C(Cc1ccc(-c2ccnc(F)c2)cc1)Nc1ccc(-c2cnccn2)cn1] | 386.10 | 1.837 | 0.2 |
| 201 | 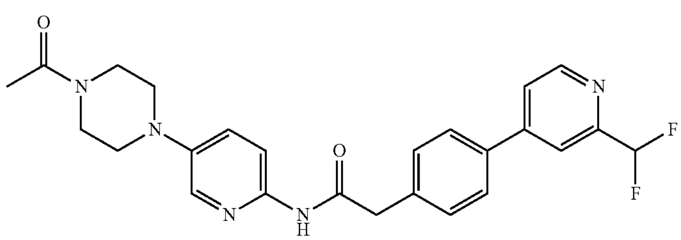 [SMILES: CC(=O)N1CCN(c2ccc(NC(=O)Cc3ccc(-c4ccnc(C(F)F)c4)cc3)nc2)CC1] | 466.3 | 1.339 | 2.5 |
| 202 | 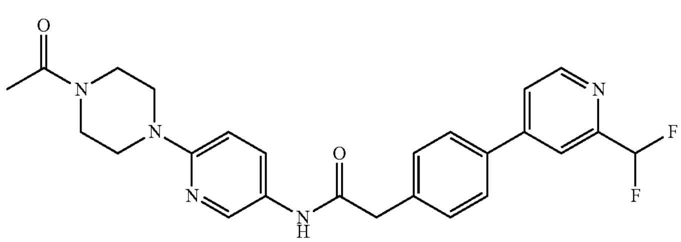 [SMILES: CC(=O)N1CCN(c2ccc(NC(=O)Cc3ccc(-c4ccnc(C(F)F)c4)cc3)cn2)CC1] | 466.3 | 1.430 | |

TABLE 1-continued

| Cpd | Structure | MS (m/z) (M + 1) | LC retention time (min) | IC$_{50}$ (nM) |
|---|---|---|---|---|
| 203 | 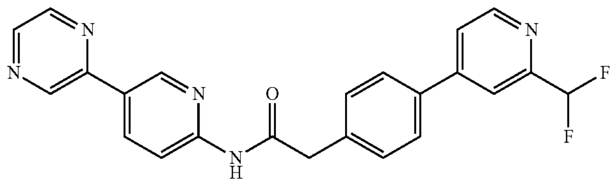 [SMILES: O=C(Cc1ccc(-c2ccnc(C(F)F)c2)cc1)Nc1ccc(-c2cnccn2)cn1] | 418.2 | 1.860 | 4.7 |
| 204 | 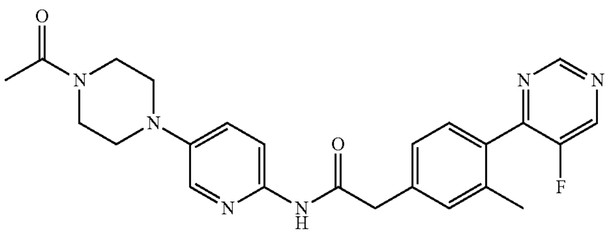 [SMILES: CC(=O)N1CCN(c2ccc(NC(=O)Cc3ccc(-c4ncncc4F)c(C)c3)nc2)CC1] | 449.10 | 1.239 | 7 |
| 205 | 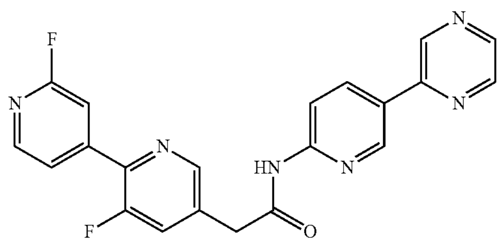 [SMILES: O=C(Cc1cnc(-c2ccnc(F)c2)c(F)c1)Nc1ccc(-c2cnccn2)cn1] | 405.20 | 1.851 | 0.1 |
| 206 | 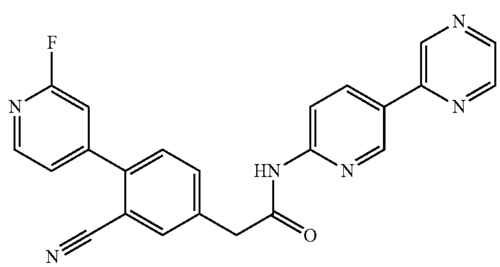 | 411.2 | 1.888 | 0.2 |
| 207 | 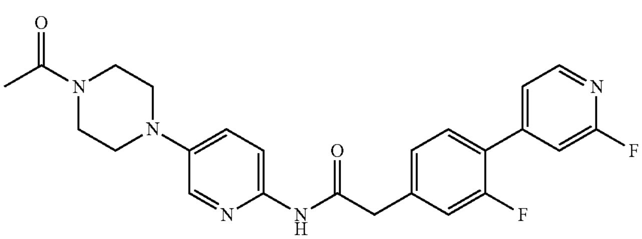 [SMILES: CC(=O)N1CCN(c2ccc(NC(=O)Cc3ccc(-c4ccnc(F)c4)c(F)c3)nc2)CC1] | 452.2 | 1.752 | 0.2 |
| 208 | 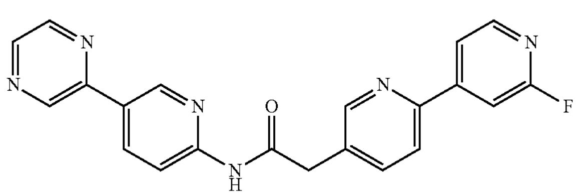 [SMILES: O=C(Cc1ccc(-c2ccnc(F)c2)nc1)Nc1ccc(-c2cnccn2)cn1] | 387.10 | 1.683 | 0.4 |

TABLE 1-continued

| Cpd | Structure | MS (m/z) (M + 1) | LC retention time (min) | IC$_{50}$ (nM) |
|---|---|---|---|---|
| 209 | 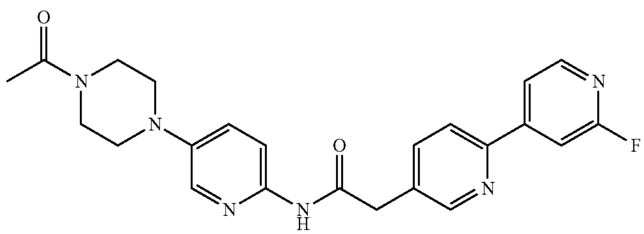 [SMILES: CC(=O)N1CCN(c2ccc(NC(=O)Cc3ccc(-c4ccnc(F)c4)nc3)nc2)CC1] | 435.20 | 1.331 | 5.4 |
| 210 | 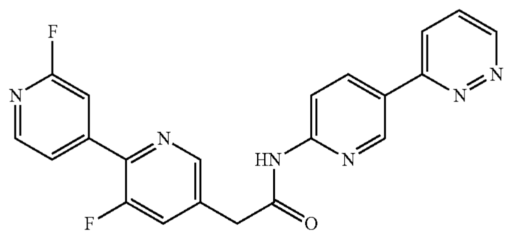 | 405.10 | 1.725 | 0.4 |
| 211 | 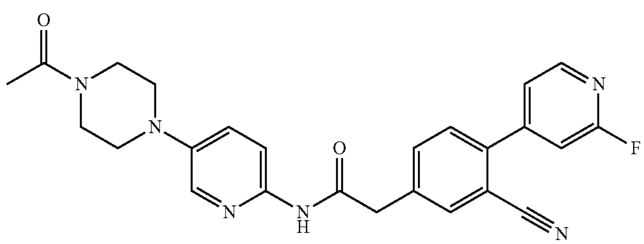 [SMILES: CC(=O)N1CCN(c2ccc(NC(=O)Cc3ccc(-c4ccnc(F)c4)c(C#N)c3)nc2)CC1] | 459.2 | 1.638 | 0.1 |
| 212 | 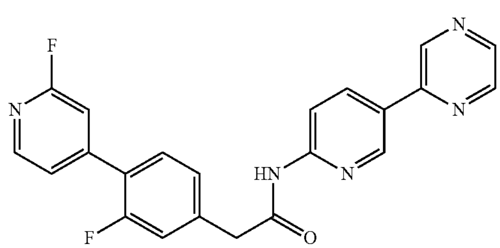 [SMILES: O=C(Cc1ccc(-c2ccnc(F)c2)c(F)c1)Nc1ccc(-c2cnccn2)cn1] | 404.1 | 2.043 | 0.2 |
| 213 | 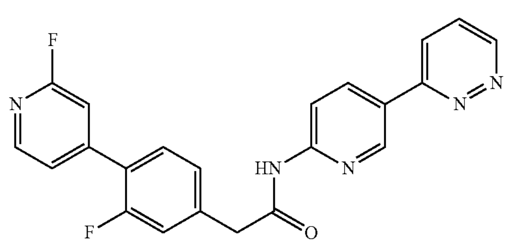 [SMILES: O=C(Cc1ccc(-c2ccnc(F)c2)c(F)c1)Nc1ccc(-c2cccnn2)cn1] | 404.2 | 2.069 | 0.1 |
| 214 | 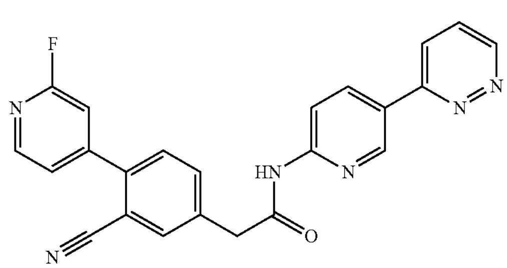 [SMILES: N#Cc1cc(CC(=O)Nc2ccc(-c3cccnn3)cn2)ccc1-c1ccnc(F)c1] | 411.2 | 1.905 | 0.2 |

TABLE 1-continued

| Cpd | Structure | MS (m/z) (M + 1) | LC retention time (min) | IC$_{50}$ (nM) |
|---|---|---|---|---|
| 215 | 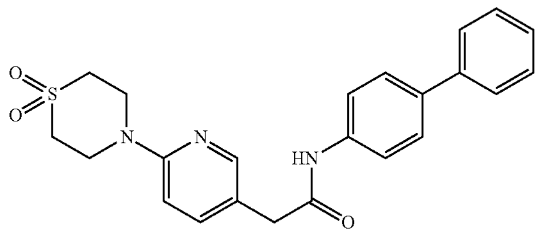 [SMILES: O=C(Cc1ccc(N2CCS(=O)(=O)CC2)nc1)Nc1ccc(-c2ccccc2)cc1] | 422.20 | 1.720 | 4.2 |
| 216 | 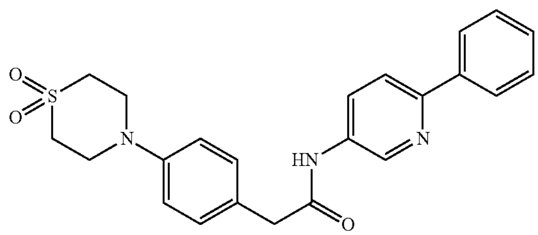 [SMILES: O=C(Cc1ccc(N2CCS(=O)(=O)CC2)cc1)Nc1ccc(-c2ccccc2)nc1] | 422.20 | 1.444 | 2.1 |
| 217 | 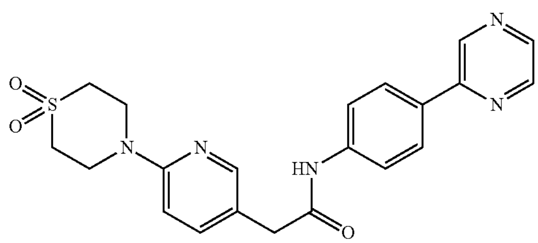 [SMILES: O=C(Cc1ccc(N2CCS(=O)(=O)CC2)nc1)Nc1ccc(-c2cnccn2)cc1] | 424.20 | 1.086 | 6.7 |
| 218 | 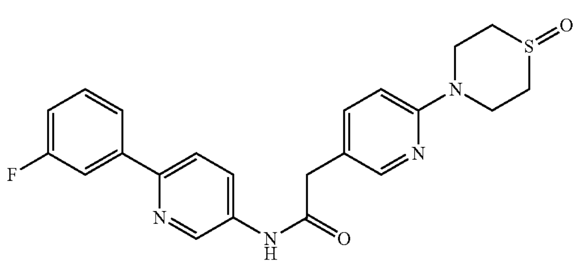 [SMILES: O=C(Cc1ccc(N2CCS(=O)CC2)nc1)Nc1ccc(-c2cccc(F)c2)nc1] | 425.20 | 0.272 | 2.3 |
| 219 | 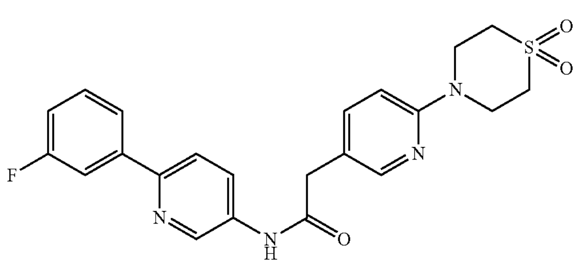 [SMILES: O=C(Cc1ccc(N2CCS(=O)(=O)CC2)nc1)Nc1ccc(-c2cccc(F)c2)nc1] | 441.20 | 0.331 | 0.8 |
| 220 | 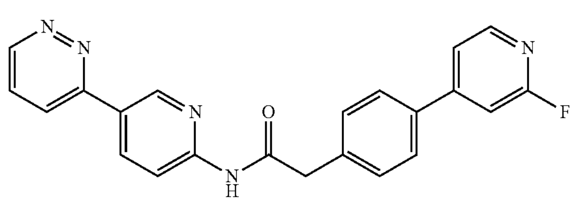 [SMILES: O=C(Cc1ccc(-c2ccnc(F)c2)cc1)Nc1ccc(-c2cccnn2)cn1] | 386.10 | 1.644 | 0.3 |

TABLE 1-continued

| Cpd | Structure | MS (m/z) (M + 1) | LC retention time (min) | IC$_{50}$ (nM) |
|---|---|---|---|---|
| 221 | 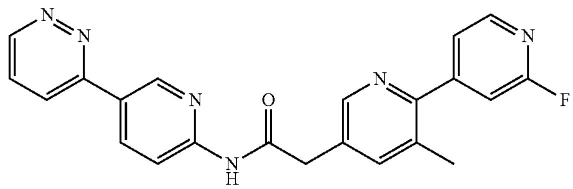 [SMILES: Cc1cc(CC(=O)Nc2ccc(-c3cccnn3)cn2)cnc1-c1ccnc(F)c1] | 401.10 | 1.216 | 0.3 |
| 222 | 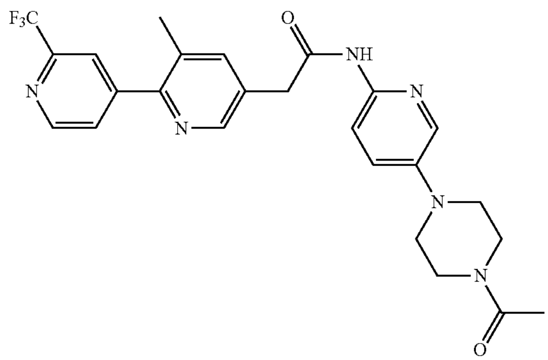 [SMILES: CC(=O)N1CCN(c2ccc(NC(=O)Cc3cnc(-c4ccnc(C(F)(F)F)c4)c(C)c3)nc2)CC1] | 498.8 | 2.218 | |
| 223 | 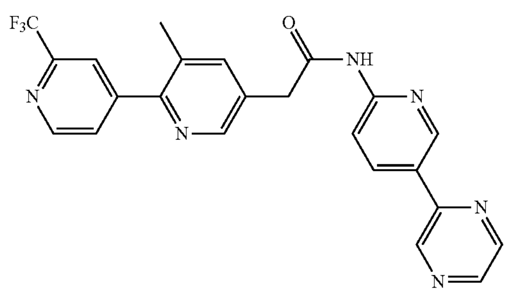 [SMILES: Cc1cc(CC(=O)Nc2ccc(-c3cnccn3)cn2)cnc1-c1ccnc(C(F)(F)F)c1] | 450.8 | 1.859 | |
| 224 | 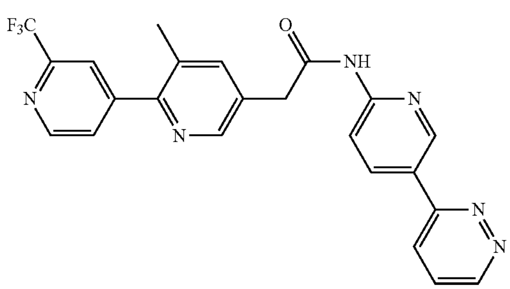 [SMILES: Cc1cc(CC(=O)Nc2ccc(-c3cccnn3)cn2)cnc1-c1ccnc(C(F)(F)F)c1] | | | |
| 225 | 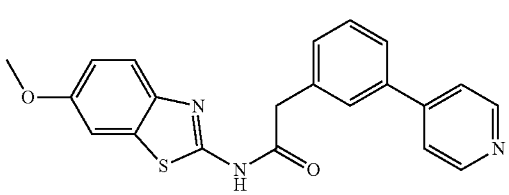 [SMILES: COc1ccc2nc(NC(=O)Cc3cccc(-c4ccncc4)c3)sc2c1] | 376.10 | 1.761 | 118 |

TABLE 1-continued

| Cpd | Structure | MS (m/z) (M + 1) | LC retention time (min) | IC$_{50}$ (nM) |
|---|---|---|---|---|
| 226 | 1H NMR 400 MHz (DMSO-d$_6$) δ 10.57 (s, 1H), 8.85 (d, 1H), 8.65 (d, 2H), 8.17 (dd, 1H), 8.05-8.02 (m, 2H), 7.92 (d, 1H), 7.79 (s, 1H), 7.69 (m, 3H), 7.50-7.44 (m, 4H), 7.39-7.36 (m, 1H), 3.83 (s, 2H). | 366.20 | 1.190 | 1.9 |
| 227 | 1H NMR 400 MHz (DMSO-d$_6$) δ 10.63 (s, 1H), 8.85 (d, 1H), 8.50 (d, 1H), 8.17 (dd, 1H), 8.04-8.02 (m, 2H), 7.92 (d, 1H), 7.78 (s, 1H), 7.67 (dt, 1H), 7.58 (s, 1H), 7.50-7.44 (m, 5H), 7.40-7.36 (m, 1H), 3.83 (s, 2H), 2.54 (s, 3H). | 380.20 | 1.189 | 0.6 |
| 228 | 1H NMR 400 MHz (DMSO-d$_6$) δ 10.57 (s, 1H), 9.65 (m,1H), 9.29 (dd, 1H), 8.84 (d, 1H), 8.16 (dd, 1H), 8.04-8.00 (m, 3H), 7.94-7.91 (m, 2H), 7.83 (dt, 1H), 7.55-7.44 (m, 4H), 7.40-7.37 (m, 1H), 3.84 (s, 2H). | 367.20 | 1.356 | 22 |
| 229 | 1H NMR 400 MHz (DMSO-d$_6$) δ 10.62 (s, 1H), 8.85 (d, 1H), 8.24 (d, 1H), 8.17 (dd, 1H), 8.04-8.02 (m, 2H), 7.92 (d, 1H), 7.78 (s, 1H), 7.66 (dt, 1H), 7.48-7.44 (m, 4H), 7.40-7.38 (m, 1H), 7.31 (dd, 1H), 7.10 (m, 1H), 3.90 (s, 3H), 3.82 (s, 2H). | 396.20 | 1.705 | 95 |

TABLE 1-continued

| Cpd | Structure | MS (m/z) (M + 1) | LC retention time (min) | IC$_{50}$ (nM) |
|---|---|---|---|---|
| 230 | 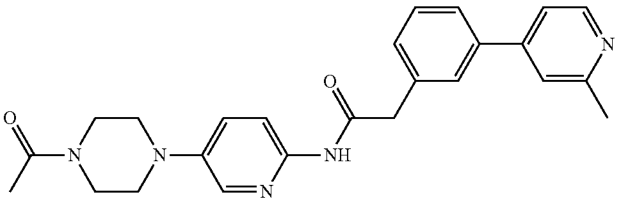 [SMILES: CC(=O)N1CCN(c2ccc(NC(=O)Cc3cccc(-c4ccnc(C)c4)c3)nc2)CC1] | 430.30 | 0.917 | 29 |
| | 1H NMR 400 MHz (DMSO-d$_6$) δ 10.56 (s, 1H), 8.50 (d, 1H), 8.02 (d, 1H), 7.92 (d, 1H), 7.76 (s, 1H), 7.65 (dt, 1H), 7.55 (s, 1H), 7.46-7.40 (m, 4H), 3.76 (s, 2H), 3.56-3.54 (m, 4H), 3.14-3.04 (m, 4H), 2.53 (s, 3H), 2.03 (s, 3H). | | | |
| 231 | 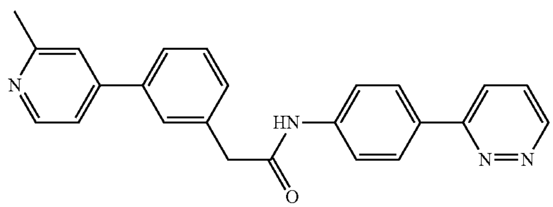 [SMILES: Cc1cc(-c2cccc(CC(=O)Nc3ccc(-c4cccnn4)cc3)c2)ccn1] | 380.80 | 1.483 | 6 |
| | 1H NMR 400 MHz (DMSO-d$_6$) δ 10.48 (s, 1H), 9.15 (dd, 1H), 8.50 (d, 1H), 8.17 (dd, 1H), 8.14-8.12 (m, 2H), 7.81-7.79 (m, 3H), 7.75 (dd, 1H), 7.67 (dt, 1H), 7.57 (s, 1H), 7.46-7.44 (m, 3H), 3.80 (s, 2H), 2.54 (s, 3H). | | | |
| 232 | 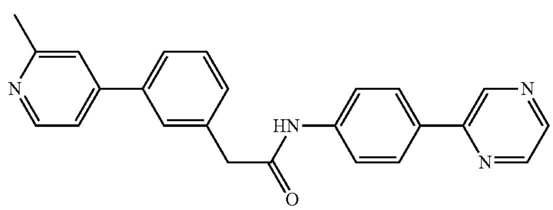 [SMILES: Cc1cc(-c2cccc(CC(=O)Nc3ccc(-c4cnccn4)cc3)c2)ccn1] | 381.20 | 1.289 | 1.3 |
| 233 | 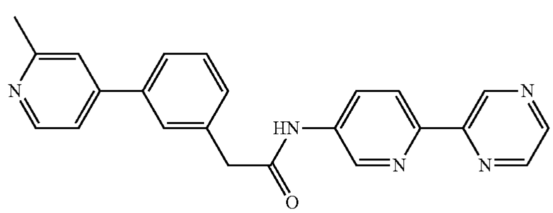 [SMILES: Cc1cc(-c2cccc(CC(=O)Nc3ccc(-c4cnccn4)nc3)c2)ccn1] | 382.20 | 1.156 | 14 |
| 234 | 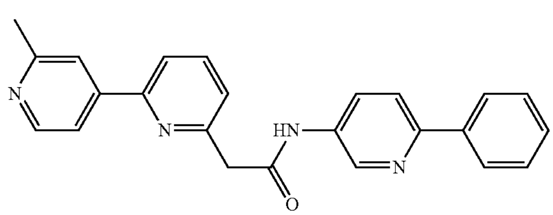 [SMILES: Cc1cc(-c2cccc(CC(=O)Nc3ccc(-c4ccccc4)nc3)n2)ccn1] | 381.20 | 0.241 | 2.9 |

TABLE 1-continued

| Cpd | Structure | MS (m/z) (M + 1) | LC retention time (min) | IC$_{50}$ (nM) |
|---|---|---|---|---|
| 235 | 1H NMR 400 MHz (DMSO-d$_6$) δ 10.63 (s, 1H), 8.83 (d, 1H), 8.68 (d, 1H), 8.57 (d, 1H), 8.14 (dd, 1H), 8.08 9s, 1H), 8.04-8.02 (m, 2H), 7.94 (d, 2H), 7.84 (dd, 1H), 7.48-7.45 (m, 3H), 7.40-7.37 (m, 1H), 3.90 (s, 2H), 2.56 (s, 3H). | 380.90 | 1.499 | 0.2 |
| 236 | 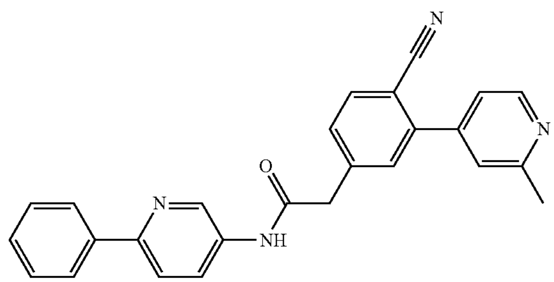 [SMILES: Cc1cc(-c2cc(CC(=O)Nc3ccc(-c4ccccc4)nc3)ccc2C#N)ccn1] | 405.20 | 1.267 | 0.2 |
| 237 | 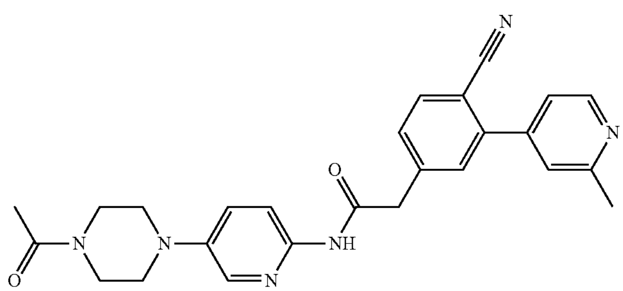 [SMILES: CC(=O)N1CCN(c2ccc(NC(=O)Cc3ccc(C#N)c(-c4ccnc(C)c4)c3)nc2)CC1] | 455.20 | 0.653 | 1.5 |
| 238 | 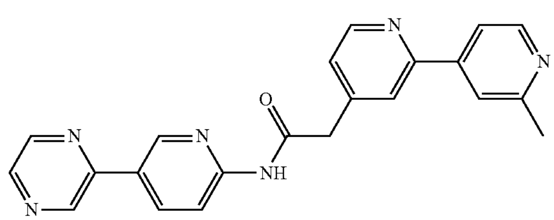 [SMILES: Cc1cc(-c2cc(CC(=O)Nc3ccc(-c4cnccn4)cn3)ccn2)ccn1] | 383.20 | 1.621 | 0.9 |
| 239 | 1H NMR 400 MHz (DMSO-d$_6$) δ 10.65 (s, 1H), 8.65 (d, 1H), 8.56 (d, 1H), 8.05-8.04 (m, 2H), 7.93-7.90 (m, 2H), 7.82 (dd, 1H), 7.42-7.40 (m, 2H), 3.84 (s, 2H), 3.57-3.55 (m, 4H), 3.15-3.06 (m, 4H), 2.56 (s, 3H), 2.03 (s, 3H). | 431.30 | 0.770 | 123 |

TABLE 1-continued

| Cpd | Structure | MS (m/z) (M + 1) | LC retention time (min) | IC$_{50}$ (nM) |
|---|---|---|---|---|
| 240 | 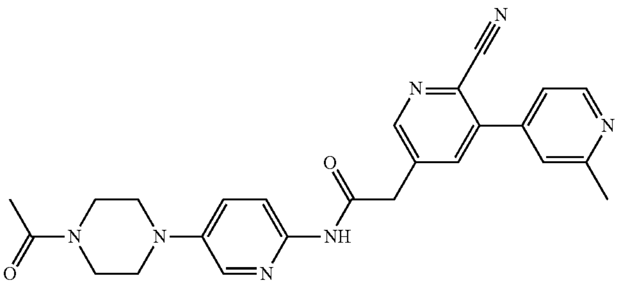 [SMILES: CC(=O)N1CCN(c2ccc(NC(=O)Cc3cnc(C#N)c(-c4ccnc(C)c4)c3)nc2)CC1] | 456.20 | 1.087 | 10 |

ASSAYS

Wnt-Luc Reporter Assay for Pathway Inhibition of Wnt Signaling

Mouse leydig cell TM3 cells (obtained from American Type Culture Collection, ATCC, Manassas, Va.) are cultured in 1:1 mixture of Ham's F12 medium and Dulbecco's modified Eagle's medium (Gibco/Invitrogen, Carlsbad, Calif.) supplemented with 2.5% FBS (Gibco/Invitrogen, Carlsbad, Calif.) and 5% horse serum (Gibco/Invitrogen, Carlsbad, Calif.), 50 unit/mL penicillin and 50 µg/mL of streptomycin (Gibco/Invitrogen, Carlsbad, Calif.) at 37° C. with 5% $CO_2$ in air atmosphere. TM3 cells in a 10 cm dish are co-transfected with 8 µg of STF-reporter plasmid containing a luciferase gene driven by Wnt-responsive elements and 2 µg of pcDNA3.1-Neo (Gibco/Invitrogen, Carlsbad, Calif.) with 30 µL of FuGENE6 (Roche Diagnostics, Indianapolis, Ind.) following the manufacturer's protocol. Stable cell lines (TM3 Wnt-Luc) were selected with 400 µg/mL of G418 (Gibco/Invitrogen, Carlsbad, Calif.). The TM3 Wnt-Luc cells and L-cell Wnt3a cells (obtained from American Type Culture Collection, ATCC, Manassas, Va.; cultured in Dulbecco's modified Eagle's medium (Gibco/Invitrogen, Carlsbad, Calif.) supplemented with 10% FBS (Gibco/Invitrogen, Carlsbad, Calif.) and 50 unit/mL penicillin and 50 µg/mL of streptomycin (Gibco/Invitrogen, Carlsbad, Calif.) at 37° C. with 5% $CO_2$ in air atmosphere) are trypsinized and co-cultured into a 384-well plate with DMEM medium supplemented with 2% FBS, and treated with different concentrations of a compound of the invention. After 24 hours, the firefly luciferase activities are assayed with the Bright-Glo™ Luciferase Assay System (Promega, Madison, Wis.). The IC$_{50}$ is measured when the effect of the compound reduces the luminescence signal by 50%.

Wnt-Luc Reporter Assay for Pathway Inhibition of Wnt Signaling

Human embryonic kidney 293 cells (obtained from American Type Culture Collection, ATCC, Manassas, Va.) are cultured in DMEM medium (Gibco/Invitrogen, Carlsbad, Calif.) supplemented with 10% FBS (Gibco/Invitrogen, Carlsbad, Calif.), 50 unit/mL penicillin and 50 µg/mL of streptomycin (Gibco/Invitrogen, Carlsbad, Calif.) at 37° C. with 5% $CO_2$ in air atmosphere. 293 cells in a 10 cm dish are co-transfected with 8 µg of STF-reporter plasmid containing a luciferase gene driven by Wnt-responsive elements and 2 µg of pcDNA3.1-Neo (Gibco/Invitrogen, Carlsbad, Calif.) with 30 µL of FuGENE6 (Roche Diagnostics, Indianapolis, Ind.) following the manufacturer's protocol. Stable cell lines (293 Wnt-Luc) were selected with 400 µg/mL of G418 (Gibco/Invitrogen, Carlsbad, Calif.). The 293 Wnt-Luc cells and L-cell Wnt3a cells (obtained from American Type Culture Collection, ATCC, Manassas, Va.) are trypsinized and co-cultured into a 384-well plate with DMEM medium supplemented with 2% FBS, and treated with different concentrations of a compound of the invention. After 24 hours, the firefly luciferase activities are assayed with the Bright-Glo™ Luciferase Assay System (Promega, Madison, Wis.). The IC$_{50}$ is measured when the effect of the compound reduces the luminescence signal by 50%.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound having Formula (5):

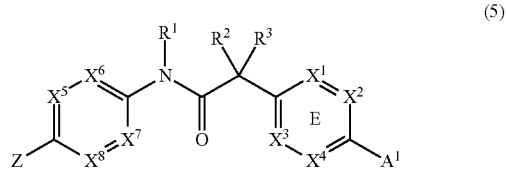

(5)

an N-oxide derivative, or a physiologically acceptable salt thereof, wherein:

wherein $A^1$ is piperazinyl substituted with —C(O)CH$_3$,

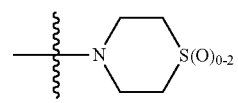

or selected from:

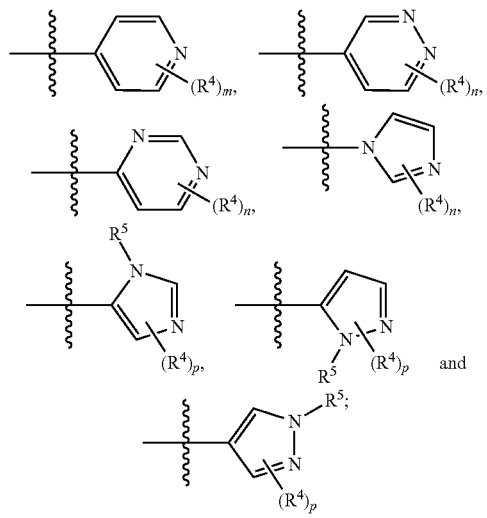

ring E is phenyl or one of $X^1$, $X^2$, $X^3$ and $X^4$ is N and the others are $CR^7$;
one of $X^5$, $X^6$, $X^7$ and $X^8$ is N and the others are $CR^{11}$;
Z is a 6-membered heterocycle or a 6-membered heteroaryl, each containing 1-2 nitrogen heteroatoms and each of which is optionally substituted with 1-2 $R^6$ groups;
$R^1$, $R^2$ and $R^3$ are H;
$R^4$ and $R^6$ are independently hydrogen, cyano, $C_{1-6}$alkoxy, —S(O)$_2$R$^{10}$, —C(O)NR$^8$R$^9$, -L -C(O)R$^{10}$, -L-C(O)OR$^{10}$, $C_{1-6}$ alkyl optionally substituted with halo, $C_{2-6}$ alkenyl or $C_{2-6}$ alkynyl;
$R^5$ is H or $C_{1-6}$ alkyl;
L is a bond or $(CR_2)_{1-4}$ wherein R is H or $C_{1-6}$ alkyl;
W is $C_{3-7}$cycloalkyl;
$R^7$ and $R^{11}$ are independently H, halo, cyano, $C_{1-6}$alkoxy, —S(O)$_2$R$^{10}$, or an optionally halogenated $C_{1-6}$ alkyl;
$R^8$ and $R^9$ are independently H, -L-W, or $C_{1-6}$ alkyl, $C_{2-6}$ alkenyl or $C_{2-6}$ alkynyl, each of which may be optionally substituted with halo, amino, hydroxyl, alkoxy or cyano;
$R^{10}$ is $C_{1-6}$ alkyl or -L-W; and
m, n and p are independently 0-2.

2. The compound of claim 1, wherein $A^1$ is piperazinyl substituted with —C(O)CH$_3$,

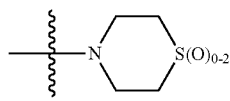

or selected from:

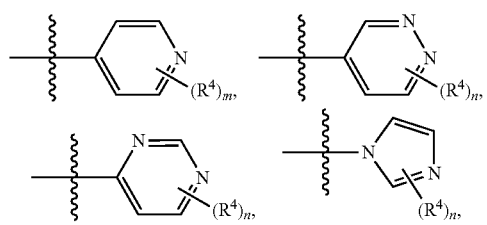

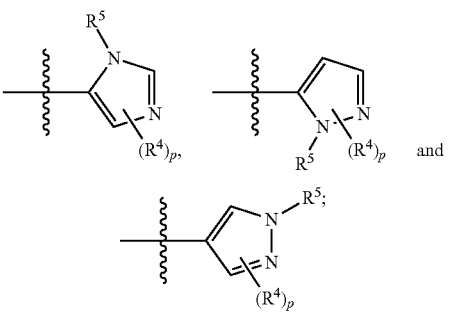

and m is 0-1.

3. The compound of claim 1, wherein said compound is selected from:

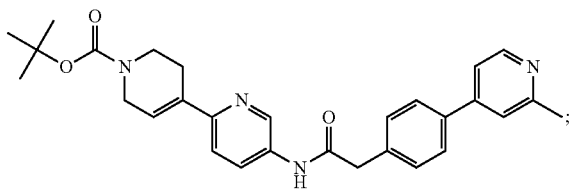

1

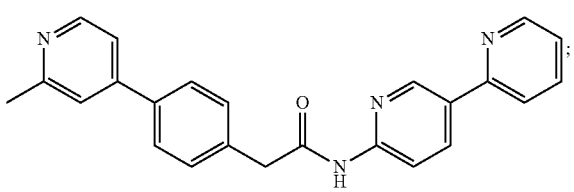

43

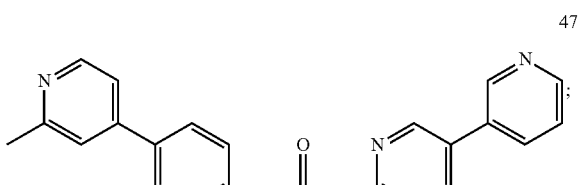

47

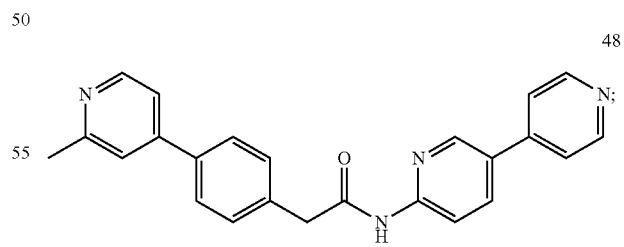

48

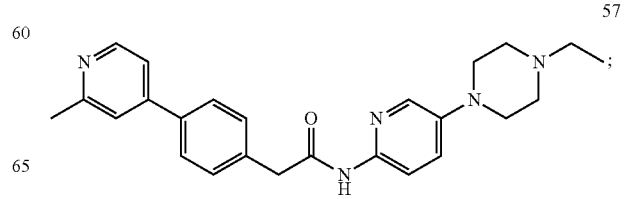

57

58
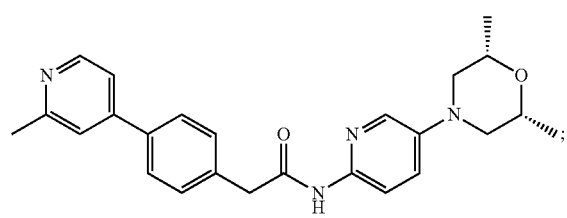
66
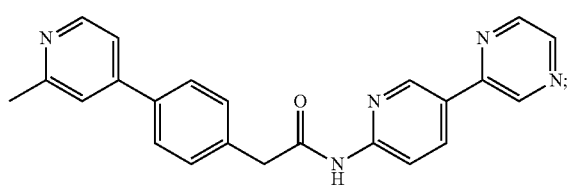
67
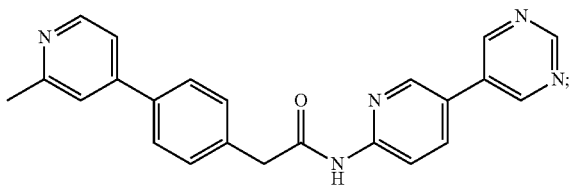
69
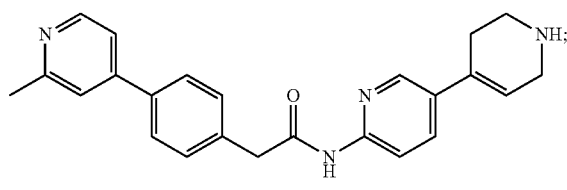
70
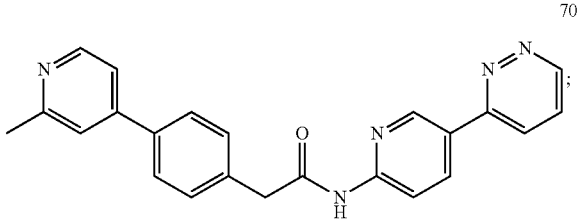
72
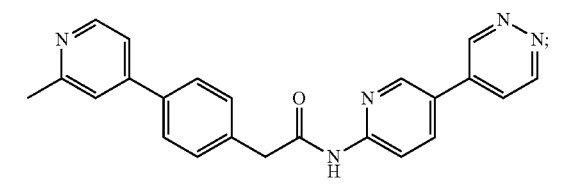
73
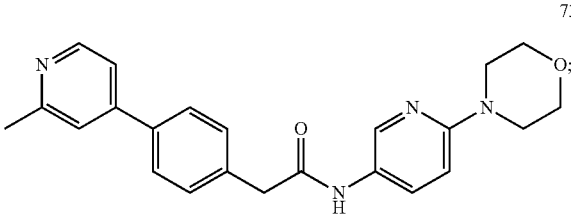
75
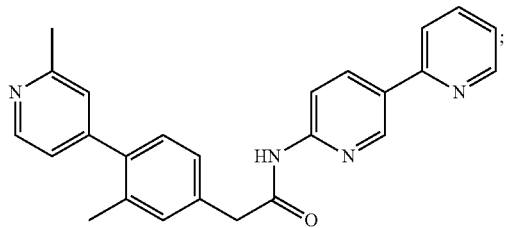
76
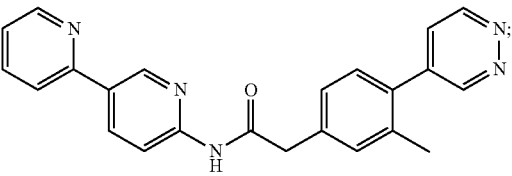
79
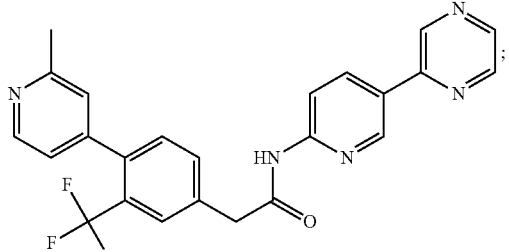
82
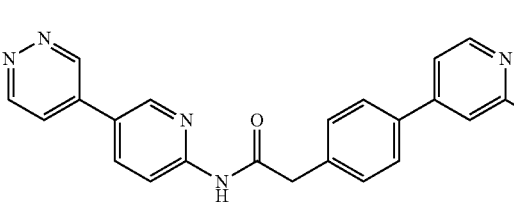
85
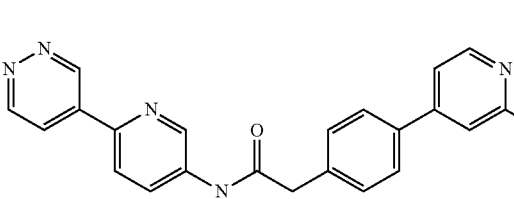
90
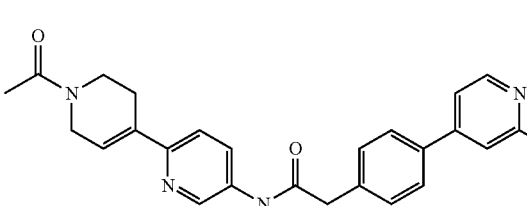
91
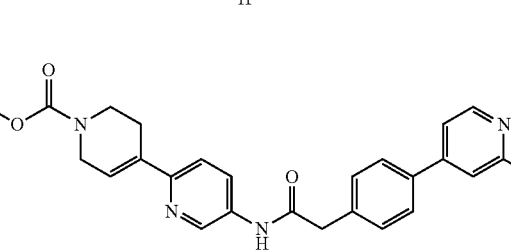

-continued

-continued
122
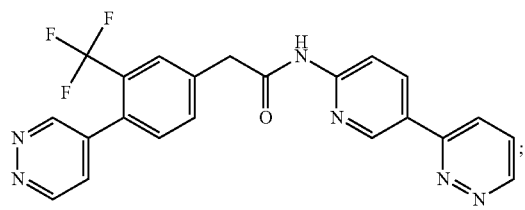
137
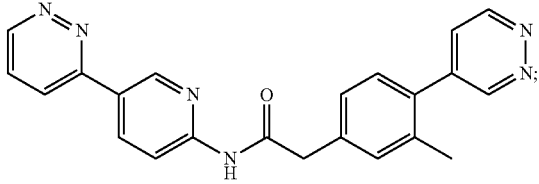
125
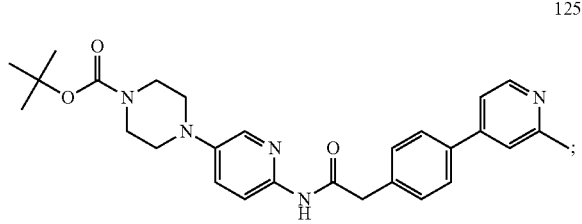
138
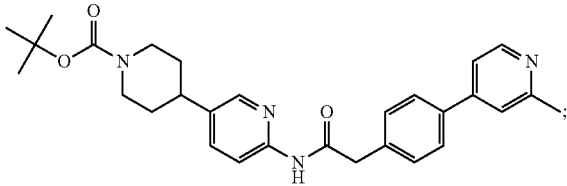
127
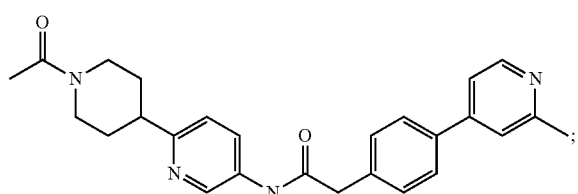
139
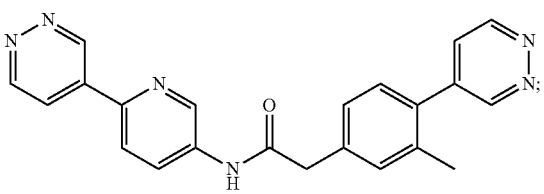
131
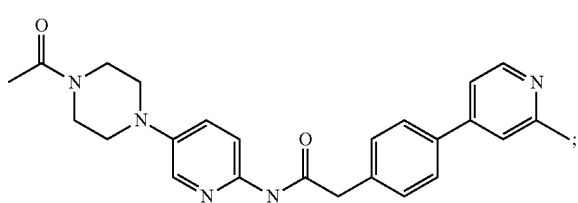
141
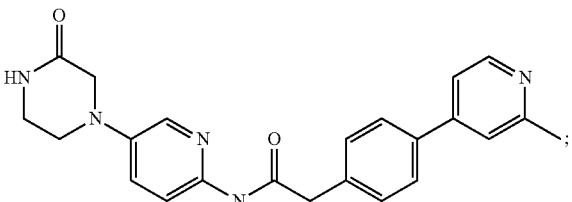
132
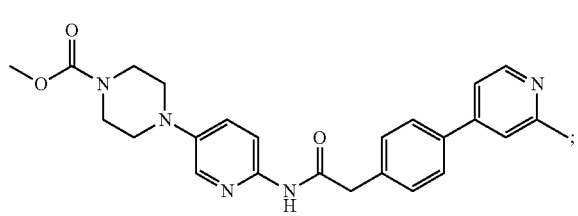
142
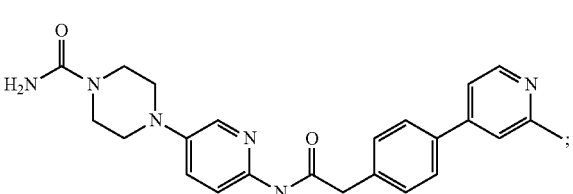
133
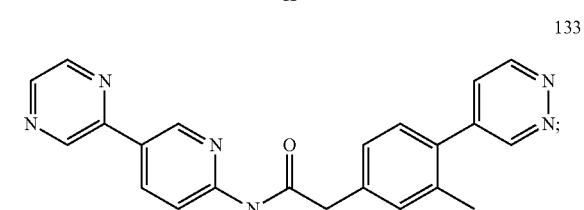
144
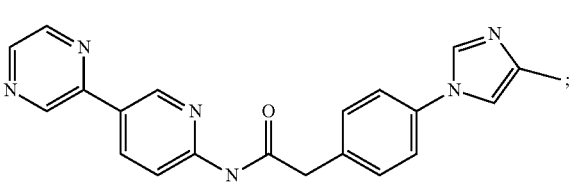
134
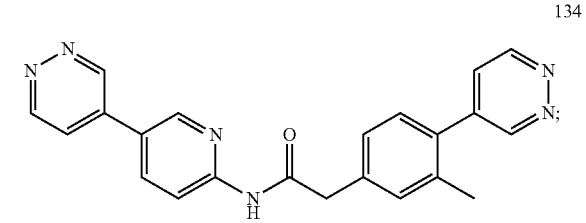
149
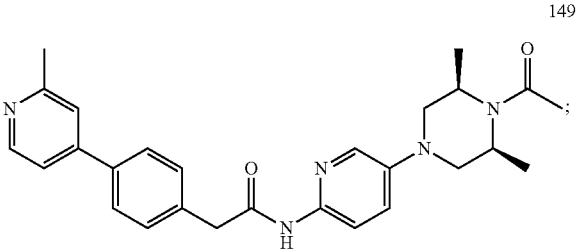

-continued
158
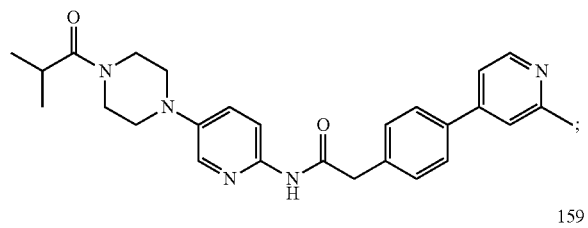
159
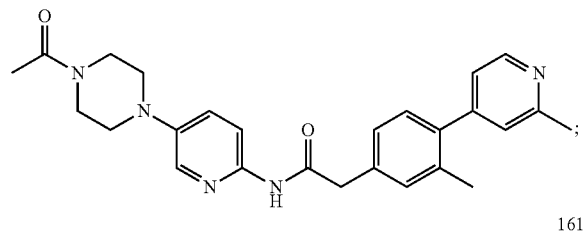
161
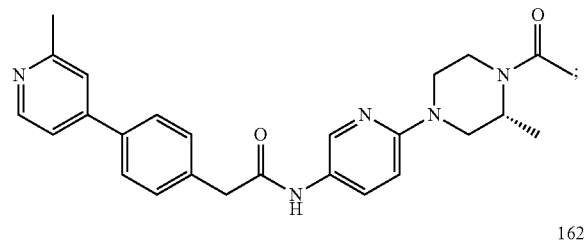
162
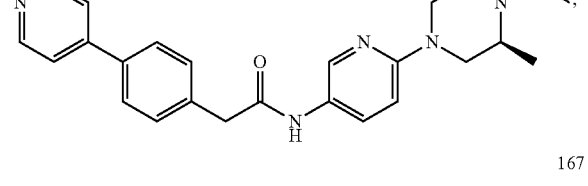
167
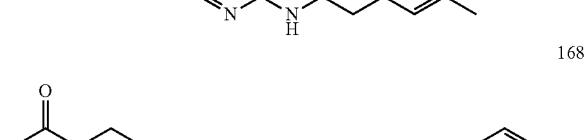
168
-continued
172
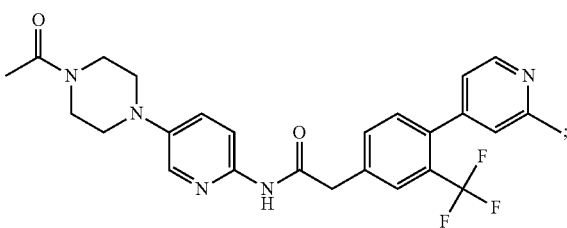
176
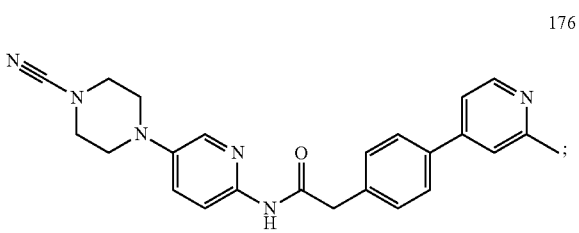
179
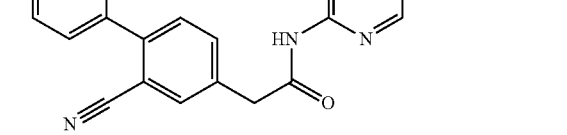
180
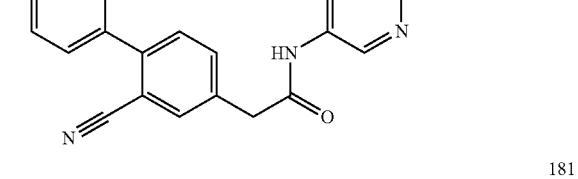
181
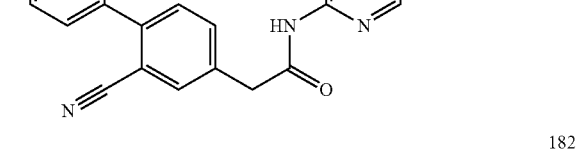
182
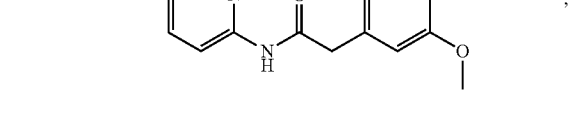

-continued

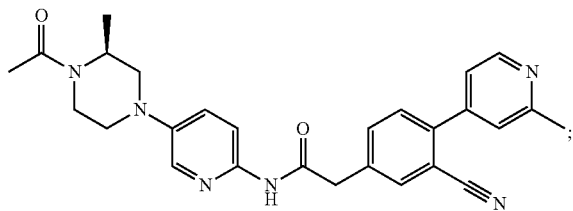

185

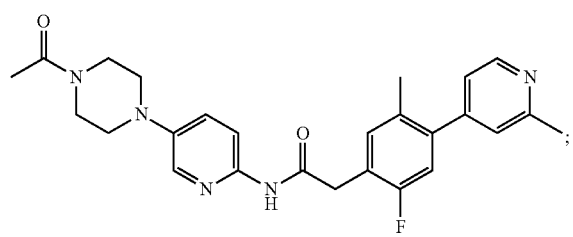

191

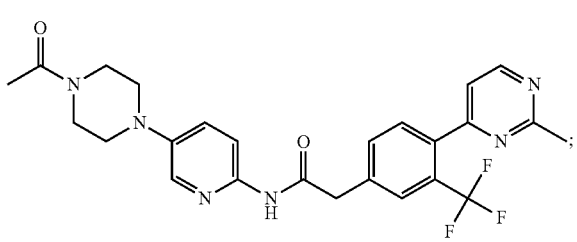

192

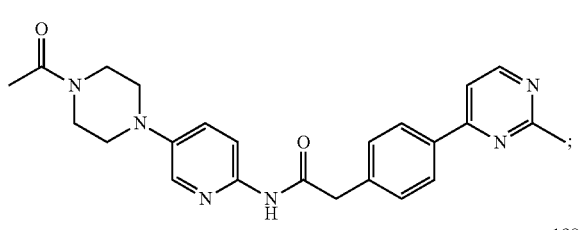

195

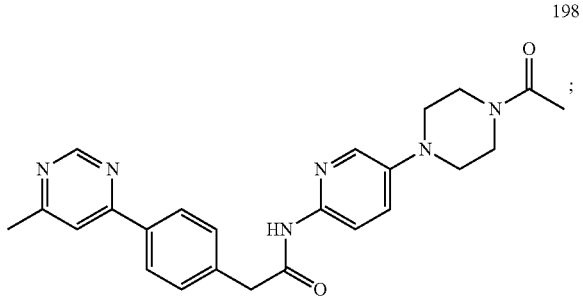

198

-continued

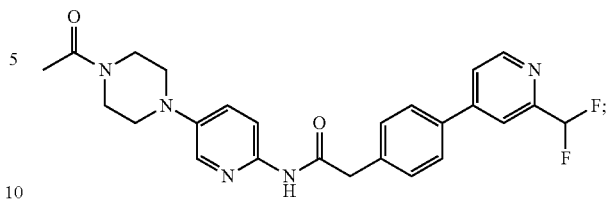

201

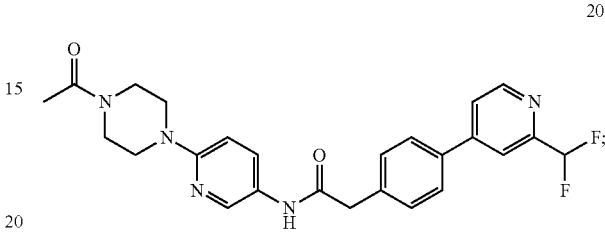

202

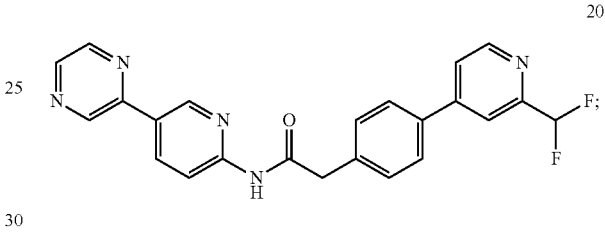

203 or a physiologically acceptable salt thereof.

4. A compound selected from: 2-(2-(2',3-dimethyl-2,4'-bipyridin-5-yl)acetamido)-5-(pyrazin-2-yl)pyridine 1-oxide; and 2',3-dimethyl-5-(2-oxo-2-(5-(pyrazin-2-yl)pyridin-2-ylamino)ethyl)-2,4'-bipyridine 1'-oxide; or a pharmaceutically acceptable salt thereof.

5. A pharmaceutical composition comprising a therapeutically effective amount of a compound of claim 1 and a pharmaceutically acceptable salt thereof, and a physiologically acceptable carrier.

6. A pharmaceutical composition comprising a therapeutically effective amount of a compound of claim 3 or a pharmaceutically acceptable salt thereof, and a physiologically acceptable carrier.

7. A pharmaceutical composition comprising a therapeutically effective amount of a compound of claim 4 or a pharmaceutically acceptable salt thereof, and a physiologically acceptable carrier.

* * * * *